(12) United States Patent
Wainer et al.

(10) Patent No.: US 7,749,984 B2
(45) Date of Patent: Jul. 6, 2010

(54) COMPUTER-BASED MODEL FOR IDENTIFICATION AND CHARACTERIZATION OF NON-COMPETITIVE INHIBITORS OF NICOTINIC ACETYLCHOLINE RECEPTORS AND RELATED LIGAND-GATED ION CHANNEL RECEPTORS

(75) Inventors: Irving W. Wainer, Washington, DC (US); Krzysztof Jozwiak, Abingdon, MD (US); Ruin Moaddel, Germantown, MD (US); Sarangan Ravichandran, Frederick, MD (US); Jack R. Collins, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1102 days.

(21) Appl. No.: 10/820,809

(22) Filed: Apr. 9, 2004

(65) Prior Publication Data
US 2005/0033522 A1    Feb. 10, 2005

Related U.S. Application Data

(63) Continuation-in-part of application No. 10/411,206, filed on Apr. 11, 2003, now abandoned.

(51) Int. Cl.
*A61K 314/85* (2006.01)
*C07C 69/88* (2006.01)

(52) U.S. Cl. .................. 514/80; 514/89; 546/74; 548/100

(58) Field of Classification Search ................ None
See application file for complete search history.

(56) References Cited

U.S. PATENT DOCUMENTS

| | | | |
|---|---|---|---|
| 2,970,147 A * | 1/1961 | Grussner et al. ............ 546/74 |
| 2,974,142 A | 3/1961 | Grüssner et al. |
| 3,341,538 A | 9/1967 | Block et al. |
| 3,634,429 A | 1/1972 | Leimgruber et al. |
| 3,767,658 A | 10/1973 | Atsumi et al. |
| 3,803,150 A | 4/1974 | Monkovic et al. |
| 3,910,919 A | 10/1975 | Monkovic et al. |
| 4,089,855 A | 5/1978 | Chatterjie et al. |
| 4,374,139 A | 2/1983 | Mohacsi |
| 4,912,114 A | 3/1990 | Revesz et al. |
| 5,905,153 A | 5/1999 | Wehrli et al. |
| 6,139,735 A | 10/2000 | Wainer et al. |
| 6,273,598 B1 | 8/2001 | Keck et al. |
| 6,387,268 B1 | 5/2002 | Wainer et al. |
| 6,784,186 B1 | 8/2004 | Jackson et al. |
| 6,844,438 B2 | 1/2005 | Neumeyer et al. |
| 2003/0073716 A1 | 4/2003 | Neumeyer et al. |
| 2004/0204862 A1 | 10/2004 | Wainer et al. |
| 2004/0242616 A1 | 12/2004 | Jackson et al. |
| 2005/0033522 A1 | 2/2005 | Wainer et al. |
| 2005/0107415 A1* | 5/2005 | Wu et al. ............... 514/282 |
| 2005/0159440 A1 | 7/2005 | Neumeyer et al. |
| 2005/0256147 A1 | 11/2005 | Kim |
| 2006/0069086 A1 | 3/2006 | Michalow |
| 2006/0111381 A1 | 5/2006 | Jackson et al. |

FOREIGN PATENT DOCUMENTS

| | | |
|---|---|---|
| EP | 0612730 A1 | 8/1994 |
| WO | 0055624 A2 | 9/2000 |

OTHER PUBLICATIONS

Eddy et al (Bull Narcotics, U.N., Dept. Social Affairs, 1958, 10(No. 4), 23-41). Abstract in Database.HCAPlus, 53:95845.*
Database Biosis, AN 2003:381659, "Molecular interactions of alpha3beta4 nicotinic acetylcholine receptor with its luminal non-competitive inhibitors: comparison of experimental chromatographic data with in silico docking studies," K. Joswiak et al., FASEB Journal (Mar. 2003), vol. 17, No. 4-5, pp. Abstract No. 390.0.
Ortells et al., "A mixed helix-beta-sheet model of the transmembrane region of the nicotinic acetylcholine receptor," Protein Engineering, vol. 9, No. 1, pp. 51-59, 1996.
1959:95845 HCAPLUS, DN:53:95845, "Synthetic analgesics", Bull. Narcotics, U.N., Dept. (1958), 10(No. 4), 23-41.
2005:431407 CAPLUS, DN:142:56393, "Preparation of opioid and opiod-like compounds as opiate receptor ligands . . . ", Wu, Edwin S.C., et al.
F.J. Barrantes et al., The Journal of Biological Chemistry, vol. 275, No. 48, Dec. 1, 2000, pp. 37333-37339.
M. Schapira et al., "Structural model of nicotinic acetylcholine receptor isotypes bound to acetylcholine and nicotine", BMC Structural Biology 2002, 2:1.
S.J. Opella et al., Nature Structural Biology, vol. 6, No. 4, Apr. 1999, pp. 374-379.
S.D. Vinarov, Journal of Structural and Functional Genomics, vol. 4, 2003, pp. 191-209.
S.C. Hernandez et al., The Journal of Pharmacology and Experimental Therapeutics, vol. 293, No. 3, 2000, pp. 962-967.
K. Jozwiak et al., Journal of Chromatography B, vol. 797, 2003, pp. 373-379.
K. Jozwiak et al., Journal of Medicinal Chemistry, vol. 47, No. 16, 2004, pp. 4008-4021.
Abagyan et al. Curr. Opinion in Chem. Biology, 20015, 375-382, 2001.
Aqvist et al. Nature 404, 881-884 (Apr. 20, 2000).

(Continued)

Primary Examiner—Michael Borin
(74) Attorney, Agent, or Firm—Cantor Colburn LLP

(57) ABSTRACT

A computer readable medium holding data of a molecular model of a ligand-gated ion channel receptor and/or a computer system for modeling said receptor are provided by the instant invention. The molecular model can be used to design novel compounds having activity as non-competitive inhibitors of the ion channel. A preferred embodiment of the invention relates to nicotinic acetylcholine receptors. Compounds having activity as non-competitive inhibitors of ligand-gated ion channel receptors and methods for inhibiting the receptor and treating diseases or disorders mediated by function of the receptor are also disclosed.

5 Claims, 16 Drawing Sheets
(4 of 16 Drawing Sheet(s) Filed in Color)

OTHER PUBLICATIONS

Arias H.R., Binding sites for exogenous and endogenous non-competitive inhibitors of the nicotrinic acetylcholine receptor, (1998), Biochimica et Biophysica Acta, vol. 1376, pp. 173-220.

Arias H.R., Topology of ligand binding sites on the nicotinic acetylcholine receptor (1997), Brain Research Reviews, vol. 25, pp. 133-191.

Arias H.R. Localization of agonist and competitive antagonist binding sites on nicotinic acetylcholine receptors (2000), Neurochemistry International, vol. 36, pp. 595-645.

Johnston, G.A.R., Medicinal Chemistry and Molecular Pharmacology of GABA-C Receptors, (Aug. 1, 2002), Current Topics in Medicinal Chemistry, vol. 2, No. 8, Abstract.

Lloyd G.K., Neuronal Nicotinic Acetylcholine Receptors as Novel Drug Targets, The Journal of Pharmacology and Experimental Therapeutics, vol. 292, No. 2, pp. 461-467.

Capener C.E, et al., Ion channels: structural bioinformatics and modeling, Human Molecular Genetics, (2002), vol. 11, No. 20, pp. 2425-2433.

Kaliszan R., et al., Combination of Biochromatography and Chemometrics: A Potential New Research Strategy in Molecular Pharmacology and Drug Design, (1997), Chromatographic Separations Based on Molecular Recognition, pp. 273-302.

R. Moaddel, et al., Immobilized nicotinic receptor stationary phases: going with the flow in high-throughput screening and pharmacological studies, Journal of Pharmaceutical and Biomedical Analysis, (2003), vol. 30, pp. 1715-1724.

Jozwiak K, et al., Displacement and Nonlinear Chromatographic Techniques . . . Chromatographic Stationary Phase, (2002), Anal. Chem., vol. 74, pp. 4618-4624.

Pearlman D.A., et al., AMBER, a package of computer programs for applying molecular . . . structural and energetic properties of molecules, (1995), Computer Physics Communications, vol. 91, pp. 1-41.

Laskowski R.A. et al., Procheck: A program to check the stereochemical quality of protein structures, (1993), J. Appl. Cryst., vol. 26, Abstract.

Bertaccini E., et al., Predicting the transmembrane secondary structure of ligand-gated ion channels, (2002), Protein Engineering, vol. 15, No. 6, pp. 443-453.

Jozwiak K, et al., Enantioselective interactions of dextromethorphan and levomethorphan with . . . chromatographic and functional data, (2003), Journal of Chromatography B, vol. 797, pp. 373-379.

Cornell W.D., et al., A Second Generation Force Field for the Simulation of Proteins, Nucleic Acids, and Organic Molecules, (1995), J. Am. Chem. Soc., vol. 117, pp. 5179-5197.

Cheng W., et al., Investigating the dielectric effects of channel pore water on the electrostatic barriers of the permeation ion by the finite difference Poisson-Boltzmann method, (1998), Eur Biophys J, vol. 27, pp. 105-112.

Wade J.L., et al., Theoretical Description of Nonlinear Chromatography, with Applications to Physicochemical . . . for Preparative-Scale Separations, (1987), Anal. Chem., vol. 59, pp. 1286-1295.

Wainer I.W., et al., Liquid chromatographic studies with immobilized neuronal nicotinic acetylcholine receptor stationary phases: effects of . . . On drug-receptor interactions, (1999), Journal of Chromatography B Sci Appl, vol. 724 pp. 65-72.

Zhang Y., et al., Immobilized Nicotinic Receptor Stationary Phase for On-Line Liquid Chromatographic Determination of Drug-Receptor Affinities, (1998), Analytical Biochemistry, vol. 264, pp. 22-25.

Barrantes F.J., Lipid matters: nicotinic acetylcholine receptor-lipid interactions (Review), (2002), Molecular Membrane Biology, vol. 19, pp. 277-284.

Morris G.M., et al., Automated Docking Using a Lamarckian Genetic Algorithm and an Empirical Binding Free Energy Function, (1998), Journal of Computational Chemistry, vol. 19, No. 14, pp. 1639-1662.

Hucho F., et al., The emerging three-dimensional structure of a receptor, the nicotinic acetylcholine receptor, (1996), Eur. J. Biochem., vol. 239, pp. 539-557.

Elgoyhen A.B., et al., $\alpha 10$: A determinant of nicotinic cholinergic receptor function in mammalian vestibular and cochlear mechanosensory hair cells, (March 13, 2001), Proc Natl Acad Sci USA, vol. 98, No. 6, pp. 3501-3506.

Maelicke A. Angew. Chem. Internat. Ed. Engl, 23, 195-221, 1984.

\* cited by examiner

SEQUENCE LISTING

```
<160> NUMBER OF SEQ ID NOS: 15

<210> SEQ ID NO 1
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Delta Sequence - Transmembrane domain
      of ligand gated ion channel subunit

<400> SEQUENCE: 1

Glu Lys Met Ser Thr Ala Ile Ser Val Leu Leu Ala Gly Ala Val Phe
1               5                   10                  15

Leu Leu Leu Thr Ser Gly Arg
            20

<210> SEQ ID NO 2
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Gamma Sequence - Transmembrane domain
      of ligand gated ion channel subunit

<400> SEQUENCE: 2

Gln Lys Cys Thr Leu Ser Ile Ser Val Leu Leu Ala Gln Thr Ile Phe
1               5                   10                  15

Leu Phe Leu Ile Ala Gln Lys
            20

<210> SEQ ID NO 3
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Alpha 1 Sequence - Transmembrane domain
      of ligand gated ion channel subunit

<400> SEQUENCE: 3

Glu Lys Met Thr Leu Ser Ile Ser Val Leu Leu Ser Leu Thr Val Phe
1               5                   10                  15

Leu Leu Val Ile Val Glu Leu
            20

<210> SEQ ID NO 4
<211> LENGTH: 23
<212> TYPE: PRT
<213> ORGANISM: Unknown
<220> FEATURE:
<221> NAME/KEY: misc_feature
<222> LOCATION: (1)..(23)
```

```
<223> OTHER INFORMATION: Table 1 Alpha 3 Sequence - Transmembrane domain
      of ligand gated ion channel subunit

<400> SEQUENCE: 4

Glu Lys Val Thr Leu Cys Ile Ser Val Leu Leu Ser Leu Thr Val Phe
1               5                   10                  15

Leu Leu Val Ile Thr Glu Thr
            20

<210> SEQ ID NO 5
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Alpha 4 Sequence - Transmembrane domain
      of ligand gated ion channel subunit

<400> SEQUENCE: 5

Glu Lys Ile Thr Leu Cys Ile Ser Val Leu Leu Ser Leu Thr Val Phe
1               5                   10                  15

Leu Leu Leu Ile Thr Glu Ile
            20

<210> SEQ ID NO 6
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Alpha 5 Sequence - Transmembrane domain
      of ligand gated ion channel subunit

<400> SEQUENCE: 6

Glu Lys Ile Cys Leu Cys Thr Ser Val Leu Val Ser Leu Thr Val Phe
1               5                   10                  15

Leu Leu Val Ile Glu Glu Ile
            20

<210> SEQ ID NO 7
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Alpha 6 Sequence - Transmembrane domain
      of ligand gated ion channel subunit

<400> SEQUENCE: 7

Glu Lys Val Thr Leu Cys Ile Ser Val Leu Leu Ser Leu Thr Val Phe
1               5                   10                  15

Leu Leu Val Ile Thr Glu Thr
            20

<210> SEQ ID NO 8
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Alpha 7 Sequence - Transmembrane domain
      of ligand gated ion channel subunit
```

```
<400> SEQUENCE: 8

Glu Lys Ile Ser Leu Gly Ile Thr Val Leu Leu Ser Leu Thr Val Phe
1               5                   10                  15

Met Leu Leu Val Ala Glu Ile
            20

<210> SEQ ID NO 9
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Alpha 9 Sequence - Transmembrane domain
      of ligand gated ion channel subunit

<400> SEQUENCE: 9

Glu Lys Val Ser Leu Gly Val Thr Ile Leu Leu Ala Met Thr Val Phe
1               5                   10                  15

Gln Leu Met Val Ala Glu Ile
            20

<210> SEQ ID NO 10
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Alpha 10 Sequence - Transmembrane
      domain of ligand gated ion channel subunit

<400> SEQUENCE: 10

Glu Lys Val Ser Leu Gly Val Thr Val Leu Leu Ala Leu Thr Val Phe
1               5                   10                  15

Gln Leu Ile Leu Ala Glu Ser
            20

<210> SEQ ID NO 11
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Beta 1 Sequence - Transmembrane domain
      of ligand gated ion channel subunit

<400> SEQUENCE: 11

Glu Lys Met Gly Leu Ser Ile Phe Ala Leu Leu Thr Leu Thr Val Phe
1               5                   10                  15

Leu Leu Leu Leu Ala Asp Lys
            20

<210> SEQ ID NO 12
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Beta 2 Sequence - Transmembrane domain
      of ligand gated ion channel subunit

<400> SEQUENCE: 12

Glu Lys Met Thr Leu Cys Ile Ser Val Leu Leu Ala Leu Thr Val Phe
```

```
                1               5               10              15
Leu Leu Leu Ile Ser Lys Ile
                20

<210> SEQ ID NO 13
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Beta 3 Sequence - Transmembrane domain
      of ligand gated ion channel subunit

<400> SEQUENCE: 13

Glu Lys Leu Ser Leu Ser Thr Ser Val Leu Val Ser Leu Thr Val Phe
1               5                   10                  15
Leu Leu Val Ile Glu Glu Ile
                20

<210> SEQ ID NO 14
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Beta 4 Sequence - Transmembrane domain
      of ligand gated ion channel subunit

<400> SEQUENCE: 14

Glu Lys Met Thr Leu Cys Ile Ser Val Leu Leu Ala Leu Thr Phe Phe
1               5                   10                  15
Leu Leu Leu Ile Ser Lys Ile
                20

<210> SEQ ID NO 15
<211> LENGTH: 23
<212> TYPE: PRT
<213> ORGANISM: Unknown
<220> FEATURE:
<221> NAME/KEY: misc_feature
<222> LOCATION: (1)..(23)
<223> OTHER INFORMATION: Table 1 Epsilon Sequence - Transmembrane domain
      of ligand gated ion channel subunit

<400> SEQUENCE: 15

Gln Lys Cys Thr Val Ser Ile Asn Val Leu Leu Ala Gln Thr Val Phe
1               5                   10                  15
Leu Phe Phe Leu Ile Ala Gln
                20
```

COMPUTER-BASED MODEL FOR IDENTIFICATION AND CHARACTERIZATION OF NON-COMPETITIVE INHIBITORS OF NICOTINIC ACETYLCHOLINE RECEPTORS AND RELATED LIGAND-GATED ION CHANNEL RECEPTORS

The present application is a Continuation-In-Part of U.S. application Ser. No. 10/411,206, filed Apr. 11, 2003 now abandoned, the entire contents of which are hereby incorporated by reference and for which priority is claimed under 35 U.S.C. §120.

The present application includes an appended Sequence Listing of 15 amino acid sequences and Appendices 1 to 5 providing computer programming scripts, parameter files and atomic coordinates of computer models of the luminal channel portion of the ligand-gated ion channel subtypes.

The patent or application file contains at least one drawing executed in color. Copies of this patent or patent application publication with color drawing(s) will be provided by the Office upon request and payment of the necessary fee.

FIELD OF THE INVENTION

The present invention relates to a computer system for generating molecular models of ligand-gated ion channels and in particular, molecular models of the inner lumen of a ligand-gated ion channel and associated binding pockets. The present invention further relates to a computer system simulating interaction of the computer-based model of the ligand-gated channel and non-competitive inhibitor compounds for identification and characterization of non-competitive inhibitors and to inhibitor compounds so discovered. The present invention also relates to methods for treating various disorders related to ligand-gated ion channel receptor function. The invention also provides a way to examine compounds for "off-target" activity that may cause undesirable side effects to a desired target activity or that may represent a new therapeutic activity for a known compound.

BACKGROUND OF THE INVENTION

Ligand gated ion channels (LGICs) are currently very important targets for drug discovery in the pharmaceutical industry. The superfamily is separated into the nicotinic receptor superfamily (muscular and neuronal nicotinic, GABA-A and-C, glycine and 5-HT3 receptors), the excitatory amino acid superfamily (glutamate, aspartate and kainate receptors) and the ATP purinergic ligand gated ion channels. These families only differ in the number of transmembrane domains found in each subunit (nicotinic—4 transmembrane domains, excitatory amino acid receptors—3 transmembrane domains, ATP purinergic LGICs—2 transmembrane domains).

Nicotinic acetylcholine receptors (nAChRs) are a family of ligand gated ion channels that control the fast permeation of cations through the postsynaptic cell membrane when stimulated by acetylcholine. Physiologically, nAChRs are key targets in drug discovery for a number of diseases, including Alzheimer's and Parkinson's disease, and have been widely discussed and investigated.

Structural and functional studies of nAChRs have led to the elucidation of three physiological states of the receptor: 1) resting (channel closed); 2) acetylcholine stimulated (channel open); and 3) a desensitized state where the ion flux is inhibited even in the presence of neurotransmitter. The overall structure of nicotinic acetylcholine receptor of *Torpedo marmorata* has been examined by Unwin and coworkers using cryo-electron microscopy and revealed the conical shape of the channel portion of the receptor and the relationship of the membrane-spanning helices to each other (see FIG. 1). In spite of these unprecedented advances in resolving the structures of transmembrane proteins, the detailed, atomic resolution, structure of the entire nAChR family remains unresolved.

Muscular nAChRs are located at the nerve-muscle junctions and are responsible for triggering motor motion, and neuronal nAChRs, widely distributed in the nervous system, are involved in the fast synaptic transmission of inter-neuronal communication. It is known that these receptors are structurally similar in their overall composition but differ in the exact make-up of the protein subunits forming the receptors.

The nicotinic acetylcholine receptor (nAChR) is presently the best characterized member of the ligand-gated ion channel superfamily. The nicotinic receptors are of great therapeutic importance. The subunits assemble combinatorily to form a variety of pentameric transmembrane protein subtypes.

Each receptor is formed by bringing together five separate trans-membrane proteins, each containing a large extra-cellular N-terminal domain, four membrane spanning alpha helices (M1, M2, M3, and M4) and a small C-terminal domain (see FIG. 1). Two, homologous, neurotransmitter binding sites are formed by the N-terminal domains where cholinergic agonist and competitive antagonists bind, and are the usual targets for drug design. The ion channel is formed by a pentameric arrangement of the M2 helical segments contributed by the five proteins (see FIG. 2). The channel specificity, characteristic of each receptor subtype, is controlled by the identity of each of the M2 helices.

Neuronal nicotinic acetylcholine receptors (nAChRs) are the class of ligand-gated ion channels of the central and peripheral nervous system that regulate synaptic activity. The basic structure of the nAChR is shown in FIGS. 1 and 2. Referring to FIG. 1, nAChR consists of five transmembrane subunits 1, 2, 3, 4, 5 oriented around a central pore 6 permeable to cations. Cations flow through the pore is regulated by ligand binding. The subunits in nAChR are typically α subunits and β subunits.

At present, 12 different homologous subunits have been identified in neuronal nAChRs, 9 α subunits (α2-α10) and 3 β subunits (β2-β4). The major difference between α and β subunits is the presence and location of the disulfide bond formed by two adjacent cysteines in the α systems, the absence of this feature distinguishes non-α subunits. This disulfide bond located on the extracellular domain plays an important role in neurotransmitter binding as well as the mechanism of channel opening. These subunits combine to form multiple nAChR subtypes and predominant stoichiometry is $(\alpha)_2(\beta)_3$, however pentamers containing only α subunit are also known e.g., $(\alpha 7)_5$. In case of muscular nAChR the stoichiometry is more complicated, the muscular nAChR receptor is predominantly described as $(\alpha)_2\beta\delta\gamma$.

The nAChRs are very complex systems with dozens of potential different binding domains for different classes of compounds of both endo- and exogenous origin (Arias H. R., (1997) Topology of ligand binding sites on the nicotinic acetylcholine receptor. *Brain Res. Rev.* 25: 133-91). Two primary cholinergic binding sites are located on the extracellular side 7 (refer to FIG. 1, approximately 30-35 Å above the membrane) in the pocket at the interface between the α and β subunits. The nAChR contains several other classes of binding sites at which non-competitive inhibitors (NCIs) bind (Arias H. R. (1998) Binding sites for exogenous and endogenous non-competitive inhibitors of the nicotinic acetylcholine receptor. *Biochim. Biophys. Act.* 1376: 173-220). One, so-called "luminal high affinity" NCI binding domain is located on the surface of the internal lumen forming the ion channel. This site is a highly polar and negatively charged domain, which primarily plays the role as a cation selector. In general, an NCI compound does not compete with the neurotransmitter ligand of the receptor for binding to the neurotransmitter ligand binding site of the receptor located on the external surface both α subunits in a pocket approximately 30-35 Å from the transmembrane portion of the subunit (that is, above the surface membrane when the receptor is expressed on in a cell), as described by Arias [Arias, H. R. (2000) Localization of agonist and competitive antagonist binding sites on nicotinic acetylcholine receptors *Neurochem. Int* 36, 595-645].

Such drugs as mecamylamine, ketamine, bupropion or barbiturates bind in the narrowest region of the channel on the cell membrane level. Inhibitors acting there are mainly amines. It is believed that the ligands bind into this region and sterically plug the channel, blocking the flux of ions.

"Non-luminal" sites are the population of 10-30 binding sites located mostly at the lipid-protein interface for which an allosteric mechanism of non-competitive inhibition was proposed. Agents of different origin (steroids, fatty acids, alcohols, local anesthetics etc.) can bind to those sites and modulate nAChR activity.

Other classes of ligand-gated ion channels include GABA (Johnston G. A. (2002) Medicinal chemistry and molecular pharmacology of GABA(C) receptors. *Curr Top Med Chem* 2, 903-13), 5HT3 (D. C. Reeves, S. C. Lummis, (2002) The molecular basis of the structure and function of the 5-HT3 receptor: a model ligand-gated ion channel (review). *Mol. Membr. Biol.* 19, 11-26), AMPA (T. B. Stensbol, U Madsen, P. Krogsgaard-Larsen, (2002) The AMPA receptor binding site: focus on agonists and competitive antagonists. *Curr. Pharm. Des.* 8, 857-72) and NMDA (K. A. Macritchie, A. H. Young, (2001) Emerging targets for the treatment of depressive disorder. *Expert Opin. Ther. Targets* 5, 601-612) receptors, etc. Although the molecular structure of these receptors differ significantly, it is believed that the luminal domains are homologous to the luminal domain of nAChRs. There are five (or occasionally four) transmembrane helices forming the wall of the channel with "rings" of polar amino-acids exposed on the pre-forming surface and the same non-competitive inhibition phenomenon can be observed.

In summary, the luminal high affinity NCI binding domain is located on the surface of the internal lumen forming the ion channel. Drugs of different origin bind in this region and sterically plug the channel blocking the flux of ions.

Non-competitive inhibition of the nAChR can be responsible for severe adverse drug effects. On the other hand, designing ligands that specifically interact with this site can be part of the development of new treatments of Alzheimer's and Parkinson's diseases, for example by identifying compounds likely to exhibit side effects through non-competitive inhibition of a LGIC. Furthermore, the compounds identified as NCIs by the present method are likely to find use in treating Tourette's syndrome and cognitive disorders, schizophrenia, pain [see, Lloyd, G. K. and Williams, M. (2000) *J. Pharmacol. Exper. Ther.* 292, 461-467.], anxiety, depression, neurodegeneration and addictions caused by an overactive LGIC receptor, especially diseases in which nicotine agonist activity against a neuronal nAChR is part of the etiology (e.g. smoking addiction). The invention can also be used to evaluate cardiovascular toxicity of a compound mediated by non-competitive inhibition of a LGIC receptor, e.g. arrhythmia and GI spasming or diarrheal side effects of a compound caused by inhibition of a muscular nAChR.

Classical methods of NCI identification are time consuming and not effective in rapid screening of chemical libraries of drug candidates.

Several different molecular models of the nAChR transmembrane domain have been reported (Capener C E, Kim H J, Arinaminpathy Y, Sansom M S (2002) Ion channels: structural bioinformatics and modelling. *Hum Mol Genet* 11:2425-33). However, none of those models were used to investigate interaction with channel blockers. A computer based model for in silico simulations of NCI interactions with the luminal domain of LGICs is needed to better understand the phenomenon of the receptor's inhibition by NCIs.

Furthermore, in drug discovery, the potential adverse effects of drug candidates are of great importance. In-depth understanding of mechanistic interaction of luminal NCIs with different subtypes of LGICs, especially of nAChRs, is required to remove potential unwanted side effects at this site. In this respect, a rapid screening technology that would identify NCIs of LGICs, and especially of nAChRs would be greatly desired.

The functional determination and characterization of a NCI of a LGIC is very complex and time consuming. One approach is affinity chromatography based on immobilized receptor protein. This is a versatile tool for investigation of intermolecular interactions of a receptor with its ligands. The chemometric approach of affinity chromatography can be employed for determination of reliable relative affinities of ligands as well as kinetic characterization, which otherwise would be inaccessible, for a large set of compounds (Kaliszan R., Wainer I. W. (1997) Combination of Biochromatography and Chemometrics: A Potential New Research Strategy in Molecular Pharmacology and Drug Design. In Chromatographic Separations Based on Molecular Recognition. K. Jinno, editors Wiley-VCH).

Methods using nAChR and other receptors immobilized on a chromatographic support have been elaborated (U.S. Pat. Nos. 6,387,268, 6,139,735, provisional application No. 60/337,172). It was shown that the obtained stationary phases worked as selective binding materials for competitive cholinergic ligands and can be used for high throughput screening of various competitive agonists and antagonists (R. Moaddel, I. W. Wainer, (2003) Immobilized nicotinic receptor stationary phases: going with the flow in high-throughput screening and pharmacological studies *J Pharm Biomed Anal.* 30, 1715-24). The usefulness of such columns based on immobilized nAChR for investigations and modeling of NCI affinity has also been demonstrated. Using a novel non-linear chromatography approach off and on kinetics of ligand interaction with the receptor can be determined. (K. Jozwiak, J. Haginaka et al., (2002) Displacement and nonlinear chromatographic techniques in the investigation of interaction of noncompetitive inhibitors with an immobilized α3β4 nicotinic acetylcholine receptor liquid chromatographic stationary phase. *Anal Chem* 74: 4618-4624).

BRIEF DESCRIPTION OF THE DRAWINGS

The features of the invention may be better understood by reference to the drawings described below.

FIG. 3 shows the luminal domain of α3β2 and α3β4 channels. Red—negatively charged (e.g., aspartic acid, glutamic acid), orange—polar (e.g., serine or threonine), green—hydrophobic (e.g., leucine, valine), light blue—positively charged (e.g., lysine), dark blue—aromatic (e.g., phenylalanine).

DETAILED DESCRIPTION OF THE INVENTION

The present invention results from understanding of the interactions between a particular subtype of the neuronal nAChRs and molecules that inhibit the flow of ions through the cell membrane. A first step in this understanding is to characterize the composition of the membrane-spanning M2 helices. So far, twelve distinct M2 helices (known as subunits of the channel), nine labeled alpha (α2-α10) and three labeled beta (β2-β4), have been shown to form channels of a wide variety of both homomeric and heteromeric subtypes of neuronal nAChRs. The most common subunit stoichiometry has been determined to be $(αX)_2(βY)_3$, (X=2-4; Y=2-4), respectively for heteromeric subtypes and $(αZ)_5$, (Z=7-10) for the homomeric subtypes. However, other, more complex, combinations have also been reported. These various subtypes have been found in different locations of the central and peripheral nervous system and can be assigned to different functions. For instance: the α4β2 and α4β4 subtypes appear to play a role in cognition, neurodegeneration, pain, anxiety and depression; the α3β2 subtype in dopamine release and Parkinson's disease; the α7 in GABA release; the α9 in auditory function and development; and the α3β4 in norepinephrine release, cardiovascular and gastrointestinal action. In addition, NCIs of ligand-gated ion channels are expected to have therapeutic benefit in treatment of cognitive dysfunction/attentional disorders such as ADHD, neurodegenerative diseases such as Alzheimer's disease, schizophrenia, depression, epilepsy, Tourette's syndrome and in smoking cessation.

Non-competitive inhibition of nAChRs may be responsible for many of the adverse effects attributed to drug therapy. For example, the impairment of cardiovascular function observed during ketamine anesthesia has been associated with the inhibitory action of ketamine on ganglionic nAChRs. The administration of such drugs as methadone (opioid antagonist) mecamylamine or verapamil (antihypertensive agents) often results in gut motility impairment and constipation, which has been associated with their NCI activity on the α3β4 nAChR.

Figure 1:
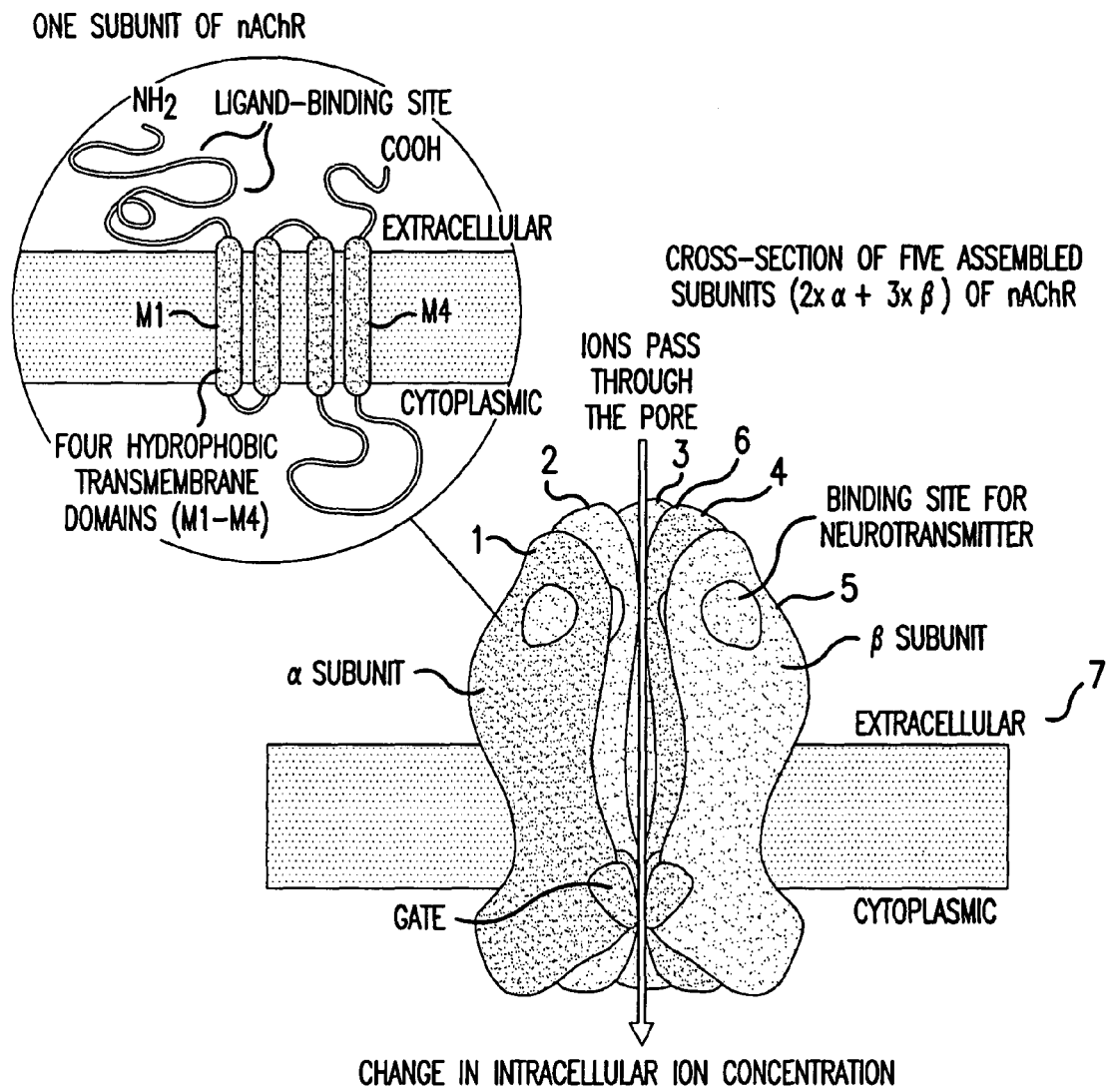
FIG. 1 and FIG. 2 schematically show the general structure of a neuronal nicotinic acetylcholine receptor (nAChR).

The pentameric bundle of M2 helices forms the "lumen" (FIGS. 1-3), the central surface of the narrowest part of the channel, which takes part in channel gating and ion selection. The amino acid residues forming the surface of the lumen are quite conserved across different subunits, and form distinct regions of the channel, or "rings" (see FIG. 2 and Table 2). These rings are important for proper function and selectivity of the neuronal nAChRs and are common to all subtypes. An illustration of this importance is the fact that even a single point mutation in this domain can lead to a variety of serious diseases e.g., autosomal dominant nocturnal frontal lobe epilepsy, associated with a serine (S)→phenylalanine (F) mutation in the M2 segment of the α4 subunit of nAChR (Steinlein, O. K. Nicotinic acetylcholine receptors and epilepsy. Curr. Drug Target CNS Neurol. Disord. 2002, 1, 443-448.). Therefore, the sequence and structure of the M2 subunits forming the luminal domain are important for understanding disease states associated with nAChRs.

The luminal domain of the ion channel has been identified as a high affinity binding site for a large number of exogenous and endogenous substances in both the open and desensitized state. Many drugs, particularly ionizable amines, can elicit deleterious side effects by binding to the surface of the lumen, sterically plugging the channel and blocking the flux of ions.

This mechanism is distinct from the traditional cholinergic mechanism of receptor regulation, and ligands inhibiting the receptor in this way are called non-competitive inhibitors (NCIs) or channel blockers. Noncompetitive action on the neuronal nAChR has been assigned to a large number of marketed drugs and their metabolites and can be responsible for many toxic side effects of various therapies. For example clinical side effects observed during ketamine anesthesia (i.e., the impairment of the cardiovascular function, etc.) have been associated with the inhibitory action of ketamine on ganglionic nAChRs (Friederich, P.; Dybek, A.; Urban, B. W. Stereospecific interaction of ketamine with nicotinic acetylcholine receptors in human sympathetic ganglion-like SH-SY5Y cells. *Anesth.* 2000, 93, 818-24.). Thus, there is a need to develop models to identify ligands that might be NCIs of nAChRs.

tion. Thus, the invention constitutes a system for drug discovery and for screening of a drug candidate for unexpected side effects and toxicities.

Figure 4:
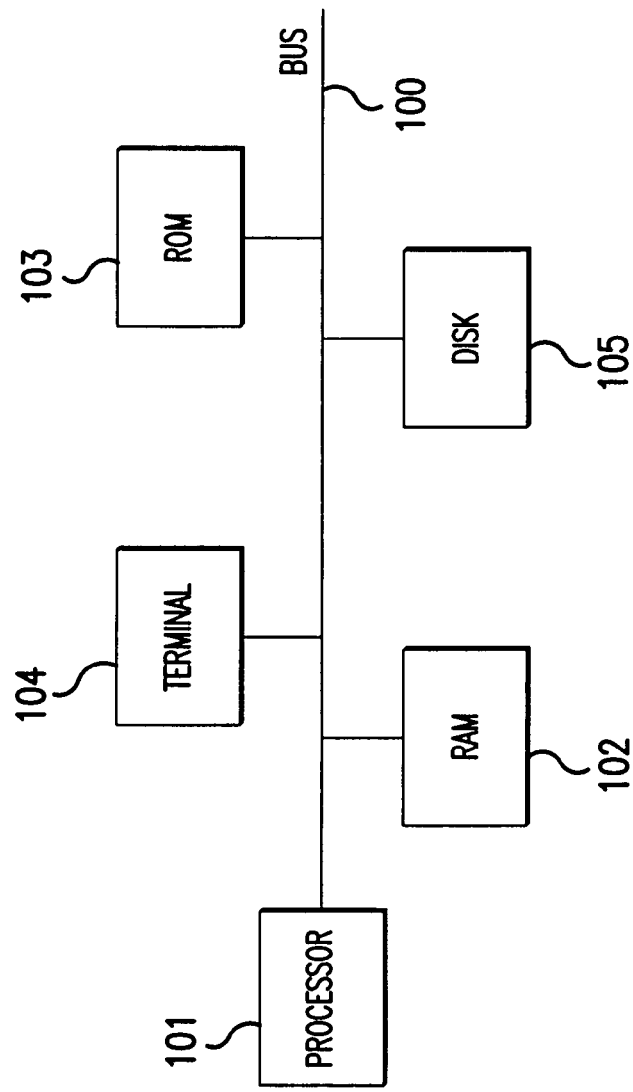
FIG. 4 is a schematic representation of a computer system useful in the practice of the invention.

In an embodiment of the present invention, as shown in FIG. 4, the computer system comprises a memory, e.g. disk 105, storing positional data of the atomic coordinates of the transmembrane portion of at least one subunit of a ligand-gated neurotransmitter receptor protein, and a processor 101 generating a molecular model having a three dimensional shape representative of the pore portion of the ligand-gated neurotransmitter receptor based on positional data. During execution of the process for generating the molecular model, it is understood that the positional data would be stored in, for example, RAM 102, or other memory readily accessible by the processor 101.

TABLE 1

| Residue No | 1' | 2' | 3' | 4' | 5' | 6' | 7' | 8' | 9' | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| delta[1]) SEQ ID NO: 1 | E | K | M | S | T | A | I | S | V | L | L | A | G | A | V | F | L | L | L | T | S | G | R |
| gamma[2]) SEQ ID NO: 2 | Q | K | C | T | L | S | I | S | V | L | L | A | Q | T | I | F | L | F | L | I | A | Q | K |
| alpha 1[3]) SEQ ID NO: 3 | E | K | M | T | L | S | I | S | V | L | L | S | L | T | V | F | L | L | V | I | V | E | L |
| alpha 3[3]) SEQ ID NO: 4 | E | K | V | T | L | C | I | S | V | L | L | S | L | T | V | F | L | L | V | I | T | E | T |
| alpha 4[5]) SEQ ID NO: 5 | E | K | I | T | L | C | I | S | V | L | L | S | L | T | V | F | L | L | L | I | T | E | I |
| alpha 5[8]) SEQ ID NO: 6 | E | K | I | C | L | C | T | S | V | L | V | S | L | T | V | F | L | L | V | I | E | E | I |
| alpha 6[8]) SEQ ID NO: 7 | E | K | V | T | L | C | I | S | V | L | L | S | L | T | V | F | L | L | V | I | T | E | T |
| alpha 7[6]) SEQ ID NO: 8 | E | K | I | S | L | G | I | T | V | L | L | S | L | T | V | F | M | L | L | V | A | E | I |
| alpha 9[8]) SEQ ID NO: 9 | E | K | V | S | L | G | V | T | I | L | L | A | M | T | V | F | Q | L | M | V | A | E | I |
| alpha 10[7]) SEQ ID NO: 10 | E | K | V | S | L | G | V | T | V | L | L | A | L | T | V | F | Q | L | I | L | A | E | S |
| beta 1[3]) SEQ ID NO: 11 | E | K | M | G | L | S | I | F | A | L | L | T | L | T | V | F | L | L | L | L | A | D | K |
| beta 2[4]) SEQ ID NO: 12 | E | K | M | T | L | C | I | S | V | L | L | A | L | T | V | F | L | L | L | I | S | K | I |
| beta 3[8]) SEQ ID NO: 13 | E | K | L | S | L | S | T | S | V | L | V | S | L | T | V | F | L | L | V | I | E | E | I |
| beta 4[3]) SEQ ID NO: 14 | E | K | M | T | L | C | I | S | V | L | L | A | L | T | F | F | L | L | L | I | S | K | I |
| epsilon[8]) SEQ ID NO: 15 | Q | K | C | T | V | S | I | N | V | L | L | A | Q | T | V | F | L | F | F | L | I | A | Q |

[1])S. J. Opella, F. M. Marassi, et al., Nat. Struc. Biol., 1999, 6, 374-379.
[2])Hucho, F.; Tsetlin, V. I.; Machold, J. Eur. J. Biochem. 1996, 239, 539-55.
[3])J. C. Webster, M. M. Francis, et al., Brit. J. Pharmacol., 1999, 127, 1337-1348.
[4])M. W. Francis, R. W. Pazquez, et al., Mol. Pharmacol. 2000, 58, 109-119.
[5])O. K. Steinlein, A Magnusson, et al., Hum. Mol. Genet., 1997, 6, 943-947.
[6])E Bertacini, JR Trudell, Protein Eng. 2002, 15, 443-453.
[7])A B Elgoyhen, D E Vetter et al., Proc Natl Acad Sci USA 2001, 98, 3501-6.
[8])ENTREZ protein databank at the US National Library of Medicine The present invention lies in part in a computer system that generates molecular models of ligand-gated neuronal receptors and a method of using the same. The computer system generates a computer-based model of the inner lumen of a ligand-gated ion channel having binding pockets for non-competitive inhibitors. The computer system simulates interaction of structures from chemical libraries or of any desired compound with the generated computer-based model of the ligand-gated ion channel. The simulation can serve to predict and describe the pharmacological importance of the interac- The memory, in particular, stores data of the atomic coordinates of at least an α chain and a β chain of a nicotinic acetylcholine receptor. The data of the atomic coordinates can include atomic coordinates of at least one polypeptide having an amino acid sequence selected from the group consisting of the polypeptides shown in Table 1 (SEQ ID NOS: 1-15). The data of the atomic coordinates should include atomic coordinates of the portion of the transmembrane portion of the subunit consisting of at least the amino acid sequence of residues 8 to 19 of SEQ. ID NOS: 1-15.

The processor 101 can generate a molecular model of the luminal domain portion, especially the pore, of a ligand-gated neurotransmitter receptor having a subunit stoichiometry ranging from $(\alpha)_5(\beta)_0$ to $(\alpha)_0(\beta)_5$. For example, the subunit stoichiometry can include $(\alpha)_2(\beta)_3$ useful for modeling the neuronal nAChR regulating cardiovascular and GI actions. The model may be generated with only four helices to model other LGIC families.

Modeling Step:

In generating a molecular model and simulating its interaction with various molecules, the computer system of the present invention first generates a molecular model of the receptor channel based on a template structure determined in an NMR investigation of synthetic channel model (Opella S. J., Marassi F. M., Gesell J. J., Valente A. P., Kim Y., Oblatt-Montal M., Montal M., (1999) Structures of the M2 channel-lining segments from nicotinic acetylcholine and NMDA receptors by NMR spectroscopy. *Nat. Struct. Biol.* 6:374-9). Using this model, the molecular structures of all of the neuronal subtypes of nAChR can be built. All subtypes of nAChR share several common structural arrangements in the luminal domain, which makes it possible to build the model of a particular subtype using a homology modeling approach.

Once a molecular model is generated, the model is refined. A preferred software package for refining the molecular model is the AMBER molecular modeling package, e.g. AMBER version 7, (D. A. Pearlman, D. A. Case, J. W. Caldwell, W. S. Ross, T. E. Cheatham III, S. De Bolt, D. M. Ferguson, G. L. Seibel and P. A. Kollman, (1995) AMBER, a package of computer programs for applying molecular mechanics, normal mode analysis, molecular dynamics and free energy calculations to simulate the structural and energetic properties of molecules. *Comp. Phys. Comm.* 91, 1-41). The AMBER package contains a set of molecular mechanical force fields for the simulation of biomolecules and a package of molecular simulation programs. In particular, the model is preferably refined using the "SANDER" program (for Simulated Annealing with NMR-Derived Energy Restraints) was used. SANDER is the main program used for molecular dynamics simulations. SANDER allows for NMR refinement based on NOE-derived distance restraints, torsion angle restraints, and penalty functions based on chemical shifts and NOESY volumes.

Once the model has been refined using the SANDER program of AMBER, the final model is evaluated. A preferred software package for evaluating the final model is the PROCHECK package, e.g. version 3.5.4 (Laskowski R A, MacArthur M W, Moss D S & Thornton J M, (1993) PROCHECK: a program to check the stereochemical quality of protein structures. *J. Appl. Cryst.*, 26, 283-291). PROCHECK checks the stereochemical quality of a protein structure, producing a number of PostScript plots analyzing its overall and residue-by-residue geometry.

In order to construct subtype-specific molecular models, the primary structures of the particular subtypes are required. Different subtypes can be found in different region of the human brain and peripheral nervous system and are responsible for specific functions. Subtype-specific models of the nAChR luminal domain can be utilized in designing subtype-specific NCIs.

The procedure of building the luminal model can be easily adopted to constrain models of luminal domain of other subtypes of the nAChR and with some modification to constrain lumen models of other classes of ligand-gated ion channels. The procedure is basically explained in the modeling step of Example 1. The model of the α3β4-nAChR can serve as the template to constrain other neuronal and muscular subtypes: since those subtypes are very homologous (see Table 1). Only a few residues need to be modified in order to obtain new subtype. The new model after residue modification must be subjected to energy minimization by AMBER procedures described previously and finally should be evaluated using PROCHECK. Elaborated docking procedures can be applied to those models and the entire approach can be used in detailed molecular characterization of the luminal domain of specific subtypes of nAChR and moreover, subtype specific interaction with different classes of NCIs.

More complicated procedures must be applied if one want to obtain a model of the domain formed by other classes of ligand-gated ion channels (GABA, NMDA, 5HT3 etc). First, amino-acid sequence alignment modeling is performed. An example and detailed description of such analysis can be found in the paper by Bertaccini and Trudel [E. Bertaccini and J. R. Trudell, (2002) Predicting the transmembrane secondary structure of ligand-gated ion channels *Protein Eng.* 15, 443-453]. Thus, homologous parts of the ion channel can be found and a new model of transmembrane domain LGIC can be made. For some LGICs, the transmembrane domain is formed by four transmembrane helices instead of five as in the case of nAChR. In such case one of the helices must be removed and the remaining four need to be properly repositioned in order to form the channel structure. Then the model can be relaxed and refined in AMBER procedures and finally evaluated in PROCHECK. In case of such distinct models the docking procedures need be parameterized by initial studies as described in the simulation step of Example 1 below. The values of the size of the grid box, the dielectric constant and the ga_num_evals must be optimized, since the size and environment of the channel would have been changed significantly.

Using the modeling method of the invention, it has been discovered that there are NCI binding sites at the interface between α and β helices of LGICs, especially of nicotinic AchRs. Among modeled candidate NCIs, the compound enters into a small hydrophobic pocket formed by residues 12, 15 and 18 of the transmembrane domains of the receptor subunits (e.g. SEQ ID NOS: 1-15, Table 1). A hydrophobic group of the NCI compound will interact with this portion of the NCI binding site. A polar group (e.g. an amino group) of a putative NCI can interact by hydrogen bonding with surrounding polar residues (e.g. residues 12 and 14 of SEQ ID NOS: 1-10).

Simulation Step:

After generating the molecular model, the final molecular model is used as a target protein for docking simulation for compounds that may be potential inhibitors. A preferred software package for docking simulation is the AutoDock package, e.g. version 3.5. AutoDock allows docking of a flexible ligand into a rigid structure of the target protein using genetic algorithms as the search method.

A particular genetic algorithm included in the AutoDock package is the Lamarckian genetic algorithm. The Lamarckian genetic algorithm was preferably used with local search in order to improve efficiency. The Lamarckian genetic algorithm works in a reverse order compared to typical genetic algorithms. In particular, new traits in an organism develop because of a need created by the environment and these acquired characteristics are transmitted to its offspring. In AutoDock the ligand's atomic coordinates represent a genotype and fitness is represented by interaction free energy with the proteins. Genotypes are found through interactions of the local search and then the atomic coordinates are translated into the ligand's state coordinates as the phenotype. In other words, in AutoDock local search is used to update the fitness associated with an individual in the genetic algorithm selection.

The Lamarckian genetic algorithm uses as input a grid data set produced by the AutoGrid module. The AutoGrid module is used to create 3-dimensional maps over the host protein using several atom specific and electronic probes at each grid point.

Results of these simulations allow the classification of tested compounds in terms of free energy of binding, which leads to the identification of ligands that may be potent inhibitors. The same approach can be used to design new compounds with high affinity binding properties to a specific subtype of the nAChR. A compound that is identified as a non-competitive inhibitor of a LGIC is one having a ΔG less than −6 kcal/mol, preferably less than −7 kcal/mol, still more preferably one having a ΔG less than −10 kcal/mol.

The ligand structures used in docking simulations are preferably made using the HyperChem package (of HyperCube Inc., Gainsville, Fla.). In particular, it is preferred that the AM1 semiempirical method implemented in HyperChem be used to minimize the system energy and to calculate atomic charges in final structures (J. J. P. Stewart, Semiempirical molecular orbital methods, in: K. B. Lipkowitz, D. B. Boyd (Eds.), *Reviews in Computational Chemistry*, vol. 1, VCH, New York, 1990, pp. 45-81).

The in silico approach described above can be supported by examining the NCI-nAChR interaction by affinity chromatography (Jozwiak K, Haginaka J, Moaddel R and Wainer I W (2002) Displacement and nonlinear chromatographic techniques in the investigation of interaction of noncompetitive inhibitors with an immobilized nicotinic acetylcholine receptor liquid chromatographic stationary phase. *Anal Chem* 74: 4618-4624), preferably in an iterative fashion. Chromatographic affinity screening can provide experimental data that is then employed for proper parameterization of the computer-based molecular simulation. Alternatively, the results of computer-based simulation can be related and evaluated by further chromatographic and functional experiments.

Until recently, the screening of drug candidates for activity as NCIs was not a standard procedure in the drug development process. However, the present invention will permit pharmaceutical companies to rapidly screen their potential drugs for NCI properties. In addition, the luminal domain of nAChR can be used as a target in drug discovery programs, which represents a new therapeutic approach to the treatment of diseases such as Alzheimer's and Parkinson's diseases and for treatment of drug and tobacco dependency, which are related to LGIC functions, especially to nAChR functions.

The nAChR, for example, was found to contain two cholinergic agonist binding sites located at the interface between the α and β subunits and on the extracellular N-terminal of the α subunits. These sites are key targets for drug discovery in a variety of diseases, including Alzheimer's disease ($\alpha_4\beta_2$), Parkinson's disease ($\alpha_3\beta_2$), cardiovascular and GI actions ($\alpha_3\beta_4$), anxiety and depression ($\alpha_4\beta_4$), short term memory ($\alpha 7$) and auditory function and development ($\alpha 9$).

Candidate NCI compounds discovered by the computational modeling method of the invention can be confirmed by in vitro experimental methods. Two preferred methods are by binding experiments or by functional assays. Either of these methods may employ the target LGIC, a population of LGICs representing the target receptor and receptors that the compound should preferably not inhibit (to avoid side effects), or a population of LGICs representing a group of target receptors (with or without a group representing LGICs that the compound should preferably not inhibit). The LGICs for the in vitro functional assays can be present either as expression products in cells, as partially purified proteins, e.g. membrane preparations made as known in the art, or as isolated proteins. If isolated proteins are used in binding experiments, the proteins are preferably immobilized.

A preferred binding assay is a displacement assay performed as described by Jozwiak et al. [Jozwiak K, Haginaka J, Moaddel R and Wainer I W (2002) Displacement and Nonlinear chromatographic techniques in the investigation of interaction of noncompetitive inhibitors with an immobilized α3β4 nicotinic acetylcholine receptor liquid chromatographic stationary phase. *Anal Chem* 74: 4618-4624.] Using this assay, a compound is identified as a non-competitive inhibitor of the ligand-gated neurotransmitter receptor as one that specifically binds to the ligand-gated neurotransmitter receptor with a k' value greater than 8, preferably with a k' value greater than 9 or even more preferably a k' value greater than 10.

Specificity of NCI binding to particular LGICs can be shown by displacement of compounds that are selective for the pore portion of the desired LGIC. Specificity of the binding to a nicotinic AChR and homologous receptors can be shown by displacement by mecamylamine. Displacement of mecamylamine at a concentration of 10 μM (of mecamylamine) indicates good specific binding, ability to displace mecamylamine at a concentration of 40 μM indicates strong specific binding. Preferably it is possible to displace mecamylamine at a concentration of 100 μM. Thus, a compound that is a preferred NCI of a nicotinic AChR is one that exhibits a k' of greater than 8 in a chromatographic binding experiment and can be displaced by mecamylamine at a concentration of 10 to 100 μM.

Preferred functional ion channel activity assays are described by Hernandez et al. [Hernandez S C, Bertolino M, Xiao Y, Pringle K E, Caruso F S and Kellar K J (2000) Dextromethorphan and its metabolite dextrorphan block α3β4 neuronal nicotinic receptors. *J Pharmacol Exp Ther* 293: 962-967] and by Jozwiak et al. [K. Jozwiak, S C Hernandez, K J Kellar, I W Wainer (2003) The Enantioselective Interactions of Dextromethorphan and Levomethorphan with the α3β4-Nicotinic Acetylcholine Receptor: Comparison of Chromatographic and Functional Data submitted to J Pharmacol Exp Ther]. In brief, 1-ml aliquots of cells in growth medium were plated onto 24-well plates coated with poly(D-lysine). The plated cells were grown at 37° C. for 16 to 18 h until reaching 90 to 100% confluence. On the day of the experiment, the growth medium was aspirated and the cells were incubated in fresh medium containing 2 μCi/ml $^{86}$RbCl for 4 h at 37° C. After this loading procedure, the medium was aspirated and the cells were washed three times with 1 ml aliquots of buffer (15 mH HEPES, 140 mM NaCl, 2 mM KCl, 1 mM MgSO$_4$, 1.8 mM CaCl$_2$, and 11 mM glucose at pH 7.4) to remove $^{86}$Rb$^+$ free in the medium. After washing, 1 ml of buffer with or without the drugs under study was added to each well, and the cells were incubated for 2 min. The incubation buffer was then collected, after which the cells were lysed in 0.1 N NaOH. The radioactivity in the buffer samples and cell lysates was measured by liquid scintillation counting. The total $^{86}$Rb$^+$ loaded into the cells (after washing) was calculated as the sum of the buffer samples and the cell lysates from each well, and the amount of $^{86}$Rb$^+$ efflux was then expressed as a percentage of the total $^{86}$Rb$^+$ loaded (fractional release). Stimulated efflux was defined as the difference between efflux in the presence and absence of nicotine (i.e., total minus basal efflux). The maximum $^{86}$Rb$^+$ efflux, found at a nicotine concentration of ~300 μM or higher, was ~45% of the amount loaded and was independent of the amount of $^{86}$Rb$^+$ loaded into the cell. In studies to determine the inhibition of nicotine-stimulated $^{86}$Rb$^+$ efflux by the drugs under study, data were expressed as a percentage of control values measured with 100 μM nicotine.

In these assays a compound is identified as a NCI that inhibits the ion channel activity of the ligand-gated neurotransmitter receptor in nicotine stimulated $^{86}$Rb$^+$ efflux with an IC$_{50}$ lower than 50 μM. A more preferred NCI compound is one that inhibits ion efflux with an IC$_{50}$ lower than 5 μM. Even more preferable compounds are those that inhibit ion efflux with an IC$_{50}$ lower than 500 nM. One of skill in the art will recognize that compounds that are effective at even lower concentrations are still more preferable, and IC$_{50}$ of 50 nM, or even 5 nM might be observed.

In some instances as described above, it might be preferred to have a NCI that is selective for a particular LGIC. By "selective" is meant that the NCI inhibits the target LGIC with an IC$_{50}$ that is at least 5-fold higher than the IC$_{50}$ of the one or more LGICs that it is desired not to inhibit. The degree of selectivity is preferably 10-fold, more preferably 20- to 50-fold, and still more preferably 100- to 500-fold or more.

On the other hand, the binding assays or functional assays also can be used to provide initial data that can be used to constrain the in silico modeling method described above. Alternatively, the in silico modeling and the in vitro assays can be run iteratively to converge upon NCI compounds that have desired properties.

Methods for synthesis of compounds of the invention are considered within the skill of the ordinary synthetic chemist. Preferred NCI compounds have the above structural features and exhibit activity of inhibiting the ion-channel activity of a ligand-gated neurotransmitter receptor in nicotine stimulated $^{86}$Rb$^+$ efflux with an IC$_{50}$ lower than 100 μM or other activities as set forth in detail above.

Dosage of compounds used for treatment of a subject can be easily determined by the ordinarily-skilled pharmacologist using known pharmacokinetic and pharmacodynamic assays and calculations from IC$_{50}$ data obtained by the inventive method. Doses of from 100 μg to 500 mg per dose are typical. Formulation and administration of compounds useful for treatment is also well-known in the art. For example, many of the compounds listed in Table 2 have been administered therapeutically and it is expected that compounds of the invention can be similarly formulated and administered.

EXAMPLE 1

Modeling of the Lumen of a α3β4 nAChR and Docking of a Putative NCI

The molecular model of a δ-M2-nAChR transmembrane channel determined by frozen state NMR was used as the template for further modification (atomic coordinates were found in Protein Data Bank—PDB id: 1EQ8). This model represents a channel that mimics the transmembrane arrangement of known LGICs (Opella S. J., Marassi F. M., Gesell J. J., Valente A. P., Kim Y., Oblatt-Montal M., Montal M., (1999) Structures of the M2 channel-lining segments from nicotinic acetylcholine and NMDA receptors by NMR spectroscopy. *Nat. Struct. Biol.* 6:374-9). The model channel consisted of 5 uniform polypeptides oriented around a central pore. The amino-acid sequence of this polypeptide is analogous to the sequence of transmembrane M2 segment of δ subunit of nAChR found in *Torpedo californica*.

In the δ-M2-nAChR transmembrane channel, the spatial arrangement of polypeptide helices conserves five-fold symmetry, with certain residues exposed to the center of the pore. These residues (predominantly polar) form an explicit surface of the channel. This is consistent with the concept of the presence of amino acid rings distributed along the pore and is a common property found in all subtypes of nAChR and also other ligand-gated ion channels [Changeux J. P., Galzi J. L., Devillers-Thiery A., Bertrand D., (1992) The functional architecture of the acetylcholine nicotinic receptor explored by affinity labelling and site-directed mutagenesis. *Q. Rev. Biophys.* 25: 395-432].

With respect to the spatial arrangement of five helices in the luminal domain, distribution of certain amino-acid rings along the channel is a common property of all subtypes of nAChR. Since primary sequences across different subtypes are predominantly homologous as presented in Table 1, and essential (exposed) residues are highly conserved, a subtype specific model of the luminal domain can be built using homology modeling techniques.

Based on the sequence comparison presented in Table 1, the initial model was modified by exchange of δ helix residues into α3 and β4 using the SYBYL 6.8 molecular modeling system (Tripos Inc., 1699 South Hanley Road, St. Louis, Mo., 63144, USA). Therefore, the channel containing α3, β4, α3, β4 and β4 helices, respectively, was constrained.

The model was further refined by energy minimization using the Sander_Classic module of AMBER 6.0 software. Both termini of each helix were blocked in a standard AMBER procedure: acetyl beginning groups (ACE) and N-methylamine ending group (NME) groups were attached, respectively, to each helix. The AMBER '94 force field (Cornell, W. D., Cieplak, P., Bayly, C. I., Gould, I. R., Merz, Jr. K. M., Ferguson, D. M., Spellmeyer, D. C., Fox, T., Caldwell, J. W., Kollman, P. A., (1995) *J. Am. Chem. Soc.* 117, 5179-5197) parameters were used for energy minimization with the convergence criterion of the root-mean-square of the gradient to be less than 1.0E-4 kcal/mole Å. Each minimization run was started with the steepest descent followed by the conjugate gradient method. A distance-dependent dielectric function was used to evaluate the electrostatic energy. The energy minimization run was carried-out in stages by relaxing i) only hydrogen atoms, ii) hydrogen+side-chain atoms, or iii) all atoms except alpha-carbons. Finally, a restrained minimization was also performed on the alpha-carbons of all the chains/residues of the model. This was to relax the structure but keep it near the initial position of the known template structure (PDB accession no. 1EQ8). Respective scripts used to run model refining with AMBER are presented in Apendix 1.

Using PROCHECK to evaluate the model it was found that the whole luminal domain is constrained fully by α-helix secondary structure. Along the lumen model seven rings of residues exposed to the center of the channel can be found; three polar residues (E, T and S) and then three apolar residues (L, V/F and LL) and the last polar residue (E/K).

It is believed that apolar rings in the middle of the structure form the actual "gate" of the channel and play a role in conformational change of the receptor from a closed to an open state. Polar residues on both sides of the "gate" participate in the cation selective function of the receptor. An important structural parameter found in the obtained model is the change in position from valine in the α3 sequence to phenylalanine in the β4 sequence (see residue 15 in Table 1). This provides the formation of small pockets between α3 and β4 subunits, found during the simulation of NCI-α3β4-nAChR interactions. The developed model of α3β4-nAChR luminal domain can be used as a template to constrain homologous systems of other nicotinic receptors, especially neuronal nicotinic receptors, and other ligand-gated ion channels.

Figure 3A:
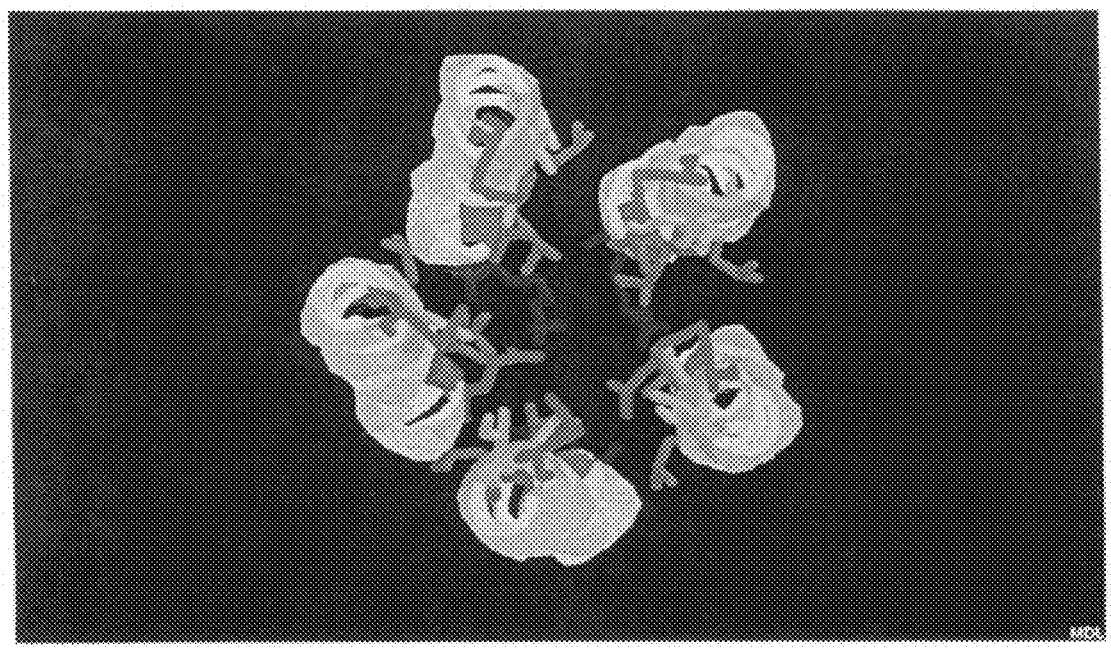
FIG. 3a shows a model of the α3β2 luminal domain having five helices forming the wall of the ion channel.
Figure 3B:
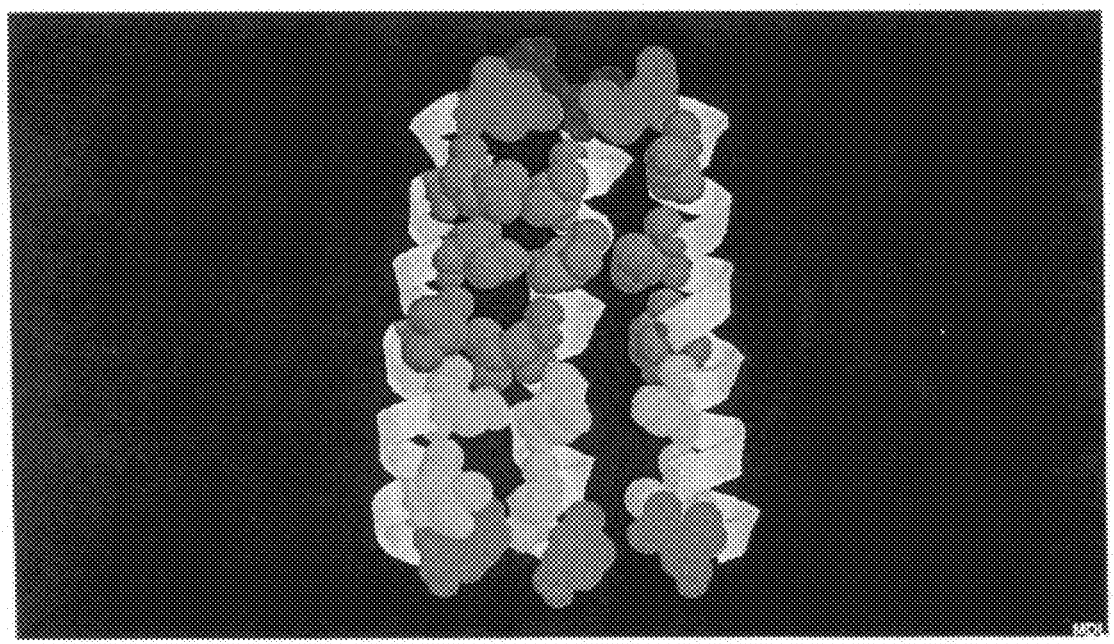
FIG. 3b shows the α3β2 luminal domain model (in ribbon and CPK rendering) in perpendicular view. Only 3 helices are shown for clarity.
Figure 3C:
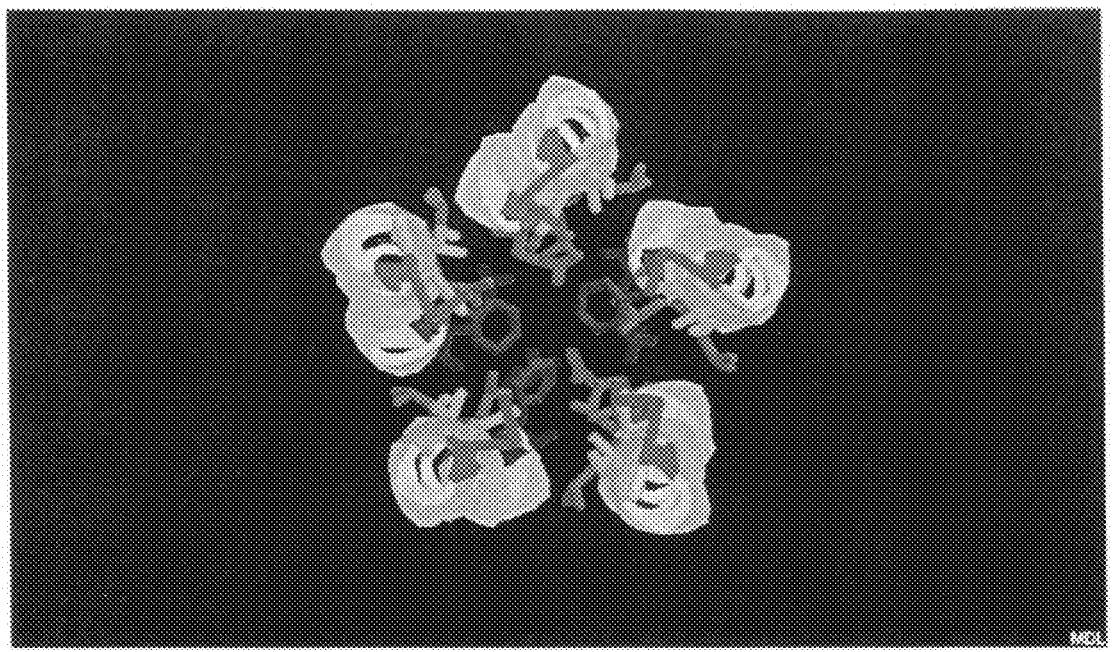
FIG. 3c shows a model of the α3β4 luminal domain having five helices forming the wall of the ion channel.
Figure 3D:
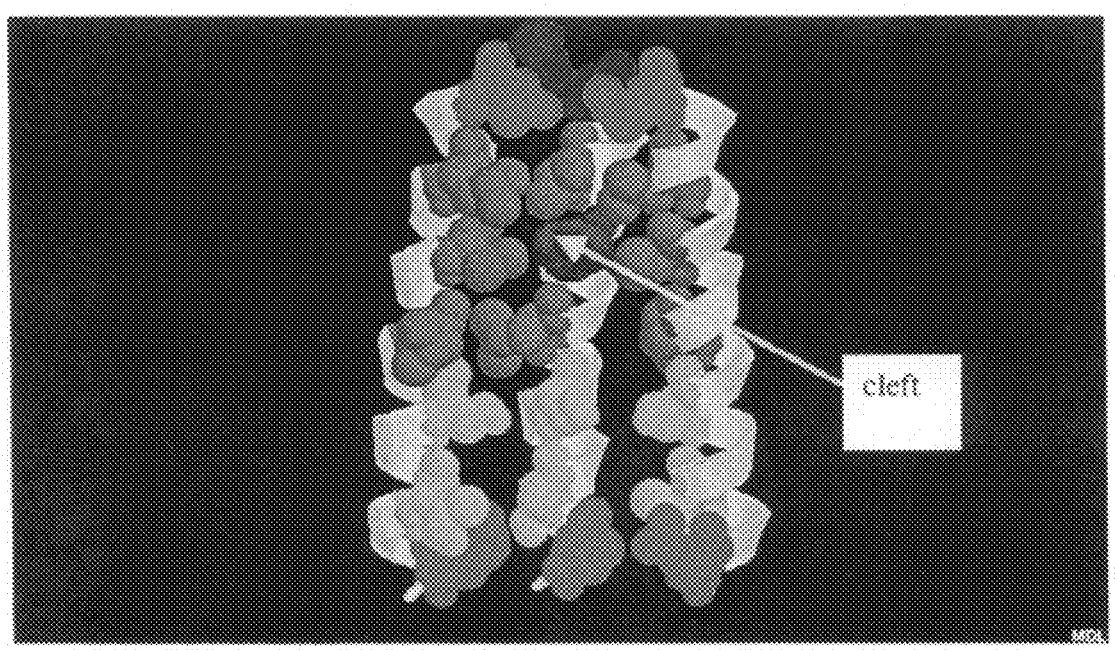
FIG. 3d shows the α3β4 luminal domain model (in ribbon and CPK rendering) in perpendicular view. Again, only 3 helices are shown for clarity. The cleft formed by the substitution of phenylalanine for valine at position 15 in the helix is noted by the arrow.
Figure 5:
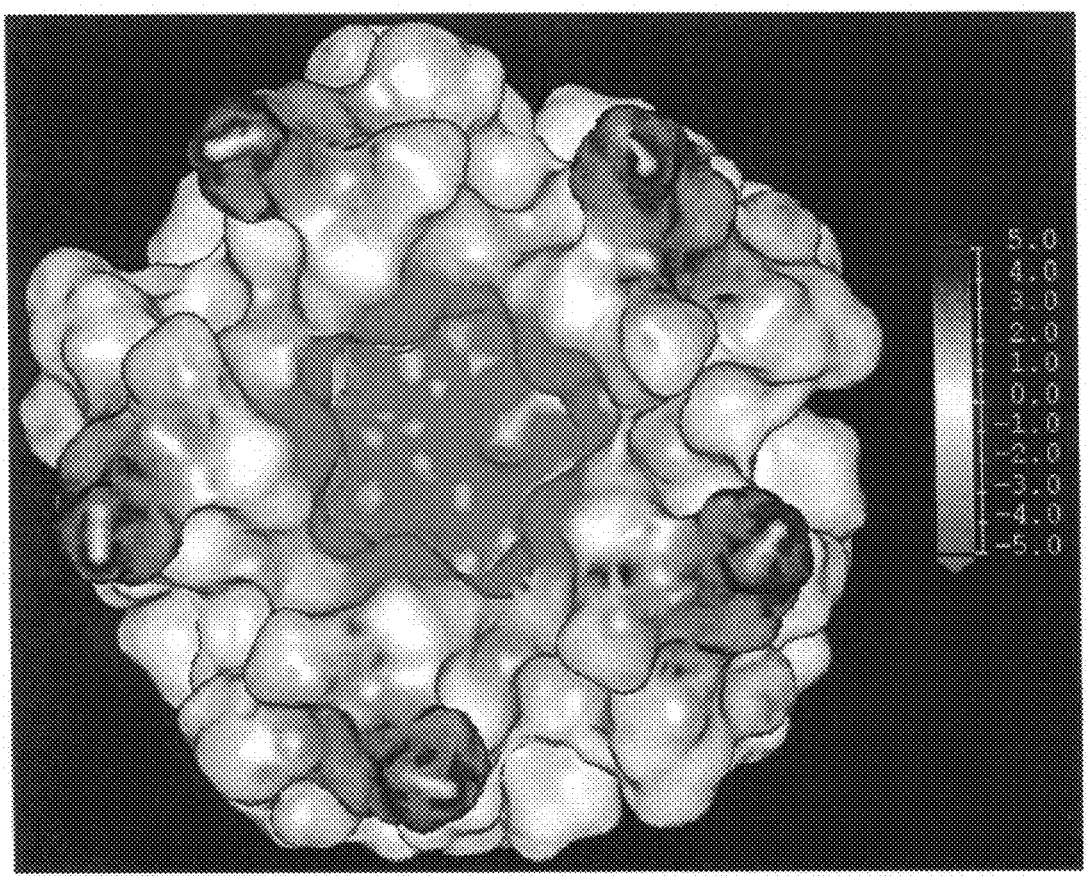
FIG. 5 is a model of luminal domain of α3β4 subtype of nAChR illustrating its electrostatic potential of the inner surface of the channel. The Figure particularly shows the electronegative potential of the cation selector region of the channel. Negative potentials are shown in red, and the positive potentials are shown in blue.

The resulting atomic coordinates represent the final model. FIG. 5 illustrates the electrostatic potential of the inner surface of the ion channel, and especially the electronegative potential of the cation selector of the channel. FIG. 3c shows an example of the resulting luminal domain model having five helices forming the wall of the ion channel. FIG. 3d shows a luminal domain model in perpendicular view with residue rings.

In order to perform docking simulations, the AutoGrid module was first used to create 3-dimensional maps over the host protein using several atom specific and electronic probes at each grid point. An example parameterization file for the AutoGrid module used in this example can be found in Appendix 2. The optimal size of constrained grid maps was a 22.5×22.5×45 Å box (i.e., a grid of 60×60×120 points, each separated by 0.375 Å). This allowed exploration of the whole internal space of the lumen domain but prevented ligands from being bound on the external side. The grid-box size can be altered in the $3^{rd}$ dimension (along the lumen) in order to explore interaction with a particular segment of the lumen or to calculate the interaction profile along the model.

An important parameter to properly explore electronic interaction in ligand receptor complexes is the dielectric constant value (d) used to calculate the electronic grid map. During the initial evaluation tests, the standard distant-dependent dielectric constant did not produce proper results: the electrostatic interaction were almost zero. The simulation did not discriminate between neutral and protonated ligands.

the lowest energy of interaction. An example parameterization file for the AutoDock module used in this example can be found in Appendix 3.

The Lamarckian genetic algorithm with local search was used from the AutoDock package. Atomic coordinate files of ligands were transformed into a format suitable to AutoDock using the HIN2PDBQ script (Johansson M. (2002) Some computational chemistry related python conversion scripts. See Web site helsinki.fi/%7Empjohans/python/).

The ligand structures used in the docking simulations were made using the HyperChem software package. Further, the AM1 semiempirical method implemented in HyperChem was used to minimize the system energy and to calculate atomic charges in final structures.

An initial simulation was performed in order to optimize the docking settings. Since previously described docking space seemed to be large in the model of α3β4-nAChR active site (22,781.25 $Å^3$) it was important to optimize the maximum number of energy evaluations (ga_num_evals) required in each search run. It was found that too low a value of ga_num_evals could result in finishing the simulation too quickly, and the global minimum of the complex conformation may not be found. A set of test simulations on several ligands including conformationally flexible and rigid systems was performed. It was found that a ga_num_evals value of at least 5 million is required to assure obtaining a statistically significant number of lowest energy complexes. In the case of bigger ligand molecules with more than 2 rotatable bonds, the

TABLE 2

| | ΔG (kcal/mol) of best docked conformation obtained in different dielectric environment. | | | | | | | |
|---|---|---|---|---|---|---|---|---|
| Diel. const. | Dist. dependent | 40 | 30 | 20 | 15 | 10 | 5 | 1 |
| MCM | −6.23 | −6.22 | −6.22 | −6.23 | −6.26 | −6.43 | −6.76 | −19.52 |
| MCM+ | −6.60 | −7.56 | −8.13 | −9.29 | −11.01 | −14.47 | −27.25 | −138.2 |
| DMT | −8.65 | −8.66 | −8.68 | −8.71 | −8.73 | −8.81 | −8.99 | |
| DMT+ | −8.74 | −9.46 | −9.77 | −10.39 | −11.87 | −15.72 | −28.00 | |
| LMT | −8.31 | −8.33 | −8.34 | −8.38 | −8.40 | −8.49 | −8.70 | |
| LMT+ | −8.95 | −9.53 | −9.81 | −10.59 | −12.28 | −15.69 | −27.85 | |

A detailed test of several d values was carried out using three pairs of ligands and the results are presented in Table 2. Table 2 shows an unexpected diminished difference between neutral and protonated systems when distant-dependent d was used; differences gradually increase with decreasing d. Simultaneously the increase in electrostatic impact in the ligand receptor interaction was noticed when a low dielectric value was used. However, a very low value (d≦10) produced unrealistic ΔG values. Finally, as a mater of compromising these two effects, d=15 was chosen for final calculations as the value producing suitable electronic properties of the ligand-receptor complex in the transmembrane ion channel system. This approach is in agreement with values of the dielectric constant in transmembrane pores obtained by theoretical calculations (Cheng et al., (1998) *Eur. Biophys J.*, 27 105-112 and Gutman et al., (1992) *Biochim. Biophys Acta* 1109: 141-148) where it was found that the actual dielectric constant in transmembrane channels remains low and ranges from 25 to 5 depending on the structure. Thus, in the case of the NCI-nAChR docking simulations d value can vary from 10 to 20.

The resulting ligand 3D structure was loaded into the AutoDock system and was iteratively sampled over previously created grid-maps in order to find optimal positions and optimal value should be at least 50 million. Higher values are acceptable; however higher values may dramatically increase the time of each simulation.

The optimal number of docking search runs was found to be 50. Again the number of docking search runs can be higher, but would take more time for simulation and have no effect on the final result.

AutoDock 3.5 implemented a free-energy scoring function that is based on a linear regression analysis, the AMBER force field, and a large set of diverse protein-ligand complexes with known inhibition constants (e.g. see Web site at scripps.edu/pub/olson-web/doc/autodock/). This function was employed to estimate the free energy change of the NCI-nAChR complex and eventually lead to an estimated inhibition constant of a particular ligand. Docking simulations allow quantitative classification of the stability of the NCI-nAChR complexes formed by tested ligands in terms of free energy of binding, which eventually lead to the identification of ligands exerting potent inhibitory properties. It was found that molecular systems forming the complex with ΔG value lower than −6.0 kcal/mol should be considered as potential NCIs. Lower ΔG values represent more potent NCI compounds. Preferred NCI compounds exhibit a ΔG value lower than −7.0 kcal/mol; more preferred compounds exhibit a ΔG value lower than −10.0 kcal/mol.

Detailed exploration of the spatial arrangement of ligand-receptor conformations leads to building a pharmacophore model of a subtype specific NCI-nAChR. Simulations on the α3β4 model showed that NCIs bind predominantly in the channel in the apolar domain (F/V ring). Tested structures primarily entered a small hydrophobic pocket formed between α3 and β4 subunits and subsequently interacted with protein side chains, forming hydrogen bonds. It is expected that this is a type of interaction that would not be found in those receptor subtypes that lack the bulky phenylalanine residue in this position. Since there are two quasi-symmetrical pockets between α3 and β4 helices in the model, ligands most likely form two separate clusters on these two symmetrical sites (e.g, FIG. 6) at which the energy of interaction does not significantly differ. Estimated free energies of docking are in the range of experimental $IC_{50}$ of tested inhibitors and also can be related to experimental affinity chromatography results. The model can be applied to a variety of compounds and is useful for in silico designing of new drugs with particularly high non-competitive inhibitory activity.

EXAMPLE 2

Chromatographic Assay of NCI Activity

Chromatographic studies based on immobilized nAChRs were performed to characterize ligand binding for broad groups of compounds. In order to further understand the mechanistic action of NCIs on the molecular level, the model of the transmembrane domain of the α3β4 nAChR was built and used for computer simulations of docking inhibitors into the receptor. The entire approach allowed the classification of NCIs in terms of their functional effectiveness.

Figure 7:
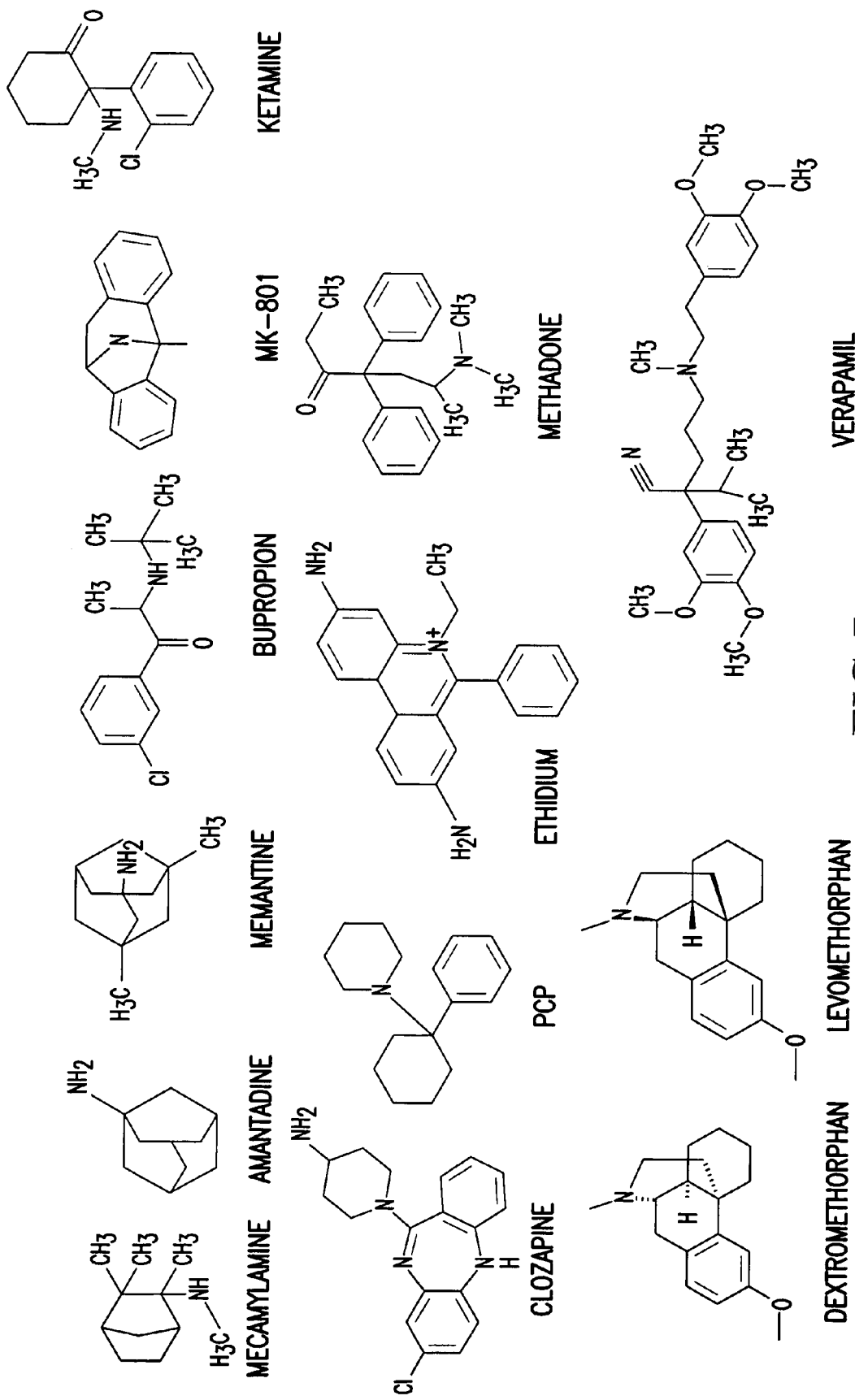
FIG. 7 shows example compounds tested by chromatography on an $α_3β_4$ nAChR affinity column. Among the tested drugs are aliphatic amines like mecamylamine, amantadine, memantine and such compound like bupropion, ketamine and mk-801. Also, some examples of more complicated structures include clozapine, pcp, methadone and verapamil. Further, the structures of two enantiomers dextromethorphan and levomethorphan. Finally, there is a structure for ethidium: the only compound permanently ionized and that binds to its specific site.

FIG. 7 presents compounds tested on an α3β4 nAChR column. The chemicals can be divided into several subgroups. The first group contains drugs from different origin, which are well known as non-competitive inhibitors of nAChRs. The second group is of the dextromethorphan family, levomethorphan, dextromethorphan and its analogues, and the final group is verapamil, its congeners, and metabolites. In order to properly assess the influence of non-specific retention, five other chemicals (acetanilide, acetaminophen, 2,4-dinitrobenzoic acid, 3,4-dimethoxybenzoic acid and phenylbutazone) were tested as negative controls. The affinity of ligands was investigated by non-linear chromatography on an α3β4 nicotinic receptor affinity column.

$10^6$ Cells from the KXα3β4R2 cell line were suspended in Tris-HCl [50 mM, pH 7.4] (buffer A), homogenized for 30 sec, and centrifuged at 35,000×g for 10 min at 4° C. The pellet was resuspended in 2% cholate in buffer A and stirred for 2 h. The mixture was centrifuged at 35,000×g for 30 min, and the supernatant containing α3β4 nAChR-cholate solution was collected. 200 mg of the IAM stationary phase was added to the α3β4 nAChR-cholate solution. Subsequently the solution was stirred for 1 h. The suspension was dialyzed against 2×1 L buffer A for 24 h at 4° C. The IAM liquid chromatographic support containing the α3β4-nAChR was packed into a HR5/2 glass column to form a chromatographic bed of 20 mm×5 mm i.d. The α3β4-nAChR column was then placed in the chromatographic system and used.

Aqueous solutions [10 μM] of each compound were prepared and 20 μl aliquots were injected into column. The mobile phase was composed of ammonium acetate [10 mM, pH 7.4] modified with methanol in the ratio 85:15 (v/v). The flow rate was 0.2 ml/min and the experiments were carried out at ambient temperature.

DM and LM were monitored in the positive ion mode (ESI+). The compounds were detected using single ion monitoring at m/z=272 {[MW+H]$^+$ion}. The chromatograms were recorded and processed using MassLynx v. 3.5. (Micromass).

The non-linear chromatography approach was used to determine kinetics of the NCI-nAChR interaction in affinity chromatography studies.

The mathematical model assumes limited (and a relatively low) number of active sites on the column. Slow association and dissociation of the drug-protein complex are the main cause of band broadening and asymmetry of the peak profile. The chromatographic peak profiles were analyzed using PeakFit v4.11 for Windows Software (SPSS Inc., Chicago, Ill.). The mathematical approach used was the non-linear chromatography (NLC) model derived from Impulse Input Solution [Wade J L, Bergold A F and Carr P W (1987) Theoretical description of nonlinear chromatography, with applications to psychochemical measurements in affinity chromatography and implications for preparative-scale separations. *Anal Chem* 59:1286-1295.] and described by Equation 1 (PeakFit User's Manual, p. 8-25):

$$y = \frac{a_0}{a_3}\left[1 - \exp\left(-\frac{a_3}{a_2}\right)\right]\left[\frac{\sqrt{\frac{a_1}{x}} I_1\left(\frac{2\sqrt{a_1 x}}{a_2}\right)\exp\left(\frac{-x-a_1}{a_2}\right)}{1 - T\left(\frac{a_1}{a_2}, \frac{x}{a_2}\right)\left[1 - \exp\left(-\frac{a_3}{a_2}\right)\right]}\right] \quad \text{Eqn. 1}$$

where:
y—intensity of signal,
x—reduced retention time, $$T(u, v) = \exp(-v)\int_0^u \exp(-t)I_o(2\sqrt{vt})dt$$

$I_0(\ )$ and $I_1(\ )$ are Modified Bessel functions
$a_0$—area parameter,
$a_1$—center parameter, reveal to true thermodynamic capacity factor,
$a_2$—width parameter,
$a_3$—distortion parameter.

Experimental chromatograms obtained by single injection of ligand into the chromatographic column with immobilized receptor were processed with PeakFit v4.11 software. After standard linear baseline subtraction, each peak profile was fitted to the NLC function. The set of NLC parameters ($a_0$, $a_1$, $a_2$ and $a_3$) was collected for each profile and used for the calculation of descriptors of the kinetic interactions with the immobilized nAChR, dissociation rate constant ($k_{off}$); equilibrium constant ($K_a$); association rate constant ($k_{on}$) real thermodynamic capacity factor (k'), according to the following equations:

$$k' = a_1 \quad \text{Eqn. 2}$$

$$k_{off} = \frac{1}{a_2 t_0} \quad \text{Eqn. 3}$$

-continued $$K = \frac{a_3}{C_0}$$ Eqn. 4

$$k_{on} = k_{off} K$$ Eqn. 5 where: $t_0$ is the dead time of a column (time needed by non-retained substance to reach the detector); $C_0$ is a concentration of solute injected multiplied by a width of the injection pulse (as a fraction of column dead volume).

Thus, by analyzing the ligand in an immobilized receptor system four descriptors can be collected: retention (k'), association rate constant ($k_{on}$), dissociation rate constant ($k_{off}$) and equilibrium constant (logK). It was found that ligands which are non-competitive inhibitors have k' greater than 8, $k_{on}$ greater than $10 \times 10^{-6}$ $M^{-1}s^{-1}$ (preferred inhibitors have $k_{on}$ of greater than $15 \times 10^{-6}$ $M^{-1}s^{-1}$ especially potent inhibitors have $k_{on}$ greater than $30 \times 10^{-6}$ $M^{-1}s^{-1}$), $k_{off}$ smaller than 15 $s^{-1}$ (preferably lower than 2 $s^{-1}$) and logK greater than 5.9 (preferably greater than 6.5).

The $k_{on}$ value obtained in chromatographic experiments is the one which is closely correlated with $IC_{50}$ values from functional in vitro or in vivo experiments. In the docking simulation, it is preferred that ΔG be lower than −6 kcal/mol (preferably less than −7 kcal/mol, most preferably less than −10 kcal/mol). In functional nicotine stimulated Rb+ efflux experiments, the $IC_{50}$ value is preferrably lower than 100μM (preferred inhibitors exhibit an $IC_{50}$<10 μM).

TABLE 3

Detailed chromatographic characterization of tested non-competitive inhibitors k' - retention capacity factor, $k_{on}$ and $k_{off}$ are association and dissociation constant rates, respectively (kinetics of formation and disformation of the complex in chromatographic system), logK is chromatographic equilibrium constant.

| | k'$_{(NLC)}$ | $k_{on}$ [*10$^{-6}$] [M$^{-1}$s$^{-1}$] | $k_{off}$ [s$^{-1}$] | log K [M$^{-1}$] |
|---|---|---|---|---|
| tested drugs | | | | |
| amantadine | 8.98 | 30.8 | 6.73 | 6.66 |
| bupropion | 12.97 | 28.7 | 5.14 | 6.75 |
| chlorpromazine | — | — | — | — |
| clozapine | 155.17 | 24.8 | 0.55 | 7.65 |
| dilthiazem | 43.53 | 26.8 | 1.60 | 7.22 |
| ketamine | 8.25 | 38.4 | 8.50 | 6.65 |
| laudanosine | 22.87 | 25.0 | 2.18 | 7.06 |
| mecamylamine | 10.89 | 40.1 | 5.96 | 6.83 |
| memantine | 16.71 | 18.8 | 3.45 | 6.74 |
| methadone | 44.45 | 15.9 | 1.37 | 7.06 |
| methamphetamine | 8.38 | 29.1 | 6.81 | 6.63 |
| MK-801 | 19.10 | 27.1 | 3.48 | 6.89 |
| phenylcyclidine | 24.06 | 23.2 | 2.69 | 6.94 |
| quinacrine | — | — | — | — |
| ethidium | 191.82 | 35.9 | 0.18 | 8.30 |
| dextromethorphan | 61.30 | 23.7 | 1.01 | 7.37 |
| levomethorphan | 35.81 | 18.6 | 1.55 | 7.08 |
| dextrorphan | 26.79 | 20.7 | 2.30 | 6.95 |
| 3 MM | 56.47 | 18.8 | 1.00 | 7.28 |
| 3 OM | 26.45 | 14.3 | 1.97 | 6.86 |
| verapamil-R | 96.86 | 31.0 | 0.68 | 7.66 |
| verapamil-S | 96.32 | 30.6 | 0.66 | 7.66 |
| nor-verapamil-R | 97.99 | 16.0 | 0.58 | 7.44 |
| nor-verapamil-S | 97.86 | 15.6 | 0.61 | 7.40 |
| galapamil | 75.93 | 20.0 | 0.74 | 7.43 |
| D-617 | 22.22 | 15.0 | 2.72 | 6.74 |
| D-620 | 17.72 | 11.6 | 3.43 | 6.53 |
| PR-22 | 99.29 | 16.0 | 0.53 | 7.48 |
| PR-25 | 19.42 | 10.6 | 2.52 | 6.63 |

TABLE 3-continued

Detailed chromatographic characterization of tested non-competitive inhibitors k' - retention capacity factor, $k_{on}$ and $k_{off}$ are association and dissociation constant rates, respectively (kinetics of formation and disformation of the complex in chromatographic system), logK is chromatographic equilibrium constant.

| | k'$_{(NLC)}$ | $k_{on}$ [*10$^{-6}$] [M$^{-1}$s$^{-1}$] | $k_{off}$ [s$^{-1}$] | log K [M$^{-1}$] |
|---|---|---|---|---|
| control compounds | | | | |
| acetaminophen | 5.30 | 8.4 | 17.17 | 5.69 |
| acetanilide | 5.95 | 8.2 | 25.54 | 5.51 |
| dimethoxybenzoic ac. | 4.46 | 9.8 | 18.21 | 5.73 |
| dinitrobenzoic acid | 7.77 | 9.1 | 12.12 | 5.87 |
| phenylbutazone | 6.29 | 8.7 | 22.22 | 5.59 |

Values of log K and k' presented in Table 3 can be regarded as a measure of relative affinity of tested NCI compounds for the nicotinic AChR. Among tested compounds, ethidium, clozapine, verapamil and some of its congeners (PR-22, nor-verapamil and galapamil) have the highest affinities towards the α3β4 nicotinic receptor column as reflected by both log K and k'. Both verapamil and nor-verapamil were tested for enantioselectivity of binding towards nicotinic affinity column but chromatographic experiments as well as NLC data did not exhibit noticeable differences between enantiomers. Interestingly, dextromethorphan exhibited markedly increased affinity compared to the optical enantiomer levomethorphan.

The NLC approach allows estimating the kinetic rates of the complex formation and dissociation, $k_{on}$ and $k_{off}$, respectively. The well-known and potent NCIs mecamylamine, ketamine, ethidium and bupropion had high association constant rates. Ketamine, methamphetamine, amantadine and mecamylamine dissociated markedly quicker than other tested ligands. The lowest dissociation constant rates were exhibited by ethidium, clozapine and verapamil congeners.

TABLE 4

QSAR models build on of chromatographic data
In general, it was found that different molecular properties correlated with chromatographic experimental characteristics: non specific bulkiness (Vol) and lipophilicity (log P; TASA) descriptors, specific shape descriptors (like X$_{length}$), another group were electronic properties: ability to form hydrogen bonds, E$_{HOMO}$ and N$_{order}$. Two latter descriptors can be associated with ability of a ligand molecule to protonation. Both bulkiness/shape and Hbond/protonation seem to be important in respect of known mechanism of inhibition by luminal NCIs: ligand must enter the polar pore, interact with negative and polar surface (primarily designated for cation selection) and eventually block or inhibit the flux of ion during receptor's open stage.

| Equation | R | F | n |
|---|---|---|---|
| log k' = 5.328(±0.745) + 0.00633(±0.000715) Volume + 0.519(±0.0740)E$_{HOMO}$ − −0.165 (±0.0317)Hbond$_{acceptors}$ − 0.2087(±0.0538)N$_{order}$ | .961 | 63.021 | 26 |
| log k$_{on}$ = 4.152(±0.595) + 1.474(±0.483)RASA + 2.383(±0.499)XY$_{fract}$ + 0.117 (±0.033)N$_{order}$ + 0.0486(±0.0161)Hbond$_{acceptors}$ | .802 | 9.441 | 26 |
| log k$_{off}$ = −3.440(±0.653) − 0.00654(±0.000635) Volume − 0.507(±0.0657)E$_{HOMO}$ + 0.168 (±0.0281)Hbond$_{acceptors}$ + 0.2308(±0.0478)N$_{order}$ | .969 | 80.326 | 26 |
| log K = 9.830(±0.752) + 0.00321(±0.000652) TASA + 0.3982(±0.0794)E$_{HOMO}$ − 0.057 (±0.022)X$_{length}$ | .908 | 34.654 | 26 |

Figure 6:
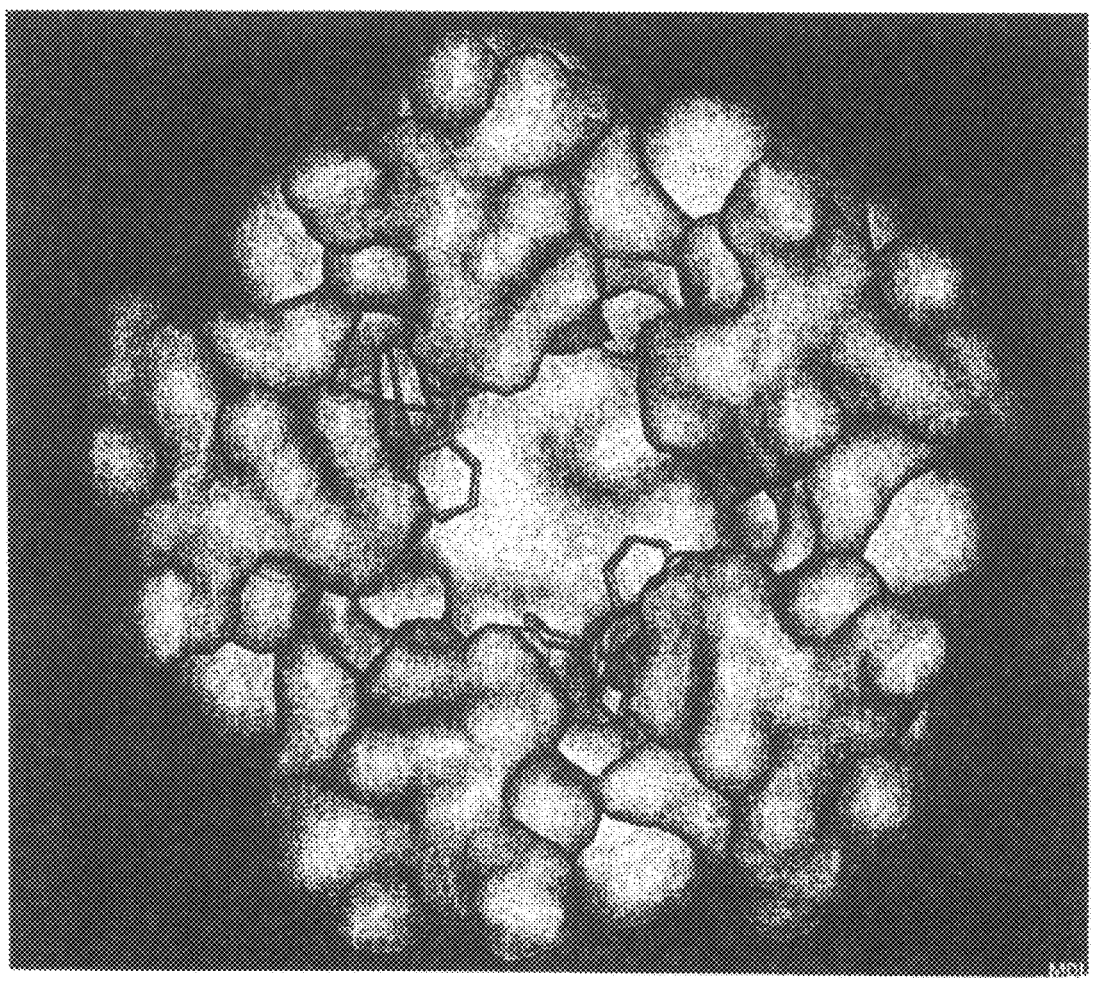
FIG. 6 shows a two cluster interaction of the ligand PCP with α3β4. Generally NCIs bind into the small pocket formed on the apolar domain (Phenylalanine/Valine rings). Tested structures primarily entered a hydrophobic pocket formed between the α3 and β4 helices and subsequently interacted with protein side chains forming hydrogen bonds. Ligands most likely form two separate clusters on two symmetrical active sites. Estimated free energies of docking are in the range of experimental $IC_{50}$ of tested inhibitors.
Figure 8:
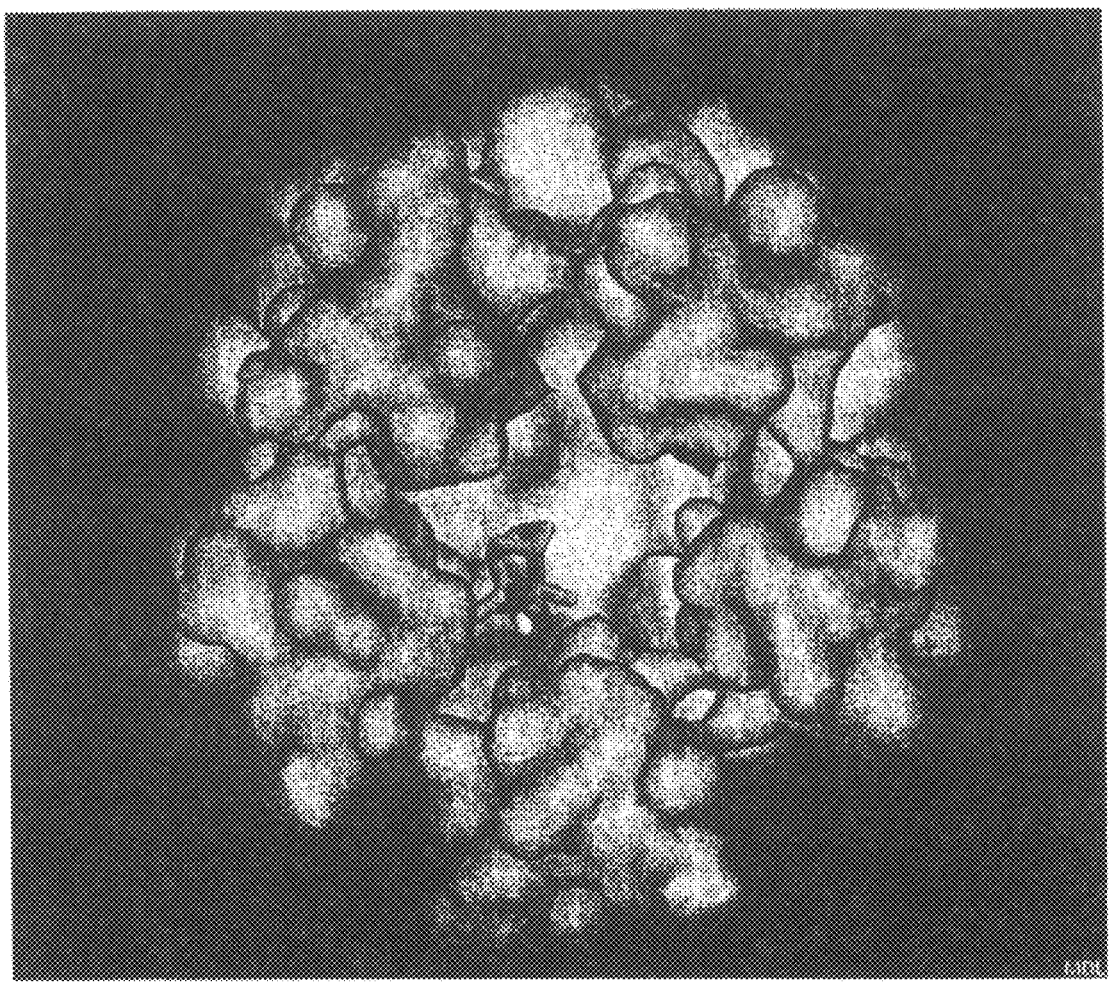
FIG. 8 shows the mecamylamine binding to the luminal domain of α3β4.
Figure 9:
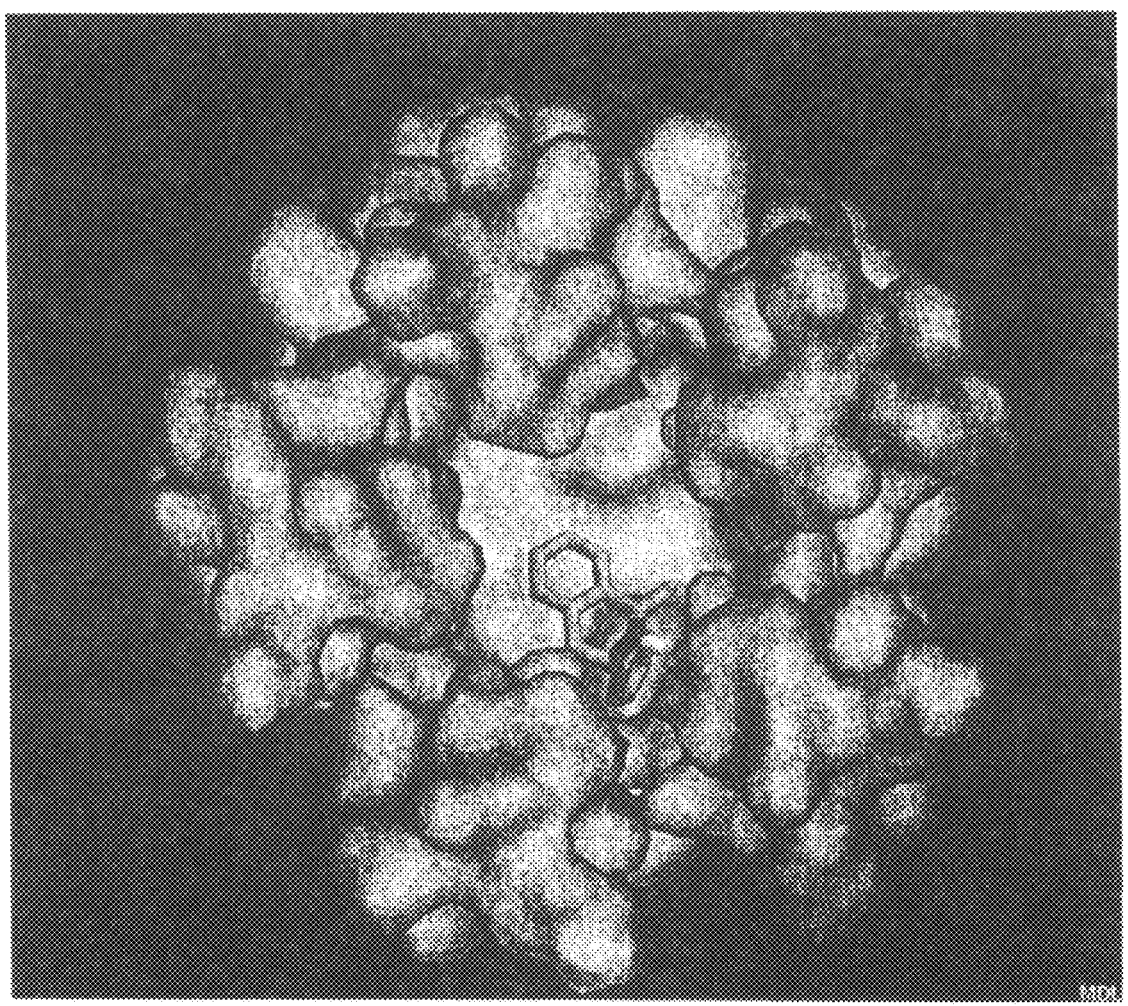
FIG. 9 shows the MK-801 binding to the luminal domain of α3β4.

Examples of complexes resulting from simulations are provided in FIGS. 6, 8 and 9. FIG. 6 shows a two cluster interaction of the ligand PCP with α3β4. FIG. 8 shows the mecamylamine luminal domain of α3β4. FIG. 9 shows the MK-801 luminal domain of α3β4.

Figure 10:
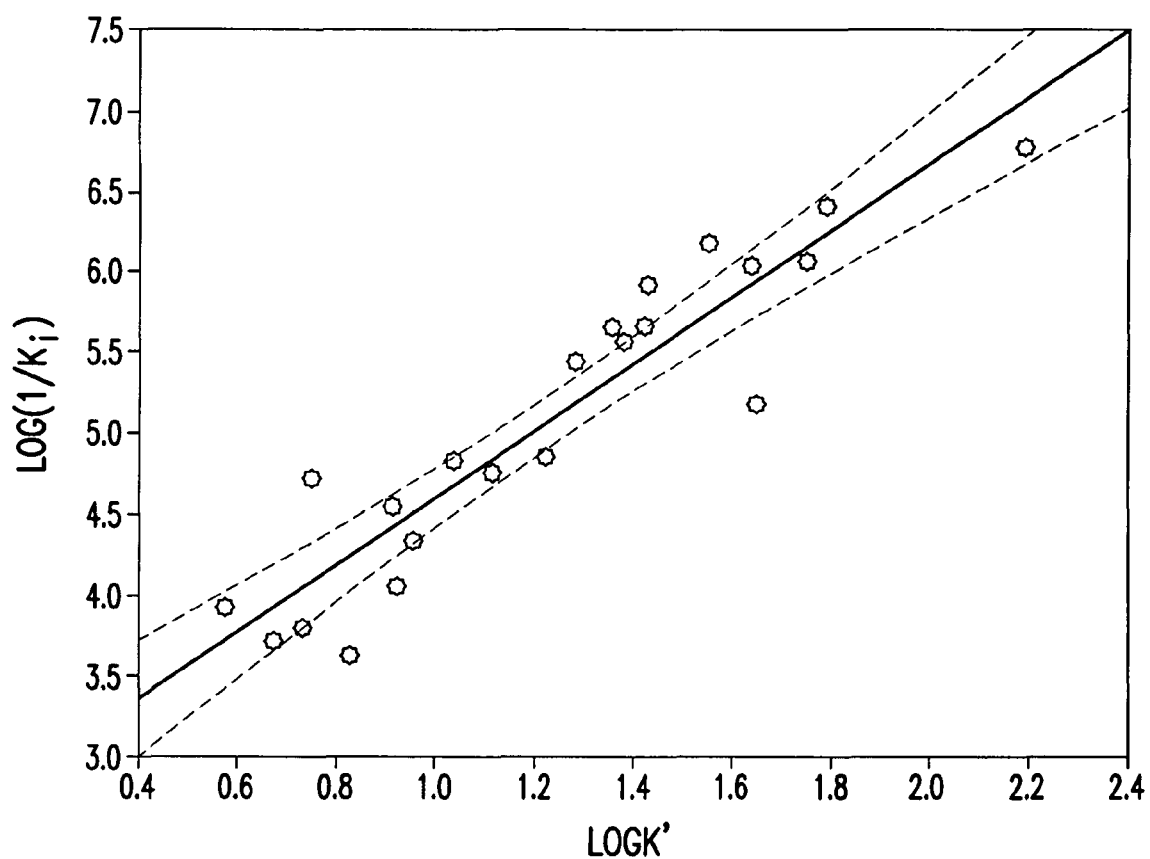
FIG. 10 shows a correlation of log k' (chromatographic) with log $(1/k_i)$ (docking simulation).

Quantitative results of simulated docking affinities were related to experimental results from chromatographic studies. Using AutoDock's scoring function, estimated inhibition constant were calculated. These values exhibited very good correlations with affinity data from NLC calculations (FIG. 10). This correlation can be illustrated by equation:

$$\log k' = 0.418(\pm 0.037)\log(1/K_i) - 0.89(\pm 0.19)$$

$$r = 0.930\ F = 127.7\ n = 22$$

TABLE 5 the collection of dextromethorphan (DM)/(LM) levomethorphan characterization by different approaches (chromatographic and docking were explained above), functional in vivo is nicotine stimulated Rb+ efflux experiments: it was found that DM has significantly longer recovery time than LM, which was predicted by chromatographic and docking modeling. The $IC_{50}$ does not significantly differ.

| Descriptor | DM | LM |
|---|---|---|
| functional in vivo | | |
| $IC_{50}$ [µM] | 10.10 (±1.10) | 10.90 (±1.08) |
| % recovery after 7 min. washout | 49.83 (±5.16) | 79.00 (±3.50) |
| % recovery after 4 h. washout | 82.09 (±3.64) | 94.09 (±4.43) |
| chromatographic (NLC and van't Hoff) | | |
| K' | 61.30 (±0.27) | 35.81 (±0.15) |
| $K_{on}$ [µM$^{-1}$sec$^{-1}$] | 23.66 (±0.61) | 18.61 (±0.38) |
| $K_{off}$ [sec$^{-1}$] | 1.01 (±0.01) | 1.549 (±0.002) |
| $K_a$ [µM$^{-1}$] | 23.40 (±0.36) | 12.01 (±0.23) |
| $\log K_a$ | 7.37 | 7.08 |
| ΔH° [kcal mol$^{-1}$] | −6.92 (±0.19) | −6.59 (±0.18) |
| ΔS° [cal mol$^{-1}$T$^{-1}$] | −15.70 (±0.7) | −15.20 (0.6) |
| ΔG° [kcal mol$^{-1}$] | −2.33 (±0.4) | −2.04 (±0.4) |
| docking | | |
| ΔG [kcal mol$^{-1}$] | −8.73 | −8.40 |
| $E_{docked}$ [kcal mol$^{-1}$] | −8.84 | −8.52 |
| $K_i$ [M] | 3.98 * 10$^{-07}$ | 6.91 * 10$^{-07}$ |
| $\log K_i$ | −6.40 | −6.16 |

Figure 11:
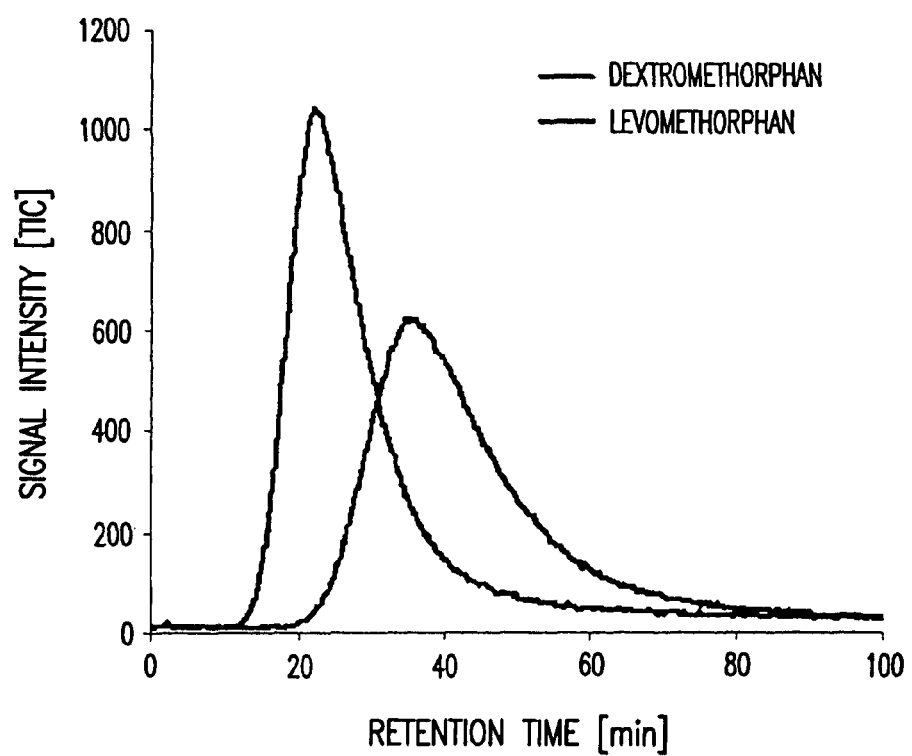
FIG. 11 shows the enantioselectivity of the dextromethorphan/levomethorphan pair determined in chromatographic experiments. Dextromethorphan had a longer retention time and the profile was more asymmetric.
Figure 12A:
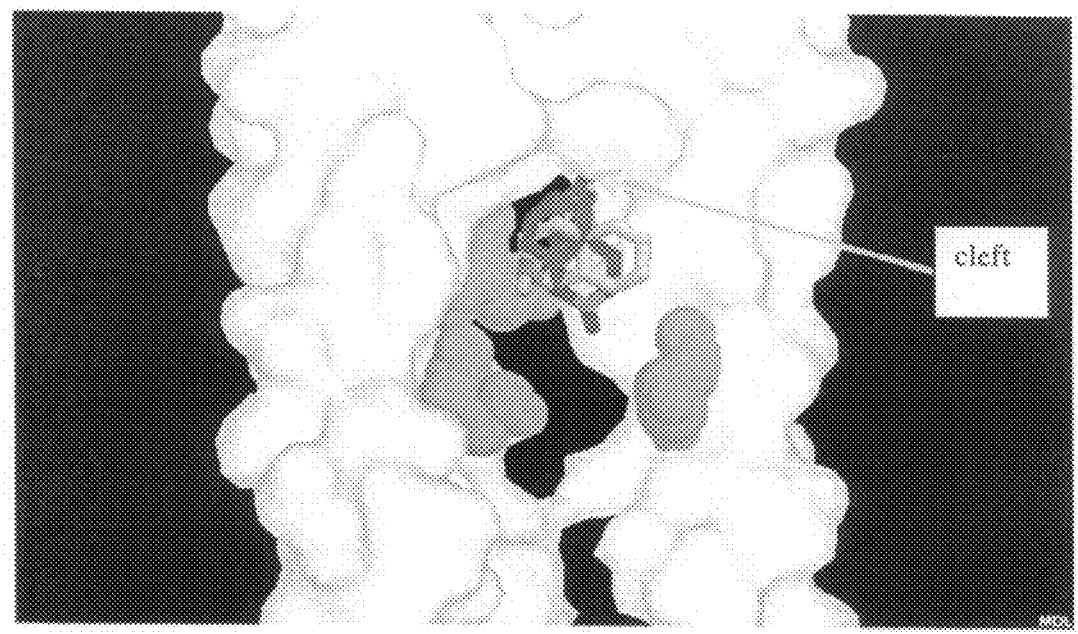
FIG. 12 shows an overlay of the most stable docked orientations of dextromethorphan (grey) and levomethorphan (magenta) complexes with the α3β4-nAChR luminal domain (FIG. 12a) and the α3β2-nAChR luminal domain (FIG. 12b). Only two helices (one α3 and one β) are presented for clarity. The serine residues (position 8, and also in position 12 in FIG. 12a) are rendered as CPK models and colored in orange. The cleft formed by the valine to phenylalanine substitution in the β4 subtype helix is indicated by the arrow in FIG. 12a and its absence is similarly indicated in FIG. 12b.

Enantiomers have identical physiochemical properties and, therefore, all possible non-specific interactions between the enantiomers of a chiral NCI and an immobilized nAChR stationary phase should be equivalent. Any differences in the chromatographic retention between the enantiomers will be due to specific binding interactions with the active site of the protein. FIG. 11 shows chromatograms of dextromethorphan (DM) and its enantiomer—levomethorphan (LM). The pair of enantiomers was further investigated by chromatographic, docking and functional studies (Table 5). It was learned from the chromatographic experiments that the drug dextromethorphan (DM) exert higher affinity on α3β4-nAChR than its enantiomer levomethorphan (LM) and the difference in ΔG of the complexes was 0.3 kcal/mol. These data were valuable in evaluating parameter selection during initial tests of the docking simulations to optimally choose the channel dielectric constant or evaluate the usefulness of the scoring function for calculating estimated ΔG implemented in AutoDock. The docking simulations give insights into chiral recognition on the molecular level (FIG. 12). In binding to the α3β4 luminal domain, both molecules interact initially with a hydrophobic pocket on the border between the α3 and β4 helices (FIG. 12a). This binding determines the positions of the terminal amine group (blue) differently for dextromethorphan (grey) than levomethorphan (magenta). The amine group of dextromethorphan can easily form secondary interaction hydrogen bonds with neighboring polar residues (orange balls), while levomethorphan is less likely to form such interaction. This makes a difference in stabilities of two complexes by ca. 0.3 kcal/mol determined by both docking and chromatographic analysis (FIG. 11).

Furthermore, the estimated inhibition constant obtained during the simulations is very well correlated with equilibrium measures obtained in affinity chromatographic experiments.

EXAMPLE 3

QSAR—3D Clustering Technique

Classical methods for the identification and characterization of non-competitive inhibitors to ligand gated ion channels are time consuming. They are not applicable to the rapid screening of chemical libraries for potential new drug candidates nor can they be routinely used in the new drug development process. An important advancement in the area is the development of a method of identification of potent NCIs. The method is based of the chemometric processing of the chromatographic data obtained using a stationary phase modified by immobilization of particular subtype of the receptor. The non-linear chromatography approach allows description of the NCI-receptor interactions in terms of real thermodynamic capacity factor (k'), equilibrium constant for binding ($K_a$) and kinetics rate constants for association ($k_a$) and dissociation ($k_d$). We have determined that a strong correlation exists between the drug $k_d$ parameter obtained in affinity chromatography experiments and the relative length of the effect of this drug in functional studies (nicotine stimulated efflux of $^{86}$Rb$^+$, from cells expressing the target nAChR) (K. Jozwiak, J. Haginaka et al., *Anal. Chem.*, 2002, 74, 4618-4624. and K. Jozwiak, S. C. Hernandez et al., J. Chromatogr. B. 2003, 797, 423-431).

A strong relationship between the chromatographic rate constant and the length of the functional effect was found. However, more than chromatographic affinity has been found necessary to predict the $IC_{50}$ value for NCI activity. The non-linear chromatographic parameters determined in these studies were obtained in a dynamic system but under simplified conditions when compared to a functional assay (i.e. no neurotransmitter stimulation, no transmembrane potential, etc.). Thus, the efficacy of the NCI's expressed as $IC_{50}$ values were not directly correlated with the calculated non-linear chromatographic parameters.

Quantitative Structure-Activity Relationship (QSAR) analysis provided models of the chromatographic affinity (Table 6). Each of the derived equations contains a descriptor related to the electronic properties of the NCI's, $E_{HOMO}$ (Energy of the Highest Occupied Molecular Orbital), TPSA (Total Polar Surface Area) or a number of hydrogen bond acceptors. These models are consistent with the fact that NCI's bind at the internal surface of the nAChR ion channel, which is highly polar and negatively charged. Three of the four equations also contain a shape descriptor (Shadow-YZ), which is consistent with the fact that the NCI's bind within a defined space on the receptor. Thus, the QSAR analyses describe a chromatographic and, as discussed above, NCI-receptor process where the primary driving force is electrostatic interactions between positively charged ligands and a negatively charged nAChR, which take place in the structurally defined central pore of the receptor.

TABLE 6

QSAR equation describing affinity chromatography parameters.

| | |
|---|---|
| log k' = 5.255(±0.942) + 0.491(±0.092) $E_{HOMO}$ + 0.0118(±0.0049)YZ<br>r = 0.894, s = 0.168, F = 27.929, n = 17 | Eqn. 1 |
| log $k_{on}$ = 7.693(±0.111) − 0.00787(±0.00257)YZ + 0.0700(±0.0237)Hbond$_{acceptors}$ − −0.00276 (±0.00118)TPSA r = 0.762, s = 0.0883, F = 5.997, n = 17 | Eqn. 2<br>Outlier:<br>mecamylamine |
| log $k_{off}$ = −3.096(±0.926) − 0.454(±0.090)$E_{HOMO}$ − 0.0128(±0.00471)YZ<br>r = 0.891, s = 0.165, F = 26.961, n = 17 | Eqn. 3 |
| log K = 11.412(±0.604) + 0.492(±0.0669)$E_{HOMO}$<br>r = 0.885, s = 0.135, F = 54.130, n = 17 | Eqn. 4 |

Figure 13:
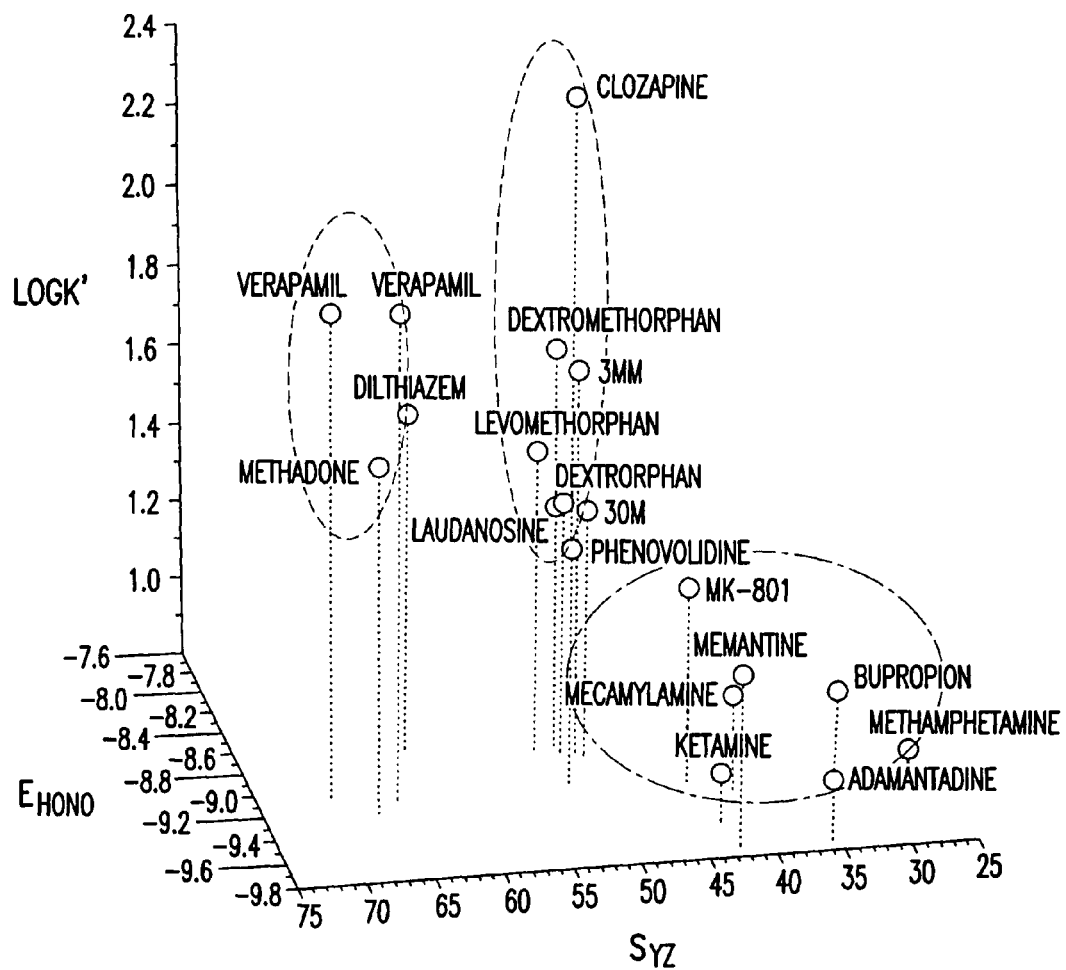
FIG. 13 illustrates cluster analysis according to the present invention. Three clusters were identified among tested NCIs. Cluster 1—red, cluster, 2—magenta, cluster 3—green.

A 3-dimensional scatterplot of the variables associated with Eqn. 1, i.e. log k', $E_{HOMO}$ and YZ, suggested that the whole cassette of tested NCI's could be subdivided into three separate clusters, FIG. 13.

The parameter k' is derived from chromatographic experiments using the non-linear chromatography approach described by Jozwiak et al. (Jozwiak K, Haginaka J, Moaddel R, Wainer I W. Displacement and nonlinear chromatographic techniques in the investigation of interaction of noncompetitive inhibitors with an immobilized alpha3beta4 nicotinic acetylcholine receptor liquid chromatographic stationary phase. *Anal. Chem.* 2002 Sep. 15;74(18):4618-24) and applied in Example 2 above. $E_{HOMO}$ is given in electron volts (eV) and is the highest occupied molecular orbital energy. $E_{HOMO}$ is an electronic descriptor of the molecule obtained in molecular simulation. In the present Example $E_{HOMO}$ was calculated using the MOPAC module in Cerius$^2$ software (Cerius2 v. 4.8. Accelrys Inc., San Diego, Calif.). Additional information about the $E_{HOMO}$ parameter can be found in J. M. Goodman, *Chemical application of Molecular Modeling*, c. Royal Society of Chemistry. 1998. p. 139.

"Shadow YZ" is a surface area projection descriptor—the molecular surface is projected the YZ plane (determined by principal axis of inertia of the molecule) and the shadow is calculated in Å$^2$. In the present example, we used the QSAR+ module of Cerius$^2$ software (Cerius2 v. 4.8. Accelrys Inc., San Diego, Calif.). More information about the surface area projection descriptor can be found in Rohrbaugh et al. (Rohrbaugh R H, Jurs P C. Molecular shape and the prediction of high-performance liquid chromatographic retention indexes of polycyclic aromatic hydrocarbons. Anal Chem. 1987 Apr. 1;59(7):1048-54).

A cluster analysis based on the three properties was carried out using K-mean clustering method of variables and the results confirm that there are 3 distinct clusters. K-mean clustering is a standard clustering method that determines a user-specified number of clusters with the goal of minimizing within-cluster variability while maximizing between-cluster variability. In the present example, the method was implemented as in Statistica (STATISTICA v. 6.0. Statsoft Inc., Tulsa, Okla.).

Cluster 1 was formed by four compounds (dilthiazem and methadone verapamil and nor-verapamil) and can be characterized by high values of log k' and $E_{HOMO}$ and YZ parameters (mean values/range:1.645/1.3 to 2.2; −8.93/−9.2 to −8.6 and 64.5/60 to 70, respectively); Cluster 2 included 8 compounds (dextromethorphan analogs, clozapine, laudanosine and phencyclidine) with high values of log k' and $E_{HOMO}$ but moderate YZ (mean values/range:1.61/1.3 to 2.2; −8.64/−9.0 to −7.7; and 50.0/45 to 60, respectively); and Cluster 3 contained 7 compounds (MK-801, adamantadine, bupropion, ketamine, mecamylamine, memantine, methamphetamine) with low values of log k', $E_{HOMO}$ and YZ parameters (mean value/range:1.06/0.9 to 1.3; −9.45/−9.8 to −9.1 and 37.9/25 to 45, respectively).

The analysis segregates the compounds by size and charge, with the smaller, more electronegative compounds appearing in Cluster 3. This division reflects a pharmacological reality since compounds contained in Cluster 3 can rapidly and deeply penetrate the luminal pore of the nAChR producing a high percentage of blockade per concentration of molecules. This would be reflected in lower IC$_{50}$ values.

The IC$_{50}$ values have been established for 4 in Cluster 1, 4 of the 8 in Cluster 2 and 6 of the 8 in Cluster 3 using the Rb$^+$efflux assay described above using cell lines expressing the relevant receptor. KXa3b4R2 is a line of human embryonic kidney 293 cells stably transfected with rat neuronal nicotinic acetylcholine receptor (nAChR) α3 and β4 subunit genes. This cell line can be obtained from Dr. Kenneth Kellar—Department of Pharmacology, Georgetown University, Washington, D.C. K177 is a line of human embryonic kidney 293 cells stably transfected with human neuronal nicotinic acetylcholine receptor (nAChR) α3 and β4 subunit genes. These cells can be obtained from Dr. Daniel Bertrand, Dept. of Physiology, University of Geneva, Switzerland. SH-SY5Y cells are a human neuroblastoma clonal subline of the neuroepithelioma cell line SK-N-SH from the bone marrow. This cell line can be obtained from the European Collection of Cell Cultures (ECACC), catalogue no. 94030304. PC-12 Rat adrenal gland pheochromocytoma cells are available from the American Type Culture Collection, ATCC Number CRL-1721. Results are shown in (Table 7).

When these values were considered in relationship to the compounds in Clusters 2 and 3, 3 of the 4 compounds in Cluster 2 had IC$_{50}$ values≧10 μM while 5 of the 6 compounds in Cluster 3 had IC$_{50}$ values≦10 μM.

TABLE 7

The IC$_{50}$ values of Rb$^+$ efflux of various compounds.

| Ligand | IC$_{50}$ | Cluster Number | Cell line |
|---|---|---|---|
| methadone | 1.9 (±0.2) | 1 | KXα3β4R2 |
| Verapamil | 8.1 (±1.3) | 1 | KXα3β4R2 |
| nor-verapamil | 2.6 (±1.0) | 1 | KXα3β4R2 |
| Dilthiazem | 2.26 (±1.0) | 1 | KXα3β4R2 |
| dextromethorphan | 8.9 (±1.1) | 2 | KXα3β4R2 |
|  | 10.1 (±1.10) |  | KXα3β4R2 |
| levomethorphan | 10.9 (±1.08) | 2 | KXα3β4R2 |
| dextrorphan | 29.6 (±5.7) | 2 | KXα3β4R2 |
| phencyclidine | 7.0 (±1.3) | 2 | KXα3β4R2 |
|  | 5.9 |  | SH-SY5Y |
| MK-801 | 26.6 (±9.6) | 3 | KXα3β4R2 |
| mecamylamine | 1.0 (±0.04) | 3 | KXα3β4R2 |
| memantine | 6.60 (±0.92) | 3 | K177 (α4β2) |
| amantadine | 3.44 (±0.67) | 3 | K177 (α4β2) |
| Bupropion | 1.4 | 3 | SH-SY5Y |
| Ketamine | 5.2 (±0.5) | 3 | PC-12 |
|  | 1.4 |  | SH-SY5Y |

The method of NCI clustering using Equation 1, above, identifies potent NCIs, i.e. those with low IC$_{50}$. Compounds belonging to cluster 3 are considered as potential NCIs and are expected to be effective in functional tests. Compounds in the cluster 2 are expected to express weaker inhibition properties. The compounds of cluster 1, which consists of large, bulky compounds with strong chromatographic affinity, are also expected to be potent NCIs. Initially, the $IC_{50}$ value of only one of the four compounds in cluster 1 was known, methadone. The cluster analysis predicted that verapamil, nor-verapamil and diltiazem should be effective NCIs of the α3β4 nAChR and functional studies confirmed this prediction.

Functional studies were carried out using a nicotine-stimulated $^{86}Rb^+$efflux assay on KXα3β4R2 cell line expressing α3β4 subtype of neuronal nAChR. The studies revealed that the $IC_{50}$ values of dilthiazem, verapamil and nor-verapamil are 2.3 µM, 8.2µM and 2.1 µM respectively. Thus all compounds in cluster 1 are strong inhibitors. The cluster analysis technique is applied in Example 6 below to identify compounds with high potency as NCIs, which was identification was further verified by functional studies of $Rb^+$ efflux.

The technique of cluster analysis using Eqn. 1 also suggests that high NCI potency can be attributed to two structurally different groups of compounds. It can be speculated that the two groups of compounds may express their inhibitory properties by two different molecular mechanisms.

EXAMPLE 4

Investigation of α3β2 nAChR Subtype

The α3β4 subtype of the nAChR is extensively characterized, easily accessible in stably transfected cell lines (e.g., KXα3β4R2) and widely tested in functional studies. Moreover, functional studies of this subtype are relatively easy. However, the transmembrane domain of α3β4-subtype has some unique features not found in other subtypes. As previously stated, the general structure of the luminal domain is believed to be fairly well conserved among the subtypes of the nAChRs. However, the M2 transmembrane part of β4 subunit has one critical mutation (phenylalanine (F) in the β4 subunit at position 15 while most other subunits have a valine (V) in this position (Table 1). As a result the nAChRs containing the β4 subunit may display significantly different properties than would other subunit types and may exhibit differences in the interaction of the nAChR channel with NCIs. The introduction of the phenylalanine moieties on the β4 subunits produces small clefts in the surface of the luminal domain of the channel. These clefts play an important role in in the binding of NCIs, as described further below. The cleft explains the observed enantioselectivity between dextroemthorphan and levomethorphan (Jozwiak, K.; Hernandez, S. C.; Kellar, K. J.; Wainer, I. W. The enantioselective interactions of dextromethorphan and levomethorphan with the α3β4-nicotinic acetylcholine receptor: comparison of chromatographic and functional data. J. Chromatogr. B. 2003, 797,423-431).

The clefts are associated with the presence of phenylalanine in β4 M2 domain and will not exist in other, non-β4 subtypes of the nAChR. Interestingly, the results from a chromatographic study which utilize an immobilized α3β2-nAChR column showed enantioselectivity for dextromethorphan and levomethorphan significantly diminished as compared to the immobilized α3β4-nAChR column (Table 7), further supporting the conclusion that the cleft is a feature of β4 subtype receptors that can be important for NCI activity.

TABLE 7

Comparison of enantioselectivity of DM/LM pair of enantiomers on two different nAChR systems. Experimental data from affinity chromatography - selectivity factor (α)

|  | α3β4 | α3β2 |
|---|---|---|
| $\alpha = \dfrac{k'_{DM}}{k'_{LM}}$ | 1.62 | 1.03 |
| $\Delta\Delta G° = -RTln\alpha$ | −0.29 kcal/mol | −0.02 kcal/mol |

Based on these observations, a molecular model of α3β2 luminal domain was constructed. The main difference in the structure of the β2-type channel is the exchange of phenylalanines from β4 helices for valines associated with β2 helices (See Table 1). A graphic representation of the model is presented in FIGS. 3a and 3b. FIG. 3b shows the residues forming the surface of the channel. The distribution of the particular rings along the channel can be easily noticed. The rings are distributed as follows (from top to bottom): extracellular ring, leucine ring, valine ring, leucine ring, serine ring, threonine ring and intermediate ring (consisting of glutamic acid residues) and this is consistent with general considerations. The α3β2 model revealed some important differences when compared with the α3β4 channel. The most important is the lack of clefts formed on the apolar surface of the lumen. The α3β2 model is considered the more general of the two and represents the shape of the channel associated with majority of subtypes of neuronal nAChR, since there is no substantial difference in the sequence of the exposed residues along the channel when compared with other subunits. Only the β4 subunit possesses a significant mutation of Val→Phe in the valine ring. Therefore, the new model of the α3β2 subtype is more homologous to other important subtypes of nAChR than the α3β4 model and should be considered as a general template for detailed studies of other nAChRs and in some perspective other members of the ligand gated ion channel superfamily.

Figure 12B:
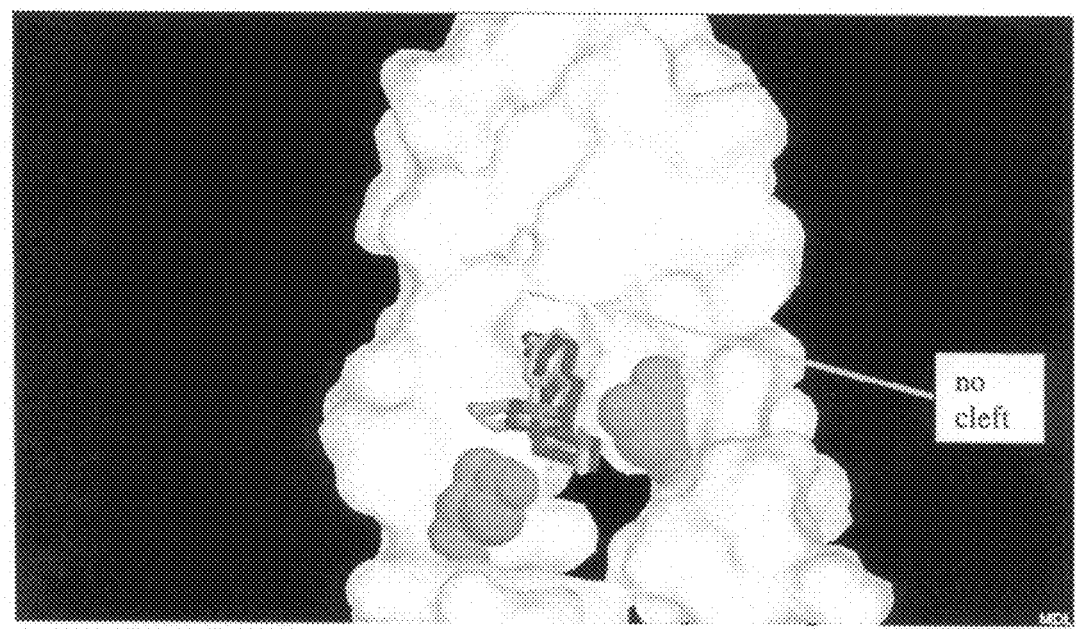

The different structure of the luminal domain of the α3β2 channel produces a profound change in the docking interaction of NCIs. Since there is no apolar cleft on the surface of the channel, the NCI molecules must find alternative interaction in the binding site. The case of special interest are docking simulations: dextromethorphan and levomethorphan. FIGS. 12a and 12b present the overlaid lowest energy conformations of these two enantiomers docked onto the model of α3β2 luminal domain. Two molecules adopt different orientations compared to docking onto α3β4 model: the ligands binds primarily to the apolar part of the lumen with nitrogen atom interacting with serine ring. However, in contrast to α3β4 docking, there is no defined cavity on the surface and only side interactions are possible which results in the significantly weaker energy of interaction and, what is even more important, the ΔG difference between DM-α3β2-nAChR complex and LM-α3β2-nAChR complex is significantly diminished when compared to simulations on α3β4-nAChR model (Table 8).

The presence of the hydrophobic cleft in the α3β4 receptor subtype and its absence from the α3β2 subtype presents a target for designing of compounds that are specific for one subtype over the other.

TABLE 8

Enantiospecificity of dextromethorphan and levomethorphan in docking simulation studies of the α3β4 and α3β2 luminal channels.

|  | α3β4 | α3β2 |
|---|---|---|
| $\Delta G_{DM}$ [kcal/mol] | −8.73 | −7.10 |
| $\Delta G_{LM}$ [kcal/mol] | −8.40 | −6.93 |
| $\Delta\Delta G$ [kcal/mol] | −0.33 | −0.17 |

EXAMPLE 5

Designing of New NCI Molecules

The molecular models, clustering analysis and dynamic chromatographic method of the invention can be used to design molecules that possess enhanced activity as NCIs of nAChRs. The molecular model of the NCI binding site and docking studies provide an understanding of the mechanism of non-competitive inhibition. Using the docking orientations of molecular NCI-nAChR complexes, we have designed modifications of known molecules to more strongly accommodate the active site and as a result obtained new compounds that express stronger NCI activity. Such new molecules are of interest in the pharmaceutical industry as new treatments of disorders associated with nAChR overactivity, e.g., as aids in smoking cessation.

In general, the docking orientation of a putative NCI is such that the molecule occupies a position within the luminal channel and exhibits a ΔG of about −8.5 kcal/mol. The molecule will generally be designed to have molecular contacts with at least one, preferably 2, 3 or 4 of the side chains of the amino acids lining the luminal channel. Molecular contacts that are useful in providing high binding energies (i.e. negative ΔG), include hydrogen bonds and pi orbital overlaps.

A structure-activity relation for a NCI of a LGIC has been derived using the above-described methods. Thus, a compound having a bulky hydrophobic moiety (e.g., a phenyl or napthyl ring system or other fused aromatic ring system, cyclopentyl or cyclohexyl ring system, a fused ring system including but not limited to bicyclo [2.2.1] heptane, bicyclo [2.2.2] octane, morphinan and dibenzo [1.4] diazepine) and a primary, secondary or tertiary amino group in proximity to (i.e, approximately 5 to 10 Å from, preferably from 5 to 8 Å from, more preferably less than 7 Å from) said hydrophobic moiety. The amino group can be directly bonded to the bulky hydrophobic moiety or can be linked by a spacer moiety, such as, but not limited to, a short hydrocarbon chain. The amino group can be substituted (—$NR_1R_2$, where $R_1$ and $R_2$ are the same or different and are selected from the group consisting of H, $C_1$-$C_3$ alkyl, $C_1$-$C_4$ alkoxy, dialkyl keto). The substituent is preferably one that retains a hydrogen-bonding potential; a preferred substituent is a keto- group, for example a dialkyl keto group, especially $CH_2(C=O)CH_3$. Another preferred substituent is a hydroxyl or alkoxyl (—$CH_2OH$) group, e.g. a $C_1$-$C_4$ normal or branched alkoxyl group. Preferred substituted amino groups are a dialkyl keto amino group (e.g., $HNCH_2(C=O)CH_3$), a hydroxyl amino group or a methoxy amino group. An example of such a compound is 3-methoxy-17-propane-2-one 9α, 13α, 14α morphinan.

A preferred compound designed using the method of the above considerations is one comprising a hydrophobic group. A preferred hydrophobic group comprises at least one ring that includes at least two conjugated unsaturated bonds, said ring optionally being fused to additional rings to form a ring system and said additional rings optionally including one or more hetero atoms. Alternatively, the hydrophobic group can be a hydrocarbon chain or saturated cyclic compound. The hydrocarbon chain can be linear or branched and preferably contains from 4 to 10 carbon atoms, more preferably from 4 to 7 carbon atoms. The hydrocarbon chain can further include alkenyl or alkynl unsaturations at one or two positions.

The compound will also preferably contain a hydrogen bond accepting group, which more preferably is selected from the group consisting of a keto group, a nitrogen-containing heterocyclic group and a guanidinium group. Typically, the ring or ring system and said hydrogen bond accepting group are joined by a linker comprising 1 to 4 carbon atoms and optionally containing an oxygen or sulfur atom.

Figure 2:
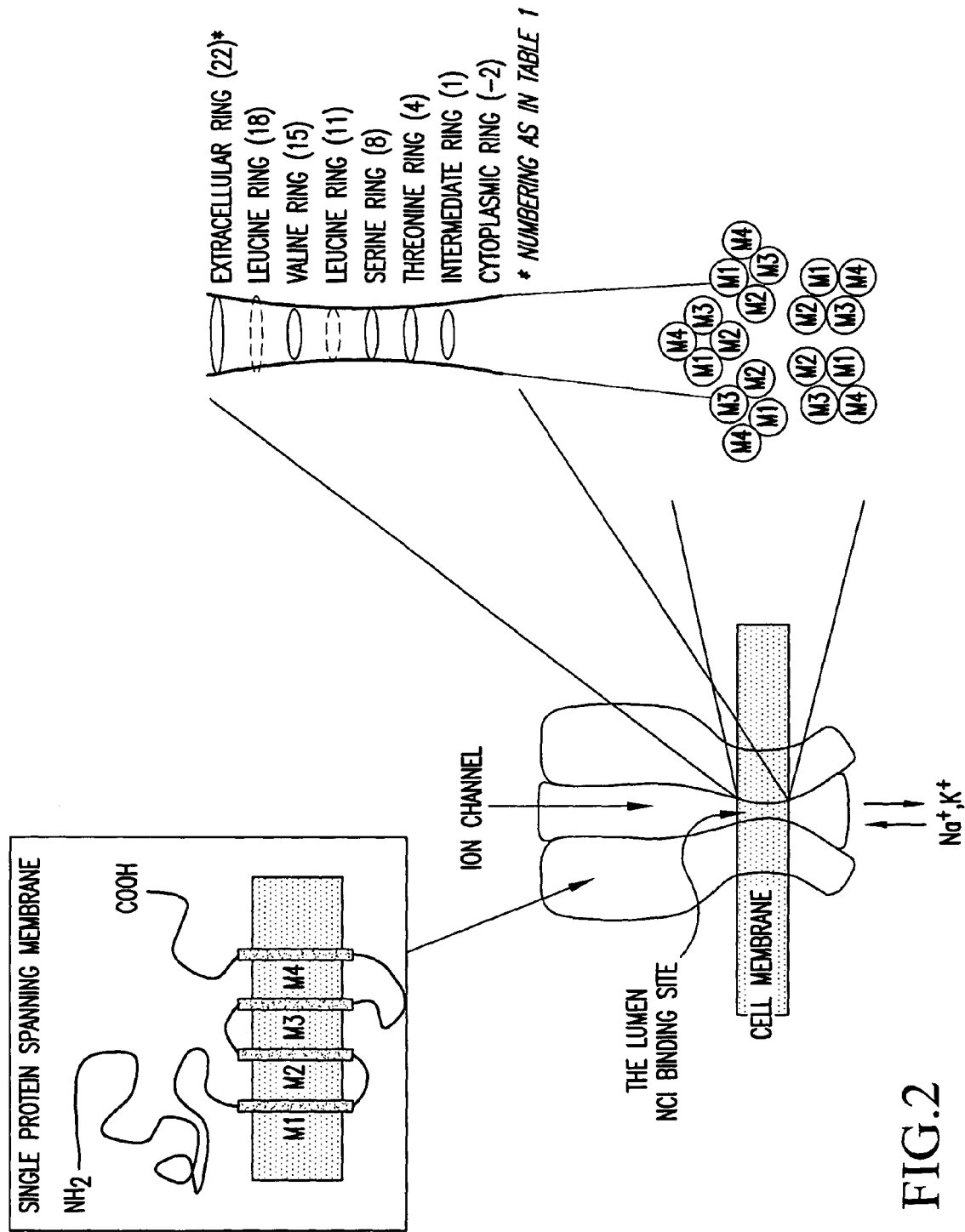

One consideration for design of effective NCI molecules is that the molecule will preferably span portion of the luminal domain from the hydrophobic region defined by the leucine and/or valine rings to the more polar region defined by the serine and/or threonine rings (FIG. 2).

The compound will preferably have activity as a non-competitive inhibitor of $Rb^+$ efflux of a ligand-gated neurotransmitter ion channel receptor with an $IC_{50}$ of less than 10 μM.

Figure 14:
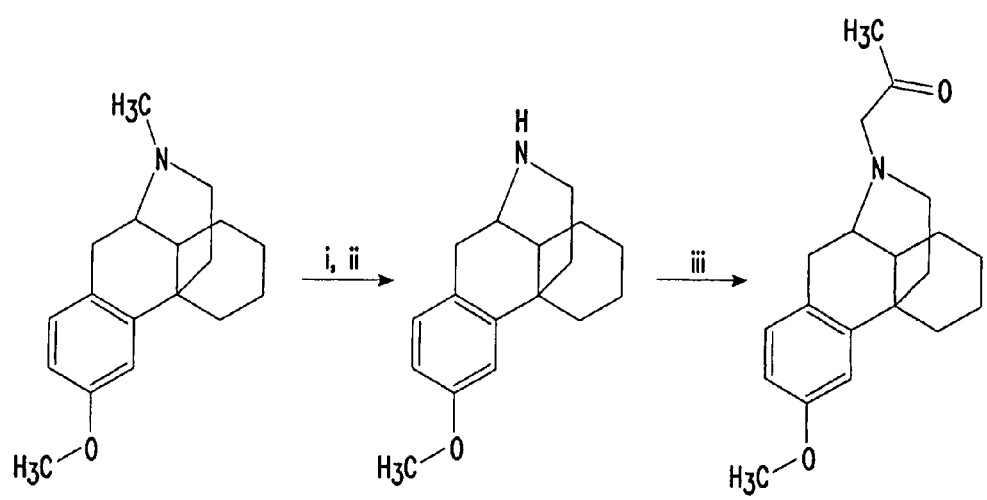
FIG. 14 shows the synthetic scheme for novel compound DM-01; i—1-chloroethyl chloroformate; ii—methanol; iii—1-chloroacetone.
Figure 15:
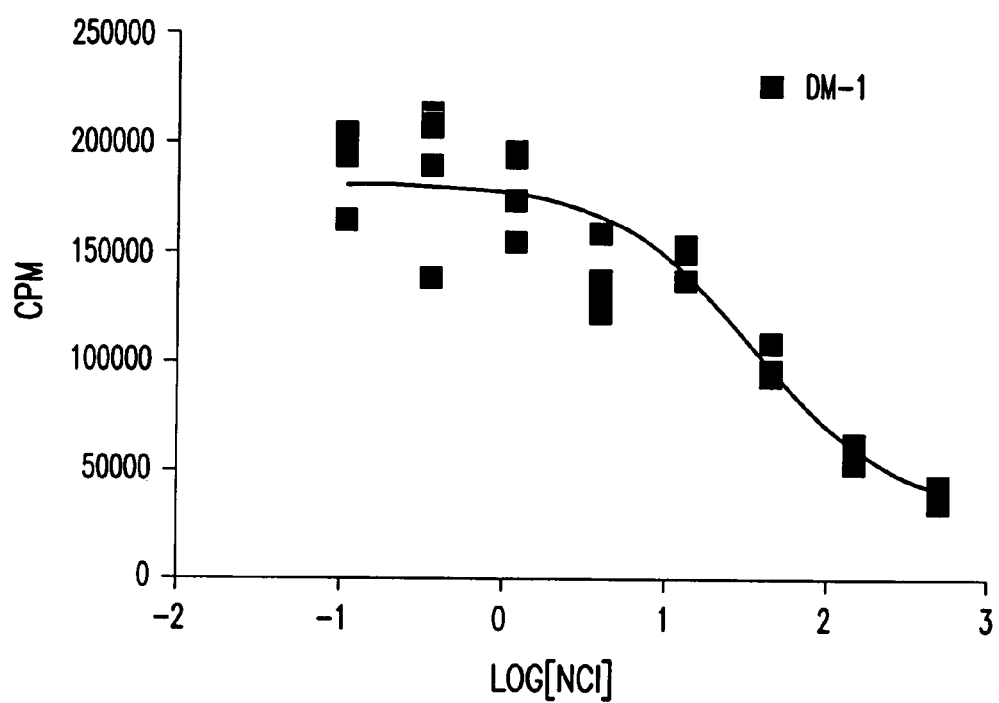
FIG. 15 shows the NCI activity in the $Rb^+$ efflux assay of compound DM-01.

As an example of such an approach, we undertook modifications of dextromethorphan (DM). DM possesses strong activity as a NCIs ($IC_{50}$=10 μM on α3β4-nAChR with a greatly prolonged duration of the NCI action), it easily passes blood-brain barrier and unlike as its enantiomer levomethorphan expresses little action on opioid receptors. The docking orientation of the DM-α3β4-nAChR complex is presented in FIG. 15. The molecule occupies the valine/phenylalanine cleft on the border between α3-M2 helix and β4-M2 helix with an amino- group exposed for interaction with polar residues below this cleft. The interaction would be even stronger if the amino group could interact with the serine residues forming the serine ring, but this interaction is prevented by the distance of ca. 5 Å separating two moieties. Study of the complex showed that the energy of interaction should be significantly enhanced if a methyl group attached to nitrogen would be exchanged into a longer moiety with hydrogen bond acceptors in order to allow forming strong hydrogen bonds and therefore stabilizing the complex. Several possible patterns of dextromethorphan modification were designed and these are shown in Table 9. Those molecules are based on the interaction with α3β4-nAChR and may be possibly selective blockers for this subtype. Compound DM-01 was synthesized and tested for activity in a $Rb^+$ efflux assay. The synthesis of DM-01 is described in FIG. 14 and the data are presented in FIG. 15.

TABLE 9

Molecules designed to inhibit α3β4-nAChR followed by ΔG values obtained in docking simulations (reference ΔG of dextromethorphan = −8.73 kcal/mol).

| Compound | Formula | ΔG |
|---|---|---|
| dextrometorphan | | −8.73 kcal/mol |

TABLE 9-continued

Molecules designed to inhibit α3β4-nAChR followed by ΔG values obtained in docking simulations (reference ΔG of dextromethorphan = −8.73 kcal/mol).

| Compound | Formula | ΔG |
|---|---|---|
| DM-01 | | −9.09 kcal/mol |
| DM-02 | | −9.35 kcal/mol |
| DM-03 | | −10.31 kcal/mol |
| DM-04 | | −9.39 kcal/mol |
| DM-05 | | −10.18 kcal/mol |

EXAMPLE 6

Prediction of Side Effects of Compounds Mediated by Non-Competitive Inhibition of Ligand-Gated Ion Channels The analytic methods of the present invention can also be applied to assessment of NCI activity of compounds compounds, both known drugs and novel compounds, to predict side effects. For example, the drugs verapamil, nor-verapamil and dilthiazem are commonly administered for treatment of high blood pressure. An undesirable side effect of these drugs is constipation.

As explained above, the α3β4 nAChR subtype plays a role in regulation of gut motility and the side effects of verapamil, nor-verapamil and dilthiazem on gut motility have been related to NCI activity of these compounds against the nAChR. As an example of application of the analytic methods of the present invention to the investigation of drug side effects, we applied the cluster analysis method to predict the NCI activity of various compounds used as calcium channel blockers for treatment of high blood pressure, or their metabolites (MA-M6 and D-620) and listed in Table 10. NCI activity is predicted if the compound falls into Cluster 1. Predicted NCI activity (or lack thereof was then confirmed using the $Rb^+$ efflux assay. Results are shown in Table 10.

The ranges defining clusters are as above and are: Cluster 1 (low $IC_{50}$ values) log k' from 1.3 to 2.2 and $E_{HOMO}$ from −9.2 to −8.6 and YZ from 60 to 70; Cluster 2 (high $IC_{50}$ values) log k' from 1.3 to 2.2 and $E_{HOMO}$ from −9.0 to −7.7 and YZ from 60 to 45; and Cluster 3 (low $IC_{50}$ values) log k' from 0.9 to 1.3; $E_{HOMO}$ from −9.8 to −9.1 and YZ from 45 to 25.

The chromatographic method using α3β4 nAChR column was used to obtain experimental affinity for 13 structures (diltiazem and 5 of its metabolites; verapamil and 3 of its metabolites; nicardapine, nifedipine and amlodipine). The computational method of the invention was use to calculate $E_{HOMO}$ and YZ descriptors and the data are presented in Table 10. Based on this data all compounds were assigned to respective clusters (Table 10).

After the prediction has been done based on clustering the actual values of $IC_{50}$ were determined using the nicotine-stimulated $^{86}Rb^+$ efflux assay on cell line KXα3β4R2. These data are also presented in Table 10 and the comparison of cluster method prediction with actual activity gives very good agreement—all tested ligands falls into proper categories.

As it can be seen from Table 10 all of the tested compounds could be assigned to either cluster 1 or to cluster 2, which segregate them into two groups: very effective NCIs ($IC_{50}$<10 µM—cluster No. 1) and less effective NCIs ($IC_{50}$>10 µM—cluster No. 2). The cluster analysis properly predicted the NCI activity of all 13 drugs and metabolites. Furthermore, the results suggest that the cardiovascular benefit attributed to calcium channel blocking activity may derive at least in part from previously unrecognized activity of inhibition of ligand-gated ion channels.

TABLE 10

Results of the cluster analysis characterization of tested calcium channel blockers.

| Ligand | logk' | $E_{HOMO}$ | YZ | Cluster No. | $IC_{50}$ [µM] |
|---|---|---|---|---|---|
| Dilthiazem | 1.64 | −8.66306 | 62.29732 | 1 | 2.2 |
| MA | 1.61 | −8.6465 | 66.535 | 1 | 4.2 |
| M1 | 1.6 | −8.5788 | 62.40288 | 2 | 30.4 |
| M2 | 1.61 | −8.58 | 57.4339 | 2 | 77.6 |
| M4 | 1.45 | −8.4067 | 61.84228 | 2 | 73.2 |
| M6 | 1.48 | −8.6465 | 58.1142 | 2 | 63.1 |
| verapamil | 1.99 | −9.05746 | 64.80137 | 1 | 8.1 |
| Nor-verapamil | 1.99 | −9.12446 | 64.82286 | 1 | 2.6 |
| galapamil | 1.88 | −9.04879 | 66.25418 | 1 | 6.4 |
| D-620 | 1.25 | −9.34918 | 48.52653 | 2 | 48.9 |
| nicardapine | 2.33 | −8.8397 | 65.20084 | 1 | 2.5 |
| amlodipine | 2 | −8.7228 | 62.93348 | 1 | 5.8 |
| nifedipine | 1.27 | −8.6323 | 58.42415 | 2 | 24.7 |

Compounds named in Table 3, Table 7 or Table 10, or specifically named in FIG. 9 or FIG. 13, and bupropion, ketamine, laudanosine, mecamylamine, methadone, MK-801, phenylcylclidine, ethidium, and dextromethorphan are compounds known in the prior art and so are not considered to be inventive compounds per se within the scope of the present invention. Methods of the invention for non-competitively inhibiting a LGIC, especially a nicotinic AChR, or for treatment of a disease mediated by overactivity of a nicotinic AChR, exclude the use of bupropion, ketamine, laudanosine, mecamylamine, methadone, MK-801, phenylcylclidine, ethidium, and dextromethorphan.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

All patent and literature references cited herein are hereby incorporated by reference in their entirety and for all purposes, including the following references:

1. Wainer I W, Zhang Y, Xiao Y, Kellar K J (1999) Liquid chromatographic studies with immobilized neuronal nicotinic acetylcholine receptor stationary phases: effects of receptor subtypes, pH and ionic strength on drug-receptor interactions. *J Chromatogr B Biomed Sci Appl* 724:65-72.
2. Zhang Y, Xiao Y, Kellar K J, Wainer I W (1998) Immobilized nicotinic receptor stationary phase for on-line liquid chromatographic determination of drug-receptor affinities. *Anal Biochem* 264:22-5.
3. Barrantes F J. (2002) Lipid matters: nicotinic acetylcholine receptor-lipid interactions (Review). *Mol Membr Biol* 19:277-84.
4. Morris G M, Goodsell D S, Halliday R S, et al. (1998) Automated docking using a Lamarckian genetic algorithm and empirical binding free energy function. 19:1639-62.

Appendix 1 AMBER Scripts for Stepwise Refining the Model

All Runs were made in AMBER 6.0. The computer used was SGI Octane.

SGI Octane information is given below:

```
-----------------------------------------
1 195 MHZ IP30 Processor
CPU: MIPS R10000 Processor Chip Revision: 2.7
FPU: MIPS R10010 Floating Point Chip Revision: 0.0
Main memory size: 1536 Mbytes
Xbow ASIC: Revision 1.3
Instruction cache size: 32 Kbytes
Data cache size: 32 Kbytes
Secondary unified instruction/data cache size: 1 Mbyte
Integral SCSI controller 0: Version QL1040B (rev. 2), single ended
Disk drive: unit 1 on SCSI controller 0
Disk drive: unit 2 on SCSI controller 0
Integral SCSI controller 1: Version QL1040B (rev. 2), single ended
IOC3 serial port: tty1
IOC3 serial port: tty2
IOC3 parallel port: plp1
Graphics board: SI
Integral Fast Ethernet: ef0, version 1, pci 2
Iris Audio Processor: version RAD revision 12.0, number 1
-----------------------------------------
```

The Amber runs were made on a potassium channel receptor model that was built using the template structure of PDB entry 1EQ8 on Sybyl 6.8. Amber 6.0 was used to refine the structure that was built in sybyl 6.8. Scripts used to do the energy minimization are attached below:

```
#++++++++++++++++++++++++++++++++++++++++++++++++++++++++++++++++
SCRIPT 1
#-------------------------------------------------------
#Script for running Sander_Classic in AMBER 6.0
#Relaxing only Hydrogen atoms ----Ravi (May 23, 2002)

#ALL Hs are relaxed IBELLY OPTION, \epsilon(r)
#-------------------------------------------------------
&cntrl
timlim=36000., imin=1, nmropt=0,
ntx=1, irest=0, ntrx=1,
ntxo=1, ntpr=10, ntwr=0, ntwx=50, ntwv=0, ntwe=50, ntwxm=0, ntwvm=0, ntwem=0,
```

-continued

```
ioutfm=0, ntwprt=0,
ntf=1, ntb=0, idiel=0, dielc=4.0, cut=9.0, ntnb=1, nsnb=25,
ntid=0, scnb=2.0,scee=1.2, cut2nd=0.0
ichdna=0,
isftrp=0, rwell=0.0,
ipol=0,
ibelly=1, ntr=0,
maxcyc=5000, ncyc=550, ntmin=1, dx0=0.01, dxm=0.05,
&end
GROUP NUMBER 1
FIND
* H * *
* H1 * *
* HC * *
* HP * *
* HO * *
* HA * *
* HS * *
SEARCH
RES 1 125
END
END
#+++++++++++++++++++++++++++++++++++++++++++++++++++++++++++++++++
SCRIPT 2
#------------------------------------------------------
#Script for running Sander_Classic in AMBER 6.0
#Relaxing Hydrogen + Side-Chains ----Ravi (May 23, 2002)

#------------------------------------------------------
# Channel ALL H+SC are moving

&cntrl
timlim=36000., imin=1, nmropt=0,
ntx=1, irest=0, ntrx=1,
ntxo=1, ntpr=5, ntwr=0, ntwx=50, ntwv=0, ntwe=50, ntwxm=0, ntwvm=0, ntwem=0,
ioutfm=0, ntwprt=0,
ntf=1, ntb=0, idiel=0, dielc=4.0, cut=9.0, ntnb=1, nsnb=25,
ntid=0, scnb=2.0,scee=1.2, cut2nd=0.0
ichdna=0,
isftrp=0, rwell=0.0,
ipol=0,
ibelly=1, ntr=0,
maxcyc=5000, ncyc=250, ntmin=1, dx0=0.01, dxm=0.05,
&end
GROUP NUMBER 1
FIND
* CT 3 *
* CA B *
* CA S *
* OH S *
* SH S *
* S S *
* C B *
* N3 3 *
* * E *
SEARCH
RES 1 125
END
END
#+++++++++++++++++++++++++++++++++++++++++++++++++++++++++++++++++
SCRIPT 3:
#------------------------------------------------------
#Script for running Sander_Classic in AMBER 6.0
#Relaxing everything except alpha-Carbons
#----Ravi (May 23, 2002)

#------------------------------------------------------
# Except Alpha C, all other atoms move

&cntrl
timlim=36000., imin=1, nmropt=0,
ntx=1, irest=0, ntrx=1,
ntxo=1, ntpr=5, ntwr=0, ntwx=50, ntwv=0, ntwe=50, ntwxm=0, ntwvm=0, ntwem=0,
ioutfm=0, ntwprt=0,
ntf=1, ntb=0, idiel=0, dielc=4.0, cut=9.0, ntnb=1, nsnb=25,
ntid=0, scnb=2.0,scee 1.2, cut2nd=0.0
ichdna=0,
```

-continued

```
isftrp=0, rwell=0.0,
ipol=0,
ibelly=1, ntr=0,
maxcyc=5000, ncyc=250, ntmin=1, dx0=0.01, dxm=0.05,
&end
GROUP NUMBER 1
FIND
* * 3 *
* * B *
* * S *
* * E *
N N M *
C C M *
CH3 CT M *
* HC M *
SEARCH
RES 1 125
END
END
#++++++++++++++++++++++++++++++++++++++++++++++++++++++++++++++++++
SCRIPT 4:
#-------------------------------------------------------
#Script for running Sander_Classic in AMBER 6.0
#Restrained minimization of the alpha-Carbons of the channel
#----Ravi (May 23, 2002)

#-------------------------------------------------------
# Restrained minimization of the alpha-Carbons

&cntrl
timlim=36000., imin=1, nmropt=0,
ntx=1, irest=0, ntrx=1,
ntxo=1, ntpr=5, ntwr=0, ntwx=50, ntwv=0, ntwe=50, ntwxm=0, ntwvm=0, ntwem=0,
ioutfm=0, ntwprt=0,
ntf=1, ntb=0, idiel=0, dielc=4.0, cut=9.0, ntnb=1, nsnb=25,
ntid=0, scnb=2.0,scee=1.2, cut2nd=0.0
ichdna=0,
isftrp=0, rwell=0.0,
ipol=0,
ibelly=0, ntr=1,
maxcyc=2000, ncyc=250, ntmin=1, dx0=0.01, dxm=0.05,
&end
GROUP NUMBER 1
10.0
FIND
CA * * *
SEARCH
RES 1 125
END
END
#++++++++++++++++++++++++++++++++++++++++++++++++++++++++++++++++++
```

Appendix 2 AutoGrid Parameter File

```
receptor M3.pdbqs      # macromolecule model
gridfld M3.maps.fld    # grid_data_file
npts 60 60 120         # num.grid points in xyz
spacing 0.375          # spacing(A)
gridcenter 0.009 0.026 −0.172   # xyz-coordinates or auto
types CANOH            # atom type names
smooth 0.5             # store minimum energy w/in rad(A)
map M3.C.map           # atom-specific affinity map
nbp_r_eps 4.00 0.0222750 12 6 # C-C lj
nbp_r_eps 3.75 0.0230026 12 6 # C-N lj
nbp_r_eps 3.60 0.0257202 12 6 # C-O lj
nbp_r_eps 4.00 0.0257202 12 6 # C-S lj
nbp_r_eps 3.00 0.0081378 12 6 # C-H lj
nbp_r_eps 3.00 0.0081378 12 6 # C-H lj
nbp_r_eps 3.00 0.0081378 12 6 # C-H lj
sol_par 12.77 0.6844   # C atomic fragmental volume,
                         solvation parameters
constant 0.000         # C grid map constant energy
map M3.A.map           # atom-specific affinity map
nbp_r_eps 4.00 0.0222750 12 6 # A-C lj
nbp_r_eps 3.75 0.0230026 12 6 # A-N lj
nbp_r_eps 3.60 0.0257202 12 6 # A-O lj
nbp_r_eps 4.00 0.0257202 12 6 # A-S lj
nbp_r_eps 3.00 0.0081378 12 6 # A-H lj
nbp_r_eps 3.00 0.0081378 12 6 # A-H lj
nbp_r_eps 3.00 0.0081378 12 6 # A-H lj
sol_par 10.80 0.1027   # A atomic fragmental volume,
                         solvation parameters
constant 0.000         # A grid map constant energy
map M3.N.map           # atom-specific affinity map
nbp_r_eps 3.75 0.0230026 12 6 # N-C lj
nbp_r_eps 3.50 0.0237600 12 6 # N-N lj
nbp_r_eps 3.35 0.0265667 12 6 # N-O lj
nbp_r_eps 3.75 0.0265667 12 6 # N-S lj
nbp_r_eps 1.90 0.3280000 12 10 # N-H hb
nbp_r_eps 1.90 0.3280000 12 10 # N-H hb
nbp_r_eps 1.90 0.3280000 12 10 # N-H hb
sol_par 0.00 0.0000    # N atomic fragmental volume,
                         solvation parameters
```

-continued

```
constant 0.000      # N grid map constant energy
map M3.O.map        # atom-specific affinity map
nbp_r_eps 3.60 0.0257202 12 6 # O-C lj
nbp_r_eps 3.35 0.0265667 12 6 # O-N lj
nbp_r_eps 3.20 0.0297000 12 6 # O-O lj
nbp_r_eps 3.60 0.0297000 12 6 # O-S lj
nbp_r_eps 1.90 0.3280000 12 10 # O-H hb
nbp_r_eps 1.90 0.3280000 12 10 # O-H hb
nbp_r_eps 1.90 0.3280000 12 10 # O-H hb
sol_par 0.00 0.0000     # O atomic fragmental volume,
                          solvation parameters
constant 0.236      # O grid map constant energy
map M3.H.map        # atom-specific affinity map
nbp_r_eps 3.00 0.0081378 12 6 # H-C lj
```

-continued

```
nbp_r_eps 1.90 0.3280000 12 10 # H-N hb
nbp_r_eps 1.90 0.3280000 12 10 # H-O hb
nbp_r_eps 3.00 0.0093852 12 6 # H-S lj
nbp_r_eps 2.00 0.0029700 12 6 # H-H lj
nbp_r_eps 2.00 0.0029700 12 6 # H-H lj
nbp_r_eps 2.00 0.0029700 12 6 # H-H lj
sol_par 0.00 0.0000     # H atomic fragmental volume,
                          solvation parameters
constant 0.118      # H grid map constant energy
elecmap M3.e.map        # electrostatic potential map
dielectric 15.0     # <0, distance-dep.diel;>0, constant
fmap M3.f.map           # floating point potential gridmap
```

Appendix 3 AutoDock Parameter File

```
seed pid time       # seeds for random generator
types CANOH         # atom type names
fld M3.maps.fld     # grid_data_file
map M3.C.map        # atom-specific affinity map
map M3.A.map        # atom-specific affinity map
map M3.N.map        # atom-specific affinity map
map M3.O.map        # atom-specific affinity map
map M3.H.map        # atom-specific affinity map
map M3.e.map        # electrostatics map
move DMT.out.pdbq       # small molecule
about -0.088 0.126 0.069    # small molecule center
tran0 random        # initial coordinates/A or random
quat0 random        # initial quaternion
ndihe 1             # number of active torsions
dihe0 random        # initial dihedrals (relative) or random
tstep 2.0           # translation step/A
qstep 50.0          # quaternion step/deg
dstep 50.0          # torsion step/deg
torsdof 1 0.3113        # torsional degrees of freedom and coefficent
intnbp_r_eps 4.00 0.0222750 12 6    # C-C lj
intnbp_r_eps 4.00 0.0222750 12 6    # C-A lj
intnbp_r_eps 3.75 0.0230026 12 6    # C-N lj
intnbp_r_eps 3.60 0.0257202 12 6    # C-O lj
intnbp_r_eps 3.00 0.0081378 12 6    # C-H lj
intnbp_r_eps 4.00 0.0222750 12 6    # A-A lj
intnbp_r_eps 3.75 0.0230026 12 6    # A-N lj
intnbp_r_eps 3.60 0.0257202 12 6    # A-O lj
intnbp_r_eps 3.00 0.0081378 12 6    # A-H lj
intnbp_r_eps 3.50 0.0237600 12 6    # N-N lj
intnbp_r_eps 3.35 0.0265667 12 6    # N-O lj
intnbp_r_eps 2.75 0.0084051 12 6    # N-H lj
intnbp_r_eps 3.20 0.0297000 12 6    # O-O lj
intnbp_r_eps 2.60 0.0093852 12 6    # O-H lj
intnbp_r_eps 2.00 0.0029700 12 6    # H-H lj
outlev 1            # diagnostic output level
rmstol 0.5          # cluster_tolerance/A
extnrg 1000.0       # external grid energy
e0max 0.0 10000     # max initial ernergy; max number of retries
ga_pop_size 50      # number of individuals in population
ga_num_evals 5000000    # maximum number of energy evaluations
ga_num_generations 27000    # maximum number of generations
ga_elitism 1        # number of top individuals to survive to next generation
ga_mutation_rate 0.02   # rate of gene mutation
ga_crossover_rate 0.8   # rate of crossover
ga_window_size 10       #
ga_cauchy_alpha 0.0     # Alpha parameter of Cauchy distribution
ga_cauchy_beta 1.0      # Beta parameter Cauchy distribution
set_ga              # set the above parameters for GA or LGA
sw_max_its 300      # iterations of Solis & Wets local search
sw_max_succ 4       # consecutive successes before changing rho
sw_max_fail 4       # consecutive failures before changing rho
sw_rho 1.0          # size of local search space to sample
sw_lb_rho 0.01      # lower bound on rho
ls_search_freq 0.06     # probability of performing local search on individual
set_psw1            # set the above pseudo-Solis & Wets parameters
ga_run 50           # do this many hybrid GA-LS runs
analysis            # perform a ranked cluster analysis
```

Appendix 4: Atomic Coordinates of the Luminal Channel of a α3β4 nAChR Ion Channel

| pdb file of the α3β4 nAChR model | | | | | | | | | |
|---|---|---|---|---|---|---|---|---|---|
| ATOM | 1 | CA | ACE | 1 | 9.270 | 5.413 | −18.665 | 0.00 | 0.00 |
| ATOM | 2 | C | ACE | 1 | 9.064 | 4.649 | −17.364 | 0.00 | 0.00 |
| ATOM | 3 | O | ACE | 1 | 9.286 | 5.198 | −16.285 | 0.00 | 0.00 |
| ATOM | 4 | N | GLU | 2 | 8.656 | 3.377 | −17.484 | 0.00 | 0.00 |
| ATOM | 5 | H | GLU | 2 | 8.496 | 3.014 | −18.412 | 0.00 | 0.00 |
| ATOM | 6 | CA | GLU | 2 | 8.345 | 2.482 | −16.365 | 0.00 | 0.00 |
| ATOM | 7 | CB | GLU | 2 | 7.781 | 1.164 | −16.930 | 0.00 | 0.00 |
| ATOM | 8 | CG | GLU | 2 | 7.274 | 0.164 | −15.874 | 0.00 | 0.00 |
| ATOM | 9 | CD | GLU | 2 | 6.311 | 0.782 | −14.852 | 0.00 | 0.00 |
| ATOM | 10 | OE1 | GLU | 2 | 6.525 | 0.540 | −13.643 | 0.00 | 0.00 |
| ATOM | 11 | OE2 | GLU | 2 | 5.381 | 1.495 | −15.291 | 0.00 | 0.00 |
| ATOM | 12 | C | GLU | 2 | 9.541 | 2.246 | −15.422 | 0.00 | 0.00 |
| ATOM | 13 | O | GLU | 2 | 9.344 | 1.832 | −14.284 | 0.00 | 0.00 |
| ATOM | 14 | N | LYS | 3 | 10.771 | 2.539 | −15.863 | 0.00 | 0.00 |
| ATOM | 15 | H | LYS | 3 | 10.867 | 2.901 | −16.800 | 0.00 | 0.00 |
| ATOM | 16 | CA | LYS | 3 | 11.990 | 2.351 | −15.083 | 0.00 | 0.00 |
| ATOM | 17 | CB | LYS | 3 | 13.218 | 2.415 | −16.010 | 0.00 | 0.00 |
| ATOM | 18 | CG | LYS | 3 | 13.496 | 1.120 | −16.797 | 0.00 | 0.00 |
| ATOM | 19 | CD | LYS | 3 | 12.434 | 0.760 | −17.851 | 0.00 | 0.00 |
| ATOM | 20 | CE | LYS | 3 | 12.843 | −0.456 | −18.690 | 0.00 | 0.00 |
| ATOM | 21 | NZ | LYS | 3 | 13.984 | −0.166 | −19.580 | 0.00 | 0.00 |
| ATOM | 22 | HZ1 | LYS | 3 | 14.784 | 0.109 | −19.027 | 0.00 | 0.00 |
| ATOM | 23 | HZ2 | LYS | 3 | 14.216 | −0.990 | −20.116 | 0.00 | 0.00 |
| ATOM | 24 | HZ3 | LYS | 3 | 13.741 | 0.585 | −20.211 | 0.00 | 0.00 |
| ATOM | 25 | C | LYS | 3 | 12.132 | 3.373 | −13.949 | 0.00 | 0.00 |
| ATOM | 26 | O | LYS | 3 | 12.566 | 3.010 | −12.857 | 0.00 | 0.00 |
| ATOM | 27 | N | VAL | 4 | 11.753 | 4.634 | −14.194 | 0.00 | 0.00 |
| ATOM | 28 | H | VAL | 4 | 11.400 | 4.864 | −15.112 | 0.00 | 0.00 |
| ATOM | 29 | CA | VAL | 4 | 11.662 | 5.664 | −13.159 | 0.00 | 0.00 |
| ATOM | 30 | CB | VAL | 4 | 11.627 | 7.065 | −13.814 | 0.00 | 0.00 |
| ATOM | 31 | CG1 | VAL | 4 | 11.499 | 8.186 | −12.768 | 0.00 | 0.00 |
| ATOM | 32 | CG2 | VAL | 4 | 12.901 | 7.325 | −14.639 | 0.00 | 0.00 |
| ATOM | 33 | C | VAL | 4 | 10.413 | 5.416 | −12.307 | 0.00 | 0.00 |
| ATOM | 34 | O | VAL | 4 | 10.455 | 5.677 | −11.110 | 0.00 | 0.00 |
| ATOM | 35 | N | THR | 5 | 9.329 | 4.884 | −12.897 | 0.00 | 0.00 |
| ATOM | 36 | H | THR | 5 | 9.350 | 4.704 | −13.891 | 0.00 | 0.00 |
| ATOM | 37 | CA | THR | 5 | 8.083 | 4.583 | −12.195 | 0.00 | 0.00 |
| ATOM | 38 | CB | THR | 5 | 6.994 | 4.125 | −13.184 | 0.00 | 0.00 |
| ATOM | 39 | CG2 | THR | 5 | 5.633 | 3.934 | −12.505 | 0.00 | 0.00 |
| ATOM | 40 | OG1 | THR | 5 | 6.830 | 5.082 | −14.210 | 0.00 | 0.00 |
| ATOM | 41 | HG1 | THR | 5 | 6.121 | 4.783 | −14.784 | 0.00 | 0.00 |
| ATOM | 42 | C | THR | 5 | 8.300 | 3.535 | −11.096 | 0.00 | 0.00 |
| ATOM | 43 | O | THR | 5 | 7.868 | 3.747 | −9.963 | 0.00 | 0.00 |
| ATOM | 44 | N | LEU | 6 | 8.984 | 2.425 | −11.414 | 0.00 | 0.00 |
| ATOM | 45 | H | LEU | 6 | 9.287 | 2.286 | −12.369 | 0.00 | 0.00 |
| ATOM | 46 | CA | LEU | 6 | 9.311 | 1.394 | −10.436 | 0.00 | 0.00 |
| ATOM | 47 | CB | LEU | 6 | 9.642 | 0.056 | −11.127 | 0.00 | 0.00 |
| ATOM | 48 | CG | LEU | 6 | 10.932 | −0.001 | −11.976 | 0.00 | 0.00 |
| ATOM | 49 | CD1 | LEU | 6 | 12.185 | −0.332 | −11.150 | 0.00 | 0.00 |
| ATOM | 50 | CD2 | LEU | 6 | 10.789 | −1.070 | −13.070 | 0.00 | 0.00 |
| ATOM | 51 | C | LEU | 6 | 10.367 | 1.852 | −9.428 | 0.00 | 0.00 |
| ATOM | 52 | O | LEU | 6 | 10.366 | 1.351 | −8.308 | 0.00 | 0.00 |
| ATOM | 53 | N | CYS | 7 | 11.216 | 2.830 | −9.782 | 0.00 | 0.00 |
| ATOM | 54 | H | CYS | 7 | 11.170 | 3.204 | −10.719 | 0.00 | 0.00 |
| ATOM | 55 | CA | CYS | 7 | 12.155 | 3.443 | −8.852 | 0.00 | 0.00 |
| ATOM | 56 | CB | CYS | 7 | 13.169 | 4.290 | −9.630 | 0.00 | 0.00 |
| ATOM | 57 | SG | CYS | 7 | 14.449 | 4.908 | −8.504 | 0.00 | 0.00 |
| ATOM | 58 | HG | CYS | 7 | 15.153 | 5.565 | −9.430 | 0.00 | 0.00 |
| ATOM | 59 | C | CYS | 7 | 11.403 | 4.271 | −7.805 | 0.00 | 0.00 |
| ATOM | 60 | O | CYS | 7 | 11.653 | 4.083 | −6.616 | 0.00 | 0.00 |
| ATOM | 61 | N | ILE | 8 | 10.477 | 5.155 | −8.222 | 0.00 | 0.00 |
| ATOM | 62 | H | ILE | 8 | 10.302 | 5.265 | −9.212 | 0.00 | 0.00 |
| ATOM | 63 | CA | ILE | 8 | 9.741 | 6.010 | −7.292 | 0.00 | 0.00 |
| ATOM | 64 | CB | ILE | 8 | 9.018 | 7.206 | −7.957 | 0.00 | 0.00 |
| ATOM | 65 | CG2 | ILE | 8 | 10.056 | 8.149 | −8.595 | 0.00 | 0.00 |
| ATOM | 66 | CG1 | ILE | 8 | 7.912 | 6.794 | −8.950 | 0.00 | 0.00 |
| ATOM | 67 | CD1 | ILE | 8 | 7.033 | 7.955 | −9.431 | 0.00 | 0.00 |
| ATOM | 68 | C | ILE | 8 | 8.822 | 5.213 | −6.360 | 0.00 | 0.00 |
| ATOM | 69 | O | ILE | 8 | 8.715 | 5.561 | −5.187 | 0.00 | 0.00 |
| ATOM | 70 | N | SER | 9 | 8.223 | 4.116 | −6.842 | 0.00 | 0.00 |
| ATOM | 71 | H | SER | 9 | 8.348 | 3.884 | −7.819 | 0.00 | 0.00 |
| ATOM | 72 | CA | SER | 9 | 7.430 | 3.207 | −6.022 | 0.00 | 0.00 |
| ATOM | 73 | CB | SER | 9 | 6.746 | 2.198 | −6.952 | 0.00 | 0.00 |

-continued pdb file of the α3β4 nAChR model

| ATOM | 74 | OG | SER | 9 | 5.880 | 1.355 | −6.222 | 0.00 | 0.00 |
|---|---|---|---|---|---|---|---|---|---|
| ATOM | 75 | HG | SER | 9 | 5.455 | 0.749 | −6.834 | 0.00 | 0.00 |
| ATOM | 76 | C | SER | 9 | 8.299 | 2.487 | −4.981 | 0.00 | 0.00 |
| ATOM | 77 | O | SER | 9 | 7.865 | 2.322 | −3.841 | 0.00 | 0.00 |
| ATOM | 78 | N | VAL | 10 | 9.527 | 2.092 | −5.355 | 0.00 | 0.00 |
| ATOM | 79 | H | VAL | 10 | 9.822 | 2.259 | −6.308 | 0.00 | 0.00 |
| ATOM | 80 | CA | VAL | 10 | 10.488 | 1.439 | −4.467 | 0.00 | 0.00 |
| ATOM | 81 | CB | VAL | 10 | 11.590 | 0.739 | −5.301 | 0.00 | 0.00 |
| ATOM | 82 | CG1 | VAL | 10 | 12.857 | 0.370 | −4.510 | 0.00 | 0.00 |
| ATOM | 83 | CG2 | VAL | 10 | 11.028 | −0.564 | −5.898 | 0.00 | 0.00 |
| ATOM | 84 | C | VAL | 10 | 11.045 | 2.397 | −3.397 | 0.00 | 0.00 |
| ATOM | 85 | O | VAL | 10 | 11.425 | 1.934 | −2.323 | 0.00 | 0.00 |
| ATOM | 86 | N | LEU | 11 | 11.046 | 3.718 | −3.626 | 0.00 | 0.00 |
| ATOM | 87 | H | LEU | 11 | 10.741 | 4.069 | −4.523 | 0.00 | 0.00 |
| ATOM | 88 | CA | LEU | 11 | 11.403 | 4.680 | −2.585 | 0.00 | 0.00 |
| ATOM | 89 | CB | LEU | 11 | 11.629 | 6.081 | −3.186 | 0.00 | 0.00 |
| ATOM | 90 | CG | LEU | 11 | 12.881 | 6.204 | −4.080 | 0.00 | 0.00 |
| ATOM | 91 | CD1 | LEU | 11 | 12.881 | 7.571 | −4.779 | 0.00 | 0.00 |
| ATOM | 92 | CD2 | LEU | 11 | 14.187 | 6.047 | −3.287 | 0.00 | 0.00 |
| ATOM | 93 | C | LEU | 11 | 10.331 | 4.735 | −1.493 | 0.00 | 0.00 |
| ATOM | 94 | O | LEU | 11 | 10.673 | 4.708 | −0.310 | 0.00 | 0.00 |
| ATOM | 95 | N | LEU | 12 | 9.046 | 4.773 | −1.879 | 0.00 | 0.00 |
| ATOM | 96 | H | LEU | 12 | 8.829 | 4.798 | −2.866 | 0.00 | 0.00 |
| ATOM | 97 | CA | LEU | 12 | 7.933 | 4.712 | −0.936 | 0.00 | 0.00 |
| ATOM | 98 | CB | LEU | 12 | 6.609 | 5.114 | −1.618 | 0.00 | 0.00 |
| ATOM | 99 | CG | LEU | 12 | 6.349 | 6.629 | −1.800 | 0.00 | 0.00 |
| ATOM | 100 | CD1 | LEU | 12 | 6.475 | 7.424 | −0.490 | 0.00 | 0.00 |
| ATOM | 101 | CD2 | LEU | 12 | 7.205 | 7.290 | −2.885 | 0.00 | 0.00 |
| ATOM | 102 | C | LEU | 12 | 7.813 | 3.333 | −0.273 | 0.00 | 0.00 |
| ATOM | 103 | O | LEU | 12 | 7.270 | 3.253 | 0.827 | 0.00 | 0.00 |
| ATOM | 104 | N | SER | 13 | 8.359 | 2.271 | −0.884 | 0.00 | 0.00 |
| ATOM | 105 | H | SER | 13 | 8.775 | 2.394 | −1.797 | 0.00 | 0.00 |
| ATOM | 106 | CA | SER | 13 | 8.421 | 0.946 | −0.280 | 0.00 | 0.00 |
| ATOM | 107 | CB | SER | 13 | 8.951 | −0.077 | −1.282 | 0.00 | 0.00 |
| ATOM | 108 | OG | SER | 13 | 9.099 | −1.310 | −0.623 | 0.00 | 0.00 |
| ATOM | 109 | HG | SER | 13 | 9.427 | −1.956 | −1.252 | 0.00 | 0.00 |
| ATOM | 110 | C | SER | 13 | 9.273 | 0.950 | 0.990 | 0.00 | 0.00 |
| ATOM | 111 | O | SER | 13 | 8.819 | 0.466 | 2.026 | 0.00 | 0.00 |
| ATOM | 112 | N | LEU | 14 | 10.492 | 1.503 | 0.918 | 0.00 | 0.00 |
| ATOM | 113 | H | LEU | 14 | 10.813 | 1.877 | 0.035 | 0.00 | 0.00 |
| ATOM | 114 | CA | LEU | 14 | 11.374 | 1.623 | 2.074 | 0.00 | 0.00 |
| ATOM | 115 | CB | LEU | 14 | 12.797 | 2.007 | 1.620 | 0.00 | 0.00 |
| ATOM | 116 | CG | LEU | 14 | 13.726 | 0.831 | 1.239 | 0.00 | 0.00 |
| ATOM | 117 | CD1 | LEU | 14 | 14.038 | −0.075 | 2.441 | 0.00 | 0.00 |
| ATOM | 118 | CD2 | LEU | 14 | 13.201 | −0.019 | 0.073 | 0.00 | 0.00 |
| ATOM | 119 | C | LEU | 14 | 10.837 | 2.631 | 3.101 | 0.00 | 0.00 |
| ATOM | 120 | O | LEU | 14 | 11.157 | 2.497 | 4.282 | 0.00 | 0.00 |
| ATOM | 121 | N | THR | 15 | 9.988 | 3.588 | 2.690 | 0.00 | 0.00 |
| ATOM | 122 | H | THR | 15 | 9.772 | 3.661 | 1.705 | 0.00 | 0.00 |
| ATOM | 123 | CA | THR | 15 | 9.285 | 4.477 | 3.614 | 0.00 | 0.00 |
| ATOM | 124 | CB | THR | 15 | 8.678 | 5.685 | 2.862 | 0.00 | 0.00 |
| ATOM | 125 | CG2 | THR | 15 | 7.178 | 5.937 | 3.069 | 0.00 | 0.00 |
| ATOM | 126 | OG1 | THR | 15 | 9.358 | 6.857 | 3.261 | 0.00 | 0.00 |
| ATOM | 127 | HG1 | THR | 15 | 9.005 | 7.597 | 2.762 | 0.00 | 0.00 |
| ATOM | 128 | C | THR | 15 | 8.292 | 3.705 | 4.503 | 0.00 | 0.00 |
| ATOM | 129 | O | THR | 15 | 8.154 | 4.016 | 5.685 | 0.00 | 0.00 |
| ATOM | 130 | N | VAL | 16 | 7.654 | 2.667 | 3.948 | 0.00 | 0.00 |
| ATOM | 131 | H | VAL | 16 | 7.830 | 2.479 | 2.969 | 0.00 | 0.00 |
| ATOM | 132 | CA | VAL | 16 | 6.734 | 1.752 | 4.625 | 0.00 | 0.00 |
| ATOM | 133 | CB | VAL | 16 | 5.717 | 1.249 | 3.563 | 0.00 | 0.00 |
| ATOM | 134 | CG1 | VAL | 16 | 4.800 | 0.106 | 4.030 | 0.00 | 0.00 |
| ATOM | 135 | CG2 | VAL | 16 | 4.835 | 2.427 | 3.122 | 0.00 | 0.00 |
| ATOM | 136 | C | VAL | 16 | 7.478 | 0.592 | 5.321 | 0.00 | 0.00 |
| ATOM | 137 | O | VAL | 16 | 6.869 | −0.166 | 6.077 | 0.00 | 0.00 |
| ATOM | 138 | N | PHE | 17 | 8.795 | 0.456 | 5.118 | 0.00 | 0.00 |
| ATOM | 139 | H | PHE | 17 | 9.260 | 1.083 | 4.476 | 0.00 | 0.00 |
| ATOM | 140 | CA | PHE | 17 | 9.611 | −0.530 | 5.817 | 0.00 | 0.00 |
| ATOM | 141 | CB | PHE | 17 | 10.708 | −1.033 | 4.870 | 0.00 | 0.00 |
| ATOM | 142 | CG | PHE | 17 | 11.522 | −2.193 | 5.415 | 0.00 | 0.00 |
| ATOM | 143 | CD1 | PHE | 17 | 12.914 | −2.068 | 5.585 | 0.00 | 0.00 |
| ATOM | 144 | CE1 | PHE | 17 | 13.666 | −3.150 | 6.076 | 0.00 | 0.00 |
| ATOM | 145 | CZ | PHE | 17 | 13.028 | −4.358 | 6.409 | 0.00 | 0.00 |
| ATOM | 146 | CE2 | PHE | 17 | 11.637 | −4.484 | 6.249 | 0.00 | 0.00 |
| ATOM | 147 | CD2 | PHE | 17 | 10.886 | −3.405 | 5.750 | 0.00 | 0.00 |
| ATOM | 148 | C | PHE | 17 | 10.230 | 0.041 | 7.098 | 0.00 | 0.00 |
| ATOM | 149 | O | PHE | 17 | 10.403 | −0.691 | 8.068 | 0.00 | 0.00 |
| ATOM | 150 | N | LEU | 18 | 10.526 | 1.346 | 7.130 | 0.00 | 0.00 |

-continued pdb file of the α3β4 nAChR model

| | | | | | | | | |
|---|---|---|---|---|---|---|---|---|
| ATOM | 151 | H | LEU | 18 | 10.403 | 1.897 | 6.291 | 0.00 | 0.00 |
| ATOM | 152 | CA | LEU | 18 | 10.896 | 2.050 | 8.354 | 0.00 | 0.00 |
| ATOM | 153 | CB | LEU | 18 | 11.530 | 3.403 | 7.987 | 0.00 | 0.00 |
| ATOM | 154 | CG | LEU | 18 | 12.879 | 3.286 | 7.245 | 0.00 | 0.00 |
| ATOM | 155 | CD1 | LEU | 18 | 13.301 | 4.670 | 6.731 | 0.00 | 0.00 |
| ATOM | 156 | CD2 | LEU | 18 | 13.990 | 2.715 | 8.140 | 0.00 | 0.00 |
| ATOM | 157 | C | LEU | 18 | 9.673 | 2.268 | 9.259 | 0.00 | 0.00 |
| ATOM | 158 | O | LEU | 18 | 9.849 | 2.384 | 10.469 | 0.00 | 0.00 |
| ATOM | 159 | N | LEU | 19 | 8.455 | 2.272 | 8.688 | 0.00 | 0.00 |
| ATOM | 160 | H | LEU | 19 | 8.412 | 2.195 | 7.682 | 0.00 | 0.00 |
| ATOM | 161 | CA | LEU | 19 | 7.175 | 2.286 | 9.391 | 0.00 | 0.00 |
| ATOM | 162 | CB | LEU | 19 | 6.037 | 2.266 | 8.350 | 0.00 | 0.00 |
| ATOM | 163 | CG | LEU | 19 | 4.564 | 2.181 | 8.822 | 0.00 | 0.00 |
| ATOM | 164 | CD1 | LEU | 19 | 3.673 | 2.526 | 7.617 | 0.00 | 0.00 |
| ATOM | 165 | CD2 | LEU | 19 | 4.122 | 0.794 | 9.310 | 0.00 | 0.00 |
| ATOM | 166 | C | LEU | 19 | 7.100 | 1.105 | 10.352 | 0.00 | 0.00 |
| ATOM | 167 | O | LEU | 19 | 7.062 | 1.310 | 11.560 | 0.00 | 0.00 |
| ATOM | 168 | N | VAL | 20 | 7.099 | −0.124 | 9.817 | 0.00 | 0.00 |
| ATOM | 169 | H | VAL | 20 | 7.136 | −0.212 | 8.812 | 0.00 | 0.00 |
| ATOM | 170 | CA | VAL | 20 | 7.026 | −1.355 | 10.600 | 0.00 | 0.00 |
| ATOM | 171 | CB | VAL | 20 | 6.989 | −2.580 | 9.653 | 0.00 | 0.00 |
| ATOM | 172 | CG1 | VAL | 20 | 8.119 | −2.645 | 8.621 | 0.00 | 0.00 |
| ATOM | 173 | CG2 | VAL | 20 | 6.980 | −3.921 | 10.402 | 0.00 | 0.00 |
| ATOM | 174 | C | VAL | 20 | 8.206 | −1.469 | 11.574 | 0.00 | 0.00 |
| ATOM | 175 | O | VAL | 20 | 8.066 | −2.124 | 12.595 | 0.00 | 0.00 |
| ATOM | 176 | N | ILE | 21 | 9.352 | −0.836 | 11.298 | 0.00 | 0.00 |
| ATOM | 177 | H | ILE | 21 | 9.423 | −0.304 | 10.442 | 0.00 | 0.00 |
| ATOM | 178 | CA | ILE | 21 | 10.528 | −0.887 | 12.162 | 0.00 | 0.00 |
| ATOM | 179 | CB | ILE | 21 | 11.791 | −0.637 | 11.286 | 0.00 | 0.00 |
| ATOM | 180 | CG2 | ILE | 21 | 13.035 | −0.126 | 12.041 | 0.00 | 0.00 |
| ATOM | 181 | CG1 | ILE | 21 | 12.131 | −1.951 | 10.542 | 0.00 | 0.00 |
| ATOM | 182 | CD1 | ILE | 21 | 13.210 | −1.823 | 9.459 | 0.00 | 0.00 |
| ATOM | 183 | C | ILE | 21 | 10.424 | 0.026 | 13.399 | 0.00 | 0.00 |
| ATOM | 184 | O | ILE | 21 | 11.224 | −0.096 | 14.325 | 0.00 | 0.00 |
| ATOM | 185 | N | THR | 22 | 9.416 | 0.897 | 13.457 | 0.00 | 0.00 |
| ATOM | 186 | H | THR | 22 | 8.797 | 0.973 | 12.660 | 0.00 | 0.00 |
| ATOM | 187 | CA | THR | 22 | 9.194 | 1.847 | 14.547 | 0.00 | 0.00 |
| ATOM | 188 | CB | THR | 22 | 9.414 | 3.264 | 14.009 | 0.00 | 0.00 |
| ATOM | 189 | CG2 | THR | 22 | 10.872 | 3.533 | 13.616 | 0.00 | 0.00 |
| ATOM | 190 | OG1 | THR | 22 | 8.581 | 3.498 | 12.893 | 0.00 | 0.00 |
| ATOM | 191 | HG1 | THR | 22 | 8.828 | 4.336 | 12.498 | 0.00 | 0.00 |
| ATOM | 192 | C | THR | 22 | 7.815 | 1.661 | 15.193 | 0.00 | 0.00 |
| ATOM | 193 | O | THR | 22 | 7.609 | 2.107 | 16.321 | 0.00 | 0.00 |
| ATOM | 194 | N | GLU | 23 | 6.921 | 0.913 | 14.532 | 0.00 | 0.00 |
| ATOM | 195 | H | GLU | 23 | 7.134 | 0.672 | 13.574 | 0.00 | 0.00 |
| ATOM | 196 | CA | GLU | 23 | 5.869 | 0.133 | 15.163 | 0.00 | 0.00 |
| ATOM | 197 | CB | GLU | 23 | 4.942 | −0.441 | 14.072 | 0.00 | 0.00 |
| ATOM | 198 | CG | GLU | 23 | 4.169 | 0.583 | 13.237 | 0.00 | 0.00 |
| ATOM | 199 | CD | GLU | 23 | 3.536 | 1.675 | 14.085 | 0.00 | 0.00 |
| ATOM | 200 | OE1 | GLU | 23 | 3.811 | 2.853 | 13.765 | 0.00 | 0.00 |
| ATOM | 201 | OE2 | GLU | 23 | 2.807 | 1.311 | 15.035 | 0.00 | 0.00 |
| ATOM | 202 | C | GLU | 23 | 6.524 | −1.009 | 15.951 | 0.00 | 0.00 |
| ATOM | 203 | O | GLU | 23 | 6.407 | −1.064 | 17.174 | 0.00 | 0.00 |
| ATOM | 204 | N | THR | 24 | 7.207 | −1.911 | 15.230 | 0.00 | 0.00 |
| ATOM | 205 | H | THR | 24 | 7.247 | −1.772 | 14.230 | 0.00 | 0.00 |
| ATOM | 206 | CA | THR | 24 | 7.853 | −3.115 | 15.730 | 0.00 | 0.00 |
| ATOM | 207 | CB | THR | 24 | 7.648 | −4.324 | 14.798 | 0.00 | 0.00 |
| ATOM | 208 | CG2 | THR | 24 | 8.232 | −5.603 | 15.416 | 0.00 | 0.00 |
| ATOM | 209 | OG1 | THR | 24 | 6.269 | −4.511 | 14.554 | 0.00 | 0.00 |
| ATOM | 210 | HG1 | THR | 24 | 6.167 | −5.285 | 13.990 | 0.00 | 0.00 |
| ATOM | 211 | C | THR | 24 | 9.332 | −2.850 | 16.043 | 0.00 | 0.00 |
| ATOM | 212 | O | THR | 24 | 9.669 | −2.599 | 17.199 | 0.00 | 0.00 |
| ATOM | 213 | N | NME | 25 | 10.210 | −2.958 | 15.034 | 0.00 | 0.00 |
| ATOM | 214 | H | NME | 25 | 9.852 | −3.136 | 14.107 | 0.00 | 0.00 |
| ATOM | 215 | CA | NME | 25 | 11.655 | −2.967 | 15.204 | 0.00 | 0.00 |
| TER | | | | | | | | | |
| ATOM | 216 | CA | ACE | 26 | −2.283 | 10.455 | −18.657 | 0.00 | 0.00 |
| ATOM | 217 | C | ACE | 26 | −1.621 | 10.026 | −17.355 | 0.00 | 0.00 |
| ATOM | 218 | O | ACE | 26 | −2.076 | 10.406 | −16.276 | 0.00 | 0.00 |
| ATOM | 219 | N | GLU | 27 | −0.535 | 9.247 | −17.473 | 0.00 | 0.00 |
| ATOM | 220 | H | GLU | 27 | −0.238 | 8.982 | −18.401 | 0.00 | 0.00 |
| ATOM | 221 | CA | GLU | 27 | 0.219 | 8.675 | −16.354 | 0.00 | 0.00 |
| ATOM | 222 | CB | GLU | 27 | 1.299 | 7.732 | −16.918 | 0.00 | 0.00 |
| ATOM | 223 | CG | GLU | 27 | 2.095 | 6.942 | −15.861 | 0.00 | 0.00 |
| ATOM | 224 | CD | GLU | 27 | 1.211 | 6.217 | −14.838 | 0.00 | 0.00 |
| ATOM | 225 | OE1 | GLU | 27 | 1.511 | 6.346 | −13.630 | 0.00 | 0.00 |
| ATOM | 226 | OE2 | GLU | 27 | 0.245 | 5.554 | −15.275 | 0.00 | 0.00 |

-continued pdb file of the α3β4 nAChR model

| ATOM | 227 | C | GLU | 27 | 0.813 | 9.739 | −15.411 | 0.00 | 0.00 |
|------|-----|------|-----|----|-------|--------|---------|------|------|
| ATOM | 228 | O | GLU | 27 | 1.147 | 9.425 | −14.273 | 0.00 | 0.00 |
| ATOM | 229 | N | LYS | 28 | 0.913 | 11.001 | −15.851 | 0.00 | 0.00 |
| ATOM | 230 | H | LYS | 28 | 0.598 | 11.204 | −16.789 | 0.00 | 0.00 |
| ATOM | 231 | CA | LYS | 28 | 1.469 | 12.100 | −15.071 | 0.00 | 0.00 |
| ATOM | 232 | CB | LYS | 28 | 1.786 | 13.290 | −15.996 | 0.00 | 0.00 |
| ATOM | 233 | CG | LYS | 28 | 3.109 | 13.161 | −16.775 | 0.00 | 0.00 |
| ATOM | 234 | CD | LYS | 28 | 3.135 | 12.037 | −17.826 | 0.00 | 0.00 |
| ATOM | 235 | CE | LYS | 28 | 4.426 | 12.051 | −18.653 | 0.00 | 0.00 |
| ATOM | 236 | NZ | LYS | 28 | 4.509 | 13.225 | −19.543 | 0.00 | 0.00 |
| ATOM | 237 | HZ1 | LYS | 28 | 4.489 | 14.071 | −18.991 | 0.00 | 0.00 |
| ATOM | 238 | HZ2 | LYS | 28 | 5.370 | 13.192 | −20.071 | 0.00 | 0.00 |
| ATOM | 239 | HZ3 | LYS | 28 | 3.726 | 13.225 | −20.181 | 0.00 | 0.00 |
| ATOM | 240 | C | LYS | 28 | 0.543 | 12.544 | −13.934 | 0.00 | 0.00 |
| ATOM | 241 | O | LYS | 28 | 1.027 | 12.826 | −12.838 | 0.00 | 0.00 |
| ATOM | 242 | N | MET | 29 | −0.774 | 12.590 | −14.176 | 0.00 | 0.00 |
| ATOM | 243 | H | MET | 29 | −1.112 | 12.342 | −15.095 | 0.00 | 0.00 |
| ATOM | 244 | CA | MET | 29 | −1.764 | 12.813 | −13.125 | 0.00 | 0.00 |
| ATOM | 245 | CB | MET | 29 | −3.085 | 13.267 | −13.769 | 0.00 | 0.00 |
| ATOM | 246 | CG | MET | 29 | −4.161 | 13.651 | −12.744 | 0.00 | 0.00 |
| ATOM | 247 | SD | MET | 29 | −3.692 | 14.972 | −11.590 | 0.00 | 0.00 |
| ATOM | 248 | CE | MET | 29 | −5.246 | 15.139 | −10.676 | 0.00 | 0.00 |
| ATOM | 249 | C | MET | 29 | −1.955 | 11.542 | −12.291 | 0.00 | 0.00 |
| ATOM | 250 | O | MET | 29 | −2.253 | 11.652 | −11.107 | 0.00 | 0.00 |
| ATOM | 251 | N | THR | 30 | −1.747 | 10.351 | −12.877 | 0.00 | 0.00 |
| ATOM | 252 | H | THR | 30 | −1.520 | 10.320 | −13.862 | 0.00 | 0.00 |
| ATOM | 253 | CA | THR | 30 | −1.852 | 9.072 | −12.179 | 0.00 | 0.00 |
| ATOM | 254 | CB | THR | 30 | −1.754 | 7.896 | −13.169 | 0.00 | 0.00 |
| ATOM | 255 | CG2 | THR | 30 | −1.994 | 6.541 | −12.493 | 0.00 | 0.00 |
| ATOM | 256 | OG1 | THR | 30 | −2.715 | 8.038 | −14.195 | 0.00 | 0.00 |
| ATOM | 257 | HG1 | THR | 30 | −2.650 | 7.272 | −14.770 | 0.00 | 0.00 |
| ATOM | 258 | C | THR | 30 | −0.788 | 8.952 | −11.081 | 0.00 | 0.00 |
| ATOM | 259 | O | THR | 30 | −1.121 | 8.605 | −9.948 | 0.00 | 0.00 |
| ATOM | 260 | N | LEU | 31 | 0.480 | 9.258 | −11.400 | 0.00 | 0.00 |
| ATOM | 261 | H | LEU | 31 | 0.706 | 9.505 | −12.355 | 0.00 | 0.00 |
| ATOM | 262 | CA | LEU | 31 | 1.562 | 9.251 | −10.421 | 0.00 | 0.00 |
| ATOM | 263 | CB | LEU | 31 | 2.937 | 9.148 | −11.113 | 0.00 | 0.00 |
| ATOM | 264 | CG | LEU | 31 | 3.392 | 10.353 | −11.965 | 0.00 | 0.00 |
| ATOM | 265 | CD1 | LEU | 31 | 4.096 | 11.445 | −11.142 | 0.00 | 0.00 |
| ATOM | 266 | CD2 | LEU | 31 | 4.365 | 9.882 | −13.057 | 0.00 | 0.00 |
| ATOM | 267 | C | LEU | 31 | 1.454 | 10.399 | −9.416 | 0.00 | 0.00 |
| ATOM | 268 | O | LEU | 31 | 1.930 | 10.247 | −8.295 | 0.00 | 0.00 |
| ATOM | 269 | N | CYS | 32 | 0.786 | 11.507 | −9.773 | 0.00 | 0.00 |
| ATOM | 270 | H | CYS | 32 | 0.420 | 11.576 | −10.712 | 0.00 | 0.00 |
| ATOM | 271 | CA | CYS | 32 | 0.488 | 12.593 | −8.848 | 0.00 | 0.00 |
| ATOM | 272 | CB | CYS | 32 | −0.021 | 13.806 | −9.638 | 0.00 | 0.00 |
| ATOM | 273 | SG | CYS | 32 | −0.259 | 15.217 | −8.524 | 0.00 | 0.00 |
| ATOM | 274 | HG | CYS | 32 | −0.695 | 16.067 | −9.459 | 0.00 | 0.00 |
| ATOM | 275 | C | CYS | 32 | −0.529 | 12.134 | −7.800 | 0.00 | 0.00 |
| ATOM | 276 | O | CYS | 32 | −0.267 | 12.312 | −6.612 | 0.00 | 0.00 |
| ATOM | 277 | N | ILE | 33 | −1.659 | 11.529 | −8.216 | 0.00 | 0.00 |
| ATOM | 278 | H | ILE | 33 | −1.826 | 11.401 | −9.205 | 0.00 | 0.00 |
| ATOM | 279 | CA | ILE | 33 | −2.684 | 11.082 | −7.275 | 0.00 | 0.00 |
| ATOM | 280 | CB | ILE | 33 | −4.048 | 10.729 | −7.917 | 0.00 | 0.00 |
| ATOM | 281 | CG2 | ILE | 33 | −4.660 | 11.993 | −8.547 | 0.00 | 0.00 |
| ATOM | 282 | CG1 | ILE | 33 | −3.996 | 9.546 | −8.906 | 0.00 | 0.00 |
| ATOM | 283 | CD1 | ILE | 33 | −5.371 | 9.049 | −9.368 | 0.00 | 0.00 |
| ATOM | 284 | C | ILE | 33 | −2.165 | 9.989 | −6.339 | 0.00 | 0.00 |
| ATOM | 285 | O | ILE | 33 | −2.443 | 10.052 | −5.146 | 0.00 | 0.00 |
| ATOM | 286 | N | SER | 34 | −1.357 | 9.045 | −6.837 | 0.00 | 0.00 |
| ATOM | 287 | H | SER | 34 | −1.155 | 9.048 | −7.828 | 0.00 | 0.00 |
| ATOM | 288 | CA | SER | 34 | −0.735 | 8.012 | −6.015 | 0.00 | 0.00 |
| ATOM | 289 | CB | SER | 34 | 0.006 | 7.043 | −6.945 | 0.00 | 0.00 |
| ATOM | 290 | OG | SER | 34 | 0.534 | 5.957 | −6.216 | 0.00 | 0.00 |
| ATOM | 291 | HG | SER | 34 | 0.980 | 5.365 | −6.827 | 0.00 | 0.00 |
| ATOM | 292 | C | SER | 34 | 0.223 | 8.612 | −4.976 | 0.00 | 0.00 |
| ATOM | 293 | O | SER | 34 | 0.245 | 8.145 | −3.839 | 0.00 | 0.00 |
| ATOM | 294 | N | VAL | 35 | 0.977 | 9.659 | −5.348 | 0.00 | 0.00 |
| ATOM | 295 | H | VAL | 35 | 0.909 | 9.995 | −6.300 | 0.00 | 0.00 |
| ATOM | 296 | CA | VAL | 35 | 1.896 | 10.368 | −4.458 | 0.00 | 0.00 |
| ATOM | 297 | CB | VAL | 35 | 2.886 | 11.226 | −5.285 | 0.00 | 0.00 |
| ATOM | 298 | CG1 | VAL | 35 | 3.608 | 12.321 | −4.481 | 0.00 | 0.00 |
| ATOM | 299 | CG2 | VAL | 35 | 3.967 | 10.314 | −5.894 | 0.00 | 0.00 |
| ATOM | 300 | C | VAL | 35 | 1.161 | 11.169 | −3.369 | 0.00 | 0.00 |
| ATOM | 301 | O | VAL | 35 | 1.709 | 11.328 | −2.279 | 0.00 | 0.00 |
| ATOM | 302 | N | LEU | 36 | −0.080 | 11.622 | −3.604 | 0.00 | 0.00 |
| ATOM | 303 | H | LEU | 36 | −0.499 | 11.480 | −4.513 | 0.00 | 0.00 |

-continued pdb file of the α3β4 nAChR model

| | | | | | | | | |
|---|---|---|---|---|---|---|---|---|
| ATOM | 304 | CA | LEU | 36 | −0.880 | 12.257 | −2.558 | 0.00 | 0.00 |
| ATOM | 305 | CB | LEU | 36 | −2.151 | 12.903 | −3.141 | 0.00 | 0.00 |
| ATOM | 306 | CG | LEU | 36 | −1.895 | 14.123 | −4.052 | 0.00 | 0.00 |
| ATOM | 307 | CD1 | LEU | 36 | −3.205 | 14.536 | −4.738 | 0.00 | 0.00 |
| ATOM | 308 | CD2 | LEU | 36 | −1.332 | 15.324 | −3.278 | 0.00 | 0.00 |
| ATOM | 309 | C | LEU | 36 | −1.235 | 11.257 | −1.456 | 0.00 | 0.00 |
| ATOM | 310 | O | LEU | 36 | −1.056 | 11.566 | −0.279 | 0.00 | 0.00 |
| ATOM | 311 | N | LEU | 37 | −1.689 | 10.055 | −1.837 | 0.00 | 0.00 |
| ATOM | 312 | H | LEU | 37 | −1.806 | 9.870 | −2.825 | 0.00 | 0.00 |
| ATOM | 313 | CA | LEU | 37 | −1.984 | 8.972 | −0.906 | 0.00 | 0.00 |
| ATOM | 314 | CB | LEU | 37 | −2.887 | 7.925 | −1.582 | 0.00 | 0.00 |
| ATOM | 315 | CG | LEU | 37 | −4.345 | 8.358 | −1.869 | 0.00 | 0.00 |
| ATOM | 316 | CD1 | LEU | 37 | −5.010 | 9.090 | −0.690 | 0.00 | 0.00 |
| ATOM | 317 | CD2 | LEU | 37 | −4.546 | 9.184 | −3.141 | 0.00 | 0.00 |
| ATOM | 318 | C | LEU | 37 | −0.716 | 8.338 | −0.311 | 0.00 | 0.00 |
| ATOM | 319 | O | LEU | 37 | −0.817 | 7.630 | 0.692 | 0.00 | 0.00 |
| ATOM | 320 | N | ALA | 38 | 0.471 | 8.626 | −0.867 | 0.00 | 0.00 |
| ATOM | 321 | H | ALA | 38 | 0.497 | 9.193 | −1.702 | 0.00 | 0.00 |
| ATOM | 322 | CA | ALA | 38 | 1.740 | 8.226 | −0.280 | 0.00 | 0.00 |
| ATOM | 323 | CB | ALA | 38 | 2.864 | 8.324 | −1.312 | 0.00 | 0.00 |
| ATOM | 324 | C | ALA | 38 | 2.066 | 9.043 | 0.973 | 0.00 | 0.00 |
| ATOM | 325 | O | ALA | 38 | 2.474 | 8.464 | 1.980 | 0.00 | 0.00 |
| ATOM | 326 | N | LEU | 39 | 1.855 | 10.367 | 0.926 | 0.00 | 0.00 |
| ATOM | 327 | H | LEU | 39 | 1.526 | 10.778 | 0.063 | 0.00 | 0.00 |
| ATOM | 328 | CA | LEU | 39 | 2.012 | 11.251 | 2.080 | 0.00 | 0.00 |
| ATOM | 329 | CB | LEU | 39 | 2.100 | 12.720 | 1.618 | 0.00 | 0.00 |
| ATOM | 330 | CG | LEU | 39 | 3.511 | 13.226 | 1.241 | 0.00 | 0.00 |
| ATOM | 331 | CD1 | LEU | 39 | 4.467 | 13.237 | 2.446 | 0.00 | 0.00 |
| ATOM | 332 | CD2 | LEU | 39 | 4.151 | 12.457 | 0.077 | 0.00 | 0.00 |
| ATOM | 333 | C | LEU | 39 | 0.881 | 11.068 | 3.102 | 0.00 | 0.00 |
| ATOM | 334 | O | LEU | 39 | 1.101 | 11.338 | 4.283 | 0.00 | 0.00 |
| ATOM | 335 | N | THR | 40 | −0.291 | 10.561 | 2.686 | 0.00 | 0.00 |
| ATOM | 336 | H | THR | 40 | −0.432 | 10.397 | 1.699 | 0.00 | 0.00 |
| ATOM | 337 | CA | THR | 40 | −1.360 | 10.158 | 3.602 | 0.00 | 0.00 |
| ATOM | 338 | CB | THR | 40 | −2.627 | 9.753 | 2.826 | 0.00 | 0.00 |
| ATOM | 339 | CG2 | THR | 40 | −3.778 | 9.334 | 3.747 | 0.00 | 0.00 |
| ATOM | 340 | OG1 | THR | 40 | −3.079 | 10.847 | 2.055 | 0.00 | 0.00 |
| ATOM | 341 | HG1 | THR | 40 | −3.887 | 10.588 | 1.606 | 0.00 | 0.00 |
| ATOM | 342 | C | THR | 40 | −0.873 | 9.037 | 4.530 | 0.00 | 0.00 |
| ATOM | 343 | O | THR | 40 | −1.089 | 9.092 | 5.741 | 0.00 | 0.00 |
| ATOM | 344 | N | PHE | 41 | −0.182 | 8.048 | 3.954 | 0.00 | 0.00 |
| ATOM | 345 | H | PHE | 41 | −0.043 | 8.088 | 2.953 | 0.00 | 0.00 |
| ATOM | 346 | CA | PHE | 41 | 0.382 | 6.891 | 4.637 | 0.00 | 0.00 |
| ATOM | 347 | CB | PHE | 41 | 0.495 | 5.780 | 3.579 | 0.00 | 0.00 |
| ATOM | 348 | CG | PHE | 41 | 0.506 | 4.374 | 4.138 | 0.00 | 0.00 |
| ATOM | 349 | CD1 | PHE | 41 | −0.701 | 3.756 | 4.512 | 0.00 | 0.00 |
| ATOM | 350 | CE1 | PHE | 41 | −0.689 | 2.457 | 5.050 | 0.00 | 0.00 |
| ATOM | 351 | CZ | PHE | 41 | 0.523 | 1.771 | 5.204 | 0.00 | 0.00 |
| ATOM | 352 | CE2 | PHE | 41 | 1.723 | 2.376 | 4.804 | 0.00 | 0.00 |
| ATOM | 353 | CD2 | PHE | 41 | 1.717 | 3.679 | 4.279 | 0.00 | 0.00 |
| ATOM | 354 | C | PHE | 41 | 1.737 | 7.181 | 5.315 | 0.00 | 0.00 |
| ATOM | 355 | O | PHE | 41 | 2.285 | 6.307 | 5.986 | 0.00 | 0.00 |
| ATOM | 356 | N | PHE | 42 | 2.270 | 8.402 | 5.164 | 0.00 | 0.00 |
| ATOM | 357 | H | PHE | 42 | 1.783 | 9.065 | 4.577 | 0.00 | 0.00 |
| ATOM | 358 | CA | PHE | 42 | 3.482 | 8.875 | 5.827 | 0.00 | 0.00 |
| ATOM | 359 | CB | PHE | 42 | 4.246 | 9.781 | 4.851 | 0.00 | 0.00 |
| ATOM | 360 | CG | PHE | 42 | 5.642 | 10.167 | 5.296 | 0.00 | 0.00 |
| ATOM | 361 | CD1 | PHE | 42 | 5.921 | 11.481 | 5.719 | 0.00 | 0.00 |
| ATOM | 362 | CE1 | PHE | 42 | 7.227 | 11.835 | 6.101 | 0.00 | 0.00 |
| ATOM | 363 | CZ | PHE | 42 | 8.255 | 10.876 | 6.071 | 0.00 | 0.00 |
| ATOM | 364 | CE2 | PHE | 42 | 7.980 | 9.564 | 5.650 | 0.00 | 0.00 |
| ATOM | 365 | CD2 | PHE | 42 | 6.676 | 9.213 | 5.258 | 0.00 | 0.00 |
| ATOM | 366 | C | PHE | 42 | 3.150 | 9.624 | 7.120 | 0.00 | 0.00 |
| ATOM | 367 | O | PHE | 42 | 3.879 | 9.495 | 8.097 | 0.00 | 0.00 |
| ATOM | 368 | N | LEU | 43 | 2.031 | 10.360 | 7.154 | 0.00 | 0.00 |
| ATOM | 369 | H | LEU | 43 | 1.484 | 10.457 | 6.309 | 0.00 | 0.00 |
| ATOM | 370 | CA | LEU | 43 | 1.473 | 10.924 | 8.382 | 0.00 | 0.00 |
| ATOM | 371 | CB | LEU | 43 | 0.398 | 11.963 | 8.019 | 0.00 | 0.00 |
| ATOM | 372 | CG | LEU | 43 | 0.943 | 13.203 | 7.276 | 0.00 | 0.00 |
| ATOM | 373 | CD1 | LEU | 43 | −0.231 | 14.055 | 6.775 | 0.00 | 0.00 |
| ATOM | 374 | CD2 | LEU | 43 | 1.853 | 14.063 | 8.168 | 0.00 | 0.00 |
| ATOM | 375 | C | LEU | 43 | 0.874 | 9.828 | 9.281 | 0.00 | 0.00 |
| ATOM | 376 | O | LEU | 43 | 0.769 | 10.036 | 10.491 | 0.00 | 0.00 |
| ATOM | 377 | N | LEU | 44 | 0.536 | 8.658 | 8.710 | 0.00 | 0.00 |
| ATOM | 378 | H | LEU | 44 | 0.627 | 8.573 | 7.707 | 0.00 | 0.00 |
| ATOM | 379 | CA | LEU | 44 | 0.132 | 7.461 | 9.440 | 0.00 | 0.00 |
| ATOM | 380 | CB | LEU | 44 | −0.237 | 6.330 | 8.461 | 0.00 | 0.00 |

-continued pdb file of the α3β4 nAChR model

| | | | | | | | | |
|---|---|---|---|---|---|---|---|---|
| ATOM | 381 | CG | LEU | 44 | −0.598 | 4.940 | 9.053 | 0.00 | 0.00 |
| ATOM | 382 | CD1 | LEU | 44 | −1.120 | 4.095 | 7.887 | 0.00 | 0.00 |
| ATOM | 383 | CD2 | LEU | 44 | 0.548 | 4.126 | 9.682 | 0.00 | 0.00 |
| ATOM | 384 | C | LEU | 44 | 1.236 | 7.030 | 10.392 | 0.00 | 0.00 |
| ATOM | 385 | O | LEU | 44 | 1.015 | 7.010 | 11.603 | 0.00 | 0.00 |
| ATOM | 386 | N | LEU | 45 | 2.406 | 6.671 | 9.845 | 0.00 | 0.00 |
| ATOM | 387 | H | LEU | 45 | 2.516 | 6.707 | 8.841 | 0.00 | 0.00 |
| ATOM | 388 | CA | LEU | 45 | 3.519 | 6.170 | 10.638 | 0.00 | 0.00 |
| ATOM | 389 | CB | LEU | 45 | 4.613 | 5.598 | 9.712 | 0.00 | 0.00 |
| ATOM | 390 | CG | LEU | 45 | 5.541 | 6.618 | 9.012 | 0.00 | 0.00 |
| ATOM | 391 | CD1 | LEU | 45 | 6.887 | 6.784 | 9.737 | 0.00 | 0.00 |
| ATOM | 392 | CD2 | LEU | 45 | 5.832 | 6.220 | 7.559 | 0.00 | 0.00 |
| ATOM | 393 | C | LEU | 45 | 4.079 | 7.261 | 11.561 | 0.00 | 0.00 |
| ATOM | 394 | O | LEU | 45 | 4.821 | 6.946 | 12.478 | 0.00 | 0.00 |
| ATOM | 395 | N | ILE | 46 | 3.724 | 8.534 | 11.345 | 0.00 | 0.00 |
| ATOM | 396 | H | ILE | 46 | 3.121 | 8.734 | 10.560 | 0.00 | 0.00 |
| ATOM | 397 | CA | ILE | 46 | 4.148 | 9.666 | 12.160 | 0.00 | 0.00 |
| ATOM | 398 | CB | ILE | 46 | 4.432 | 10.867 | 11.210 | 0.00 | 0.00 |
| ATOM | 399 | CG2 | ILE | 46 | 4.416 | 12.260 | 11.869 | 0.00 | 0.00 |
| ATOM | 400 | CG1 | ILE | 46 | 5.801 | 10.618 | 10.528 | 0.00 | 0.00 |
| ATOM | 401 | CD1 | ILE | 46 | 6.159 | 11.602 | 9.409 | 0.00 | 0.00 |
| ATOM | 402 | C | ILE | 46 | 3.185 | 9.956 | 13.327 | 0.00 | 0.00 |
| ATOM | 403 | O | ILE | 46 | 3.473 | 10.794 | 14.180 | 0.00 | 0.00 |
| ATOM | 404 | N | SER | 47 | 2.082 | 9.209 | 13.426 | 0.00 | 0.00 |
| ATOM | 405 | H | SER | 47 | 1.886 | 8.542 | 12.690 | 0.00 | 0.00 |
| ATOM | 406 | CA | SER | 47 | 1.150 | 9.252 | 14.548 | 0.00 | 0.00 |
| ATOM | 407 | CB | SER | 47 | −0.126 | 9.962 | 14.095 | 0.00 | 0.00 |
| ATOM | 408 | OG | SER | 47 | −0.740 | 9.307 | 13.001 | 0.00 | 0.00 |
| ATOM | 409 | HG | SER | 47 | −0.178 | 9.413 | 12.226 | 0.00 | 0.00 |
| ATOM | 410 | C | SER | 47 | 0.919 | 7.870 | 15.169 | 0.00 | 0.00 |
| ATOM | 411 | O | SER | 47 | 0.237 | 7.783 | 16.189 | 0.00 | 0.00 |
| ATOM | 412 | N | LYS | 48 | 1.561 | 6.825 | 14.617 | 0.00 | 0.00 |
| ATOM | 413 | H | LYS | 48 | 2.046 | 6.979 | 13.746 | 0.00 | 0.00 |
| ATOM | 414 | CA | LYS | 48 | 1.788 | 5.536 | 15.262 | 0.00 | 0.00 |
| ATOM | 415 | CB | LYS | 48 | 1.158 | 4.403 | 14.455 | 0.00 | 0.00 |
| ATOM | 416 | CG | LYS | 48 | −0.354 | 4.284 | 14.642 | 0.00 | 0.00 |
| ATOM | 417 | CD | LYS | 48 | −0.773 | 3.894 | 16.077 | 0.00 | 0.00 |
| ATOM | 418 | CE | LYS | 48 | −1.189 | 5.103 | 16.921 | 0.00 | 0.00 |
| ATOM | 419 | NZ | LYS | 48 | −1.702 | 4.693 | 18.239 | 0.00 | 0.00 |
| ATOM | 420 | HZ1 | LYS | 48 | −1.012 | 4.132 | 18.717 | 0.00 | 0.00 |
| ATOM | 421 | HZ2 | LYS | 48 | −1.914 | 5.513 | 18.789 | 0.00 | 0.00 |
| ATOM | 422 | HZ3 | LYS | 48 | −2.552 | 4.158 | 18.112 | 0.00 | 0.00 |
| ATOM | 423 | C | LYS | 48 | 3.272 | 5.283 | 15.588 | 0.00 | 0.00 |
| ATOM | 424 | O | LYS | 48 | 3.543 | 4.430 | 16.432 | 0.00 | 0.00 |
| ATOM | 425 | N | ILE | 49 | 4.204 | 6.096 | 15.057 | 0.00 | 0.00 |
| ATOM | 426 | H | ILE | 49 | 3.931 | 6.719 | 14.311 | 0.00 | 0.00 |
| ATOM | 427 | CA | ILE | 49 | 5.427 | 6.457 | 15.769 | 0.00 | 0.00 |
| ATOM | 428 | CB | ILE | 49 | 6.732 | 5.740 | 15.337 | 0.00 | 0.00 |
| ATOM | 429 | CG2 | ILE | 49 | 7.308 | 6.108 | 13.955 | 0.00 | 0.00 |
| ATOM | 430 | CG1 | ILE | 49 | 7.793 | 5.862 | 16.468 | 0.00 | 0.00 |
| ATOM | 431 | CD1 | ILE | 49 | 8.665 | 7.127 | 16.501 | 0.00 | 0.00 |
| ATOM | 432 | C | ILE | 49 | 5.527 | 7.970 | 16.024 | 0.00 | 0.00 |
| ATOM | 433 | O | ILE | 49 | 5.311 | 8.399 | 17.157 | 0.00 | 0.00 |
| ATOM | 434 | N | NME | 50 | 5.876 | 8.773 | 15.013 | 0.00 | 0.00 |
| ATOM | 435 | H | NME | 50 | 5.998 | 8.361 | 14.099 | 0.00 | 0.00 |
| ATOM | 436 | CA | NME | 50 | 6.271 | 10.165 | 15.177 | 0.00 | 0.00 |
| TER | | | | | | | | | |
| ATOM | 437 | CA | ACE | 51 | −10.666 | 1.083 | −18.631 | 0.00 | 0.00 |
| ATOM | 438 | C | ACE | 51 | −10.046 | 1.575 | −17.331 | 0.00 | 0.00 |
| ATOM | 439 | O | ACE | 51 | −10.544 | 1.258 | −16.251 | 0.00 | 0.00 |
| ATOM | 440 | N | GLU | 52 | −8.968 | 2.364 | −17.452 | 0.00 | 0.00 |
| ATOM | 441 | H | GLU | 52 | −8.628 | 2.567 | −18.381 | 0.00 | 0.00 |
| ATOM | 442 | CA | GLU | 52 | −8.186 | 2.902 | −16.335 | 0.00 | 0.00 |
| ATOM | 443 | CB | GLU | 52 | −6.955 | 3.634 | −16.901 | 0.00 | 0.00 |
| ATOM | 444 | CG | GLU | 52 | −5.951 | 4.138 | −15.847 | 0.00 | 0.00 |
| ATOM | 445 | CD | GLU | 52 | −5.535 | 3.066 | −14.831 | 0.00 | 0.00 |
| ATOM | 446 | OE1 | GLU | 52 | −5.559 | 3.384 | −13.621 | 0.00 | 0.00 |
| ATOM | 447 | OE2 | GLU | 52 | −5.211 | 1.942 | −15.275 | 0.00 | 0.00 |
| ATOM | 448 | C | GLU | 52 | −9.010 | 3.796 | −15.388 | 0.00 | 0.00 |
| ATOM | 449 | O | GLU | 52 | −8.603 | 4.015 | −14.251 | 0.00 | 0.00 |
| ATOM | 450 | N | LYS | 53 | −10.180 | 4.283 | −15.824 | 0.00 | 0.00 |
| ATOM | 451 | H | LYS | 53 | −10.473 | 4.046 | −16.760 | 0.00 | 0.00 |
| ATOM | 452 | CA | LYS | 53 | −11.053 | 5.150 | −15.040 | 0.00 | 0.00 |
| ATOM | 453 | CB | LYS | 53 | −12.089 | 5.818 | −15.963 | 0.00 | 0.00 |
| ATOM | 454 | CG | LYS | 53 | −11.559 | 7.029 | −16.754 | 0.00 | 0.00 |
| ATOM | 455 | CD | LYS | 53 | −10.494 | 6.696 | −17.814 | 0.00 | 0.00 |
| ATOM | 456 | CE | LYS | 53 | −10.117 | 7.919 | −18.658 | 0.00 | 0.00 |

-continued pdb file of the α3β4 nAChR model

| ATOM | 457 | NZ | LYS | 53 | −11.217 | 8.353 | −19.541 | 0.00 | 0.00 |
|---|---|---|---|---|---|---|---|---|---|
| ATOM | 458 | HZ1 | LYS | 53 | −12.022 | 8.601 | −18.983 | 0.00 | 0.00 |
| ATOM | 459 | HZ2 | LYS | 53 | −10.924 | 9.156 | −20.080 | 0.00 | 0.00 |
| ATOM | 460 | HZ3 | LYS | 53 | −11.465 | 7.602 | −20.169 | 0.00 | 0.00 |
| ATOM | 461 | C | LYS | 53 | −11.761 | 4.405 | −13.903 | 0.00 | 0.00 |
| ATOM | 462 | O | LYS | 53 | −11.891 | 4.952 | −12.809 | 0.00 | 0.00 |
| ATOM | 463 | N | VAL | 54 | −12.200 | 3.164 | −14.148 | 0.00 | 0.00 |
| ATOM | 464 | H | VAL | 54 | −12.057 | 2.773 | −15.068 | 0.00 | 0.00 |
| ATOM | 465 | CA | VAL | 54 | −12.728 | 2.277 | −13.112 | 0.00 | 0.00 |
| ATOM | 466 | CB | VAL | 54 | −13.527 | 1.124 | −13.765 | 0.00 | 0.00 |
| ATOM | 467 | CG1 | VAL | 54 | −14.079 | 0.140 | −12.718 | 0.00 | 0.00 |
| ATOM | 468 | CG2 | VAL | 54 | −14.713 | 1.664 | −14.584 | 0.00 | 0.00 |
| ATOM | 469 | C | VAL | 54 | −11.569 | 1.741 | −12.265 | 0.00 | 0.00 |
| ATOM | 470 | O | VAL | 54 | −11.753 | 1.551 | −11.068 | 0.00 | 0.00 |
| ATOM | 471 | N | THR | 55 | −10.381 | 1.536 | −12.859 | 0.00 | 0.00 |
| ATOM | 472 | H | THR | 55 | −10.295 | 1.697 | −13.853 | 0.00 | 0.00 |
| ATOM | 473 | CA | THR | 55 | −9.194 | 1.046 | −12.162 | 0.00 | 0.00 |
| ATOM | 474 | CB | THR | 55 | −8.048 | 0.775 | −13.155 | 0.00 | 0.00 |
| ATOM | 475 | CG2 | THR | 55 | −6.833 | 0.127 | −12.482 | 0.00 | 0.00 |
| ATOM | 476 | OG1 | THR | 55 | −8.483 | −0.094 | −14.180 | 0.00 | 0.00 |
| ATOM | 477 | HG1 | THR | 55 | −7.736 | −0.269 | −14.758 | 0.00 | 0.00 |
| ATOM | 478 | C | THR | 55 | −8.748 | 2.021 | −11.065 | 0.00 | 0.00 |
| ATOM | 479 | O | THR | 55 | −8.516 | 1.595 | −9.933 | 0.00 | 0.00 |
| ATOM | 480 | N | LEU | 56 | −8.652 | 3.321 | −11.382 | 0.00 | 0.00 |
| ATOM | 481 | H | LEU | 56 | −8.821 | 3.613 | −12.336 | 0.00 | 0.00 |
| ATOM | 482 | CA | LEU | 56 | −8.307 | 4.347 | −10.403 | 0.00 | 0.00 |
| ATOM | 483 | CB | LEU | 56 | −7.786 | 5.623 | −11.095 | 0.00 | 0.00 |
| ATOM | 484 | CG | LEU | 56 | −8.796 | 6.430 | −11.941 | 0.00 | 0.00 |
| ATOM | 485 | CD1 | LEU | 56 | −9.612 | 7.436 | −11.112 | 0.00 | 0.00 |
| ATOM | 486 | CD2 | LEU | 56 | −8.052 | 7.211 | −13.035 | 0.00 | 0.00 |
| ATOM | 487 | C | LEU | 56 | −9.428 | 4.598 | −9.393 | 0.00 | 0.00 |
| ATOM | 488 | O | LEU | 56 | −9.129 | 5.005 | −8.274 | 0.00 | 0.00 |
| ATOM | 489 | N | CYS | 57 | −10.690 | 4.306 | −9.743 | 0.00 | 0.00 |
| ATOM | 490 | H | CYS | 57 | −10.875 | 3.975 | −10.679 | 0.00 | 0.00 |
| ATOM | 491 | CA | CYS | 57 | −11.808 | 4.362 | −8.810 | 0.00 | 0.00 |
| ATOM | 492 | CB | CYS | 57 | −13.128 | 4.274 | −9.585 | 0.00 | 0.00 |
| ATOM | 493 | SG | CYS | 57 | −14.524 | 4.525 | −8.455 | 0.00 | 0.00 |
| ATOM | 494 | HG | CYS | 57 | −15.482 | 4.408 | −9.379 | 0.00 | 0.00 |
| ATOM | 495 | C | CYS | 57 | −11.684 | 3.250 | −7.764 | 0.00 | 0.00 |
| ATOM | 496 | O | CYS | 57 | −11.771 | 3.550 | −6.575 | 0.00 | 0.00 |
| ATOM | 497 | N | ILE | 58 | −11.457 | 1.991 | −8.183 | 0.00 | 0.00 |
| ATOM | 498 | H | ILE | 58 | −11.384 | 1.798 | −9.172 | 0.00 | 0.00 |
| ATOM | 499 | CA | ILE | 58 | −11.358 | 0.867 | −7.251 | 0.00 | 0.00 |
| ATOM | 500 | CB | ILE | 58 | −11.468 | −0.528 | −7.914 | 0.00 | 0.00 |
| ATOM | 501 | CG2 | ILE | 58 | −12.863 | −0.690 | −8.546 | 0.00 | 0.00 |
| ATOM | 502 | CG1 | ILE | 58 | −10.334 | −0.841 | −8.910 | 0.00 | 0.00 |
| ATOM | 503 | CD1 | ILE | 58 | −10.300 | −2.298 | −9.389 | 0.00 | 0.00 |
| ATOM | 504 | C | ILE | 58 | −10.147 | 0.986 | −6.321 | 0.00 | 0.00 |
| ATOM | 505 | O | ILE | 58 | −10.272 | 0.671 | −5.140 | 0.00 | 0.00 |
| ATOM | 506 | N | SER | 59 | −9.013 | 1.503 | −6.811 | 0.00 | 0.00 |
| ATOM | 507 | H | SER | 59 | −8.973 | 1.742 | −7.793 | 0.00 | 0.00 |
| ATOM | 508 | CA | SER | 59 | −7.835 | 1.772 | −5.994 | 0.00 | 0.00 |
| ATOM | 509 | CB | SER | 59 | −6.690 | 2.182 | −6.928 | 0.00 | 0.00 |
| ATOM | 510 | OG | SER | 59 | −5.491 | 2.352 | −6.204 | 0.00 | 0.00 |
| ATOM | 511 | HG | SER | 59 | −4.792 | 2.591 | −6.818 | 0.00 | 0.00 |
| ATOM | 512 | C | SER | 59 | −8.108 | 2.867 | −4.953 | 0.00 | 0.00 |
| ATOM | 513 | O | SER | 59 | −7.648 | 2.750 | −3.818 | 0.00 | 0.00 |
| ATOM | 514 | N | VAL | 60 | −8.876 | 3.905 | −5.322 | 0.00 | 0.00 |
| ATOM | 515 | H | VAL | 60 | −9.223 | 3.940 | −6.272 | 0.00 | 0.00 |
| ATOM | 516 | CA | VAL | 60 | −9.265 | 4.998 | −4.432 | 0.00 | 0.00 |
| ATOM | 517 | CB | VAL | 60 | −9.741 | 6.215 | −5.265 | 0.00 | 0.00 |
| ATOM | 518 | CG1 | VAL | 60 | −10.541 | 7.263 | −4.472 | 0.00 | 0.00 |
| ATOM | 519 | CG2 | VAL | 60 | −8.517 | 6.933 | −5.864 | 0.00 | 0.00 |
| ATOM | 520 | C | VAL | 60 | −10.280 | 4.554 | −3.361 | 0.00 | 0.00 |
| ATOM | 521 | O | VAL | 60 | −10.318 | 5.159 | −2.290 | 0.00 | 0.00 |
| ATOM | 522 | N | LEU | 61 | −11.052 | 3.480 | −3.581 | 0.00 | 0.00 |
| ATOM | 523 | H | LEU | 61 | −11.008 | 3.009 | −4.474 | 0.00 | 0.00 |
| ATOM | 524 | CA | LEU | 61 | −11.901 | 2.915 | −2.534 | 0.00 | 0.00 |
| ATOM | 525 | CB | LEU | 61 | −12.909 | 1.910 | −3.123 | 0.00 | 0.00 |
| ATOM | 526 | CG | LEU | 61 | −13.994 | 2.537 | −4.025 | 0.00 | 0.00 |
| ATOM | 527 | CD1 | LEU | 61 | −14.799 | 1.424 | −4.710 | 0.00 | 0.00 |
| ATOM | 528 | CD2 | LEU | 61 | −14.957 | 3.442 | −3.241 | 0.00 | 0.00 |
| ATOM | 529 | C | LEU | 61 | −11.060 | 2.250 | −1.440 | 0.00 | 0.00 |
| ATOM | 530 | O | LEU | 61 | −11.309 | 2.485 | −0.258 | 0.00 | 0.00 |
| ATOM | 531 | N | LEU | 62 | −10.049 | 1.457 | −1.829 | 0.00 | 0.00 |
| ATOM | 532 | H | LEU | 62 | −9.900 | 1.302 | −2.817 | 0.00 | 0.00 |
| ATOM | 533 | CA | LEU | 62 | −9.102 | 0.850 | −0.897 | 0.00 | 0.00 |

-continued

| pdb file of the α3β4 nAChR model | | | | | | | | |
|---|---|---|---|---|---|---|---|---|
| ATOM | 534 | CB | LEU | 62 | −8.300 | −0.270 | −1.593 | 0.00 | 0.00 |
| ATOM | 535 | CG | LEU | 62 | −9.018 | −1.623 | −1.814 | 0.00 | 0.00 |
| ATOM | 536 | CD1 | LEU | 62 | −9.643 | −2.189 | −0.530 | 0.00 | 0.00 |
| ATOM | 537 | CD2 | LEU | 62 | −10.062 | −1.618 | −2.934 | 0.00 | 0.00 |
| ATOM | 538 | C | LEU | 62 | −8.155 | 1.886 | −0.271 | 0.00 | 0.00 |
| ATOM | 539 | O | LEU | 62 | −7.590 | 1.612 | 0.785 | 0.00 | 0.00 |
| ATOM | 540 | N | SER | 63 | −8.017 | 3.082 | −0.864 | 0.00 | 0.00 |
| ATOM | 541 | H | SER | 63 | −8.482 | 3.248 | −1.746 | 0.00 | 0.00 |
| ATOM | 542 | CA | SER | 63 | −7.286 | 4.186 | −0.257 | 0.00 | 0.00 |
| ATOM | 543 | CB | SER | 63 | −7.134 | 5.342 | −1.243 | 0.00 | 0.00 |
| ATOM | 544 | OG | SER | 63 | −6.568 | 6.434 | −0.563 | 0.00 | 0.00 |
| ATOM | 545 | HG | SER | 63 | −6.465 | 7.161 | −1.181 | 0.00 | 0.00 |
| ATOM | 546 | C | SER | 63 | −7.974 | 4.660 | 1.024 | 0.00 | 0.00 |
| ATOM | 547 | O | SER | 63 | −7.322 | 4.753 | 2.063 | 0.00 | 0.00 |
| ATOM | 548 | N | LEU | 64 | −9.281 | 4.947 | 0.953 | 0.00 | 0.00 |
| ATOM | 549 | H | LEU | 64 | −9.759 | 4.859 | 0.066 | 0.00 | 0.00 |
| ATOM | 550 | CA | LEU | 64 | −10.062 | 5.363 | 2.111 | 0.00 | 0.00 |
| ATOM | 551 | CB | LEU | 64 | −11.442 | 5.887 | 1.664 | 0.00 | 0.00 |
| ATOM | 552 | CG | LEU | 64 | −11.507 | 7.384 | 1.285 | 0.00 | 0.00 |
| ATOM | 553 | CD1 | LEU | 64 | −11.224 | 8.300 | 2.487 | 0.00 | 0.00 |
| ATOM | 554 | CD2 | LEU | 64 | −10.589 | 7.768 | 0.116 | 0.00 | 0.00 |
| ATOM | 555 | C | LEU | 64 | −10.212 | 4.225 | 3.132 | 0.00 | 0.00 |
| ATOM | 556 | O | LEU | 64 | −10.375 | 4.517 | 4.317 | 0.00 | 0.00 |
| ATOM | 557 | N | THR | 65 | −10.100 | 2.951 | 2.714 | 0.00 | 0.00 |
| ATOM | 558 | H | THR | 65 | −9.981 | 2.765 | 1.727 | 0.00 | 0.00 |
| ATOM | 559 | CA | THR | 65 | −10.084 | 1.818 | 3.641 | 0.00 | 0.00 |
| ATOM | 560 | CB | THR | 65 | −10.415 | 0.492 | 2.913 | 0.00 | 0.00 |
| ATOM | 561 | CG2 | THR | 65 | −9.313 | −0.575 | 2.884 | 0.00 | 0.00 |
| ATOM | 562 | OG1 | THR | 65 | −11.537 | −0.097 | 3.538 | 0.00 | 0.00 |
| ATOM | 563 | HG1 | THR | 65 | −11.768 | −0.893 | 3.055 | 0.00 | 0.00 |
| ATOM | 564 | C | THR | 65 | −8.814 | 1.779 | 4.506 | 0.00 | 0.00 |
| ATOM | 565 | O | THR | 65 | −8.851 | 1.294 | 5.636 | 0.00 | 0.00 |
| ATOM | 566 | N | VAL | 66 | −7.719 | 2.353 | 3.997 | 0.00 | 0.00 |
| ATOM | 567 | H | VAL | 66 | −7.786 | 2.732 | 3.062 | 0.00 | 0.00 |
| ATOM | 568 | CA | VAL | 66 | −6.420 | 2.502 | 4.649 | 0.00 | 0.00 |
| ATOM | 569 | CB | VAL | 66 | −5.352 | 2.198 | 3.567 | 0.00 | 0.00 |
| ATOM | 570 | CG1 | VAL | 66 | −3.925 | 2.559 | 3.978 | 0.00 | 0.00 |
| ATOM | 571 | CG2 | VAL | 66 | −5.379 | 0.698 | 3.225 | 0.00 | 0.00 |
| ATOM | 572 | C | VAL | 66 | −6.284 | 3.892 | 5.313 | 0.00 | 0.00 |
| ATOM | 573 | O | VAL | 66 | −5.310 | 4.144 | 6.024 | 0.00 | 0.00 |
| ATOM | 574 | N | PHE | 67 | −7.276 | 4.781 | 5.148 | 0.00 | 0.00 |
| ATOM | 575 | H | PHE | 67 | −8.047 | 4.538 | 4.543 | 0.00 | 0.00 |
| ATOM | 576 | CA | PHE | 67 | −7.349 | 6.061 | 5.845 | 0.00 | 0.00 |
| ATOM | 577 | CB | PHE | 67 | −7.920 | 7.118 | 4.892 | 0.00 | 0.00 |
| ATOM | 578 | CG | PHE | 67 | −7.904 | 8.533 | 5.444 | 0.00 | 0.00 |
| ATOM | 579 | CD1 | PHE | 67 | −9.105 | 9.254 | 5.590 | 0.00 | 0.00 |
| ATOM | 580 | CE1 | PHE | 67 | −9.084 | 10.569 | 6.089 | 0.00 | 0.00 |
| ATOM | 581 | CZ | PHE | 67 | −7.863 | 11.165 | 6.452 | 0.00 | 0.00 |
| ATOM | 582 | CE2 | PHE | 67 | −6.663 | 10.445 | 6.318 | 0.00 | 0.00 |
| ATOM | 583 | CD2 | PHE | 67 | −6.684 | 9.133 | 5.813 | 0.00 | 0.00 |
| ATOM | 584 | C | PHE | 67 | −8.198 | 5.980 | 7.119 | 0.00 | 0.00 |
| ATOM | 585 | O | PHE | 67 | −7.928 | 6.700 | 8.075 | 0.00 | 0.00 |
| ATOM | 586 | N | LEU | 68 | −9.194 | 5.085 | 7.164 | 0.00 | 0.00 |
| ATOM | 587 | H | LEU | 68 | −9.408 | 4.549 | 6.335 | 0.00 | 0.00 |
| ATOM | 588 | CA | LEU | 68 | −9.898 | 4.738 | 8.397 | 0.00 | 0.00 |
| ATOM | 589 | CB | LEU | 68 | −11.193 | 3.986 | 8.045 | 0.00 | 0.00 |
| ATOM | 590 | CG | LEU | 68 | −12.237 | 4.842 | 7.296 | 0.00 | 0.00 |
| ATOM | 591 | CD1 | LEU | 68 | −13.375 | 3.941 | 6.799 | 0.00 | 0.00 |
| ATOM | 592 | CD2 | LEU | 68 | −12.818 | 5.958 | 8.179 | 0.00 | 0.00 |
| ATOM | 593 | C | LEU | 68 | −9.014 | 3.871 | 9.307 | 0.00 | 0.00 |
| ATOM | 594 | O | LEU | 68 | −9.191 | 3.913 | 10.521 | 0.00 | 0.00 |
| ATOM | 595 | N | LEU | 69 | −8.046 | 3.136 | 8.730 | 0.00 | 0.00 |
| ATOM | 596 | H | LEU | 69 | −7.987 | 3.155 | 7.722 | 0.00 | 0.00 |
| ATOM | 597 | CA | LEU | 69 | −7.027 | 2.348 | 9.420 | 0.00 | 0.00 |
| ATOM | 598 | CB | LEU | 69 | −6.105 | 1.703 | 8.363 | 0.00 | 0.00 |
| ATOM | 599 | CG | LEU | 69 | −4.888 | 0.869 | 8.834 | 0.00 | 0.00 |
| ATOM | 600 | CD1 | LEU | 69 | −4.375 | 0.064 | 7.628 | 0.00 | 0.00 |
| ATOM | 601 | CD2 | LEU | 69 | −3.704 | 1.695 | 9.357 | 0.00 | 0.00 |
| ATOM | 602 | C | LEU | 69 | −6.243 | 3.221 | 10.394 | 0.00 | 0.00 |
| ATOM | 603 | O | LEU | 69 | −6.277 | 2.978 | 11.599 | 0.00 | 0.00 |
| ATOM | 604 | N | VAL | 70 | −5.545 | 4.233 | 9.858 | 0.00 | 0.00 |
| ATOM | 605 | H | VAL | 70 | −5.571 | 4.347 | 8.854 | 0.00 | 0.00 |
| ATOM | 606 | CA | VAL | 70 | −4.762 | 5.203 | 10.615 | 0.00 | 0.00 |
| ATOM | 607 | CB | VAL | 70 | −4.039 | 6.171 | 9.644 | 0.00 | 0.00 |
| ATOM | 608 | CG1 | VAL | 70 | −4.936 | 6.845 | 8.604 | 0.00 | 0.00 |
| ATOM | 609 | CG2 | VAL | 70 | −3.279 | 7.289 | 10.371 | 0.00 | 0.00 |
| ATOM | 610 | C | VAL | 70 | −5.649 | 5.978 | 11.595 | 0.00 | 0.00 |

-continued pdb file of the α3β4 nAChR model

| ATOM | 611 | O | VAL | 70 | −5.145 | 6.438 | 12.606 | 0.00 | 0.00 |
|---|---|---|---|---|---|---|---|---|---|
| ATOM | 612 | N | ILE | 71 | −6.953 | 6.123 | 11.333 | 0.00 | 0.00 |
| ATOM | 613 | H | ILE | 71 | −7.330 | 5.720 | 10.486 | 0.00 | 0.00 |
| ATOM | 614 | CA | ILE | 71 | −7.867 | 6.881 | 12.184 | 0.00 | 0.00 |
| ATOM | 615 | CB | ILE | 71 | −8.994 | 7.473 | 11.285 | 0.00 | 0.00 |
| ATOM | 616 | CG2 | ILE | 71 | −10.325 | 7.793 | 11.995 | 0.00 | 0.00 |
| ATOM | 617 | CG1 | ILE | 71 | −8.441 | 8.747 | 10.601 | 0.00 | 0.00 |
| ATOM | 618 | CD1 | ILE | 71 | −9.348 | 9.356 | 9.524 | 0.00 | 0.00 |
| ATOM | 619 | C | ILE | 71 | −8.368 | 6.088 | 13.406 | 0.00 | 0.00 |
| ATOM | 620 | O | ILE | 71 | −8.968 | 6.678 | 14.304 | 0.00 | 0.00 |
| ATOM | 621 | N | THR | 72 | −8.079 | 4.786 | 13.497 | 0.00 | 0.00 |
| ATOM | 622 | H | THR | 72 | −7.620 | 4.331 | 12.719 | 0.00 | 0.00 |
| ATOM | 623 | CA | THR | 72 | −8.423 | 3.957 | 14.657 | 0.00 | 0.00 |
| ATOM | 624 | CB | THR | 72 | −9.641 | 3.075 | 14.346 | 0.00 | 0.00 |
| ATOM | 625 | CG2 | THR | 72 | −10.949 | 3.875 | 14.377 | 0.00 | 0.00 |
| ATOM | 626 | OG1 | THR | 72 | −9.535 | 2.482 | 13.069 | 0.00 | 0.00 |
| ATOM | 627 | HG1 | THR | 72 | −10.353 | 2.020 | 12.878 | 0.00 | 0.00 |
| ATOM | 628 | C | THR | 72 | −7.221 | 3.219 | 15.258 | 0.00 | 0.00 |
| ATOM | 629 | O | THR | 72 | −7.312 | 2.686 | 16.361 | 0.00 | 0.00 |
| ATOM | 630 | N | GLU | 73 | −6.070 | 3.306 | 14.587 | 0.00 | 0.00 |
| ATOM | 631 | H | GLU | 73 | −6.119 | 3.677 | 13.648 | 0.00 | 0.00 |
| ATOM | 632 | CA | GLU | 73 | −4.733 | 3.301 | 15.164 | 0.00 | 0.00 |
| ATOM | 633 | CB | GLU | 73 | −3.762 | 3.156 | 13.982 | 0.00 | 0.00 |
| ATOM | 634 | CG | GLU | 73 | −3.490 | 1.699 | 13.589 | 0.00 | 0.00 |
| ATOM | 635 | CD | GLU | 73 | −2.451 | 1.055 | 14.506 | 0.00 | 0.00 |
| ATOM | 636 | OE1 | GLU | 73 | −2.795 | 0.776 | 15.677 | 0.00 | 0.00 |
| ATOM | 637 | OE2 | GLU | 73 | −1.312 | 0.867 | 14.029 | 0.00 | 0.00 |
| ATOM | 638 | C | GLU | 73 | −4.533 | 4.614 | 15.932 | 0.00 | 0.00 |
| ATOM | 639 | O | GLU | 73 | −4.423 | 4.592 | 17.156 | 0.00 | 0.00 |
| ATOM | 640 | N | THR | 74 | −4.509 | 5.746 | 15.211 | 0.00 | 0.00 |
| ATOM | 641 | H | THR | 74 | −4.599 | 5.666 | 14.208 | 0.00 | 0.00 |
| ATOM | 642 | CA | THR | 74 | −4.364 | 7.101 | 15.736 | 0.00 | 0.00 |
| ATOM | 643 | CB | THR | 74 | −3.619 | 8.038 | 14.767 | 0.00 | 0.00 |
| ATOM | 644 | CG2 | THR | 74 | −3.335 | 9.399 | 15.417 | 0.00 | 0.00 |
| ATOM | 645 | OG1 | THR | 74 | −2.398 | 7.442 | 14.386 | 0.00 | 0.00 |
| ATOM | 646 | HG1 | THR | 74 | −1.910 | 8.067 | 13.839 | 0.00 | 0.00 |
| ATOM | 647 | C | THR | 74 | −5.716 | 7.672 | 16.183 | 0.00 | 0.00 |
| ATOM | 648 | O | THR | 74 | −6.035 | 7.610 | 17.370 | 0.00 | 0.00 |
| ATOM | 649 | N | NME | 75 | −6.476 | 8.270 | 15.254 | 0.00 | 0.00 |
| ATOM | 650 | H | NME | 75 | −6.161 | 8.257 | 14.295 | 0.00 | 0.00 |
| ATOM | 651 | CA | NME | 75 | −7.656 | 9.066 | 15.556 | 0.00 | 0.00 |
| ATOM | 652 | CA | ACE | 76 | −4.045 | −8.929 | −19.241 | 0.00 | 0.00 |
| ATOM | 653 | C | ACE | 76 | −4.015 | −8.111 | −17.958 | 0.00 | 0.00 |
| ATOM | 654 | O | ACE | 76 | −2.949 | −7.910 | −17.379 | 0.00 | 0.00 |
| ATOM | 655 | N | GLU | 77 | −5.198 | −7.652 | −17.527 | 0.00 | 0.00 |
| ATOM | 656 | H | GLU | 77 | −6.010 | −7.846 | −18.092 | 0.00 | 0.00 |
| ATOM | 657 | CA | GLU | 77 | −5.391 | −6.805 | −16.347 | 0.00 | 0.00 |
| ATOM | 658 | CB | GLU | 77 | −5.703 | −5.373 | −16.827 | 0.00 | 0.00 |
| ATOM | 659 | CG | GLU | 77 | −5.866 | −4.312 | −15.722 | 0.00 | 0.00 |
| ATOM | 660 | CD | GLU | 77 | −4.715 | −4.292 | −14.708 | 0.00 | 0.00 |
| ATOM | 661 | OE1 | GLU | 77 | −5.022 | −4.256 | −13.496 | 0.00 | 0.00 |
| ATOM | 662 | OE2 | GLU | 77 | −3.548 | −4.318 | −15.156 | 0.00 | 0.00 |
| ATOM | 663 | C | GLU | 77 | −6.465 | −7.361 | −15.396 | 0.00 | 0.00 |
| ATOM | 664 | O | GLU | 77 | −6.549 | −6.921 | −14.253 | 0.00 | 0.00 |
| ATOM | 665 | N | LYS | 78 | −7.269 | −8.342 | −15.829 | 0.00 | 0.00 |
| ATOM | 666 | H | LYS | 78 | −7.144 | −8.695 | −16.766 | 0.00 | 0.00 |
| ATOM | 667 | CA | LYS | 78 | −8.386 | −8.870 | −15.048 | 0.00 | 0.00 |
| ATOM | 668 | CB | LYS | 78 | −9.379 | −9.594 | −15.976 | 0.00 | 0.00 |
| ATOM | 669 | CG | LYS | 78 | −10.375 | −8.657 | −16.686 | 0.00 | 0.00 |
| ATOM | 670 | CD | LYS | 78 | −9.740 | −7.666 | −17.677 | 0.00 | 0.00 |
| ATOM | 671 | CE | LYS | 78 | −10.794 | −6.833 | −18.416 | 0.00 | 0.00 |
| ATOM | 672 | NZ | LYS | 78 | −11.598 | −7.646 | −19.349 | 0.00 | 0.00 |
| ATOM | 673 | HZ1 | LYS | 78 | −12.083 | −8.370 | −18.837 | 0.00 | 0.00 |
| ATOM | 674 | HZ2 | LYS | 78 | −12.275 | −7.058 | −19.816 | 0.00 | 0.00 |
| ATOM | 675 | HZ3 | LYS | 78 | −10.994 | −8.071 | −20.038 | 0.00 | 0.00 |
| ATOM | 676 | C | LYS | 78 | −7.926 | −9.797 | −13.917 | 0.00 | 0.00 |
| ATOM | 677 | O | LYS | 78 | −8.500 | −9.752 | −12.830 | 0.00 | 0.00 |
| ATOM | 678 | N | MET | 79 | −6.883 | −10.604 | −14.152 | 0.00 | 0.00 |
| ATOM | 679 | H | MET | 79 | −6.466 | −10.607 | −15.071 | 0.00 | 0.00 |
| ATOM | 680 | CA | MET | 79 | −6.210 | −11.357 | −13.097 | 0.00 | 0.00 |
| ATOM | 681 | CB | MET | 79 | −5.404 | −12.502 | −13.733 | 0.00 | 0.00 |
| ATOM | 682 | CG | MET | 79 | −4.757 | −13.440 | −12.706 | 0.00 | 0.00 |
| ATOM | 683 | SD | MET | 79 | −5.911 | −14.233 | −11.550 | 0.00 | 0.00 |
| ATOM | 684 | CE | MET | 79 | −4.751 | −15.290 | −10.646 | 0.00 | 0.00 |
| ATOM | 685 | C | MET | 79 | −5.312 | −10.435 | −12.263 | 0.00 | 0.00 |
| ATOM | 686 | O | MET | 79 | −5.123 | −10.703 | −11.082 | 0.00 | 0.00 |
| ATOM | 687 | N | THR | 80 | −4.794 | −9.345 | −12.850 | 0.00 | 0.00 |

-continued pdb file of the α3β4 nAChR model

| ATOM | 688 | H | THR | 80 | −4.985 | −9.175 | −13.826 | 0.00 | 0.00 |
|------|-----|-----|-----|----|--------|--------|---------|------|------|
| ATOM | 689 | CA | THR | 80 | −3.932 | −8.380 | −12.171 | 0.00 | 0.00 |
| ATOM | 690 | CB | THR | 80 | −3.313 | −7.404 | −13.188 | 0.00 | 0.00 |
| ATOM | 691 | CG2 | THR | 80 | −2.263 | −6.487 | −12.550 | 0.00 | 0.00 |
| ATOM | 692 | OG1 | THR | 80 | −2.688 | −8.125 | −14.231 | 0.00 | 0.00 |
| ATOM | 693 | HG1 | THR | 80 | −2.352 | −7.496 | −14.876 | 0.00 | 0.00 |
| ATOM | 694 | C | THR | 80 | −4.701 | −7.631 | −11.075 | 0.00 | 0.00 |
| ATOM | 695 | O | THR | 80 | −4.208 | −7.525 | −9.951 | 0.00 | 0.00 |
| ATOM | 696 | N | LEU | 81 | −5.914 | −7.146 | −11.381 | 0.00 | 0.00 |
| ATOM | 697 | H | LEU | 81 | −6.254 | −7.229 | −12.330 | 0.00 | 0.00 |
| ATOM | 698 | CA | LEU | 81 | −6.784 | −6.508 | −10.399 | 0.00 | 0.00 |
| ATOM | 699 | CB | LEU | 81 | −7.852 | −5.633 | −11.088 | 0.00 | 0.00 |
| ATOM | 700 | CG | LEU | 81 | −8.925 | −6.361 | −11.926 | 0.00 | 0.00 |
| ATOM | 701 | CD1 | LEU | 81 | −10.130 | −6.825 | −11.091 | 0.00 | 0.00 |
| ATOM | 702 | CD2 | LEU | 81 | −9.447 | −5.431 | −13.032 | 0.00 | 0.00 |
| ATOM | 703 | C | LEU | 81 | −7.354 | −7.502 | −9.385 | 0.00 | 0.00 |
| ATOM | 704 | O | LEU | 81 | −7.630 | −7.100 | −8.259 | 0.00 | 0.00 |
| ATOM | 705 | N | CYS | 82 | −7.474 | −8.790 | −9.743 | 0.00 | 0.00 |
| ATOM | 706 | H | CYS | 82 | −7.232 | −9.060 | −10.685 | 0.00 | 0.00 |
| ATOM | 707 | CA | CYS | 82 | −7.870 | −9.842 | −8.815 | 0.00 | 0.00 |
| ATOM | 708 | CB | CYS | 82 | −8.181 | −11.122 | −9.601 | 0.00 | 0.00 |
| ATOM | 709 | SG | CYS | 82 | −8.822 | −12.397 | −8.483 | 0.00 | 0.00 |
| ATOM | 710 | HG | CYS | 82 | −8.977 | −13.342 | −9.415 | 0.00 | 0.00 |
| ATOM | 711 | C | CYS | 82 | −6.773 | −10.071 | −7.771 | 0.00 | 0.00 |
| ATOM | 712 | O | CYS | 82 | −7.084 | −10.069 | −6.581 | 0.00 | 0.00 |
| ATOM | 713 | N | ILE | 83 | −5.505 | −10.239 | −8.191 | 0.00 | 0.00 |
| ATOM | 714 | H | ILE | 83 | −5.299 | −10.228 | −9.181 | 0.00 | 0.00 |
| ATOM | 715 | CA | ILE | 83 | −4.407 | −10.490 | −7.258 | 0.00 | 0.00 |
| ATOM | 716 | CB | ILE | 83 | −3.110 | −11.018 | −7.916 | 0.00 | 0.00 |
| ATOM | 717 | CG2 | ILE | 83 | −3.376 | −12.398 | −8.545 | 0.00 | 0.00 |
| ATOM | 718 | CG1 | ILE | 83 | −2.464 | −10.029 | −8.908 | 0.00 | 0.00 |
| ATOM | 719 | CD1 | ILE | 83 | −1.076 | −10.449 | −9.406 | 0.00 | 0.00 |
| ATOM | 720 | C | ILE | 83 | −4.147 | −9.303 | −6.326 | 0.00 | 0.00 |
| ATOM | 721 | O | ILE | 83 | −3.876 | −9.520 | −5.147 | 0.00 | 0.00 |
| ATOM | 722 | N | SER | 84 | −4.295 | −8.065 | −6.815 | 0.00 | 0.00 |
| ATOM | 723 | H | SER | 84 | −4.518 | −7.952 | −7.795 | 0.00 | 0.00 |
| ATOM | 724 | CA | SER | 84 | −4.185 | −6.861 | −5.999 | 0.00 | 0.00 |
| ATOM | 725 | CB | SER | 84 | −4.229 | −5.644 | −6.931 | 0.00 | 0.00 |
| ATOM | 726 | OG | SER | 84 | −4.021 | −4.452 | −6.205 | 0.00 | 0.00 |
| ATOM | 727 | HG | SER | 84 | −4.040 | −3.713 | −6.817 | 0.00 | 0.00 |
| ATOM | 728 | C | SER | 84 | −5.305 | −6.788 | −4.952 | 0.00 | 0.00 |
| ATOM | 729 | O | SER | 84 | −5.040 | −6.413 | −3.811 | 0.00 | 0.00 |
| ATOM | 730 | N | VAL | 85 | −6.535 | −7.178 | −5.324 | 0.00 | 0.00 |
| ATOM | 731 | H | VAL | 85 | −6.684 | −7.476 | −6.279 | 0.00 | 0.00 |
| ATOM | 732 | CA | VAL | 85 | −7.690 | −7.218 | −4.428 | 0.00 | 0.00 |
| ATOM | 733 | CB | VAL | 85 | −8.998 | −7.352 | −5.246 | 0.00 | 0.00 |
| ATOM | 734 | CG1 | VAL | 85 | −10.214 | −7.827 | −4.431 | 0.00 | 0.00 |
| ATOM | 735 | CG2 | VAL | 85 | −9.361 | −5.986 | −5.859 | 0.00 | 0.00 |
| ATOM | 736 | C | VAL | 85 | −7.544 | −8.290 | −3.334 | 0.00 | 0.00 |
| ATOM | 737 | O | VAL | 85 | −8.061 | −8.092 | −2.235 | 0.00 | 0.00 |
| ATOM | 738 | N | LEU | 86 | −6.811 | −9.385 | −3.579 | 0.00 | 0.00 |
| ATOM | 739 | H | LEU | 86 | −6.409 | −9.519 | −4.497 | 0.00 | 0.00 |
| ATOM | 740 | CA | LEU | 86 | −6.530 | −10.378 | −2.544 | 0.00 | 0.00 |
| ATOM | 741 | CB | LEU | 86 | −5.931 | −11.656 | −3.161 | 0.00 | 0.00 |
| ATOM | 742 | CG | LEU | 86 | −6.917 | −12.472 | −4.025 | 0.00 | 0.00 |
| ATOM | 743 | CD1 | LEU | 86 | −6.158 | −13.577 | −4.772 | 0.00 | 0.00 |
| ATOM | 744 | CD2 | LEU | 86 | −8.036 | −13.112 | −3.188 | 0.00 | 0.00 |
| ATOM | 745 | C | LEU | 86 | −5.603 | −9.815 | −1.462 | 0.00 | 0.00 |
| ATOM | 746 | O | LEU | 86 | −5.867 | −10.023 | −0.277 | 0.00 | 0.00 |
| ATOM | 747 | N | LEU | 87 | −4.555 | −9.073 | −1.855 | 0.00 | 0.00 |
| ATOM | 748 | H | LEU | 87 | −4.386 | −8.940 | −2.843 | 0.00 | 0.00 |
| ATOM | 749 | CA | LEU | 87 | −3.693 | −8.366 | −0.911 | 0.00 | 0.00 |
| ATOM | 750 | CB | LEU | 87 | −2.393 | −7.889 | −1.592 | 0.00 | 0.00 |
| ATOM | 751 | CG | LEU | 87 | −1.291 | −8.950 | −1.828 | 0.00 | 0.00 |
| ATOM | 752 | CD1 | LEU | 87 | −0.956 | −9.769 | −0.571 | 0.00 | 0.00 |
| ATOM | 753 | CD2 | LEU | 87 | −1.575 | −9.897 | −2.998 | 0.00 | 0.00 |
| ATOM | 754 | C | LEU | 87 | −4.417 | −7.191 | −0.237 | 0.00 | 0.00 |
| ATOM | 755 | O | LEU | 87 | −4.011 | −6.796 | 0.855 | 0.00 | 0.00 |
| ATOM | 756 | N | ALA | 88 | −5.496 | −6.665 | −0.837 | 0.00 | 0.00 |
| ATOM | 757 | H | ALA | 88 | −5.776 | −7.017 | −1.742 | 0.00 | 0.00 |
| ATOM | 758 | CA | ALA | 88 | −6.288 | −5.590 | −0.255 | 0.00 | 0.00 |
| ATOM | 759 | CB | ALA | 88 | −7.211 | −4.976 | −1.305 | 0.00 | 0.00 |
| ATOM | 760 | C | ALA | 88 | −7.083 | −6.048 | 0.972 | 0.00 | 0.00 |
| ATOM | 761 | O | ALA | 88 | −7.166 | −5.302 | 1.946 | 0.00 | 0.00 |
| ATOM | 762 | N | LEU | 89 | −7.629 | −7.272 | 0.946 | 0.00 | 0.00 |
| ATOM | 763 | H | LEU | 89 | −7.542 | −7.830 | 0.106 | 0.00 | 0.00 |
| ATOM | 764 | CA | LEU | 89 | −8.274 | −7.881 | 2.106 | 0.00 | 0.00 |

-continued pdb file of the α3β4 nAChR model

| | | | | | | | | | |
|---|---|---|---|---|---|---|---|---|---|
| ATOM | 765 | CB | LEU | 89 | −9.186 | −9.043 | 1.662 | 0.00 | 0.00 |
| ATOM | 766 | CG | LEU | 89 | −10.632 | −8.658 | 1.276 | 0.00 | 0.00 |
| ATOM | 767 | CD1 | LEU | 89 | −11.423 | −8.092 | 2.468 | 0.00 | 0.00 |
| ATOM | 768 | CD2 | LEU | 89 | −10.716 | −7.689 | 0.089 | 0.00 | 0.00 |
| ATOM | 769 | C | LEU | 89 | −7.245 | −8.364 | 3.140 | 0.00 | 0.00 |
| ATOM | 770 | O | LEU | 89 | −7.584 | −8.432 | 4.321 | 0.00 | 0.00 |
| ATOM | 771 | N | THR | 90 | −5.994 | −8.643 | 2.734 | 0.00 | 0.00 |
| ATOM | 772 | H | THR | 90 | −5.777 | −8.588 | 1.748 | 0.00 | 0.00 |
| ATOM | 773 | CA | THR | 90 | −4.900 | −8.941 | 3.660 | 0.00 | 0.00 |
| ATOM | 774 | CB | THR | 90 | −3.669 | −9.491 | 2.901 | 0.00 | 0.00 |
| ATOM | 775 | CG2 | THR | 90 | −2.336 | −8.768 | 3.142 | 0.00 | 0.00 |
| ATOM | 776 | OG1 | THR | 90 | −3.485 | −10.845 | 3.257 | 0.00 | 0.00 |
| ATOM | 777 | HG1 | THR | 90 | −2.755 | −11.198 | 2.741 | 0.00 | 0.00 |
| ATOM | 778 | C | THR | 90 | −4.597 | −7.729 | 4.565 | 0.00 | 0.00 |
| ATOM | 779 | O | THR | 90 | −4.396 | −7.880 | 5.770 | 0.00 | 0.00 |
| ATOM | 780 | N | PHE | 91 | −4.622 | −6.530 | 3.975 | 0.00 | 0.00 |
| ATOM | 781 | H | PHE | 91 | −4.792 | −6.522 | 2.979 | 0.00 | 0.00 |
| ATOM | 782 | CA | PHE | 91 | −4.453 | −5.213 | 4.589 | 0.00 | 0.00 |
| ATOM | 783 | CB | PHE | 91 | −4.322 | −4.228 | 3.394 | 0.00 | 0.00 |
| ATOM | 784 | CG | PHE | 91 | −3.356 | −3.056 | 3.460 | 0.00 | 0.00 |
| ATOM | 785 | CD1 | PHE | 91 | −2.423 | −2.883 | 2.414 | 0.00 | 0.00 |
| ATOM | 786 | CE1 | PHE | 91 | −1.616 | −1.734 | 2.355 | 0.00 | 0.00 |
| ATOM | 787 | CZ | PHE | 91 | −1.734 | −0.745 | 3.343 | 0.00 | 0.00 |
| ATOM | 788 | CE2 | PHE | 91 | −2.641 | −0.920 | 4.401 | 0.00 | 0.00 |
| ATOM | 789 | CD2 | PHE | 91 | −3.457 | −2.064 | 4.456 | 0.00 | 0.00 |
| ATOM | 790 | C | PHE | 91 | −5.683 | −4.789 | 5.417 | 0.00 | 0.00 |
| ATOM | 791 | O | PHE | 91 | −5.598 | −3.869 | 6.228 | 0.00 | 0.00 |
| ATOM | 792 | N | PHE | 92 | −6.842 | −5.423 | 5.194 | 0.00 | 0.00 |
| ATOM | 793 | H | PHE | 92 | −6.868 | −6.154 | 4.498 | 0.00 | 0.00 |
| ATOM | 794 | CA | PHE | 92 | −8.094 | −5.092 | 5.865 | 0.00 | 0.00 |
| ATOM | 795 | CB | PHE | 92 | −9.244 | −5.283 | 4.865 | 0.00 | 0.00 |
| ATOM | 796 | CG | PHE | 92 | −10.588 | −4.770 | 5.342 | 0.00 | 0.00 |
| ATOM | 797 | CD1 | PHE | 92 | −11.566 | −5.666 | 5.815 | 0.00 | 0.00 |
| ATOM | 798 | CE1 | PHE | 92 | −12.813 | −5.182 | 6.250 | 0.00 | 0.00 |
| ATOM | 799 | CZ | PHE | 92 | −13.082 | −3.802 | 6.223 | 0.00 | 0.00 |
| ATOM | 800 | CE2 | PHE | 92 | −12.107 | −2.905 | 5.751 | 0.00 | 0.00 |
| ATOM | 801 | CD2 | PHE | 92 | −10.866 | −3.390 | 5.305 | 0.00 | 0.00 |
| ATOM | 802 | C | PHE | 92 | −8.318 | −5.951 | 7.113 | 0.00 | 0.00 |
| ATOM | 803 | O | PHE | 92 | −8.996 | −5.514 | 8.038 | 0.00 | 0.00 |
| ATOM | 804 | N | LEU | 93 | −7.720 | −7.147 | 7.170 | 0.00 | 0.00 |
| ATOM | 805 | H | LEU | 93 | −7.216 | −7.478 | 6.358 | 0.00 | 0.00 |
| ATOM | 806 | CA | LEU | 93 | −7.607 | −7.931 | 8.393 | 0.00 | 0.00 |
| ATOM | 807 | CB | LEU | 93 | −7.337 | −9.401 | 8.029 | 0.00 | 0.00 |
| ATOM | 808 | CG | LEU | 93 | −8.505 | −10.093 | 7.292 | 0.00 | 0.00 |
| ATOM | 809 | CD1 | LEU | 93 | −8.049 | −11.471 | 6.794 | 0.00 | 0.00 |
| ATOM | 810 | CD2 | LEU | 93 | −9.743 | −10.260 | 8.187 | 0.00 | 0.00 |
| ATOM | 811 | C | LEU | 93 | −6.476 | −7.392 | 9.286 | 0.00 | 0.00 |
| ATOM | 812 | O | LEU | 93 | −6.534 | −7.605 | 10.495 | 0.00 | 0.00 |
| ATOM | 813 | N | LEU | 94 | −5.492 | −6.665 | 8.716 | 0.00 | 0.00 |
| ATOM | 814 | H | LEU | 94 | −5.499 | −6.553 | 7.712 | 0.00 | 0.00 |
| ATOM | 815 | CA | LEU | 94 | −4.451 | −5.952 | 9.457 | 0.00 | 0.00 |
| ATOM | 816 | CB | LEU | 94 | −3.480 | −5.226 | 8.501 | 0.00 | 0.00 |
| ATOM | 817 | CG | LEU | 94 | −2.353 | −4.352 | 9.118 | 0.00 | 0.00 |
| ATOM | 818 | CD1 | LEU | 94 | −1.439 | −3.925 | 7.963 | 0.00 | 0.00 |
| ATOM | 819 | CD2 | LEU | 94 | −2.778 | −3.049 | 9.821 | 0.00 | 0.00 |
| ATOM | 820 | C | LEU | 94 | −5.090 | −4.966 | 10.421 | 0.00 | 0.00 |
| ATOM | 821 | O | LEU | 94 | −4.900 | −5.085 | 11.631 | 0.00 | 0.00 |
| ATOM | 822 | N | LEU | 95 | −5.820 | −3.984 | 9.872 | 0.00 | 0.00 |
| ATOM | 823 | H | LEU | 95 | −5.919 | −3.951 | 8.867 | 0.00 | 0.00 |
| ATOM | 824 | CA | LEU | 95 | −6.449 | −2.929 | 10.650 | 0.00 | 0.00 |
| ATOM | 825 | CB | LEU | 95 | −7.031 | −1.860 | 9.702 | 0.00 | 0.00 |
| ATOM | 826 | CG | LEU | 95 | −8.254 | −2.255 | 8.847 | 0.00 | 0.00 |
| ATOM | 827 | CD1 | LEU | 95 | −9.593 | −1.964 | 9.540 | 0.00 | 0.00 |
| ATOM | 828 | CD2 | LEU | 95 | −8.260 | −1.499 | 7.512 | 0.00 | 0.00 |
| ATOM | 829 | C | LEU | 95 | −7.493 | −3.521 | 11.603 | 0.00 | 0.00 |
| ATOM | 830 | O | LEU | 95 | −7.759 | −2.920 | 12.628 | 0.00 | 0.00 |
| ATOM | 831 | N | ILE | 96 | −8.050 | −4.708 | 11.327 | 0.00 | 0.00 |
| ATOM | 832 | H | ILE | 96 | −7.793 | −5.180 | 10.472 | 0.00 | 0.00 |
| ATOM | 833 | CA | ILE | 96 | −9.022 | −5.369 | 12.197 | 0.00 | 0.00 |
| ATOM | 834 | CB | ILE | 96 | −9.920 | −6.295 | 11.322 | 0.00 | 0.00 |
| ATOM | 835 | CG2 | ILE | 96 | −10.612 | −7.453 | 12.070 | 0.00 | 0.00 |
| ATOM | 836 | CG1 | ILE | 96 | −10.979 | −5.416 | 10.613 | 0.00 | 0.00 |
| ATOM | 837 | CD1 | ILE | 96 | −11.868 | −6.145 | 9.597 | 0.00 | 0.00 |
| ATOM | 838 | C | ILE | 96 | −8.387 | −6.082 | 13.410 | 0.00 | 0.00 |
| ATOM | 839 | O | ILE | 96 | −9.102 | −6.439 | 14.344 | 0.00 | 0.00 |
| ATOM | 840 | N | SER | 97 | −7.059 | −6.234 | 13.455 | 0.00 | 0.00 |
| ATOM | 841 | H | SER | 97 | −6.507 | −5.963 | 12.651 | 0.00 | 0.00 |

-continued pdb file of the α3β4 nAChR model

| ATOM | 842 | CA | SER | 97 | −6.334 | −6.780 | 14.606 | 0.00 | 0.00 |
|---|---|---|---|---|---|---|---|---|---|
| ATOM | 843 | CB | SER | 97 | −5.760 | −8.160 | 14.256 | 0.00 | 0.00 |
| ATOM | 844 | OG | SER | 97 | −5.015 | −8.132 | 13.060 | 0.00 | 0.00 |
| ATOM | 845 | HG | SER | 97 | −4.783 | −9.033 | 12.822 | 0.00 | 0.00 |
| ATOM | 846 | C | SER | 97 | −5.306 | −5.798 | 15.185 | 0.00 | 0.00 |
| ATOM | 847 | O | SER | 97 | −4.693 | −6.100 | 16.208 | 0.00 | 0.00 |
| ATOM | 848 | N | LYS | 98 | −5.198 | −4.596 | 14.597 | 0.00 | 0.00 |
| ATOM | 849 | H | LYS | 98 | −5.681 | −4.458 | 13.721 | 0.00 | 0.00 |
| ATOM | 850 | CA | LYS | 98 | −4.651 | −3.399 | 15.233 | 0.00 | 0.00 |
| ATOM | 851 | CB | LYS | 98 | −3.647 | −2.714 | 14.287 | 0.00 | 0.00 |
| ATOM | 852 | CG | LYS | 98 | −2.211 | −3.185 | 14.574 | 0.00 | 0.00 |
| ATOM | 853 | CD | LYS | 98 | −1.468 | −2.332 | 15.616 | 0.00 | 0.00 |
| ATOM | 854 | CE | LYS | 98 | −2.219 | −2.091 | 16.926 | 0.00 | 0.00 |
| ATOM | 855 | NZ | LYS | 98 | −1.576 | −1.033 | 17.722 | 0.00 | 0.00 |
| ATOM | 856 | HZ1 | LYS | 98 | −1.606 | −0.172 | 17.188 | 0.00 | 0.00 |
| ATOM | 857 | HZ2 | LYS | 98 | −2.081 | −0.902 | 18.587 | 0.00 | 0.00 |
| ATOM | 858 | HZ3 | LYS | 98 | −0.617 | −1.281 | 17.915 | 0.00 | 0.00 |
| ATOM | 859 | C | LYS | 98 | −5.757 | −2.436 | 15.696 | 0.00 | 0.00 |
| ATOM | 860 | O | LYS | 98 | −5.464 | −1.551 | 16.499 | 0.00 | 0.00 |
| ATOM | 861 | N | ILE | 99 | −7.014 | −2.629 | 15.257 | 0.00 | 0.00 |
| ATOM | 862 | H | ILE | 99 | −7.181 | −3.351 | 14.572 | 0.00 | 0.00 |
| ATOM | 863 | CA | ILE | 99 | −8.183 | −1.910 | 15.761 | 0.00 | 0.00 |
| ATOM | 864 | CB | ILE | 99 | −8.578 | −0.611 | 14.993 | 0.00 | 0.00 |
| ATOM | 865 | CG2 | ILE | 99 | −7.440 | −0.024 | 14.128 | 0.00 | 0.00 |
| ATOM | 866 | CG1 | ILE | 99 | −9.986 | −0.568 | 14.330 | 0.00 | 0.00 |
| ATOM | 867 | CD1 | ILE | 99 | −10.151 | −1.102 | 12.907 | 0.00 | 0.00 |
| ATOM | 868 | C | ILE | 99 | −9.354 | −2.838 | 16.111 | 0.00 | 0.00 |
| ATOM | 869 | O | ILE | 99 | −9.812 | −2.824 | 17.253 | 0.00 | 0.00 |
| ATOM | 870 | N | NME | 100 | −9.856 | −3.612 | 15.142 | 0.00 | 0.00 |
| ATOM | 871 | H | NME | 100 | −9.425 | −3.578 | 14.228 | 0.00 | 0.00 |
| ATOM | 872 | CA | NME | 100 | −11.085 | −4.380 | 15.281 | 0.00 | 0.00 |
| TER | | | | | | | | | |
| ATOM | 873 | CA | ACE | 101 | 7.905 | −7.165 | −18.677 | 0.00 | 0.00 |
| ATOM | 874 | C | ACE | 101 | 7.125 | −7.203 | −17.370 | 0.00 | 0.00 |
| ATOM | 875 | O | ACE | 101 | 7.723 | −7.240 | −16.295 | 0.00 | 0.00 |
| ATOM | 876 | N | GLU | 102 | 5.788 | −7.211 | −17.481 | 0.00 | 0.00 |
| ATOM | 877 | H | GLU | 102 | 5.386 | −7.173 | −18.406 | 0.00 | 0.00 |
| ATOM | 878 | CA | GLU | 102 | 4.848 | −7.189 | −16.356 | 0.00 | 0.00 |
| ATOM | 879 | CB | GLU | 102 | 3.417 | −7.059 | −16.912 | 0.00 | 0.00 |
| ATOM | 880 | CG | GLU | 102 | 2.315 | −6.884 | −15.850 | 0.00 | 0.00 |
| ATOM | 881 | CD | GLU | 102 | 2.611 | −5.777 | −14.830 | 0.00 | 0.00 |
| ATOM | 882 | OE1 | GLU | 102 | 2.451 | −6.055 | −13.621 | 0.00 | 0.00 |
| ATOM | 883 | OE2 | GLU | 102 | 3.004 | −4.674 | −15.270 | 0.00 | 0.00 |
| ATOM | 884 | C | GLU | 102 | 4.997 | −8.397 | −15.412 | 0.00 | 0.00 |
| ATOM | 885 | O | GLU | 102 | 4.547 | −8.337 | −14.272 | 0.00 | 0.00 |
| ATOM | 886 | N | LYS | 103 | 5.656 | −9.477 | −15.853 | 0.00 | 0.00 |
| ATOM | 887 | H | LYS | 103 | 6.027 | −9.457 | −16.791 | 0.00 | 0.00 |
| ATOM | 888 | CA | LYS | 103 | 5.855 | −10.692 | −15.071 | 0.00 | 0.00 |
| ATOM | 889 | CB | LYS | 103 | 6.292 | −11.843 | −15.997 | 0.00 | 0.00 |
| ATOM | 890 | CG | LYS | 103 | 5.142 | −12.514 | −16.771 | 0.00 | 0.00 |
| ATOM | 891 | CD | LYS | 103 | 4.455 | −11.619 | −17.817 | 0.00 | 0.00 |
| ATOM | 892 | CE | LYS | 103 | 3.415 | −12.388 | −18.642 | 0.00 | 0.00 |
| ATOM | 893 | NZ | LYS | 103 | 4.035 | −13.385 | −19.536 | 0.00 | 0.00 |
| ATOM | 894 | HZ1 | LYS | 103 | 4.552 | −14.058 | −18.988 | 0.00 | 0.00 |
| ATOM | 895 | HZ2 | LYS | 103 | 3.316 | −13.863 | −20.062 | 0.00 | 0.00 |
| ATOM | 896 | HZ3 | LYS | 103 | 4.664 | −12.922 | −20.177 | 0.00 | 0.00 |
| ATOM | 897 | C | LYS | 103 | 6.870 | −10.507 | −13.939 | 0.00 | 0.00 |
| ATOM | 898 | O | LYS | 103 | 6.650 | −11.020 | −12.842 | 0.00 | 0.00 |
| ATOM | 899 | N | MET | 104 | 7.961 | −9.768 | −14.185 | 0.00 | 0.00 |
| ATOM | 900 | H | MET | 104 | 8.084 | −9.368 | −15.104 | 0.00 | 0.00 |
| ATOM | 901 | CA | MET | 104 | 8.896 | −9.366 | −13.138 | 0.00 | 0.00 |
| ATOM | 902 | CB | MET | 104 | 10.229 | −8.957 | −13.787 | 0.00 | 0.00 |
| ATOM | 903 | CG | MET | 104 | 11.329 | −8.633 | −12.766 | 0.00 | 0.00 |
| ATOM | 904 | SD | MET | 104 | 11.730 | −9.976 | −11.612 | 0.00 | 0.00 |
| ATOM | 905 | CE | MET | 104 | 13.090 | −9.197 | −10.705 | 0.00 | 0.00 |
| ATOM | 906 | C | MET | 104 | 8.305 | −8.224 | −12.304 | 0.00 | 0.00 |
| ATOM | 907 | O | MET | 104 | 8.615 | −8.137 | −11.120 | 0.00 | 0.00 |
| ATOM | 908 | N | THR | 105 | 7.436 | −7.383 | −12.888 | 0.00 | 0.00 |
| ATOM | 909 | H | THR | 105 | 7.231 | −7.492 | −13.872 | 0.00 | 0.00 |
| ATOM | 910 | CA | THR | 105 | 6.771 | −6.285 | −12.189 | 0.00 | 0.00 |
| ATOM | 911 | CB | THR | 105 | 5.997 | −5.394 | −13.179 | 0.00 | 0.00 |
| ATOM | 912 | CG2 | THR | 105 | 5.397 | −4.156 | −12.502 | 0.00 | 0.00 |
| ATOM | 913 | OG1 | THR | 105 | 6.855 | −4.945 | −14.208 | 0.00 | 0.00 |
| ATOM | 914 | HG1 | THR | 105 | 6.350 | −4.365 | −14.783 | 0.00 | 0.00 |
| ATOM | 915 | C | THR | 105 | 5.844 | −6.813 | −11.088 | 0.00 | 0.00 |
| ATOM | 916 | O | THR | 105 | 5.914 | −6.335 | −9.955 | 0.00 | 0.00 |
| ATOM | 917 | N | LEU | 106 | 4.997 | −7.805 | −11.402 | 0.00 | 0.00 |

-continued pdb file of the α3β4 nAChR model

| ATOM | 918 | H | LEU | 106 | 4.955 | −8.138 | −12.357 | 0.00 | 0.00 |
|---|---|---|---|---|---|---|---|---|---|
| ATOM | 919 | CA | LEU | 106 | 4.120 | −8.434 | −10.420 | 0.00 | 0.00 |
| ATOM | 920 | CB | LEU | 106 | 2.946 | −9.161 | −11.107 | 0.00 | 0.00 |
| ATOM | 921 | CG | LEU | 106 | 3.285 | −10.405 | −11.958 | 0.00 | 0.00 |
| ATOM | 922 | CD1 | LEU | 106 | 3.360 | −11.700 | −11.133 | 0.00 | 0.00 |
| ATOM | 923 | CD2 | LEU | 106 | 2.220 | −10.598 | −13.048 | 0.00 | 0.00 |
| ATOM | 924 | C | LEU | 106 | 4.886 | −9.297 | −9.415 | 0.00 | 0.00 |
| ATOM | 925 | O | LEU | 106 | 4.414 | −9.452 | −8.293 | 0.00 | 0.00 |
| ATOM | 926 | N | CYS | 107 | 6.076 | −9.802 | −9.775 | 0.00 | 0.00 |
| ATOM | 927 | H | CYS | 107 | 6.410 | −9.644 | −10.715 | 0.00 | 0.00 |
| ATOM | 928 | CA | CYS | 107 | 6.959 | −10.502 | −8.851 | 0.00 | 0.00 |
| ATOM | 929 | CB | CYS | 107 | 8.082 | −11.186 | −9.642 | 0.00 | 0.00 |
| ATOM | 930 | SG | CYS | 107 | 9.106 | −12.185 | −8.530 | 0.00 | 0.00 |
| ATOM | 931 | HG | CYS | 107 | 9.956 | −12.618 | −9.466 | 0.00 | 0.00 |
| ATOM | 932 | C | CYS | 107 | 7.514 | −9.531 | −7.807 | 0.00 | 0.00 |
| ATOM | 933 | O | CYS | 107 | 7.409 | −9.826 | −6.618 | 0.00 | 0.00 |
| ATOM | 934 | N | ILE | 108 | 8.071 | −8.379 | −8.226 | 0.00 | 0.00 |
| ATOM | 935 | H | ILE | 108 | 8.128 | −8.179 | −9.216 | 0.00 | 0.00 |
| ATOM | 936 | CA | ILE | 108 | 8.642 | −7.413 | −7.290 | 0.00 | 0.00 |
| ATOM | 937 | CB | ILE | 108 | 9.539 | −6.330 | −7.938 | 0.00 | 0.00 |
| ATOM | 938 | CG2 | ILE | 108 | 10.773 | −6.998 | −8.571 | 0.00 | 0.00 |
| ATOM | 939 | CG1 | ILE | 108 | 8.800 | −5.405 | −8.926 | 0.00 | 0.00 |
| ATOM | 940 | CD1 | ILE | 108 | 9.621 | −4.198 | −9.395 | 0.00 | 0.00 |
| ATOM | 941 | C | ILE | 108 | 7.585 | −6.825 | −6.352 | 0.00 | 0.00 |
| ATOM | 942 | O | ILE | 108 | 7.856 | −6.698 | −5.162 | 0.00 | 0.00 |
| ATOM | 943 | N | SER | 109 | 6.372 | −6.546 | −6.845 | 0.00 | 0.00 |
| ATOM | 944 | H | SER | 109 | 6.205 | −6.679 | −7.834 | 0.00 | 0.00 |
| ATOM | 945 | CA | SER | 109 | 5.265 | −6.074 | −6.021 | 0.00 | 0.00 |
| ATOM | 946 | CB | SER | 109 | 4.092 | −5.731 | −6.947 | 0.00 | 0.00 |
| ATOM | 947 | OG | SER | 109 | 3.028 | −5.162 | −6.216 | 0.00 | 0.00 |
| ATOM | 948 | HG | SER | 109 | 2.317 | −4.947 | −6.824 | 0.00 | 0.00 |
| ATOM | 949 | C | SER | 109 | 4.848 | −7.120 | −4.978 | 0.00 | 0.00 |
| ATOM | 950 | O | SER | 109 | 4.563 | −6.754 | −3.839 | 0.00 | 0.00 |
| ATOM | 951 | N | VAL | 110 | 4.849 | −8.412 | −5.349 | 0.00 | 0.00 |
| ATOM | 952 | H | VAL | 110 | 5.095 | −8.644 | −6.301 | 0.00 | 0.00 |
| ATOM | 953 | CA | VAL | 110 | 4.526 | −9.523 | −4.455 | 0.00 | 0.00 |
| ATOM | 954 | CB | VAL | 110 | 4.228 | −10.801 | −5.279 | 0.00 | 0.00 |
| ATOM | 955 | CG1 | VAL | 110 | 4.290 | −12.110 | −4.473 | 0.00 | 0.00 |
| ATOM | 956 | CG2 | VAL | 110 | 2.814 | −10.701 | −5.883 | 0.00 | 0.00 |
| ATOM | 957 | C | VAL | 110 | 5.595 | −9.736 | −3.370 | 0.00 | 0.00 |
| ATOM | 958 | O | VAL | 110 | 5.249 | −10.185 | −2.278 | 0.00 | 0.00 |
| ATOM | 959 | N | LEU | 111 | 6.864 | −9.373 | −3.610 | 0.00 | 0.00 |
| ATOM | 960 | H | LEU | 111 | 7.116 | −9.015 | −4.521 | 0.00 | 0.00 |
| ATOM | 961 | CA | LEU | 111 | 7.889 | −9.415 | −2.568 | 0.00 | 0.00 |
| ATOM | 962 | CB | LEU | 111 | 9.294 | −9.189 | −3.157 | 0.00 | 0.00 |
| ATOM | 963 | CG | LEU | 111 | 9.802 | −10.327 | −4.068 | 0.00 | 0.00 |
| ATOM | 964 | CD1 | LEU | 111 | 11.103 | −9.891 | −4.757 | 0.00 | 0.00 |
| ATOM | 965 | CD2 | LEU | 111 | 10.057 | −11.628 | −3.292 | 0.00 | 0.00 |
| ATOM | 966 | C | LEU | 111 | 7.591 | −8.396 | −1.466 | 0.00 | 0.00 |
| ATOM | 967 | O | LEU | 111 | 7.632 | −8.750 | −0.288 | 0.00 | 0.00 |
| ATOM | 968 | N | LEU | 112 | 7.252 | −7.156 | −1.847 | 0.00 | 0.00 |
| ATOM | 969 | H | LEU | 112 | 7.233 | −6.937 | −2.834 | 0.00 | 0.00 |
| ATOM | 970 | CA | LEU | 112 | 6.854 | −6.108 | −0.913 | 0.00 | 0.00 |
| ATOM | 971 | CB | LEU | 112 | 6.958 | −4.728 | −1.587 | 0.00 | 0.00 |
| ATOM | 972 | CG | LEU | 112 | 8.387 | −4.206 | −1.871 | 0.00 | 0.00 |
| ATOM | 973 | CD1 | LEU | 112 | 9.353 | −4.393 | −0.688 | 0.00 | 0.00 |
| ATOM | 974 | CD2 | LEU | 112 | 9.042 | −4.756 | −3.139 | 0.00 | 0.00 |
| ATOM | 975 | C | LEU | 112 | 5.460 | −6.346 | −0.311 | 0.00 | 0.00 |
| ATOM | 976 | O | LEU | 112 | 5.132 | −5.721 | 0.698 | 0.00 | 0.00 |
| ATOM | 977 | N | ALA | 113 | 4.666 | −7.274 | −0.866 | 0.00 | 0.00 |
| ATOM | 978 | H | ALA | 113 | 4.973 | −7.744 | −1.706 | 0.00 | 0.00 |
| ATOM | 979 | CA | ALA | 113 | 3.404 | −7.696 | −0.277 | 0.00 | 0.00 |
| ATOM | 980 | CB | ALA | 113 | 2.547 | −8.426 | −1.311 | 0.00 | 0.00 |
| ATOM | 981 | C | ALA | 113 | 3.618 | −8.559 | 0.969 | 0.00 | 0.00 |
| ATOM | 982 | O | ALA | 113 | 2.930 | −8.356 | 1.969 | 0.00 | 0.00 |
| ATOM | 983 | N | LEU | 114 | 4.583 | −9.491 | 0.927 | 0.00 | 0.00 |
| ATOM | 984 | H | LEU | 114 | 5.105 | −9.614 | 0.070 | 0.00 | 0.00 |
| ATOM | 985 | CA | LEU | 114 | 4.974 | −10.298 | 2.081 | 0.00 | 0.00 |
| ATOM | 986 | CB | LEU | 114 | 5.771 | −11.536 | 1.621 | 0.00 | 0.00 |
| ATOM | 987 | CG | LEU | 114 | 4.931 | −12.778 | 1.245 | 0.00 | 0.00 |
| ATOM | 988 | CD1 | LEU | 114 | 4.166 | −13.350 | 2.450 | 0.00 | 0.00 |
| ATOM | 989 | CD2 | LEU | 114 | 3.961 | −12.538 | 0.081 | 0.00 | 0.00 |
| ATOM | 990 | C | LEU | 114 | 5.779 | −9.482 | 3.103 | 0.00 | 0.00 |
| ATOM | 991 | O | LEU | 114 | 5.748 | −9.823 | 4.285 | 0.00 | 0.00 |
| ATOM | 992 | N | THR | 115 | 6.437 | −8.388 | 2.684 | 0.00 | 0.00 |
| ATOM | 993 | H | THR | 115 | 6.462 | −8.179 | 1.695 | 0.00 | 0.00 |
| ATOM | 994 | CA | THR | 115 | 7.061 | −7.429 | 3.597 | 0.00 | 0.00 |

-continued pdb file of the α3β4 nAChR model

| ATOM | 995 | CB | THR | 115 | 7.850 | −6.357 | 2.822 | 0.00 | 0.00 |
|------|-----|-----|-----|-----|-------|--------|-------|------|------|
| ATOM | 996 | CG2 | THR | 115 | 8.536 | −5.343 | 3.744 | 0.00 | 0.00 |
| ATOM | 997 | OG1 | THR | 115 | 8.856 | −6.976 | 2.049 | 0.00 | 0.00 |
| ATOM | 998 | HG1 | THR | 115 | 9.358 | −6.292 | 1.600 | 0.00 | 0.00 |
| ATOM | 999 | C | THR | 115 | 6.004 | −6.808 | 4.520 | 0.00 | 0.00 |
| ATOM | 1000 | O | THR | 115 | 6.203 | −6.724 | 5.732 | 0.00 | 0.00 |
| ATOM | 1001 | N | PHE | 116 | 4.865 | −6.420 | 3.937 | 0.00 | 0.00 |
| ATOM | 1002 | H | PHE | 116 | 4.787 | −6.534 | 2.935 | 0.00 | 0.00 |
| ATOM | 1003 | CA | PHE | 116 | 3.714 | −5.834 | 4.610 | 0.00 | 0.00 |
| ATOM | 1004 | CB | PHE | 116 | 2.906 | −5.115 | 3.515 | 0.00 | 0.00 |
| ATOM | 1005 | CG | PHE | 116 | 1.976 | −4.054 | 4.050 | 0.00 | 0.00 |
| ATOM | 1006 | CD1 | PHE | 116 | 2.473 | −2.763 | 4.304 | 0.00 | 0.00 |
| ATOM | 1007 | CE1 | PHE | 116 | 1.655 | −1.804 | 4.920 | 0.00 | 0.00 |
| ATOM | 1008 | CZ | PHE | 116 | 0.337 | −2.137 | 5.275 | 0.00 | 0.00 |
| ATOM | 1009 | CE2 | PHE | 116 | −0.178 | −3.405 | 4.957 | 0.00 | 0.00 |
| ATOM | 1010 | CD2 | PHE | 116 | 0.638 | −4.365 | 4.345 | 0.00 | 0.00 |
| ATOM | 1011 | C | PHE | 116 | 2.840 | −6.870 | 5.349 | 0.00 | 0.00 |
| ATOM | 1012 | O | PHE | 116 | 1.930 | −6.491 | 6.087 | 0.00 | 0.00 |
| ATOM | 1013 | N | PHE | 117 | 3.110 | −8.171 | 5.174 | 0.00 | 0.00 |
| ATOM | 1014 | H | PHE | 117 | 3.853 | −8.430 | 4.541 | 0.00 | 0.00 |
| ATOM | 1015 | CA | PHE | 117 | 2.400 | −9.253 | 5.851 | 0.00 | 0.00 |
| ATOM | 1016 | CB | PHE | 117 | 2.221 | −10.413 | 4.862 | 0.00 | 0.00 |
| ATOM | 1017 | CG | PHE | 117 | 1.273 | −11.497 | 5.337 | 0.00 | 0.00 |
| ATOM | 1018 | CD1 | PHE | 117 | 1.772 | −12.711 | 5.847 | 0.00 | 0.00 |
| ATOM | 1019 | CE1 | PHE | 117 | 0.881 | −13.709 | 6.281 | 0.00 | 0.00 |
| ATOM | 1020 | CZ | PHE | 117 | −0.507 | −13.495 | 6.215 | 0.00 | 0.00 |
| ATOM | 1021 | CE2 | PHE | 117 | −1.006 | −12.283 | 5.705 | 0.00 | 0.00 |
| ATOM | 1022 | CD2 | PHE | 117 | −0.117 | −11.289 | 5.264 | 0.00 | 0.00 |
| ATOM | 1023 | C | PHE | 117 | 3.141 | −9.726 | 7.108 | 0.00 | 0.00 |
| ATOM | 1024 | O | PHE | 117 | 2.504 | −10.191 | 8.048 | 0.00 | 0.00 |
| ATOM | 1025 | N | LEU | 118 | 4.470 | −9.571 | 7.159 | 0.00 | 0.00 |
| ATOM | 1026 | H | LEU | 118 | 4.952 | −9.227 | 6.340 | 0.00 | 0.00 |
| ATOM | 1027 | CA | LEU | 118 | 5.248 | −9.706 | 8.388 | 0.00 | 0.00 |
| ATOM | 1028 | CB | LEU | 118 | 6.733 | −9.887 | 8.025 | 0.00 | 0.00 |
| ATOM | 1029 | CG | LEU | 118 | 7.045 | −11.202 | 7.277 | 0.00 | 0.00 |
| ATOM | 1030 | CD1 | LEU | 118 | 8.486 | −11.161 | 6.750 | 0.00 | 0.00 |
| ATOM | 1031 | CD2 | LEU | 118 | 6.867 | −12.436 | 8.174 | 0.00 | 0.00 |
| ATOM | 1032 | C | LEU | 118 | 5.076 | −8.470 | 9.290 | 0.00 | 0.00 |
| ATOM | 1033 | O | LEU | 118 | 5.266 | −8.568 | 10.503 | 0.00 | 0.00 |
| ATOM | 1034 | N | LEU | 119 | 4.684 | −7.327 | 8.702 | 0.00 | 0.00 |
| ATOM | 1035 | H | LEU | 119 | 4.577 | −7.325 | 7.698 | 0.00 | 0.00 |
| ATOM | 1036 | CA | LEU | 119 | 4.344 | −6.095 | 9.399 | 0.00 | 0.00 |
| ATOM | 1037 | CB | LEU | 119 | 4.091 | −4.980 | 8.368 | 0.00 | 0.00 |
| ATOM | 1038 | CG | LEU | 119 | 3.542 | −3.613 | 8.849 | 0.00 | 0.00 |
| ATOM | 1039 | CD1 | LEU | 119 | 3.637 | −2.659 | 7.650 | 0.00 | 0.00 |
| ATOM | 1040 | CD2 | LEU | 119 | 2.071 | −3.607 | 9.296 | 0.00 | 0.00 |
| ATOM | 1041 | C | LEU | 119 | 3.168 | −6.312 | 10.329 | 0.00 | 0.00 |
| ATOM | 1042 | O | LEU | 119 | 3.315 | −6.088 | 11.531 | 0.00 | 0.00 |
| ATOM | 1043 | N | LEU | 120 | 2.020 | −6.742 | 9.780 | 0.00 | 0.00 |
| ATOM | 1044 | H | LEU | 120 | 1.965 | −6.893 | 8.783 | 0.00 | 0.00 |
| ATOM | 1045 | CA | LEU | 120 | 0.847 | −7.006 | 10.594 | 0.00 | 0.00 |
| ATOM | 1046 | CB | LEU | 120 | −0.389 | −7.303 | 9.718 | 0.00 | 0.00 |
| ATOM | 1047 | CG | LEU | 120 | −0.420 | −8.605 | 8.891 | 0.00 | 0.00 |
| ATOM | 1048 | CD1 | LEU | 120 | −1.031 | −9.789 | 9.656 | 0.00 | 0.00 |
| ATOM | 1049 | CD2 | LEU | 120 | −1.238 | −8.408 | 7.606 | 0.00 | 0.00 |
| ATOM | 1050 | C | LEU | 120 | 1.196 | −8.082 | 11.617 | 0.00 | 0.00 |
| ATOM | 1051 | O | LEU | 120 | 0.868 | −7.887 | 12.770 | 0.00 | 0.00 |
| ATOM | 1052 | N | ILE | 121 | 1.952 | −9.132 | 11.261 | 0.00 | 0.00 |
| ATOM | 1053 | H | ILE | 121 | 2.237 | −9.221 | 10.296 | 0.00 | 0.00 |
| ATOM | 1054 | CA | ILE | 121 | 2.309 | −10.226 | 12.171 | 0.00 | 0.00 |
| ATOM | 1055 | CB | ILE | 121 | 3.044 | −11.338 | 11.371 | 0.00 | 0.00 |
| ATOM | 1056 | CG2 | ILE | 121 | 3.910 | −12.280 | 12.235 | 0.00 | 0.00 |
| ATOM | 1057 | CG1 | ILE | 121 | 1.996 | −12.159 | 10.582 | 0.00 | 0.00 |
| ATOM | 1058 | CD1 | ILE | 121 | 2.583 | −13.151 | 9.570 | 0.00 | 0.00 |
| ATOM | 1059 | C | ILE | 121 | 3.063 | −9.794 | 13.437 | 0.00 | 0.00 |
| ATOM | 1060 | O | ILE | 121 | 2.951 | −10.474 | 14.455 | 0.00 | 0.00 |
| ATOM | 1061 | N | SER | 122 | 3.779 | −8.666 | 13.408 | 0.00 | 0.00 |
| ATOM | 1062 | H | SER | 122 | 3.814 | −8.140 | 12.545 | 0.00 | 0.00 |
| ATOM | 1063 | CA | SER | 122 | 4.547 | −8.154 | 14.544 | 0.00 | 0.00 |
| ATOM | 1064 | CB | SER | 122 | 5.983 | −7.919 | 14.082 | 0.00 | 0.00 |
| ATOM | 1065 | OG | SER | 122 | 6.054 | −6.966 | 13.038 | 0.00 | 0.00 |
| ATOM | 1066 | HG | SER | 122 | 5.710 | −7.367 | 12.233 | 0.00 | 0.00 |
| ATOM | 1067 | C | SER | 122 | 3.910 | −6.923 | 15.201 | 0.00 | 0.00 |
| ATOM | 1068 | O | SER | 122 | 4.356 | −6.504 | 16.269 | 0.00 | 0.00 |
| ATOM | 1069 | N | LYS | 123 | 2.824 | −6.407 | 14.610 | 0.00 | 0.00 |
| ATOM | 1070 | H | LYS | 123 | 2.554 | −6.785 | 13.712 | 0.00 | 0.00 |
| ATOM | 1071 | CA | LYS | 123 | 1.865 | −5.507 | 15.238 | 0.00 | 0.00 |

| | pdb file of the α3β4 nAChR model | | | | | | | |
|---|---|---|---|---|---|---|---|---|
| | | | | -continued | | | | |
| ATOM | 1072 | CB | LYS | 123 | 1.524 | −4.373 | 14.258 | 0.00 | 0.00 |
| ATOM | 1073 | CG | LYS | 123 | 2.444 | −3.153 | 14.412 | 0.00 | 0.00 |
| ATOM | 1074 | CD | LYS | 123 | 2.457 | −2.557 | 15.837 | 0.00 | 0.00 |
| ATOM | 1075 | CE | LYS | 123 | 3.740 | −2.934 | 16.588 | 0.00 | 0.00 |
| ATOM | 1076 | NZ | LYS | 123 | 3.804 | −2.279 | 17.906 | 0.00 | 0.00 |
| ATOM | 1077 | HZ1 | LYS | 123 | 3.039 | −2.591 | 18.485 | 0.00 | 0.00 |
| ATOM | 1078 | HZ2 | LYS | 123 | 4.684 | −2.505 | 18.349 | 0.00 | 0.00 |
| ATOM | 1079 | HZ3 | LYS | 123 | 3.755 | −1.276 | 17.784 | 0.00 | 0.00 |
| ATOM | 1080 | C | LYS | 123 | 0.606 | −6.239 | 15.731 | 0.00 | 0.00 |
| ATOM | 1081 | O | LYS | 123 | −0.209 | −5.615 | 16.411 | 0.00 | 0.00 |
| ATOM | 1082 | N | ILE | 124 | 0.460 | −7.540 | 15.426 | 0.00 | 0.00 |
| ATOM | 1083 | H | ILE | 124 | 1.160 | −7.964 | 14.834 | 0.00 | 0.00 |
| ATOM | 1084 | CA | ILE | 124 | −0.713 | −8.357 | 15.735 | 0.00 | 0.00 |
| ATOM | 1085 | CB | ILE | 124 | −1.737 | −8.470 | 14.570 | 0.00 | 0.00 |
| ATOM | 1086 | CG2 | ILE | 124 | −2.030 | −7.099 | 13.925 | 0.00 | 0.00 |
| ATOM | 1087 | CG1 | ILE | 124 | −1.402 | −9.547 | 13.510 | 0.00 | 0.00 |
| ATOM | 1088 | CD1 | ILE | 124 | −2.384 | −10.723 | 13.496 | 0.00 | 0.00 |
| ATOM | 1089 | C | ILE | 124 | −0.378 | −9.710 | 16.388 | 0.00 | 0.00 |
| ATOM | 1090 | O | ILE | 124 | −1.293 | −10.446 | 16.758 | 0.00 | 0.00 |
| ATOM | 1091 | N | NME | 125 | 0.912 | −10.026 | 16.573 | 0.00 | 0.00 |
| ATOM | 1092 | H | NME | 125 | 1.620 | −9.385 | 16.248 | 0.00 | 0.00 |
| ATOM | 1093 | CA | NME | 125 | 1.375 | −11.257 | 17.196 | 0.00 | 0.00 |
| TER | | | | | | | | | |
| END | | | | | | | | | |

Appendix 5: Atomic Coordinates of the Luminal Channel of a α3β2 nAChR Ion Channel

| | pdb file of the α3β2 model | | | | | | | |
|---|---|---|---|---|---|---|---|---|
| REMARK | File generated by Swiss-PdbViewer 3.70b0 | | | | | | | |
| ATOM | 1 | N | GLU | 2 | 8.656 | 3.377 | −17.484 | 0.00 | 0.00 |
| ATOM | 2 | CA | GLU | 2 | 8.345 | 2.482 | −16.365 | 0.00 | 0.00 |
| ATOM | 3 | C | GLU | 2 | 9.541 | 2.246 | −15.422 | 0.00 | 0.00 |
| ATOM | 4 | O | GLU | 2 | 9.344 | 1.832 | −14.284 | 0.00 | 0.00 |
| ATOM | 5 | CB | GLU | 2 | 7.781 | 1.164 | −16.930 | 0.00 | 0.00 |
| ATOM | 6 | CG | GLU | 2 | 7.274 | 0.164 | −15.874 | 0.00 | 0.00 |
| ATOM | 7 | CD | GLU | 2 | 6.311 | 0.782 | −14.852 | 0.00 | 0.00 |
| ATOM | 8 | OE1 | GLU | 2 | 6.525 | 0.540 | −13.643 | 0.00 | 0.00 |
| ATOM | 9 | OE2 | GLU | 2 | 5.381 | 1.495 | −15.291 | 0.00 | 0.00 |
| ATOM | 10 | H | GLU | 2 | 8.496 | 3.014 | −18.412 | 1.00 | 99.99 |
| ATOM | 11 | N | LYS | 3 | 10.771 | 2.539 | −15.863 | 0.00 | 0.00 |
| ATOM | 12 | CA | LYS | 3 | 11.990 | 2.351 | −15.083 | 0.00 | 0.00 |
| ATOM | 13 | C | LYS | 3 | 12.132 | 3.373 | −13.949 | 0.00 | 0.00 |
| ATOM | 14 | O | LYS | 3 | 12.566 | 3.010 | −12.857 | 0.00 | 0.00 |
| ATOM | 15 | CB | LYS | 3 | 13.218 | 2.415 | −16.010 | 0.00 | 0.00 |
| ATOM | 16 | CG | LYS | 3 | 13.496 | 1.120 | −16.797 | 0.00 | 0.00 |
| ATOM | 17 | CD | LYS | 3 | 12.434 | 0.760 | −17.851 | 0.00 | 0.00 |
| ATOM | 18 | CE | LYS | 3 | 12.843 | −0.456 | −18.690 | 0.00 | 0.00 |
| ATOM | 19 | NZ | LYS | 3 | 13.984 | −0.166 | −19.580 | 0.00 | 0.00 |
| ATOM | 20 | H | LYS | 3 | 10.867 | 2.901 | −16.800 | 1.00 | 99.99 |
| ATOM | 21 | HZ1 | LYS | 3 | 14.784 | 0.109 | −19.027 | 1.00 | 99.99 |
| ATOM | 22 | HZ2 | LYS | 3 | 14.216 | −0.990 | −20.116 | 1.00 | 99.99 |
| ATOM | 23 | HZ3 | LYS | 3 | 13.741 | 0.585 | −20.211 | 1.00 | 99.99 |
| ATOM | 24 | N | VAL | 4 | 11.753 | 4.634 | −14.194 | 0.00 | 0.00 |
| ATOM | 25 | CA | VAL | 4 | 11.662 | 5.664 | −13.159 | 0.00 | 0.00 |
| ATOM | 26 | C | VAL | 4 | 10.413 | 5.416 | −12.307 | 0.00 | 0.00 |
| ATOM | 27 | O | VAL | 4 | 10.455 | 5.677 | −11.110 | 0.00 | 0.00 |
| ATOM | 28 | CB | VAL | 4 | 11.627 | 7.065 | −13.814 | 0.00 | 0.00 |
| ATOM | 29 | CG1 | VAL | 4 | 11.499 | 8.186 | −12.768 | 0.00 | 0.00 |
| ATOM | 30 | CG2 | VAL | 4 | 12.901 | 7.325 | −14.639 | 0.00 | 0.00 |
| ATOM | 31 | H | VAL | 4 | 11.400 | 4.864 | −15.112 | 1.00 | 99.99 |
| ATOM | 32 | N | THR | 5 | 9.329 | 4.884 | −12.897 | 0.00 | 0.00 |
| ATOM | 33 | CA | THR | 5 | 8.083 | 4.583 | −12.195 | 0.00 | 0.00 |
| ATOM | 34 | C | THR | 5 | 8.300 | 3.535 | −11.096 | 0.00 | 0.00 |
| ATOM | 35 | O | THR | 5 | 7.868 | 3.747 | −9.963 | 0.00 | 0.00 |
| ATOM | 36 | CB | THR | 5 | 6.994 | 4.125 | −13.184 | 0.00 | 0.00 |
| ATOM | 37 | OG1 | THR | 5 | 6.830 | 5.082 | −14.210 | 0.00 | 0.00 |
| ATOM | 38 | CG2 | THR | 5 | 5.633 | 3.934 | −12.505 | 0.00 | 0.00 |
| ATOM | 39 | H | THR | 5 | 9.350 | 4.704 | −13.891 | 1.00 | 99.99 |
| ATOM | 40 | HG1 | THR | 5 | 6.121 | 4.783 | −14.784 | 1.00 | 99.99 |

-continued pdb file of the α3β2 model

| | | | | | | | | |
|---|---|---|---|---|---|---|---|---|
| ATOM | 41 | N | LEU | 6 | 8.984 | 2.425 | −11.414 | 0.00 | 0.00 |
| ATOM | 42 | CA | LEU | 6 | 9.311 | 1.394 | −10.436 | 0.00 | 0.00 |
| ATOM | 43 | C | LEU | 6 | 10.367 | 1.852 | −9.428 | 0.00 | 0.00 |
| ATOM | 44 | O | LEU | 6 | 10.366 | 1.351 | −8.308 | 0.00 | 0.00 |
| ATOM | 45 | CB | LEU | 6 | 9.642 | 0.056 | −11.127 | 0.00 | 0.00 |
| ATOM | 46 | CG | LEU | 6 | 10.932 | −0.001 | −11.976 | 0.00 | 0.00 |
| ATOM | 47 | CD1 | LEU | 6 | 12.185 | −0.332 | −11.150 | 0.00 | 0.00 |
| ATOM | 48 | CD2 | LEU | 6 | 10.789 | −1.070 | −13.070 | 0.00 | 0.00 |
| ATOM | 49 | H | LEU | 6 | 9.287 | 2.286 | −12.369 | 1.00 | 99.99 |
| ATOM | 50 | N | CYS | 7 | 11.216 | 2.830 | −9.782 | 0.00 | 0.00 |
| ATOM | 51 | CA | CYS | 7 | 12.155 | 3.443 | −8.852 | 0.00 | 0.00 |
| ATOM | 52 | C | CYS | 7 | 11.403 | 4.271 | −7.805 | 0.00 | 0.00 |
| ATOM | 53 | O | CYS | 7 | 11.653 | 4.083 | −6.616 | 0.00 | 0.00 |
| ATOM | 54 | CB | CYS | 7 | 13.169 | 4.290 | −9.630 | 0.00 | 0.00 |
| ATOM | 55 | SG | CYS | 7 | 14.449 | 4.908 | −8.504 | 0.00 | 0.00 |
| ATOM | 56 | H | CYS | 7 | 11.170 | 3.204 | −10.719 | 1.00 | 99.99 |
| ATOM | 57 | HG | CYS | 7 | 15.153 | 5.565 | −9.430 | 1.00 | 99.99 |
| ATOM | 58 | N | ILE | 8 | 10.477 | 5.155 | −8.222 | 0.00 | 0.00 |
| ATOM | 59 | CA | ILE | 8 | 9.741 | 6.010 | −7.292 | 0.00 | 0.00 |
| ATOM | 60 | C | ILE | 8 | 8.822 | 5.213 | −6.360 | 0.00 | 0.00 |
| ATOM | 61 | O | ILE | 8 | 8.715 | 5.561 | −5.187 | 0.00 | 0.00 |
| ATOM | 62 | CB | ILE | 8 | 9.018 | 7.206 | −7.957 | 0.00 | 0.00 |
| ATOM | 63 | CG1 | ILE | 8 | 7.912 | 6.794 | −8.950 | 0.00 | 0.00 |
| ATOM | 64 | CG2 | ILE | 8 | 10.056 | 8.149 | −8.595 | 0.00 | 0.00 |
| ATOM | 65 | CD1 | ILE | 8 | 7.033 | 7.955 | −9.431 | 0.00 | 0.00 |
| ATOM | 66 | H | ILE | 8 | 10.302 | 5.265 | −9.212 | 1.00 | 99.99 |
| ATOM | 67 | N | SER | 9 | 8.223 | 4.116 | −6.842 | 0.00 | 0.00 |
| ATOM | 68 | CA | SER | 9 | 7.430 | 3.207 | −6.022 | 0.00 | 0.00 |
| ATOM | 69 | C | SER | 9 | 8.299 | 2.487 | −4.981 | 0.00 | 0.00 |
| ATOM | 70 | O | SER | 9 | 7.865 | 2.322 | −3.841 | 0.00 | 0.00 |
| ATOM | 71 | CB | SER | 9 | 6.746 | 2.198 | −6.952 | 0.00 | 0.00 |
| ATOM | 72 | OG | SER | 9 | 5.880 | 1.355 | −6.222 | 0.00 | 0.00 |
| ATOM | 73 | H | SER | 9 | 8.348 | 3.884 | −7.819 | 1.00 | 99.99 |
| ATOM | 74 | HG | SER | 9 | 5.455 | 0.749 | −6.834 | 1.00 | 99.99 |
| ATOM | 75 | N | VAL | 10 | 9.527 | 2.092 | −5.355 | 0.00 | 0.00 |
| ATOM | 76 | CA | VAL | 10 | 10.488 | 1.439 | −4.467 | 0.00 | 0.00 |
| ATOM | 77 | C | VAL | 10 | 11.045 | 2.397 | −3.397 | 0.00 | 0.00 |
| ATOM | 78 | O | VAL | 10 | 11.425 | 1.934 | −2.323 | 0.00 | 0.00 |
| ATOM | 79 | CB | VAL | 10 | 11.590 | 0.739 | −5.301 | 0.00 | 0.00 |
| ATOM | 80 | CG1 | VAL | 10 | 12.857 | 0.370 | −4.510 | 0.00 | 0.00 |
| ATOM | 81 | CG2 | VAL | 10 | 11.028 | −0.564 | −5.898 | 0.00 | 0.00 |
| ATOM | 82 | H | VAL | 10 | 9.822 | 2.259 | −6.308 | 1.00 | 99.99 |
| ATOM | 83 | N | LEU | 11 | 11.046 | 3.718 | −3.626 | 0.00 | 0.00 |
| ATOM | 84 | CA | LEU | 11 | 11.403 | 4.680 | −2.585 | 0.00 | 0.00 |
| ATOM | 85 | C | LEU | 11 | 10.331 | 4.735 | −1.493 | 0.00 | 0.00 |
| ATOM | 86 | O | LEU | 11 | 10.673 | 4.708 | −0.310 | 0.00 | 0.00 |
| ATOM | 87 | CB | LEU | 11 | 11.629 | 6.081 | −3.186 | 0.00 | 0.00 |
| ATOM | 88 | CG | LEU | 11 | 12.881 | 6.204 | −4.080 | 0.00 | 0.00 |
| ATOM | 89 | CD1 | LEU | 11 | 12.881 | 7.571 | −4.779 | 0.00 | 0.00 |
| ATOM | 90 | CD2 | LEU | 11 | 14.187 | 6.047 | −3.287 | 0.00 | 0.00 |
| ATOM | 91 | H | LEU | 11 | 10.741 | 4.069 | −4.523 | 1.00 | 99.99 |
| ATOM | 92 | N | LEU | 12 | 9.046 | 4.773 | −1.879 | 0.00 | 0.00 |
| ATOM | 93 | CA | LEU | 12 | 7.933 | 4.712 | −0.936 | 0.00 | 0.00 |
| ATOM | 94 | C | LEU | 12 | 7.813 | 3.333 | −0.273 | 0.00 | 0.00 |
| ATOM | 95 | O | LEU | 12 | 7.270 | 3.253 | 0.827 | 0.00 | 0.00 |
| ATOM | 96 | CB | LEU | 12 | 6.609 | 5.114 | −1.618 | 0.00 | 0.00 |
| ATOM | 97 | CG | LEU | 12 | 6.349 | 6.629 | −1.800 | 0.00 | 0.00 |
| ATOM | 98 | CD1 | LEU | 12 | 6.475 | 7.424 | −0.490 | 0.00 | 0.00 |
| ATOM | 99 | CD2 | LEU | 12 | 7.205 | 7.290 | −2.885 | 0.00 | 0.00 |
| ATOM | 100 | H | LEU | 12 | 8.829 | 4.798 | −2.866 | 1.00 | 99.99 |
| ATOM | 101 | N | SER | 13 | 8.359 | 2.271 | −0.884 | 0.00 | 0.00 |
| ATOM | 102 | CA | SER | 13 | 8.421 | 0.946 | −0.280 | 0.00 | 0.00 |
| ATOM | 103 | C | SER | 13 | 9.273 | 0.950 | 0.990 | 0.00 | 0.00 |
| ATOM | 104 | O | SER | 13 | 8.819 | 0.466 | 2.026 | 0.00 | 0.00 |
| ATOM | 105 | CB | SER | 13 | 8.951 | −0.077 | −1.282 | 0.00 | 0.00 |
| ATOM | 106 | OG | SER | 13 | 9.099 | −1.310 | −0.623 | 0.00 | 0.00 |
| ATOM | 107 | H | SER | 13 | 8.775 | 2.394 | −1.797 | 1.00 | 99.99 |
| ATOM | 108 | HG | SER | 13 | 9.427 | −1.956 | −1.252 | 1.00 | 99.99 |
| ATOM | 109 | N | LEU | 14 | 10.492 | 1.503 | 0.918 | 0.00 | 0.00 |
| ATOM | 110 | CA | LEU | 14 | 11.374 | 1.623 | 2.074 | 0.00 | 0.00 |
| ATOM | 111 | C | LEU | 14 | 10.837 | 2.631 | 3.101 | 0.00 | 0.00 |
| ATOM | 112 | O | LEU | 14 | 11.157 | 2.497 | 4.282 | 0.00 | 0.00 |
| ATOM | 113 | CB | LEU | 14 | 12.797 | 2.007 | 1.620 | 0.00 | 0.00 |
| ATOM | 114 | CG | LEU | 14 | 13.726 | 0.831 | 1.239 | 0.00 | 0.00 |
| ATOM | 115 | CD1 | LEU | 14 | 14.038 | −0.075 | 2.441 | 0.00 | 0.00 |
| ATOM | 116 | CD2 | LEU | 14 | 13.201 | −0.019 | 0.073 | 0.00 | 0.00 |
| ATOM | 117 | H | LEU | 14 | 10.813 | 1.877 | 0.035 | 1.00 | 99.99 |

-continued pdb file of the α3β2 model

| ATOM | 118 | N | THR | 15 | 9.988 | 3.588 | 2.690 | 0.00 | 0.00 |
|---|---|---|---|---|---|---|---|---|---|
| ATOM | 119 | CA | THR | 15 | 9.285 | 4.477 | 3.614 | 0.00 | 0.00 |
| ATOM | 120 | C | THR | 15 | 8.292 | 3.705 | 4.503 | 0.00 | 0.00 |
| ATOM | 121 | O | THR | 15 | 8.154 | 4.016 | 5.685 | 0.00 | 0.00 |
| ATOM | 122 | CB | THR | 15 | 8.678 | 5.685 | 2.862 | 0.00 | 0.00 |
| ATOM | 123 | OG1 | THR | 15 | 9.358 | 6.857 | 3.261 | 0.00 | 0.00 |
| ATOM | 124 | CG2 | THR | 15 | 7.178 | 5.937 | 3.069 | 0.00 | 0.00 |
| ATOM | 125 | H | THR | 15 | 9.772 | 3.661 | 1.705 | 1.00 | 99.99 |
| ATOM | 126 | HG1 | THR | 15 | 9.005 | 7.597 | 2.762 | 1.00 | 99.99 |
| ATOM | 127 | N | VAL | 16 | 7.654 | 2.667 | 3.948 | 0.00 | 0.00 |
| ATOM | 128 | CA | VAL | 16 | 6.734 | 1.752 | 4.625 | 0.00 | 0.00 |
| ATOM | 129 | C | VAL | 16 | 7.478 | 0.592 | 5.321 | 0.00 | 0.00 |
| ATOM | 130 | O | VAL | 16 | 6.869 | −0.166 | 6.077 | 0.00 | 0.00 |
| ATOM | 131 | CB | VAL | 16 | 5.717 | 1.249 | 3.563 | 0.00 | 0.00 |
| ATOM | 132 | CG1 | VAL | 16 | 4.800 | 0.106 | 4.030 | 0.00 | 0.00 |
| ATOM | 133 | CG2 | VAL | 16 | 4.835 | 2.427 | 3.122 | 0.00 | 0.00 |
| ATOM | 134 | H | VAL | 16 | 7.830 | 2.479 | 2.969 | 1.00 | 99.99 |
| ATOM | 135 | N | PHE | 17 | 8.795 | 0.456 | 5.118 | 0.00 | 0.00 |
| ATOM | 136 | CA | PHE | 17 | 9.611 | −0.530 | 5.817 | 0.00 | 0.00 |
| ATOM | 137 | C | PHE | 17 | 10.230 | 0.041 | 7.098 | 0.00 | 0.00 |
| ATOM | 138 | O | PHE | 17 | 10.403 | −0.691 | 8.068 | 0.00 | 0.00 |
| ATOM | 139 | CB | PHE | 17 | 10.708 | −1.033 | 4.870 | 0.00 | 0.00 |
| ATOM | 140 | CG | PHE | 17 | 11.522 | −2.193 | 5.415 | 0.00 | 0.00 |
| ATOM | 141 | CD1 | PHE | 17 | 12.914 | −2.068 | 5.585 | 0.00 | 0.00 |
| ATOM | 142 | CD2 | PHE | 17 | 10.886 | −3.405 | 5.750 | 0.00 | 0.00 |
| ATOM | 143 | CE1 | PHE | 17 | 13.666 | −3.150 | 6.076 | 0.00 | 0.00 |
| ATOM | 144 | CE2 | PHE | 17 | 11.637 | −4.484 | 6.249 | 0.00 | 0.00 |
| ATOM | 145 | CZ | PHE | 17 | 13.028 | −4.358 | 6.409 | 0.00 | 0.00 |
| ATOM | 146 | H | PHE | 17 | 9.260 | 1.083 | 4.476 | 1.00 | 99.99 |
| ATOM | 147 | N | LEU | 18 | 10.526 | 1.346 | 7.130 | 0.00 | 0.00 |
| ATOM | 148 | CA | LEU | 18 | 10.896 | 2.050 | 8.354 | 0.00 | 0.00 |
| ATOM | 149 | C | LEU | 18 | 9.673 | 2.268 | 9.259 | 0.00 | 0.00 |
| ATOM | 150 | O | LEU | 18 | 9.849 | 2.384 | 10.469 | 0.00 | 0.00 |
| ATOM | 151 | CB | LEU | 18 | 11.530 | 3.403 | 7.987 | 0.00 | 0.00 |
| ATOM | 152 | CG | LEU | 18 | 12.879 | 3.286 | 7.245 | 0.00 | 0.00 |
| ATOM | 153 | CD1 | LEU | 18 | 13.301 | 4.670 | 6.731 | 0.00 | 0.00 |
| ATOM | 154 | CD2 | LEU | 18 | 13.990 | 2.715 | 8.140 | 0.00 | 0.00 |
| ATOM | 155 | H | LEU | 18 | 10.403 | 1.897 | 6.291 | 1.00 | 99.99 |
| ATOM | 156 | N | LEU | 19 | 8.455 | 2.272 | 8.688 | 0.00 | 0.00 |
| ATOM | 157 | CA | LEU | 19 | 7.175 | 2.286 | 9.391 | 0.00 | 0.00 |
| ATOM | 158 | C | LEU | 19 | 7.100 | 1.105 | 10.352 | 0.00 | 0.00 |
| ATOM | 159 | O | LEU | 19 | 7.062 | 1.310 | 11.560 | 0.00 | 0.00 |
| ATOM | 160 | CB | LEU | 19 | 6.037 | 2.266 | 8.350 | 0.00 | 0.00 |
| ATOM | 161 | CG | LEU | 19 | 4.564 | 2.181 | 8.822 | 0.00 | 0.00 |
| ATOM | 162 | CD1 | LEU | 19 | 3.673 | 2.526 | 7.617 | 0.00 | 0.00 |
| ATOM | 163 | CD2 | LEU | 19 | 4.122 | 0.794 | 9.310 | 0.00 | 0.00 |
| ATOM | 164 | H | LEU | 19 | 8.412 | 2.195 | 7.682 | 1.00 | 99.99 |
| ATOM | 165 | N | VAL | 20 | 7.099 | −0.124 | 9.817 | 0.00 | 0.00 |
| ATOM | 166 | CA | VAL | 20 | 7.026 | −1.355 | 10.600 | 0.00 | 0.00 |
| ATOM | 167 | C | VAL | 20 | 8.206 | −1.469 | 11.574 | 0.00 | 0.00 |
| ATOM | 168 | O | VAL | 20 | 8.066 | −2.124 | 12.595 | 0.00 | 0.00 |
| ATOM | 169 | CB | VAL | 20 | 6.989 | −2.580 | 9.653 | 0.00 | 0.00 |
| ATOM | 170 | CG1 | VAL | 20 | 8.119 | −2.645 | 8.621 | 0.00 | 0.00 |
| ATOM | 171 | CG2 | VAL | 20 | 6.980 | −3.921 | 10.402 | 0.00 | 0.00 |
| ATOM | 172 | H | VAL | 20 | 7.136 | −0.212 | 8.812 | 1.00 | 99.99 |
| ATOM | 173 | N | ILE | 21 | 9.352 | −0.836 | 11.298 | 0.00 | 0.00 |
| ATOM | 174 | CA | ILE | 21 | 10.528 | −0.887 | 12.162 | 0.00 | 0.00 |
| ATOM | 175 | C | ILE | 21 | 10.424 | 0.026 | 13.399 | 0.00 | 0.00 |
| ATOM | 176 | O | ILE | 21 | 11.224 | −0.096 | 14.325 | 0.00 | 0.00 |
| ATOM | 177 | CB | ILE | 21 | 11.791 | −0.637 | 11.286 | 0.00 | 0.00 |
| ATOM | 178 | CG1 | ILE | 21 | 12.131 | −1.951 | 10.542 | 0.00 | 0.00 |
| ATOM | 179 | CG2 | ILE | 21 | 13.035 | −0.126 | 12.041 | 0.00 | 0.00 |
| ATOM | 180 | CD1 | ILE | 21 | 13.210 | −1.823 | 9.459 | 0.00 | 0.00 |
| ATOM | 181 | H | ILE | 21 | 9.423 | −0.304 | 10.442 | 1.00 | 99.99 |
| ATOM | 182 | N | THR | 22 | 9.416 | 0.897 | 13.457 | 0.00 | 0.00 |
| ATOM | 183 | CA | THR | 22 | 9.194 | 1.847 | 14.547 | 0.00 | 0.00 |
| ATOM | 184 | C | THR | 22 | 7.815 | 1.661 | 15.193 | 0.00 | 0.00 |
| ATOM | 185 | O | THR | 22 | 7.609 | 2.107 | 16.321 | 0.00 | 0.00 |
| ATOM | 186 | CB | THR | 22 | 9.414 | 3.264 | 14.009 | 0.00 | 0.00 |
| ATOM | 187 | OG1 | THR | 22 | 8.581 | 3.498 | 12.893 | 0.00 | 0.00 |
| ATOM | 188 | CG2 | THR | 22 | 10.872 | 3.533 | 13.616 | 0.00 | 0.00 |
| ATOM | 189 | H | THR | 22 | 8.797 | 0.973 | 12.660 | 1.00 | 99.99 |
| ATOM | 190 | HG1 | THR | 22 | 8.828 | 4.336 | 12.498 | 1.00 | 99.99 |
| ATOM | 191 | N | GLU | 23 | 6.921 | 0.913 | 14.532 | 0.00 | 0.00 |
| ATOM | 192 | CA | GLU | 23 | 5.869 | 0.133 | 15.163 | 0.00 | 0.00 |
| ATOM | 193 | C | GLU | 23 | 6.524 | −1.009 | 15.951 | 0.00 | 0.00 |
| ATOM | 194 | O | GLU | 23 | 6.407 | −1.064 | 17.174 | 0.00 | 0.00 |

-continued pdb file of the α3β2 model

| | | | | | | | | | |
|---|---|---|---|---|---|---|---|---|---|
| ATOM | 195 | CB | GLU | 23 | 4.942 | −0.441 | 14.072 | 0.00 | 0.00 |
| ATOM | 196 | CG | GLU | 23 | 4.169 | 0.583 | 13.237 | 0.00 | 0.00 |
| ATOM | 197 | CD | GLU | 23 | 3.536 | 1.675 | 14.085 | 0.00 | 0.00 |
| ATOM | 198 | OE1 | GLU | 23 | 3.811 | 2.853 | 13.765 | 0.00 | 0.00 |
| ATOM | 199 | OE2 | GLU | 23 | 2.807 | 1.311 | 15.035 | 0.00 | 0.00 |
| ATOM | 200 | H | GLU | 23 | 7.134 | 0.672 | 13.574 | 1.00 | 99.99 |
| ATOM | 201 | N | THR | 24 | 7.207 | −1.911 | 15.230 | 0.00 | 0.00 |
| ATOM | 202 | CA | THR | 24 | 7.853 | −3.115 | 15.730 | 0.00 | 0.00 |
| ATOM | 203 | C | THR | 24 | 9.332 | −2.850 | 16.043 | 0.00 | 0.00 |
| ATOM | 204 | O | THR | 24 | 9.669 | −2.599 | 17.199 | 0.00 | 0.00 |
| ATOM | 205 | CB | THR | 24 | 7.648 | −4.324 | 14.798 | 0.00 | 0.00 |
| ATOM | 206 | OG1 | THR | 24 | 6.269 | −4.511 | 14.554 | 0.00 | 0.00 |
| ATOM | 207 | CG2 | THR | 24 | 8.232 | −5.603 | 15.416 | 0.00 | 0.00 |
| ATOM | 208 | H | THR | 24 | 7.247 | −1.772 | 14.230 | 1.00 | 99.99 |
| ATOM | 209 | HG1 | THR | 24 | 6.167 | −5.285 | 13.990 | 1.00 | 99.99 |
| HETATM | 210 | N | NME | 25 | 10.210 | −2.958 | 15.034 | 0.00 | 0.00 |
| HETATM | 211 | H | NME | 25 | 9.852 | −3.136 | 14.107 | 0.00 | 0.00 |
| HETATM | 212 | CA | NME | 25 | 11.655 | −2.967 | 15.204 | 0.00 | 0.00 |
| ATOM | 213 | N | GLU | 27 | −0.535 | 9.247 | −17.473 | 0.00 | 0.00 |
| ATOM | 214 | CA | GLU | 27 | 0.219 | 8.675 | −16.354 | 0.00 | 0.00 |
| ATOM | 215 | C | GLU | 27 | 0.813 | 9.739 | −15.411 | 0.00 | 0.00 |
| ATOM | 216 | O | GLU | 27 | 1.147 | 9.425 | −14.273 | 0.00 | 0.00 |
| ATOM | 217 | CB | GLU | 27 | 1.299 | 7.732 | −16.918 | 0.00 | 0.00 |
| ATOM | 218 | CG | GLU | 27 | 2.095 | 6.942 | −15.861 | 0.00 | 0.00 |
| ATOM | 219 | CD | GLU | 27 | 1.211 | 6.217 | −14.838 | 0.00 | 0.00 |
| ATOM | 220 | OE1 | GLU | 27 | 1.511 | 6.346 | −13.630 | 0.00 | 0.00 |
| ATOM | 221 | OE2 | GLU | 27 | 0.245 | 5.554 | −15.275 | 0.00 | 0.00 |
| ATOM | 222 | H | GLU | 27 | −0.238 | 8.982 | −18.401 | 1.00 | 99.99 |
| ATOM | 223 | N | LYS | 28 | 0.913 | 11.001 | −15.851 | 0.00 | 0.00 |
| ATOM | 224 | CA | LYS | 28 | 1.469 | 12.100 | −15.071 | 0.00 | 0.00 |
| ATOM | 225 | C | LYS | 28 | 0.543 | 12.544 | −13.934 | 0.00 | 0.00 |
| ATOM | 226 | O | LYS | 28 | 1.027 | 12.826 | −12.838 | 0.00 | 0.00 |
| ATOM | 227 | CB | LYS | 28 | 1.786 | 13.290 | −15.996 | 0.00 | 0.00 |
| ATOM | 228 | CG | LYS | 28 | 3.109 | 13.161 | −16.775 | 0.00 | 0.00 |
| ATOM | 229 | CD | LYS | 28 | 3.135 | 12.037 | −17.826 | 0.00 | 0.00 |
| ATOM | 230 | CE | LYS | 28 | 4.426 | 12.051 | −18.653 | 0.00 | 0.00 |
| ATOM | 231 | NZ | LYS | 28 | 4.509 | 13.225 | −19.543 | 0.00 | 0.00 |
| ATOM | 232 | H | LYS | 28 | 0.598 | 11.204 | −16.789 | 1.00 | 99.99 |
| ATOM | 233 | HZ1 | LYS | 28 | 4.489 | 14.071 | −18.991 | 1.00 | 99.99 |
| ATOM | 234 | HZ2 | LYS | 28 | 5.370 | 13.192 | −20.071 | 1.00 | 99.99 |
| ATOM | 235 | HZ3 | LYS | 28 | 3.726 | 13.225 | −20.181 | 1.00 | 99.99 |
| ATOM | 236 | N | MET | 29 | −0.774 | 12.590 | −14.176 | 0.00 | 0.00 |
| ATOM | 237 | CA | MET | 29 | −1.764 | 12.813 | −13.125 | 0.00 | 0.00 |
| ATOM | 238 | C | MET | 29 | −1.955 | 11.542 | −12.291 | 0.00 | 0.00 |
| ATOM | 239 | O | MET | 29 | −2.253 | 11.652 | −11.107 | 0.00 | 0.00 |
| ATOM | 240 | CB | MET | 29 | −3.085 | 13.267 | −13.769 | 0.00 | 0.00 |
| ATOM | 241 | CG | MET | 29 | −4.161 | 13.651 | −12.744 | 0.00 | 0.00 |
| ATOM | 242 | SD | MET | 29 | −3.692 | 14.972 | −11.590 | 0.00 | 0.00 |
| ATOM | 243 | CE | MET | 29 | −5.246 | 15.139 | −10.676 | 0.00 | 0.00 |
| ATOM | 244 | H | MET | 29 | −1.112 | 12.342 | −15.095 | 1.00 | 99.99 |
| ATOM | 245 | N | THR | 30 | −1.747 | 10.351 | −12.877 | 0.00 | 0.00 |
| ATOM | 246 | CA | THR | 30 | −1.852 | 9.072 | −12.179 | 0.00 | 0.00 |
| ATOM | 247 | C | THR | 30 | −0.788 | 8.952 | −11.081 | 0.00 | 0.00 |
| ATOM | 248 | O | THR | 30 | −1.121 | 8.605 | −9.948 | 0.00 | 0.00 |
| ATOM | 249 | CB | THR | 30 | −1.754 | 7.896 | −13.169 | 0.00 | 0.00 |
| ATOM | 250 | OG1 | THR | 30 | −2.715 | 8.038 | −14.195 | 0.00 | 0.00 |
| ATOM | 251 | CG2 | THR | 30 | −1.994 | 6.541 | −12.493 | 0.00 | 0.00 |
| ATOM | 252 | H | THR | 30 | −1.520 | 10.320 | −13.862 | 1.00 | 99.99 |
| ATOM | 253 | HG1 | THR | 30 | −2.650 | 7.272 | −14.770 | 1.00 | 99.99 |
| ATOM | 254 | N | LEU | 31 | 0.480 | 9.258 | −11.400 | 0.00 | 0.00 |
| ATOM | 255 | CA | LEU | 31 | 1.562 | 9.251 | −10.421 | 0.00 | 0.00 |
| ATOM | 256 | C | LEU | 31 | 1.454 | 10.399 | −9.416 | 0.00 | 0.00 |
| ATOM | 257 | O | LEU | 31 | 1.930 | 10.247 | −8.295 | 0.00 | 0.00 |
| ATOM | 258 | CB | LEU | 31 | 2.937 | 9.148 | −11.113 | 0.00 | 0.00 |
| ATOM | 259 | CG | LEU | 31 | 3.392 | 10.353 | −11.965 | 0.00 | 0.00 |
| ATOM | 260 | CD1 | LEU | 31 | 4.096 | 11.445 | −11.142 | 0.00 | 0.00 |
| ATOM | 261 | CD2 | LEU | 31 | 4.365 | 9.882 | −13.057 | 0.00 | 0.00 |
| ATOM | 262 | H | LEU | 31 | 0.706 | 9.505 | −12.355 | 1.00 | 99.99 |
| ATOM | 263 | N | CYS | 32 | 0.786 | 11.507 | −9.773 | 0.00 | 0.00 |
| ATOM | 264 | CA | CYS | 32 | 0.488 | 12.593 | −8.848 | 0.00 | 0.00 |
| ATOM | 265 | C | CYS | 32 | −0.529 | 12.134 | −7.800 | 0.00 | 0.00 |
| ATOM | 266 | O | CYS | 32 | −0.267 | 12.312 | −6.612 | 0.00 | 0.00 |
| ATOM | 267 | CB | CYS | 32 | −0.021 | 13.806 | −9.638 | 0.00 | 0.00 |
| ATOM | 268 | SG | CYS | 32 | −0.259 | 15.217 | −8.524 | 0.00 | 0.00 |
| ATOM | 269 | H | CYS | 32 | 0.420 | 11.576 | −10.712 | 1.00 | 99.99 |
| ATOM | 270 | HG | CYS | 32 | −0.695 | 16.067 | −9.459 | 1.00 | 99.99 |
| ATOM | 271 | N | ILE | 33 | −1.659 | 11.529 | −8.216 | 0.00 | 0.00 |

-continued pdb file of the α3β2 model

| | | | | | | | | |
|---|---|---|---|---|---|---|---|---|
| ATOM | 272 | CA | ILE | 33 | −2.684 | 11.082 | −7.275 | 0.00 | 0.00 |
| ATOM | 273 | C | ILE | 33 | −2.165 | 9.989 | −6.339 | 0.00 | 0.00 |
| ATOM | 274 | O | ILE | 33 | −2.443 | 10.052 | −5.146 | 0.00 | 0.00 |
| ATOM | 275 | CB | ILE | 33 | −4.048 | 10.729 | −7.917 | 0.00 | 0.00 |
| ATOM | 276 | CG1 | ILE | 33 | −3.996 | 9.546 | −8.906 | 0.00 | 0.00 |
| ATOM | 277 | CG2 | ILE | 33 | −4.660 | 11.993 | −8.547 | 0.00 | 0.00 |
| ATOM | 278 | CD1 | ILE | 33 | −5.371 | 9.049 | −9.368 | 0.00 | 0.00 |
| ATOM | 279 | H | ILE | 33 | −1.826 | 11.401 | −9.205 | 1.00 | 99.99 |
| ATOM | 280 | N | SER | 34 | −1.357 | 9.045 | −6.837 | 0.00 | 0.00 |
| ATOM | 281 | CA | SER | 34 | −0.735 | 8.012 | −6.015 | 0.00 | 0.00 |
| ATOM | 282 | C | SER | 34 | 0.223 | 8.612 | −4.976 | 0.00 | 0.00 |
| ATOM | 283 | O | SER | 34 | 0.245 | 8.145 | −3.839 | 0.00 | 0.00 |
| ATOM | 284 | CB | SER | 34 | 0.006 | 7.043 | −6.945 | 0.00 | 0.00 |
| ATOM | 285 | OG | SER | 34 | 0.534 | 5.957 | −6.216 | 0.00 | 0.00 |
| ATOM | 286 | H | SER | 34 | −1.155 | 9.048 | −7.828 | 1.00 | 99.99 |
| ATOM | 287 | HG | SER | 34 | 0.980 | 5.365 | −6.827 | 1.00 | 99.99 |
| ATOM | 288 | N | VAL | 35 | 0.977 | 9.659 | −5.348 | 0.00 | 0.00 |
| ATOM | 289 | CA | VAL | 35 | 1.896 | 10.368 | −4.458 | 0.00 | 0.00 |
| ATOM | 290 | C | VAL | 35 | 1.161 | 11.169 | −3.369 | 0.00 | 0.00 |
| ATOM | 291 | O | VAL | 35 | 1.709 | 11.328 | −2.279 | 0.00 | 0.00 |
| ATOM | 292 | CB | VAL | 35 | 2.886 | 11.226 | −5.285 | 0.00 | 0.00 |
| ATOM | 293 | CG1 | VAL | 35 | 3.608 | 12.321 | −4.481 | 0.00 | 0.00 |
| ATOM | 294 | CG2 | VAL | 35 | 3.967 | 10.314 | −5.894 | 0.00 | 0.00 |
| ATOM | 295 | H | VAL | 35 | 0.909 | 9.995 | −6.300 | 1.00 | 99.99 |
| ATOM | 296 | N | LEU | 36 | −0.080 | 11.622 | −3.604 | 0.00 | 0.00 |
| ATOM | 297 | CA | LEU | 36 | −0.880 | 12.257 | −2.558 | 0.00 | 0.00 |
| ATOM | 298 | C | LEU | 36 | −1.235 | 11.257 | −1.456 | 0.00 | 0.00 |
| ATOM | 299 | O | LEU | 36 | −1.056 | 11.566 | −0.279 | 0.00 | 0.00 |
| ATOM | 300 | CB | LEU | 36 | −2.151 | 12.903 | −3.141 | 0.00 | 0.00 |
| ATOM | 301 | CG | LEU | 36 | −1.895 | 14.123 | −4.052 | 0.00 | 0.00 |
| ATOM | 302 | CD1 | LEU | 36 | −3.205 | 14.536 | −4.738 | 0.00 | 0.00 |
| ATOM | 303 | CD2 | LEU | 36 | −1.332 | 15.324 | −3.278 | 0.00 | 0.00 |
| ATOM | 304 | H | LEU | 36 | −0.499 | 11.480 | −4.513 | 1.00 | 99.99 |
| ATOM | 305 | N | LEU | 37 | −1.689 | 10.055 | −1.837 | 0.00 | 0.00 |
| ATOM | 306 | CA | LEU | 37 | −1.984 | 8.972 | −0.906 | 0.00 | 0.00 |
| ATOM | 307 | C | LEU | 37 | −0.716 | 8.338 | −0.311 | 0.00 | 0.00 |
| ATOM | 308 | O | LEU | 37 | −0.817 | 7.630 | 0.692 | 0.00 | 0.00 |
| ATOM | 309 | CB | LEU | 37 | −2.887 | 7.925 | −1.582 | 0.00 | 0.00 |
| ATOM | 310 | CG | LEU | 37 | −4.345 | 8.358 | −1.869 | 0.00 | 0.00 |
| ATOM | 311 | CD1 | LEU | 37 | −5.010 | 9.090 | −0.690 | 0.00 | 0.00 |
| ATOM | 312 | CD2 | LEU | 37 | −4.546 | 9.184 | −3.141 | 0.00 | 0.00 |
| ATOM | 313 | H | LEU | 37 | −1.806 | 9.870 | −2.825 | 1.00 | 99.99 |
| ATOM | 314 | N | ALA | 38 | 0.471 | 8.626 | −0.867 | 0.00 | 0.00 |
| ATOM | 315 | CA | ALA | 38 | 1.740 | 8.226 | −0.280 | 0.00 | 0.00 |
| ATOM | 316 | C | ALA | 38 | 2.066 | 9.043 | 0.973 | 0.00 | 0.00 |
| ATOM | 317 | O | ALA | 38 | 2.474 | 8.464 | 1.980 | 0.00 | 0.00 |
| ATOM | 318 | CB | ALA | 38 | 2.864 | 8.324 | −1.312 | 0.00 | 0.00 |
| ATOM | 319 | H | ALA | 38 | 0.497 | 9.193 | −1.702 | 1.00 | 99.99 |
| ATOM | 320 | N | LEU | 39 | 1.855 | 10.367 | 0.926 | 0.00 | 0.00 |
| ATOM | 321 | CA | LEU | 39 | 2.012 | 11.251 | 2.080 | 0.00 | 0.00 |
| ATOM | 322 | C | LEU | 39 | 0.881 | 11.068 | 3.102 | 0.00 | 0.00 |
| ATOM | 323 | O | LEU | 39 | 1.101 | 11.338 | 4.283 | 0.00 | 0.00 |
| ATOM | 324 | CB | LEU | 39 | 2.100 | 12.720 | 1.618 | 0.00 | 0.00 |
| ATOM | 325 | CG | LEU | 39 | 3.511 | 13.226 | 1.241 | 0.00 | 0.00 |
| ATOM | 326 | CD1 | LEU | 39 | 4.467 | 13.237 | 2.446 | 0.00 | 0.00 |
| ATOM | 327 | CD2 | LEU | 39 | 4.151 | 12.457 | 0.077 | 0.00 | 0.00 |
| ATOM | 328 | H | LEU | 39 | 1.526 | 10.778 | 0.063 | 1.00 | 99.99 |
| ATOM | 329 | N | THR | 40 | −0.291 | 10.561 | 2.686 | 0.00 | 0.00 |
| ATOM | 330 | CA | THR | 40 | −1.360 | 10.158 | 3.602 | 0.00 | 0.00 |
| ATOM | 331 | C | THR | 40 | −0.873 | 9.037 | 4.530 | 0.00 | 0.00 |
| ATOM | 332 | O | THR | 40 | −1.089 | 9.092 | 5.741 | 0.00 | 0.00 |
| ATOM | 333 | CB | THR | 40 | −2.627 | 9.753 | 2.826 | 0.00 | 0.00 |
| ATOM | 334 | OG1 | THR | 40 | −3.079 | 10.847 | 2.055 | 0.00 | 0.00 |
| ATOM | 335 | CG2 | THR | 40 | −3.778 | 9.334 | 3.747 | 0.00 | 0.00 |
| ATOM | 336 | H | THR | 40 | −0.432 | 10.397 | 1.699 | 1.00 | 99.99 |
| ATOM | 337 | HG1 | THR | 40 | −3.887 | 10.588 | 1.606 | 1.00 | 99.99 |
| ATOM | 338 | N | VAL | 41 | −0.182 | 8.048 | 3.954 | 0.00 | 0.00 |
| ATOM | 339 | CA | VAL | 41 | 0.382 | 6.891 | 4.637 | 0.00 | 0.00 |
| ATOM | 340 | C | VAL | 41 | 1.737 | 7.181 | 5.315 | 0.00 | 0.00 |
| ATOM | 341 | O | VAL | 41 | 2.285 | 6.307 | 5.986 | 0.00 | 0.00 |
| ATOM | 342 | CB | VAL | 41 | 0.606 | 5.759 | 3.640 | 0.00 | 9.99 |
| ATOM | 343 | CG1 | VAL | 41 | 1.502 | 4.697 | 4.271 | 0.00 | 9.99 |
| ATOM | 344 | CG2 | VAL | 41 | −0.733 | 5.135 | 3.266 | 0.00 | 9.99 |
| ATOM | 345 | N | PHE | 42 | 2.270 | 8.402 | 5.164 | 0.00 | 0.00 |
| ATOM | 346 | CA | PHE | 42 | 3.482 | 8.875 | 5.827 | 0.00 | 0.00 |
| ATOM | 347 | C | PHE | 42 | 3.150 | 9.624 | 7.120 | 0.00 | 0.00 |
| ATOM | 348 | O | PHE | 42 | 3.879 | 9.495 | 8.097 | 0.00 | 0.00 |

-continued

| pdb file of the α3β2 model | | | | | | | | | |
|---|---|---|---|---|---|---|---|---|---|
| ATOM | 349 | CB | PHE | 42 | 4.246 | 9.781 | 4.851 | 0.00 | 0.00 |
| ATOM | 350 | CG | PHE | 42 | 5.642 | 10.167 | 5.296 | 0.00 | 0.00 |
| ATOM | 351 | CD1 | PHE | 42 | 5.921 | 11.481 | 5.719 | 0.00 | 0.00 |
| ATOM | 352 | CD2 | PHE | 42 | 6.676 | 9.213 | 5.258 | 0.00 | 0.00 |
| ATOM | 353 | CE1 | PHE | 42 | 7.227 | 11.835 | 6.101 | 0.00 | 0.00 |
| ATOM | 354 | CE2 | PHE | 42 | 7.980 | 9.564 | 5.650 | 0.00 | 0.00 |
| ATOM | 355 | CZ | PHE | 42 | 8.255 | 10.876 | 6.071 | 0.00 | 0.00 |
| ATOM | 356 | H | PHE | 42 | 1.783 | 9.065 | 4.577 | 1.00 | 99.99 |
| ATOM | 357 | N | LEU | 43 | 2.031 | 10.360 | 7.154 | 0.00 | 0.00 |
| ATOM | 358 | CA | LEU | 43 | 1.473 | 10.924 | 8.382 | 0.00 | 0.00 |
| ATOM | 359 | C | LEU | 43 | 0.874 | 9.828 | 9.281 | 0.00 | 0.00 |
| ATOM | 360 | O | LEU | 43 | 0.769 | 10.036 | 10.491 | 0.00 | 0.00 |
| ATOM | 361 | CB | LEU | 43 | 0.398 | 11.963 | 8.019 | 0.00 | 0.00 |
| ATOM | 362 | CG | LEU | 43 | 0.943 | 13.203 | 7.276 | 0.00 | 0.00 |
| ATOM | 363 | CD1 | LEU | 43 | −0.231 | 14.055 | 6.775 | 0.00 | 0.00 |
| ATOM | 364 | CD2 | LEU | 43 | 1.853 | 14.063 | 8.168 | 0.00 | 0.00 |
| ATOM | 365 | H | LEU | 43 | 1.484 | 10.457 | 6.309 | 1.00 | 99.99 |
| ATOM | 366 | N | LEU | 44 | 0.536 | 8.658 | 8.710 | 0.00 | 0.00 |
| ATOM | 367 | CA | LEU | 44 | 0.132 | 7.461 | 9.440 | 0.00 | 0.00 |
| ATOM | 368 | C | LEU | 44 | 1.236 | 7.030 | 10.392 | 0.00 | 0.00 |
| ATOM | 369 | O | LEU | 44 | 1.015 | 7.010 | 11.603 | 0.00 | 0.00 |
| ATOM | 370 | CB | LEU | 44 | −0.237 | 6.330 | 8.461 | 0.00 | 0.00 |
| ATOM | 371 | CG | LEU | 44 | −0.598 | 4.940 | 9.053 | 0.00 | 0.00 |
| ATOM | 372 | CD1 | LEU | 44 | −1.120 | 4.095 | 7.887 | 0.00 | 0.00 |
| ATOM | 373 | CD2 | LEU | 44 | 0.548 | 4.126 | 9.682 | 0.00 | 0.00 |
| ATOM | 374 | H | LEU | 44 | 0.627 | 8.573 | 7.707 | 1.00 | 99.99 |
| ATOM | 375 | N | LEU | 45 | 2.406 | 6.671 | 9.845 | 0.00 | 0.00 |
| ATOM | 376 | CA | LEU | 45 | 3.519 | 6.170 | 10.638 | 0.00 | 0.00 |
| ATOM | 377 | C | LEU | 45 | 4.079 | 7.261 | 11.561 | 0.00 | 0.00 |
| ATOM | 378 | O | LEU | 45 | 4.821 | 6.946 | 12.478 | 0.00 | 0.00 |
| ATOM | 379 | CB | LEU | 45 | 4.613 | 5.598 | 9.712 | 0.00 | 0.00 |
| ATOM | 380 | CG | LEU | 45 | 5.541 | 6.618 | 9.012 | 0.00 | 0.00 |
| ATOM | 381 | CD1 | LEU | 45 | 6.887 | 6.784 | 9.737 | 0.00 | 0.00 |
| ATOM | 382 | CD2 | LEU | 45 | 5.832 | 6.220 | 7.559 | 0.00 | 0.00 |
| ATOM | 383 | H | LEU | 45 | 2.516 | 6.707 | 8.841 | 1.00 | 99.99 |
| ATOM | 384 | N | ILE | 46 | 3.724 | 8.534 | 11.345 | 0.00 | 0.00 |
| ATOM | 385 | CA | ILE | 46 | 4.148 | 9.666 | 12.160 | 0.00 | 0.00 |
| ATOM | 386 | C | ILE | 46 | 3.185 | 9.956 | 13.327 | 0.00 | 0.00 |
| ATOM | 387 | O | ILE | 46 | 3.473 | 10.794 | 14.180 | 0.00 | 0.00 |
| ATOM | 388 | CB | ILE | 46 | 4.432 | 10.867 | 11.210 | 0.00 | 0.00 |
| ATOM | 389 | CG1 | ILE | 46 | 5.801 | 10.618 | 10.528 | 0.00 | 0.00 |
| ATOM | 390 | CG2 | ILE | 46 | 4.416 | 12.260 | 11.869 | 0.00 | 0.00 |
| ATOM | 391 | CD1 | ILE | 46 | 6.159 | 11.602 | 9.409 | 0.00 | 0.00 |
| ATOM | 392 | H | ILE | 46 | 3.121 | 8.734 | 10.560 | 1.00 | 99.99 |
| ATOM | 393 | N | SER | 47 | 2.082 | 9.209 | 13.426 | 0.00 | 0.00 |
| ATOM | 394 | CA | SER | 47 | 1.150 | 9.252 | 14.548 | 0.00 | 0.00 |
| ATOM | 395 | C | SER | 47 | 0.919 | 7.870 | 15.169 | 0.00 | 0.00 |
| ATOM | 396 | O | SER | 47 | 0.237 | 7.783 | 16.189 | 0.00 | 0.00 |
| ATOM | 397 | CB | SER | 47 | −0.126 | 9.962 | 14.095 | 0.00 | 0.00 |
| ATOM | 398 | OG | SER | 47 | −0.740 | 9.307 | 13.001 | 0.00 | 0.00 |
| ATOM | 399 | H | SER | 47 | 1.886 | 8.542 | 12.690 | 1.00 | 99.99 |
| ATOM | 400 | HG | SER | 47 | −0.178 | 9.413 | 12.226 | 1.00 | 99.99 |
| ATOM | 401 | N | LYS | 48 | 1.561 | 6.825 | 14.617 | 0.00 | 0.00 |
| ATOM | 402 | CA | LYS | 48 | 1.788 | 5.536 | 15.262 | 0.00 | 0.00 |
| ATOM | 403 | C | LYS | 48 | 3.272 | 5.283 | 15.588 | 0.00 | 0.00 |
| ATOM | 404 | O | LYS | 48 | 3.543 | 4.430 | 16.432 | 0.00 | 0.00 |
| ATOM | 405 | CB | LYS | 48 | 1.158 | 4.403 | 14.455 | 0.00 | 0.00 |
| ATOM | 406 | CG | LYS | 48 | −0.354 | 4.284 | 14.642 | 0.00 | 0.00 |
| ATOM | 407 | CD | LYS | 48 | −0.773 | 3.894 | 16.077 | 0.00 | 0.00 |
| ATOM | 408 | CE | LYS | 48 | −1.189 | 5.103 | 16.921 | 0.00 | 0.00 |
| ATOM | 409 | NZ | LYS | 48 | −1.702 | 4.693 | 18.239 | 0.00 | 0.00 |
| ATOM | 410 | H | LYS | 48 | 2.046 | 6.979 | 13.746 | 1.00 | 99.99 |
| ATOM | 411 | HZ1 | LYS | 48 | −1.012 | 4.132 | 18.717 | 1.00 | 99.99 |
| ATOM | 412 | HZ2 | LYS | 48 | −1.914 | 5.513 | 18.789 | 1.00 | 99.99 |
| ATOM | 413 | HZ3 | LYS | 48 | −2.552 | 4.158 | 18.112 | 1.00 | 99.99 |
| ATOM | 414 | N | ILE | 49 | 4.204 | 6.096 | 15.057 | 0.00 | 0.00 |
| ATOM | 415 | CA | ILE | 49 | 5.427 | 6.457 | 15.769 | 0.00 | 0.00 |
| ATOM | 416 | C | ILE | 49 | 5.527 | 7.970 | 16.024 | 0.00 | 0.00 |
| ATOM | 417 | O | ILE | 49 | 5.311 | 8.399 | 17.157 | 0.00 | 0.00 |
| ATOM | 418 | CB | ILE | 49 | 6.732 | 5.740 | 15.337 | 0.00 | 0.00 |
| ATOM | 419 | CG1 | ILE | 49 | 7.793 | 5.862 | 16.468 | 0.00 | 0.00 |
| ATOM | 420 | CG2 | ILE | 49 | 7.308 | 6.108 | 13.955 | 0.00 | 0.00 |
| ATOM | 421 | CD1 | ILE | 49 | 8.665 | 7.127 | 16.501 | 0.00 | 0.00 |
| ATOM | 422 | H | ILE | 49 | 3.931 | 6.719 | 14.311 | 1.00 | 99.99 |
| HETATM | 423 | N | NME | 50 | 5.876 | 8.773 | 15.013 | 0.00 | 0.00 |
| HETATM | 424 | H | NME | 50 | 5.998 | 8.361 | 14.099 | 0.00 | 0.00 |
| HETATM | 425 | CA | NME | 50 | 6.271 | 10.165 | 15.177 | 0.00 | 0.00 |

-continued pdb file of the α3β2 model

| ATOM | 426 | N | GLU | 52 | −8.968 | 2.364 | −17.452 | 0.00 | 0.00 |
|---|---|---|---|---|---|---|---|---|---|
| ATOM | 427 | CA | GLU | 52 | −8.186 | 2.902 | −16.335 | 0.00 | 0.00 |
| ATOM | 428 | C | GLU | 52 | −9.010 | 3.796 | −15.388 | 0.00 | 0.00 |
| ATOM | 429 | O | GLU | 52 | −8.603 | 4.015 | −14.251 | 0.00 | 0.00 |
| ATOM | 430 | CB | GLU | 52 | −6.955 | 3.634 | −16.901 | 0.00 | 0.00 |
| ATOM | 431 | CG | GLU | 52 | −5.951 | 4.138 | −15.847 | 0.00 | 0.00 |
| ATOM | 432 | CD | GLU | 52 | −5.535 | 3.066 | −14.831 | 0.00 | 0.00 |
| ATOM | 433 | OE1 | GLU | 52 | −5.559 | 3.384 | −13.621 | 0.00 | 0.00 |
| ATOM | 434 | OE2 | GLU | 52 | −5.211 | 1.942 | −15.275 | 0.00 | 0.00 |
| ATOM | 435 | H | GLU | 52 | −8.628 | 2.567 | −18.381 | 1.00 | 99.99 |
| ATOM | 436 | N | LYS | 53 | −10.180 | 4.283 | −15.824 | 0.00 | 0.00 |
| ATOM | 437 | CA | LYS | 53 | −11.053 | 5.150 | −15.040 | 0.00 | 0.00 |
| ATOM | 438 | C | LYS | 53 | −11.761 | 4.405 | −13.903 | 0.00 | 0.00 |
| ATOM | 439 | O | LYS | 53 | −11.891 | 4.952 | −12.809 | 0.00 | 0.00 |
| ATOM | 440 | CB | LYS | 53 | −12.089 | 5.818 | −15.963 | 0.00 | 0.00 |
| ATOM | 441 | CG | LYS | 53 | −11.559 | 7.029 | −16.754 | 0.00 | 0.00 |
| ATOM | 442 | CD | LYS | 53 | −10.494 | 6.696 | −17.814 | 0.00 | 0.00 |
| ATOM | 443 | CE | LYS | 53 | −10.117 | 7.919 | −18.658 | 0.00 | 0.00 |
| ATOM | 444 | NZ | LYS | 53 | −11.217 | 8.353 | −19.541 | 0.00 | 0.00 |
| ATOM | 445 | H | LYS | 53 | −10.473 | 4.046 | −16.760 | 1.00 | 99.99 |
| ATOM | 446 | HZ1 | LYS | 53 | −12.022 | 8.601 | −18.983 | 1.00 | 99.99 |
| ATOM | 447 | HZ2 | LYS | 53 | −10.924 | 9.156 | −20.080 | 1.00 | 99.99 |
| ATOM | 448 | HZ3 | LYS | 53 | −11.465 | 7.602 | −20.169 | 1.00 | 99.99 |
| ATOM | 449 | N | VAL | 54 | −12.200 | 3.164 | −14.148 | 0.00 | 0.00 |
| ATOM | 450 | CA | VAL | 54 | −12.728 | 2.277 | −13.112 | 0.00 | 0.00 |
| ATOM | 451 | C | VAL | 54 | −11.569 | 1.741 | −12.265 | 0.00 | 0.00 |
| ATOM | 452 | O | VAL | 54 | −11.753 | 1.551 | −11.068 | 0.00 | 0.00 |
| ATOM | 453 | CB | VAL | 54 | −13.527 | 1.124 | −13.765 | 0.00 | 0.00 |
| ATOM | 454 | CG1 | VAL | 54 | −14.079 | 0.140 | −12.718 | 0.00 | 0.00 |
| ATOM | 455 | CG2 | VAL | 54 | −14.713 | 1.664 | −14.584 | 0.00 | 0.00 |
| ATOM | 456 | H | VAL | 54 | −12.057 | 2.773 | −15.068 | 1.00 | 99.99 |
| ATOM | 457 | N | THR | 55 | −10.381 | 1.536 | −12.859 | 0.00 | 0.00 |
| ATOM | 458 | CA | THR | 55 | −9.194 | 1.046 | −12.162 | 0.00 | 0.00 |
| ATOM | 459 | C | THR | 55 | −8.748 | 2.021 | −11.065 | 0.00 | 0.00 |
| ATOM | 460 | O | THR | 55 | −8.516 | 1.595 | −9.933 | 0.00 | 0.00 |
| ATOM | 461 | CB | THR | 55 | −8.048 | 0.775 | −13.155 | 0.00 | 0.00 |
| ATOM | 462 | OG1 | THR | 55 | −8.483 | −0.094 | −14.180 | 0.00 | 0.00 |
| ATOM | 463 | CG2 | THR | 55 | −6.833 | 0.127 | −12.482 | 0.00 | 0.00 |
| ATOM | 464 | H | THR | 55 | −10.295 | 1.697 | −13.853 | 1.00 | 99.99 |
| ATOM | 465 | HG1 | THR | 55 | −7.736 | −0.269 | −14.758 | 1.00 | 99.99 |
| ATOM | 466 | N | LEU | 56 | −8.652 | 3.321 | −11.382 | 0.00 | 0.00 |
| ATOM | 467 | CA | LEU | 56 | −8.307 | 4.347 | −10.403 | 0.00 | 0.00 |
| ATOM | 468 | C | LEU | 56 | −9.428 | 4.598 | −9.393 | 0.00 | 0.00 |
| ATOM | 469 | O | LEU | 56 | −9.129 | 5.005 | −8.274 | 0.00 | 0.00 |
| ATOM | 470 | CB | LEU | 56 | −7.786 | 5.623 | −11.095 | 0.00 | 0.00 |
| ATOM | 471 | CG | LEU | 56 | −8.796 | 6.430 | −11.941 | 0.00 | 0.00 |
| ATOM | 472 | CD1 | LEU | 56 | −9.612 | 7.436 | −11.112 | 0.00 | 0.00 |
| ATOM | 473 | CD2 | LEU | 56 | −8.052 | 7.211 | −13.035 | 0.00 | 0.00 |
| ATOM | 474 | H | LEU | 56 | −8.821 | 3.613 | −12.336 | 1.00 | 99.99 |
| ATOM | 475 | N | CYS | 57 | −10.690 | 4.306 | −9.743 | 0.00 | 0.00 |
| ATOM | 476 | CA | CYS | 57 | −11.808 | 4.362 | −8.810 | 0.00 | 0.00 |
| ATOM | 477 | C | CYS | 57 | −11.684 | 3.250 | −7.764 | 0.00 | 0.00 |
| ATOM | 478 | O | CYS | 57 | −11.771 | 3.550 | −6.575 | 0.00 | 0.00 |
| ATOM | 479 | CB | CYS | 57 | −13.128 | 4.274 | −9.585 | 0.00 | 0.00 |
| ATOM | 480 | SG | CYS | 57 | −14.524 | 4.525 | −8.455 | 0.00 | 0.00 |
| ATOM | 481 | H | CYS | 57 | −10.875 | 3.975 | −10.679 | 1.00 | 99.99 |
| ATOM | 482 | HG | CYS | 57 | −15.482 | 4.408 | −9.379 | 1.00 | 99.99 |
| ATOM | 483 | N | ILE | 58 | −11.457 | 1.991 | −8.183 | 0.00 | 0.00 |
| ATOM | 484 | CA | ILE | 58 | −11.358 | 0.867 | −7.251 | 0.00 | 0.00 |
| ATOM | 485 | C | ILE | 58 | −10.147 | 0.986 | −6.321 | 0.00 | 0.00 |
| ATOM | 486 | O | ILE | 58 | −10.272 | 0.671 | −5.140 | 0.00 | 0.00 |
| ATOM | 487 | CB | ILE | 58 | −11.468 | −0.528 | −7.914 | 0.00 | 0.00 |
| ATOM | 488 | CG1 | ILE | 58 | −10.334 | −0.841 | −8.910 | 0.00 | 0.00 |
| ATOM | 489 | CG2 | ILE | 58 | −12.863 | −0.690 | −8.546 | 0.00 | 0.00 |
| ATOM | 490 | CD1 | ILE | 58 | −10.300 | −2.298 | −9.389 | 0.00 | 0.00 |
| ATOM | 491 | H | ILE | 58 | −11.384 | 1.798 | −9.172 | 1.00 | 99.99 |
| ATOM | 492 | N | SER | 59 | −9.013 | 1.503 | −6.811 | 0.00 | 0.00 |
| ATOM | 493 | CA | SER | 59 | −7.835 | 1.772 | −5.994 | 0.00 | 0.00 |
| ATOM | 494 | C | SER | 59 | −8.108 | 2.867 | −4.953 | 0.00 | 0.00 |
| ATOM | 495 | O | SER | 59 | −7.648 | 2.750 | −3.818 | 0.00 | 0.00 |
| ATOM | 496 | CB | SER | 59 | −6.690 | 2.182 | −6.928 | 0.00 | 0.00 |
| ATOM | 497 | OG | SER | 59 | −5.491 | 2.352 | −6.204 | 0.00 | 0.00 |
| ATOM | 498 | H | SER | 59 | −8.973 | 1.742 | −7.793 | 1.00 | 99.99 |
| ATOM | 499 | HG | SER | 59 | −4.792 | 2.591 | −6.818 | 1.00 | 99.99 |
| ATOM | 500 | N | VAL | 60 | −8.876 | 3.905 | −5.322 | 0.00 | 0.00 |
| ATOM | 501 | CA | VAL | 60 | −9.265 | 4.998 | −4.432 | 0.00 | 0.00 |
| ATOM | 502 | C | VAL | 60 | −10.280 | 4.554 | −3.361 | 0.00 | 0.00 |

-continued pdb file of the α3β2 model

| ATOM | 503 | O | VAL | 60 | −10.318 | 5.159 | −2.290 | 0.00 | 0.00 |
|---|---|---|---|---|---|---|---|---|---|
| ATOM | 504 | CB | VAL | 60 | −9.741 | 6.215 | −5.265 | 0.00 | 0.00 |
| ATOM | 505 | CG1 | VAL | 60 | −10.541 | 7.263 | −4.472 | 0.00 | 0.00 |
| ATOM | 506 | CG2 | VAL | 60 | −8.517 | 6.933 | −5.864 | 0.00 | 0.00 |
| ATOM | 507 | H | VAL | 60 | −9.223 | 3.940 | −6.272 | 1.00 | 99.99 |
| ATOM | 508 | N | LEU | 61 | −11.052 | 3.480 | −3.581 | 0.00 | 0.00 |
| ATOM | 509 | CA | LEU | 61 | −11.901 | 2.915 | −2.534 | 0.00 | 0.00 |
| ATOM | 510 | C | LEU | 61 | −11.060 | 2.250 | −1.440 | 0.00 | 0.00 |
| ATOM | 511 | O | LEU | 61 | −11.309 | 2.485 | −0.258 | 0.00 | 0.00 |
| ATOM | 512 | CB | LEU | 61 | −12.909 | 1.910 | −3.123 | 0.00 | 0.00 |
| ATOM | 513 | CG | LEU | 61 | −13.994 | 2.537 | −4.025 | 0.00 | 0.00 |
| ATOM | 514 | CD1 | LEU | 61 | −14.799 | 1.424 | −4.710 | 0.00 | 0.00 |
| ATOM | 515 | CD2 | LEU | 61 | −14.957 | 3.442 | −3.241 | 0.00 | 0.00 |
| ATOM | 516 | H | LEU | 61 | −11.008 | 3.009 | −4.474 | 1.00 | 99.99 |
| ATOM | 517 | N | LEU | 62 | −10.049 | 1.457 | −1.829 | 0.00 | 0.00 |
| ATOM | 518 | CA | LEU | 62 | −9.102 | 0.850 | −0.897 | 0.00 | 0.00 |
| ATOM | 519 | C | LEU | 62 | −8.155 | 1.886 | −0.271 | 0.00 | 0.00 |
| ATOM | 520 | O | LEU | 62 | −7.590 | 1.612 | 0.785 | 0.00 | 0.00 |
| ATOM | 521 | CB | LEU | 62 | −8.300 | −0.270 | −1.593 | 0.00 | 0.00 |
| ATOM | 522 | CG | LEU | 62 | −9.018 | −1.623 | −1.814 | 0.00 | 0.00 |
| ATOM | 523 | CD1 | LEU | 62 | −9.643 | −2.189 | −0.530 | 0.00 | 0.00 |
| ATOM | 524 | CD2 | LEU | 62 | −10.062 | −1.618 | −2.934 | 0.00 | 0.00 |
| ATOM | 525 | H | LEU | 62 | −9.900 | 1.302 | −2.817 | 1.00 | 99.99 |
| ATOM | 526 | N | SER | 63 | −8.017 | 3.082 | −0.864 | 0.00 | 0.00 |
| ATOM | 527 | CA | SER | 63 | −7.286 | 4.186 | −0.257 | 0.00 | 0.00 |
| ATOM | 528 | C | SER | 63 | −7.974 | 4.660 | 1.024 | 0.00 | 0.00 |
| ATOM | 529 | O | SER | 63 | −7.322 | 4.753 | 2.063 | 0.00 | 0.00 |
| ATOM | 530 | CB | SER | 63 | −7.134 | 5.342 | −1.243 | 0.00 | 0.00 |
| ATOM | 531 | OG | SER | 63 | −6.568 | 6.434 | −0.563 | 0.00 | 0.00 |
| ATOM | 532 | H | SER | 63 | −8.482 | 3.248 | −1.746 | 1.00 | 99.99 |
| ATOM | 533 | HG | SER | 63 | −6.465 | 7.161 | −1.181 | 1.00 | 99.99 |
| ATOM | 534 | N | LEU | 64 | −9.281 | 4.947 | 0.953 | 0.00 | 0.00 |
| ATOM | 535 | CA | LEU | 64 | −10.062 | 5.363 | 2.111 | 0.00 | 0.00 |
| ATOM | 536 | C | LEU | 64 | −10.212 | 4.225 | 3.132 | 0.00 | 0.00 |
| ATOM | 537 | O | LEU | 64 | −10.375 | 4.517 | 4.317 | 0.00 | 0.00 |
| ATOM | 538 | CB | LEU | 64 | −11.442 | 5.887 | 1.664 | 0.00 | 0.00 |
| ATOM | 539 | CG | LEU | 64 | −11.507 | 7.384 | 1.285 | 0.00 | 0.00 |
| ATOM | 540 | CD1 | LEU | 64 | −11.224 | 8.300 | 2.487 | 0.00 | 0.00 |
| ATOM | 541 | CD2 | LEU | 64 | −10.589 | 7.768 | 0.116 | 0.00 | 0.00 |
| ATOM | 542 | H | LEU | 64 | −9.759 | 4.859 | 0.066 | 1.00 | 99.99 |
| ATOM | 543 | N | THR | 65 | −10.100 | 2.951 | 2.714 | 0.00 | 0.00 |
| ATOM | 544 | CA | THR | 65 | −10.084 | 1.818 | 3.641 | 0.00 | 0.00 |
| ATOM | 545 | C | THR | 65 | −8.814 | 1.779 | 4.506 | 0.00 | 0.00 |
| ATOM | 546 | O | THR | 65 | −8.851 | 1.294 | 5.636 | 0.00 | 0.00 |
| ATOM | 547 | CB | THR | 65 | −10.415 | 0.492 | 2.913 | 0.00 | 0.00 |
| ATOM | 548 | OG1 | THR | 65 | −11.537 | −0.097 | 3.538 | 0.00 | 0.00 |
| ATOM | 549 | CG2 | THR | 65 | −9.313 | −0.575 | 2.884 | 0.00 | 0.00 |
| ATOM | 550 | H | THR | 65 | −9.981 | 2.765 | 1.727 | 1.00 | 99.99 |
| ATOM | 551 | HG1 | THR | 65 | −11.768 | −0.893 | 3.055 | 1.00 | 99.99 |
| ATOM | 552 | N | VAL | 66 | −7.719 | 2.353 | 3.997 | 0.00 | 0.00 |
| ATOM | 553 | CA | VAL | 66 | −6.420 | 2.502 | 4.649 | 0.00 | 0.00 |
| ATOM | 554 | C | VAL | 66 | −6.284 | 3.892 | 5.313 | 0.00 | 0.00 |
| ATOM | 555 | O | VAL | 66 | −5.310 | 4.144 | 6.024 | 0.00 | 0.00 |
| ATOM | 556 | CB | VAL | 66 | −5.352 | 2.198 | 3.567 | 0.00 | 0.00 |
| ATOM | 557 | CG1 | VAL | 66 | −3.925 | 2.559 | 3.978 | 0.00 | 0.00 |
| ATOM | 558 | CG2 | VAL | 66 | −5.379 | 0.698 | 3.225 | 0.00 | 0.00 |
| ATOM | 559 | H | VAL | 66 | −7.786 | 2.732 | 3.062 | 1.00 | 99.99 |
| ATOM | 560 | N | PHE | 67 | −7.276 | 4.781 | 5.148 | 0.00 | 0.00 |
| ATOM | 561 | CA | PHE | 67 | −7.349 | 6.061 | 5.845 | 0.00 | 0.00 |
| ATOM | 562 | C | PHE | 67 | −8.198 | 5.980 | 7.119 | 0.00 | 0.00 |
| ATOM | 563 | O | PHE | 67 | −7.928 | 6.700 | 8.075 | 0.00 | 0.00 |
| ATOM | 564 | CB | PHE | 67 | −7.920 | 7.118 | 4.892 | 0.00 | 0.00 |
| ATOM | 565 | CG | PHE | 67 | −7.904 | 8.533 | 5.444 | 0.00 | 0.00 |
| ATOM | 566 | CD1 | PHE | 67 | −9.105 | 9.254 | 5.590 | 0.00 | 0.00 |
| ATOM | 567 | CD2 | PHE | 67 | −6.684 | 9.133 | 5.813 | 0.00 | 0.00 |
| ATOM | 568 | CE1 | PHE | 67 | −9.084 | 10.569 | 6.089 | 0.00 | 0.00 |
| ATOM | 569 | CE2 | PHE | 67 | −6.663 | 10.445 | 6.318 | 0.00 | 0.00 |
| ATOM | 570 | CZ | PHE | 67 | −7.863 | 11.165 | 6.452 | 0.00 | 0.00 |
| ATOM | 571 | H | PHE | 67 | −8.047 | 4.538 | 4.543 | 1.00 | 99.99 |
| ATOM | 572 | N | LEU | 68 | −9.194 | 5.085 | 7.164 | 0.00 | 0.00 |
| ATOM | 573 | CA | LEU | 68 | −9.898 | 4.738 | 8.397 | 0.00 | 0.00 |
| ATOM | 574 | C | LEU | 68 | −9.014 | 3.871 | 9.307 | 0.00 | 0.00 |
| ATOM | 575 | O | LEU | 68 | −9.191 | 3.913 | 10.521 | 0.00 | 0.00 |
| ATOM | 576 | CB | LEU | 68 | −11.193 | 3.986 | 8.045 | 0.00 | 0.00 |
| ATOM | 577 | CG | LEU | 68 | −12.237 | 4.842 | 7.296 | 0.00 | 0.00 |
| ATOM | 578 | CD1 | LEU | 68 | −13.375 | 3.941 | 6.799 | 0.00 | 0.00 |
| ATOM | 579 | CD2 | LEU | 68 | −12.818 | 5.958 | 8.179 | 0.00 | 0.00 |

-continued pdb file of the α3β2 model

| | | | | | | | | | |
|---|---|---|---|---|---|---|---|---|---|
| ATOM | 580 | H | LEU | 68 | −9.408 | 4.549 | 6.335 | 1.00 | 99.99 |
| ATOM | 581 | N | LEU | 69 | −8.046 | 3.136 | 8.730 | 0.00 | 0.00 |
| ATOM | 582 | CA | LEU | 69 | −7.027 | 2.348 | 9.420 | 0.00 | 0.00 |
| ATOM | 583 | C | LEU | 69 | −6.243 | 3.221 | 10.394 | 0.00 | 0.00 |
| ATOM | 584 | O | LEU | 69 | −6.277 | 2.978 | 11.599 | 0.00 | 0.00 |
| ATOM | 585 | CB | LEU | 69 | −6.105 | 1.703 | 8.363 | 0.00 | 0.00 |
| ATOM | 586 | CG | LEU | 69 | −4.888 | 0.869 | 8.834 | 0.00 | 0.00 |
| ATOM | 587 | CD1 | LEU | 69 | −4.375 | 0.064 | 7.628 | 0.00 | 0.00 |
| ATOM | 588 | CD2 | LEU | 69 | −3.704 | 1.695 | 9.357 | 0.00 | 0.00 |
| ATOM | 589 | H | LEU | 69 | −7.987 | 3.155 | 7.722 | 1.00 | 99.99 |
| ATOM | 590 | N | VAL | 70 | −5.545 | 4.233 | 9.858 | 0.00 | 0.00 |
| ATOM | 591 | CA | VAL | 70 | −4.762 | 5.203 | 10.615 | 0.00 | 0.00 |
| ATOM | 592 | C | VAL | 70 | −5.649 | 5.978 | 11.595 | 0.00 | 0.00 |
| ATOM | 593 | O | VAL | 70 | −5.145 | 6.438 | 12.606 | 0.00 | 0.00 |
| ATOM | 594 | CB | VAL | 70 | −4.039 | 6.171 | 9.644 | 0.00 | 0.00 |
| ATOM | 595 | CG1 | VAL | 70 | −4.936 | 6.845 | 8.604 | 0.00 | 0.00 |
| ATOM | 596 | CG2 | VAL | 70 | −3.279 | 7.289 | 10.371 | 0.00 | 0.00 |
| ATOM | 597 | H | VAL | 70 | −5.571 | 4.347 | 8.854 | 1.00 | 99.99 |
| ATOM | 598 | N | ILE | 71 | −6.953 | 6.123 | 11.333 | 0.00 | 0.00 |
| ATOM | 599 | CA | ILE | 71 | −7.867 | 6.881 | 12.184 | 0.00 | 0.00 |
| ATOM | 600 | C | ILE | 71 | −8.368 | 6.088 | 13.406 | 0.00 | 0.00 |
| ATOM | 601 | O | ILE | 71 | −8.968 | 6.678 | 14.304 | 0.00 | 0.00 |
| ATOM | 602 | CB | ILE | 71 | −8.994 | 7.473 | 11.285 | 0.00 | 0.00 |
| ATOM | 603 | CG1 | ILE | 71 | −8.441 | 8.747 | 10.601 | 0.00 | 0.00 |
| ATOM | 604 | CG2 | ILE | 71 | −10.325 | 7.793 | 11.995 | 0.00 | 0.00 |
| ATOM | 605 | CD1 | ILE | 71 | −9.348 | 9.356 | 9.524 | 0.00 | 0.00 |
| ATOM | 606 | H | ILE | 71 | −7.330 | 5.720 | 10.486 | 1.00 | 99.99 |
| ATOM | 607 | N | THR | 72 | −8.079 | 4.786 | 13.497 | 0.00 | 0.00 |
| ATOM | 608 | CA | THR | 72 | −8.423 | 3.957 | 14.657 | 0.00 | 0.00 |
| ATOM | 609 | C | THR | 72 | −7.221 | 3.219 | 15.258 | 0.00 | 0.00 |
| ATOM | 610 | O | THR | 72 | −7.312 | 2.686 | 16.361 | 0.00 | 0.00 |
| ATOM | 611 | CB | THR | 72 | −9.641 | 3.075 | 14.346 | 0.00 | 0.00 |
| ATOM | 612 | OG1 | THR | 72 | −9.535 | 2.482 | 13.069 | 0.00 | 0.00 |
| ATOM | 613 | CG2 | THR | 72 | −10.949 | 3.875 | 14.377 | 0.00 | 0.00 |
| ATOM | 614 | H | THR | 72 | −7.620 | 4.331 | 12.719 | 1.00 | 99.99 |
| ATOM | 615 | HG1 | THR | 72 | −10.353 | 2.020 | 12.878 | 1.00 | 99.99 |
| ATOM | 616 | N | GLU | 73 | −6.070 | 3.306 | 14.587 | 0.00 | 0.00 |
| ATOM | 617 | CA | GLU | 73 | −4.733 | 3.301 | 15.164 | 0.00 | 0.00 |
| ATOM | 618 | C | GLU | 73 | −4.533 | 4.614 | 15.932 | 0.00 | 0.00 |
| ATOM | 619 | O | GLU | 73 | −4.423 | 4.592 | 17.156 | 0.00 | 0.00 |
| ATOM | 620 | CB | GLU | 73 | −3.762 | 3.156 | 13.982 | 0.00 | 0.00 |
| ATOM | 621 | CG | GLU | 73 | −3.490 | 1.699 | 13.589 | 0.00 | 0.00 |
| ATOM | 622 | CD | GLU | 73 | −2.451 | 1.055 | 14.506 | 0.00 | 0.00 |
| ATOM | 623 | OE1 | GLU | 73 | −2.795 | 0.776 | 15.677 | 0.00 | 0.00 |
| ATOM | 624 | OE2 | GLU | 73 | −1.312 | 0.867 | 14.029 | 0.00 | 0.00 |
| ATOM | 625 | H | GLU | 73 | −6.119 | 3.677 | 13.648 | 1.00 | 99.99 |
| ATOM | 626 | N | THR | 74 | −4.509 | 5.746 | 15.211 | 0.00 | 0.00 |
| ATOM | 627 | CA | THR | 74 | −4.364 | 7.101 | 15.736 | 0.00 | 0.00 |
| ATOM | 628 | C | THR | 74 | −5.716 | 7.672 | 16.183 | 0.00 | 0.00 |
| ATOM | 629 | O | THR | 74 | −6.035 | 7.610 | 17.370 | 0.00 | 0.00 |
| ATOM | 630 | CB | THR | 74 | −3.619 | 8.038 | 14.767 | 0.00 | 0.00 |
| ATOM | 631 | OG1 | THR | 74 | −2.398 | 7.442 | 14.386 | 0.00 | 0.00 |
| ATOM | 632 | CG2 | THR | 74 | −3.335 | 9.399 | 15.417 | 0.00 | 0.00 |
| ATOM | 633 | H | THR | 74 | −4.599 | 5.666 | 14.208 | 1.00 | 99.99 |
| ATOM | 634 | HG1 | THR | 74 | −1.910 | 8.067 | 13.839 | 1.00 | 99.99 |
| HETATM | 635 | N | NME | 75 | −6.476 | 8.270 | 15.254 | 0.00 | 0.00 |
| HETATM | 636 | H | NME | 75 | −6.161 | 8.257 | 14.295 | 0.00 | 0.00 |
| HETATM | 637 | CA | NME | 75 | −7.656 | 9.066 | 15.556 | 0.00 | 0.00 |
| ATOM | 638 | N | GLU | 77 | −5.198 | −7.652 | −17.527 | 0.00 | 0.00 |
| ATOM | 639 | CA | GLU | 77 | −5.391 | −6.805 | −16.347 | 0.00 | 0.00 |
| ATOM | 640 | C | GLU | 77 | −6.465 | −7.361 | −15.396 | 0.00 | 0.00 |
| ATOM | 641 | O | GLU | 77 | −6.549 | −6.921 | −14.253 | 0.00 | 0.00 |
| ATOM | 642 | CB | GLU | 77 | −5.703 | −5.373 | −16.827 | 0.00 | 0.00 |
| ATOM | 643 | CG | GLU | 77 | −5.866 | −4.312 | −15.722 | 0.00 | 0.00 |
| ATOM | 644 | CD | GLU | 77 | −4.715 | −4.292 | −14.708 | 0.00 | 0.00 |
| ATOM | 645 | OE1 | GLU | 77 | −5.022 | −4.256 | −13.496 | 0.00 | 0.00 |
| ATOM | 646 | OE2 | GLU | 77 | −3.548 | −4.318 | −15.156 | 0.00 | 0.00 |
| ATOM | 647 | H | GLU | 77 | −6.010 | −7.846 | −18.092 | 1.00 | 99.99 |
| ATOM | 648 | N | LYS | 78 | −7.269 | −8.342 | −15.829 | 0.00 | 0.00 |
| ATOM | 649 | CA | LYS | 78 | −8.386 | −8.870 | −15.048 | 0.00 | 0.00 |
| ATOM | 650 | C | LYS | 78 | −7.926 | −9.797 | −13.917 | 0.00 | 0.00 |
| ATOM | 651 | O | LYS | 78 | −8.500 | −9.752 | −12.830 | 0.00 | 0.00 |
| ATOM | 652 | CB | LYS | 78 | −9.379 | −9.594 | −15.976 | 0.00 | 0.00 |
| ATOM | 653 | CG | LYS | 78 | −10.375 | −8.657 | −16.686 | 0.00 | 0.00 |
| ATOM | 654 | CD | LYS | 78 | −9.740 | −7.666 | −17.677 | 0.00 | 0.00 |
| ATOM | 655 | CE | LYS | 78 | −10.794 | −6.833 | −18.416 | 0.00 | 0.00 |
| ATOM | 656 | NZ | LYS | 78 | −11.598 | −7.646 | −19.349 | 0.00 | 0.00 |

-continued pdb file of the α3β2 model

| ATOM | 657 | H | LYS | 78 | −7.144 | −8.695 | −16.766 | 1.00 | 99.99 |
|------|-----|-----|-----|----|--------|--------|---------|------|-------|
| ATOM | 658 | HZ1 | LYS | 78 | −12.083 | −8.370 | −18.837 | 1.00 | 99.99 |
| ATOM | 659 | HZ2 | LYS | 78 | −12.275 | −7.058 | −19.816 | 1.00 | 99.99 |
| ATOM | 660 | HZ3 | LYS | 78 | −10.994 | −8.071 | −20.038 | 1.00 | 99.99 |
| ATOM | 661 | N | MET | 79 | −6.883 | −10.604 | −14.152 | 0.00 | 0.00 |
| ATOM | 662 | CA | MET | 79 | −6.210 | −11.357 | −13.097 | 0.00 | 0.00 |
| ATOM | 663 | C | MET | 79 | −5.312 | −10.435 | −12.263 | 0.00 | 0.00 |
| ATOM | 664 | O | MET | 79 | −5.123 | −10.703 | −11.082 | 0.00 | 0.00 |
| ATOM | 665 | CB | MET | 79 | −5.404 | −12.502 | −13.733 | 0.00 | 0.00 |
| ATOM | 666 | CG | MET | 79 | −4.757 | −13.440 | −12.706 | 0.00 | 0.00 |
| ATOM | 667 | SD | MET | 79 | −5.911 | −14.233 | −11.550 | 0.00 | 0.00 |
| ATOM | 668 | CE | MET | 79 | −4.751 | −15.290 | −10.646 | 0.00 | 0.00 |
| ATOM | 669 | H | MET | 79 | −6.466 | −10.607 | −15.071 | 1.00 | 99.99 |
| ATOM | 670 | N | THR | 80 | −4.794 | −9.345 | −12.850 | 0.00 | 0.00 |
| ATOM | 671 | CA | THR | 80 | −3.932 | −8.380 | −12.171 | 0.00 | 0.00 |
| ATOM | 672 | C | THR | 80 | −4.701 | −7.631 | −11.075 | 0.00 | 0.00 |
| ATOM | 673 | O | THR | 80 | −4.208 | −7.525 | −9.951 | 0.00 | 0.00 |
| ATOM | 674 | CB | THR | 80 | −3.313 | −7.404 | −13.188 | 0.00 | 0.00 |
| ATOM | 675 | OG1 | THR | 80 | −2.688 | −8.125 | −14.231 | 0.00 | 0.00 |
| ATOM | 676 | CG2 | THR | 80 | −2.263 | −6.487 | −12.550 | 0.00 | 0.00 |
| ATOM | 677 | H | THR | 80 | −4.985 | −9.175 | −13.826 | 1.00 | 99.99 |
| ATOM | 678 | HG1 | THR | 80 | −2.352 | −7.496 | −14.876 | 1.00 | 99.99 |
| ATOM | 679 | N | LEU | 81 | −5.914 | −7.146 | −11.381 | 0.00 | 0.00 |
| ATOM | 680 | CA | LEU | 81 | −6.784 | −6.508 | −10.399 | 0.00 | 0.00 |
| ATOM | 681 | C | LEU | 81 | −7.354 | −7.502 | −9.385 | 0.00 | 0.00 |
| ATOM | 682 | O | LEU | 81 | −7.630 | −7.100 | −8.259 | 0.00 | 0.00 |
| ATOM | 683 | CB | LEU | 81 | −7.852 | −5.633 | −11.088 | 0.00 | 0.00 |
| ATOM | 684 | CG | LEU | 81 | −8.925 | −6.361 | −11.926 | 0.00 | 0.00 |
| ATOM | 685 | CD1 | LEU | 81 | −10.130 | −6.825 | −11.091 | 0.00 | 0.00 |
| ATOM | 686 | CD2 | LEU | 81 | −9.447 | −5.431 | −13.032 | 0.00 | 0.00 |
| ATOM | 687 | H | LEU | 81 | −6.254 | −7.229 | −12.330 | 1.00 | 99.99 |
| ATOM | 688 | N | CYS | 82 | −7.474 | −8.790 | −9.743 | 0.00 | 0.00 |
| ATOM | 689 | CA | CYS | 82 | −7.870 | −9.842 | −8.815 | 0.00 | 0.00 |
| ATOM | 690 | C | CYS | 82 | −6.773 | −10.071 | −7.771 | 0.00 | 0.00 |
| ATOM | 691 | O | CYS | 82 | −7.084 | −10.069 | −6.581 | 0.00 | 0.00 |
| ATOM | 692 | CB | CYS | 82 | −8.181 | −11.122 | −9.601 | 0.00 | 0.00 |
| ATOM | 693 | SG | CYS | 82 | −8.822 | −12.397 | −8.483 | 0.00 | 0.00 |
| ATOM | 694 | H | CYS | 82 | −7.232 | −9.060 | −10.685 | 1.00 | 99.99 |
| ATOM | 695 | HG | CYS | 82 | −8.977 | −13.342 | −9.415 | 1.00 | 99.99 |
| ATOM | 696 | N | ILE | 83 | −5.505 | −10.239 | −8.191 | 0.00 | 0.00 |
| ATOM | 697 | CA | ILE | 83 | −4.407 | −10.490 | −7.258 | 0.00 | 0.00 |
| ATOM | 698 | C | ILE | 83 | −4.147 | −9.303 | −6.326 | 0.00 | 0.00 |
| ATOM | 699 | O | ILE | 83 | −3.876 | −9.520 | −5.147 | 0.00 | 0.00 |
| ATOM | 700 | CB | ILE | 83 | −3.110 | −11.018 | −7.916 | 0.00 | 0.00 |
| ATOM | 701 | CG1 | ILE | 83 | −2.464 | −10.029 | −8.908 | 0.00 | 0.00 |
| ATOM | 702 | CG2 | ILE | 83 | −3.376 | −12.398 | −8.545 | 0.00 | 0.00 |
| ATOM | 703 | CD1 | ILE | 83 | −1.076 | −10.449 | −9.406 | 0.00 | 0.00 |
| ATOM | 704 | H | ILE | 83 | −5.299 | −10.228 | −9.181 | 1.00 | 99.99 |
| ATOM | 705 | N | SER | 84 | −4.295 | −8.065 | −6.815 | 0.00 | 0.00 |
| ATOM | 706 | CA | SER | 84 | −4.185 | −6.861 | −5.999 | 0.00 | 0.00 |
| ATOM | 707 | C | SER | 84 | −5.305 | −6.788 | −4.952 | 0.00 | 0.00 |
| ATOM | 708 | O | SER | 84 | −5.040 | −6.413 | −3.811 | 0.00 | 0.00 |
| ATOM | 709 | CB | SER | 84 | −4.229 | −5.644 | −6.931 | 0.00 | 0.00 |
| ATOM | 710 | OG | SER | 84 | −4.021 | −4.452 | −6.205 | 0.00 | 0.00 |
| ATOM | 711 | H | SER | 84 | −4.518 | −7.952 | −7.795 | 1.00 | 99.99 |
| ATOM | 712 | HG | SER | 84 | −4.040 | −3.713 | −6.817 | 1.00 | 99.99 |
| ATOM | 713 | N | VAL | 85 | −6.535 | −7.178 | −5.324 | 0.00 | 0.00 |
| ATOM | 714 | CA | VAL | 85 | −7.690 | −7.218 | −4.428 | 0.00 | 0.00 |
| ATOM | 715 | C | VAL | 85 | −7.544 | −8.290 | −3.334 | 0.00 | 0.00 |
| ATOM | 716 | O | VAL | 85 | −8.061 | −8.092 | −2.235 | 0.00 | 0.00 |
| ATOM | 717 | CB | VAL | 85 | −8.998 | −7.352 | −5.246 | 0.00 | 0.00 |
| ATOM | 718 | CG1 | VAL | 85 | −10.214 | −7.827 | −4.431 | 0.00 | 0.00 |
| ATOM | 719 | CG2 | VAL | 85 | −9.361 | −5.986 | −5.859 | 0.00 | 0.00 |
| ATOM | 720 | H | VAL | 85 | −6.684 | −7.476 | −6.279 | 1.00 | 99.99 |
| ATOM | 721 | N | LEU | 86 | −6.811 | −9.385 | −3.579 | 0.00 | 0.00 |
| ATOM | 722 | CA | LEU | 86 | −6.530 | −10.378 | −2.544 | 0.00 | 0.00 |
| ATOM | 723 | C | LEU | 86 | −5.603 | −9.815 | −1.462 | 0.00 | 0.00 |
| ATOM | 724 | O | LEU | 86 | −5.867 | −10.023 | −0.277 | 0.00 | 0.00 |
| ATOM | 725 | CB | LEU | 86 | −5.931 | −11.656 | −3.161 | 0.00 | 0.00 |
| ATOM | 726 | CG | LEU | 86 | −6.917 | −12.472 | −4.025 | 0.00 | 0.00 |
| ATOM | 727 | CD1 | LEU | 86 | −6.158 | −13.577 | −4.772 | 0.00 | 0.00 |
| ATOM | 728 | CD2 | LEU | 86 | −8.036 | −13.112 | −3.188 | 0.00 | 0.00 |
| ATOM | 729 | H | LEU | 86 | −6.409 | −9.519 | −4.497 | 1.00 | 99.99 |
| ATOM | 730 | N | LEU | 87 | −4.555 | −9.073 | −1.855 | 0.00 | 0.00 |
| ATOM | 731 | CA | LEU | 87 | −3.693 | −8.366 | −0.911 | 0.00 | 0.00 |
| ATOM | 732 | C | LEU | 87 | −4.417 | −7.191 | −0.237 | 0.00 | 0.00 |
| ATOM | 733 | O | LEU | 87 | −4.011 | −6.796 | 0.855 | 0.00 | 0.00 |

-continued pdb file of the α3β2 model

| | | | | | | | | | |
|---|---|---|---|---|---|---|---|---|---|
| ATOM | 734 | CB | LEU | 87 | −2.393 | −7.889 | −1.592 | 0.00 | 0.00 |
| ATOM | 735 | CG | LEU | 87 | −1.291 | −8.950 | −1.828 | 0.00 | 0.00 |
| ATOM | 736 | CD1 | LEU | 87 | −0.956 | −9.769 | −0.571 | 0.00 | 0.00 |
| ATOM | 737 | CD2 | LEU | 87 | −1.575 | −9.897 | −2.998 | 0.00 | 0.00 |
| ATOM | 738 | H | LEU | 87 | −4.386 | −8.940 | −2.843 | 1.00 | 99.99 |
| ATOM | 739 | N | ALA | 88 | −5.496 | −6.665 | −0.837 | 0.00 | 0.00 |
| ATOM | 740 | CA | ALA | 88 | −6.288 | −5.590 | −0.255 | 0.00 | 0.00 |
| ATOM | 741 | C | ALA | 88 | −7.083 | −6.048 | 0.972 | 0.00 | 0.00 |
| ATOM | 742 | O | ALA | 88 | −7.166 | −5.302 | 1.946 | 0.00 | 0.00 |
| ATOM | 743 | CB | ALA | 88 | −7.211 | −4.976 | −1.305 | 0.00 | 0.00 |
| ATOM | 744 | H | ALA | 88 | −5.776 | −7.017 | −1.742 | 1.00 | 99.99 |
| ATOM | 745 | N | LEU | 89 | −7.629 | −7.272 | 0.946 | 0.00 | 0.00 |
| ATOM | 746 | CA | LEU | 89 | −8.274 | −7.881 | 2.106 | 0.00 | 0.00 |
| ATOM | 747 | C | LEU | 89 | −7.245 | −8.364 | 3.140 | 0.00 | 0.00 |
| ATOM | 748 | O | LEU | 89 | −7.584 | −8.432 | 4.321 | 0.00 | 0.00 |
| ATOM | 749 | CB | LEU | 89 | −9.186 | −9.043 | 1.662 | 0.00 | 0.00 |
| ATOM | 750 | CG | LEU | 89 | −10.632 | −8.658 | 1.276 | 0.00 | 0.00 |
| ATOM | 751 | CD1 | LEU | 89 | −11.423 | −8.092 | 2.468 | 0.00 | 0.00 |
| ATOM | 752 | CD2 | LEU | 89 | −10.716 | −7.689 | 0.089 | 0.00 | 0.00 |
| ATOM | 753 | H | LEU | 89 | −7.542 | −7.830 | 0.106 | 1.00 | 99.99 |
| ATOM | 754 | N | THR | 90 | −5.994 | −8.643 | 2.734 | 0.00 | 0.00 |
| ATOM | 755 | CA | THR | 90 | −4.900 | −8.941 | 3.660 | 0.00 | 0.00 |
| ATOM | 756 | C | THR | 90 | −4.597 | −7.729 | 4.565 | 0.00 | 0.00 |
| ATOM | 757 | O | THR | 90 | −4.396 | −7.880 | 5.770 | 0.00 | 0.00 |
| ATOM | 758 | CB | THR | 90 | −3.669 | −9.491 | 2.901 | 0.00 | 0.00 |
| ATOM | 759 | OG1 | THR | 90 | −3.485 | −10.845 | 3.257 | 0.00 | 0.00 |
| ATOM | 760 | CG2 | THR | 90 | −2.336 | −8.768 | 3.142 | 0.00 | 0.00 |
| ATOM | 761 | H | THR | 90 | −5.777 | −8.588 | 1.748 | 1.00 | 99.99 |
| ATOM | 762 | HG1 | THR | 90 | −2.755 | −11.198 | 2.741 | 1.00 | 99.99 |
| ATOM | 763 | N | VAL | 91 | −4.622 | −6.530 | 3.975 | 0.00 | 0.00 |
| ATOM | 764 | CA | VAL | 91 | −4.453 | −5.213 | 4.589 | 0.00 | 0.00 |
| ATOM | 765 | C | VAL | 91 | −5.683 | −4.789 | 5.417 | 0.00 | 0.00 |
| ATOM | 766 | O | VAL | 91 | −5.598 | −3.869 | 6.228 | 0.00 | 0.00 |
| ATOM | 767 | CB | VAL | 91 | −4.233 | −4.161 | 3.507 | 0.00 | 99.99 |
| ATOM | 768 | CG1 | VAL | 91 | −4.404 | −2.769 | 4.110 | 0.00 | 99.99 |
| ATOM | 769 | CG2 | VAL | 91 | −2.825 | −4.298 | 2.941 | 0.00 | 99.99 |
| ATOM | 770 | N | PHE | 92 | −6.842 | −5.423 | 5.194 | 0.00 | 0.00 |
| ATOM | 771 | CA | PHE | 92 | −8.094 | −5.092 | 5.865 | 0.00 | 0.00 |
| ATOM | 772 | C | PHE | 92 | −8.318 | −5.951 | 7.113 | 0.00 | 0.00 |
| ATOM | 773 | O | PHE | 92 | −8.996 | −5.514 | 8.038 | 0.00 | 0.00 |
| ATOM | 774 | CB | PHE | 92 | −9.244 | −5.283 | 4.865 | 0.00 | 0.00 |
| ATOM | 775 | CG | PHE | 92 | −10.588 | −4.770 | 5.342 | 0.00 | 0.00 |
| ATOM | 776 | CD1 | PHE | 92 | −11.566 | −5.666 | 5.815 | 0.00 | 0.00 |
| ATOM | 777 | CD2 | PHE | 92 | −10.866 | −3.390 | 5.305 | 0.00 | 0.00 |
| ATOM | 778 | CE1 | PHE | 92 | −12.813 | −5.182 | 6.250 | 0.00 | 0.00 |
| ATOM | 779 | CE2 | PHE | 92 | −12.107 | −2.905 | 5.751 | 0.00 | 0.00 |
| ATOM | 780 | CZ | PHE | 92 | −13.082 | −3.802 | 6.223 | 0.00 | 0.00 |
| ATOM | 781 | H | PHE | 92 | −6.868 | −6.154 | 4.498 | 1.00 | 99.99 |
| ATOM | 782 | N | LEU | 93 | −7.720 | −7.147 | 7.170 | 0.00 | 0.00 |
| ATOM | 783 | CA | LEU | 93 | −7.607 | −7.931 | 8.393 | 0.00 | 0.00 |
| ATOM | 784 | C | LEU | 93 | −6.476 | −7.392 | 9.286 | 0.00 | 0.00 |
| ATOM | 785 | O | LEU | 93 | −6.534 | −7.605 | 10.495 | 0.00 | 0.00 |
| ATOM | 786 | CB | LEU | 93 | −7.337 | −9.401 | 8.029 | 0.00 | 0.00 |
| ATOM | 787 | CG | LEU | 93 | −8.505 | −10.093 | 7.292 | 0.00 | 0.00 |
| ATOM | 788 | CD1 | LEU | 93 | −8.049 | −11.471 | 6.794 | 0.00 | 0.00 |
| ATOM | 789 | CD2 | LEU | 93 | −9.743 | −10.260 | 8.187 | 0.00 | 0.00 |
| ATOM | 790 | H | LEU | 93 | −7.216 | −7.478 | 6.358 | 1.00 | 99.99 |
| ATOM | 791 | N | LEU | 94 | −5.492 | −6.665 | 8.716 | 0.00 | 0.00 |
| ATOM | 792 | CA | LEU | 94 | −4.451 | −5.952 | 9.457 | 0.00 | 0.00 |
| ATOM | 793 | C | LEU | 94 | −5.090 | −4.966 | 10.421 | 0.00 | 0.00 |
| ATOM | 794 | O | LEU | 94 | −4.900 | −5.085 | 11.631 | 0.00 | 0.00 |
| ATOM | 795 | CB | LEU | 94 | −3.480 | −5.226 | 8.501 | 0.00 | 0.00 |
| ATOM | 796 | CG | LEU | 94 | −2.353 | −4.352 | 9.118 | 0.00 | 0.00 |
| ATOM | 797 | CD1 | LEU | 94 | −1.439 | −3.925 | 7.963 | 0.00 | 0.00 |
| ATOM | 798 | CD2 | LEU | 94 | −2.778 | −3.049 | 9.821 | 0.00 | 0.00 |
| ATOM | 799 | H | LEU | 94 | −5.499 | −6.553 | 7.712 | 1.00 | 99.99 |
| ATOM | 800 | N | LEU | 95 | −5.820 | −3.984 | 9.872 | 0.00 | 0.00 |
| ATOM | 801 | CA | LEU | 95 | −6.449 | −2.929 | 10.650 | 0.00 | 0.00 |
| ATOM | 802 | C | LEU | 95 | −7.493 | −3.521 | 11.603 | 0.00 | 0.00 |
| ATOM | 803 | O | LEU | 95 | −7.759 | −2.920 | 12.628 | 0.00 | 0.00 |
| ATOM | 804 | CB | LEU | 95 | −7.031 | −1.860 | 9.702 | 0.00 | 0.00 |
| ATOM | 805 | CG | LEU | 95 | −8.254 | −2.255 | 8.847 | 0.00 | 0.00 |
| ATOM | 806 | CD1 | LEU | 95 | −9.593 | −1.964 | 9.540 | 0.00 | 0.00 |
| ATOM | 807 | CD2 | LEU | 95 | −8.260 | −1.499 | 7.512 | 0.00 | 0.00 |
| ATOM | 808 | H | LEU | 95 | −5.919 | −3.951 | 8.867 | 1.00 | 99.99 |
| ATOM | 809 | N | ILE | 96 | −8.050 | −4.708 | 11.327 | 0.00 | 0.00 |
| ATOM | 810 | CA | ILE | 96 | −9.022 | −5.369 | 12.197 | 0.00 | 0.00 |

-continued pdb file of the α3β2 model

| | | | | | | | | | |
|---|---|---|---|---|---|---|---|---|---|
| ATOM | 811 | C | ILE | 96 | −8.387 | −6.082 | 13.410 | 0.00 | 0.00 |
| ATOM | 812 | O | ILE | 96 | −9.102 | −6.439 | 14.344 | 0.00 | 0.00 |
| ATOM | 813 | CB | ILE | 96 | −9.920 | −6.295 | 11.322 | 0.00 | 0.00 |
| ATOM | 814 | CG1 | ILE | 96 | −10.979 | −5.416 | 10.613 | 0.00 | 0.00 |
| ATOM | 815 | CG2 | ILE | 96 | −10.612 | −7.453 | 12.070 | 0.00 | 0.00 |
| ATOM | 816 | CD1 | ILE | 96 | −11.868 | −6.145 | 9.597 | 0.00 | 0.00 |
| ATOM | 817 | H | ILE | 96 | −7.793 | −5.180 | 10.472 | 1.00 | 99.99 |
| ATOM | 818 | N | SER | 97 | −7.059 | −6.234 | 13.455 | 0.00 | 0.00 |
| ATOM | 819 | CA | SER | 97 | −6.334 | −6.780 | 14.606 | 0.00 | 0.00 |
| ATOM | 820 | C | SER | 97 | −5.306 | −5.798 | 15.185 | 0.00 | 0.00 |
| ATOM | 821 | O | SER | 97 | −4.693 | −6.100 | 16.208 | 0.00 | 0.00 |
| ATOM | 822 | CB | SER | 97 | −5.760 | −8.160 | 14.256 | 0.00 | 0.00 |
| ATOM | 823 | OG | SER | 97 | −5.015 | −8.132 | 13.060 | 0.00 | 0.00 |
| ATOM | 824 | H | SER | 97 | −6.507 | −5.963 | 12.651 | 1.00 | 99.99 |
| ATOM | 825 | HG | SER | 97 | −4.783 | −9.033 | 12.822 | 1.00 | 99.99 |
| ATOM | 826 | N | LYS | 98 | −5.198 | −4.596 | 14.597 | 0.00 | 0.00 |
| ATOM | 827 | CA | LYS | 98 | −4.651 | −3.399 | 15.233 | 0.00 | 0.00 |
| ATOM | 828 | C | LYS | 98 | −5.757 | −2.436 | 15.696 | 0.00 | 0.00 |
| ATOM | 829 | O | LYS | 98 | −5.464 | −1.551 | 16.499 | 0.00 | 0.00 |
| ATOM | 830 | CB | LYS | 98 | −3.647 | −2.714 | 14.287 | 0.00 | 0.00 |
| ATOM | 831 | CG | LYS | 98 | −2.211 | −3.185 | 14.574 | 0.00 | 0.00 |
| ATOM | 832 | CD | LYS | 98 | −1.468 | −2.332 | 15.616 | 0.00 | 0.00 |
| ATOM | 833 | CE | LYS | 98 | −2.219 | −2.091 | 16.926 | 0.00 | 0.00 |
| ATOM | 834 | NZ | LYS | 98 | −1.576 | −1.033 | 17.722 | 0.00 | 0.00 |
| ATOM | 835 | H | LYS | 98 | −5.681 | −4.458 | 13.721 | 1.00 | 99.99 |
| ATOM | 836 | HZ1 | LYS | 98 | −1.606 | −0.172 | 17.188 | 1.00 | 99.99 |
| ATOM | 837 | HZ2 | LYS | 98 | −2.081 | −0.902 | 18.587 | 1.00 | 99.99 |
| ATOM | 838 | HZ3 | LYS | 98 | −0.617 | −1.281 | 17.915 | 1.00 | 99.99 |
| ATOM | 839 | N | ILE | 99 | −7.014 | −2.629 | 15.257 | 0.00 | 0.00 |
| ATOM | 840 | CA | ILE | 99 | −8.183 | −1.910 | 15.761 | 0.00 | 0.00 |
| ATOM | 841 | C | ILE | 99 | −9.354 | −2.838 | 16.111 | 0.00 | 0.00 |
| ATOM | 842 | O | ILE | 99 | −9.812 | −2.824 | 17.253 | 0.00 | 0.00 |
| ATOM | 843 | CB | ILE | 99 | −8.578 | −0.611 | 14.993 | 0.00 | 0.00 |
| ATOM | 844 | CG1 | ILE | 99 | −9.986 | −0.568 | 14.330 | 0.00 | 0.00 |
| ATOM | 845 | CG2 | ILE | 99 | −7.440 | −0.024 | 14.128 | 0.00 | 0.00 |
| ATOM | 846 | CD1 | ILE | 99 | −10.151 | −1.102 | 12.907 | 0.00 | 0.00 |
| ATOM | 847 | H | ILE | 99 | −7.181 | −3.351 | 14.572 | 1.00 | 99.99 |
| HETATM | 848 | N | NME | 100 | −9.856 | −3.612 | 15.142 | 0.00 | 0.00 |
| HETATM | 849 | H | NME | 100 | −9.425 | −3.578 | 14.228 | 0.00 | 0.00 |
| HETATM | 850 | CA | NME | 100 | −11.085 | −4.380 | 15.281 | 0.00 | 0.00 |
| ATOM | 851 | N | GLU | 102 | 5.788 | −7.211 | −17.481 | 0.00 | 0.00 |
| ATOM | 852 | CA | GLU | 102 | 4.848 | −7.189 | −16.356 | 0.00 | 0.00 |
| ATOM | 853 | C | GLU | 102 | 4.997 | −8.397 | −15.412 | 0.00 | 0.00 |
| ATOM | 854 | O | GLU | 102 | 4.547 | −8.337 | −14.272 | 0.00 | 0.00 |
| ATOM | 855 | CB | GLU | 102 | 3.417 | −7.059 | −16.912 | 0.00 | 0.00 |
| ATOM | 856 | CG | GLU | 102 | 2.315 | −6.884 | −15.850 | 0.00 | 0.00 |
| ATOM | 857 | CD | GLU | 102 | 2.611 | −5.777 | −14.830 | 0.00 | 0.00 |
| ATOM | 858 | OE1 | GLU | 102 | 2.451 | −6.055 | −13.621 | 0.00 | 0.00 |
| ATOM | 859 | OE2 | GLU | 102 | 3.004 | −4.674 | −15.270 | 0.00 | 0.00 |
| ATOM | 860 | H | GLU | 102 | 5.386 | −7.173 | −18.406 | 1.00 | 99.99 |
| ATOM | 861 | N | LYS | 103 | 5.656 | −9.477 | −15.853 | 0.00 | 0.00 |
| ATOM | 862 | CA | LYS | 103 | 5.855 | −10.692 | −15.071 | 0.00 | 0.00 |
| ATOM | 863 | C | LYS | 103 | 6.870 | −10.507 | −13.939 | 0.00 | 0.00 |
| ATOM | 864 | O | LYS | 103 | 6.650 | −11.020 | −12.842 | 0.00 | 0.00 |
| ATOM | 865 | CB | LYS | 103 | 6.292 | −11.843 | −15.997 | 0.00 | 0.00 |
| ATOM | 866 | CG | LYS | 103 | 5.142 | −12.514 | −16.771 | 0.00 | 0.00 |
| ATOM | 867 | CD | LYS | 103 | 4.455 | −11.619 | −17.817 | 0.00 | 0.00 |
| ATOM | 868 | CE | LYS | 103 | 3.415 | −12.388 | −18.642 | 0.00 | 0.00 |
| ATOM | 869 | NZ | LYS | 103 | 4.035 | −13.385 | −19.536 | 0.00 | 0.00 |
| ATOM | 870 | H | LYS | 103 | 6.027 | −9.457 | −16.791 | 1.00 | 99.99 |
| ATOM | 871 | HZ1 | LYS | 103 | 4.552 | −14.058 | −18.988 | 1.00 | 99.99 |
| ATOM | 872 | HZ2 | LYS | 103 | 3.316 | −13.863 | −20.062 | 1.00 | 99.99 |
| ATOM | 873 | HZ3 | LYS | 103 | 4.664 | −12.922 | −20.177 | 1.00 | 99.99 |
| ATOM | 874 | N | MET | 104 | 7.961 | −9.768 | −14.185 | 0.00 | 0.00 |
| ATOM | 875 | CA | MET | 104 | 8.896 | −9.366 | −13.138 | 0.00 | 0.00 |
| ATOM | 876 | C | MET | 104 | 8.305 | −8.224 | −12.304 | 0.00 | 0.00 |
| ATOM | 877 | O | MET | 104 | 8.615 | −8.137 | −11.120 | 0.00 | 0.00 |
| ATOM | 878 | CB | MET | 104 | 10.229 | −8.957 | −13.787 | 0.00 | 0.00 |
| ATOM | 879 | CG | MET | 104 | 11.329 | −8.633 | −12.766 | 0.00 | 0.00 |
| ATOM | 880 | SD | MET | 104 | 11.730 | −9.976 | −11.612 | 0.00 | 0.00 |
| ATOM | 881 | CE | MET | 104 | 13.090 | −9.197 | −10.705 | 0.00 | 0.00 |
| ATOM | 882 | H | MET | 104 | 8.084 | −9.368 | −15.104 | 1.00 | 99.99 |
| ATOM | 883 | N | THR | 105 | 7.436 | −7.383 | −12.888 | 0.00 | 0.00 |
| ATOM | 884 | CA | THR | 105 | 6.771 | −6.285 | −12.189 | 0.00 | 0.00 |
| ATOM | 885 | C | THR | 105 | 5.844 | −6.813 | −11.088 | 0.00 | 0.00 |
| ATOM | 886 | O | THR | 105 | 5.914 | −6.335 | −9.955 | 0.00 | 0.00 |
| ATOM | 887 | CB | THR | 105 | 5.997 | −5.394 | −13.179 | 0.00 | 0.00 |

-continued pdb file of the α3β2 model

| ATOM | 888 | OG1 | THR | 105 | 6.855 | −4.945 | −14.208 | 0.00 | 0.00 |
|---|---|---|---|---|---|---|---|---|---|
| ATOM | 889 | CG2 | THR | 105 | 5.397 | −4.156 | −12.502 | 0.00 | 0.00 |
| ATOM | 890 | H | THR | 105 | 7.231 | −7.492 | −13.872 | 1.00 | 99.99 |
| ATOM | 891 | HG1 | THR | 105 | 6.350 | −4.365 | −14.783 | 1.00 | 99.99 |
| ATOM | 892 | N | LEU | 106 | 4.997 | −7.805 | −11.402 | 0.00 | 0.00 |
| ATOM | 893 | CA | LEU | 106 | 4.120 | −8.434 | −10.420 | 0.00 | 0.00 |
| ATOM | 894 | C | LEU | 106 | 4.886 | −9.297 | −9.415 | 0.00 | 0.00 |
| ATOM | 895 | O | LEU | 106 | 4.414 | −9.452 | −8.293 | 0.00 | 0.00 |
| ATOM | 896 | CB | LEU | 106 | 2.946 | −9.161 | −11.107 | 0.00 | 0.00 |
| ATOM | 897 | CG | LEU | 106 | 3.285 | −10.405 | −11.958 | 0.00 | 0.00 |
| ATOM | 898 | CD1 | LEU | 106 | 3.360 | −11.700 | −11.133 | 0.00 | 0.00 |
| ATOM | 899 | CD2 | LEU | 106 | 2.220 | −10.598 | −13.048 | 0.00 | 0.00 |
| ATOM | 900 | H | LEU | 106 | 4.955 | −8.138 | −12.357 | 1.00 | 99.99 |
| ATOM | 901 | N | CYS | 107 | 6.076 | −9.802 | −9.775 | 0.00 | 0.00 |
| ATOM | 902 | CA | CYS | 107 | 6.959 | −10.502 | −8.851 | 0.00 | 0.00 |
| ATOM | 903 | C | CYS | 107 | 7.514 | −9.531 | −7.807 | 0.00 | 0.00 |
| ATOM | 904 | O | CYS | 107 | 7.409 | −9.826 | −6.618 | 0.00 | 0.00 |
| ATOM | 905 | CB | CYS | 107 | 8.082 | −11.186 | −9.642 | 0.00 | 0.00 |
| ATOM | 906 | SG | CYS | 107 | 9.106 | −12.185 | −8.530 | 0.00 | 0.00 |
| ATOM | 907 | H | CYS | 107 | 6.410 | −9.644 | −10.715 | 1.00 | 99.99 |
| ATOM | 908 | HG | CYS | 107 | 9.956 | −12.618 | −9.466 | 1.00 | 99.99 |
| ATOM | 909 | N | ILE | 108 | 8.071 | −8.379 | −8.226 | 0.00 | 0.00 |
| ATOM | 910 | CA | ILE | 108 | 8.642 | −7.413 | −7.290 | 0.00 | 0.00 |
| ATOM | 911 | C | ILE | 108 | 7.585 | −6.825 | −6.352 | 0.00 | 0.00 |
| ATOM | 912 | O | ILE | 108 | 7.856 | −6.698 | −5.162 | 0.00 | 0.00 |
| ATOM | 913 | CB | ILE | 108 | 9.539 | −6.330 | −7.938 | 0.00 | 0.00 |
| ATOM | 914 | CG1 | ILE | 108 | 8.800 | −5.405 | −8.926 | 0.00 | 0.00 |
| ATOM | 915 | CG2 | ILE | 108 | 10.773 | −6.998 | −8.571 | 0.00 | 0.00 |
| ATOM | 916 | CD1 | ILE | 108 | 9.621 | −4.198 | −9.395 | 0.00 | 0.00 |
| ATOM | 917 | H | ILE | 108 | 8.128 | −8.179 | −9.216 | 1.00 | 99.99 |
| ATOM | 918 | N | SER | 109 | 6.372 | −6.546 | −6.845 | 0.00 | 0.00 |
| ATOM | 919 | CA | SER | 109 | 5.265 | −6.074 | −6.021 | 0.00 | 0.00 |
| ATOM | 920 | C | SER | 109 | 4.848 | −7.120 | −4.978 | 0.00 | 0.00 |
| ATOM | 921 | O | SER | 109 | 4.563 | −6.754 | −3.839 | 0.00 | 0.00 |
| ATOM | 922 | CB | SER | 109 | 4.092 | −5.731 | −6.947 | 0.00 | 0.00 |
| ATOM | 923 | OG | SER | 109 | 3.028 | −5.162 | −6.216 | 0.00 | 0.00 |
| ATOM | 924 | H | SER | 109 | 6.205 | −6.679 | −7.834 | 1.00 | 99.99 |
| ATOM | 925 | HG | SER | 109 | 2.317 | −4.947 | −6.824 | 1.00 | 99.99 |
| ATOM | 926 | N | VAL | 110 | 4.849 | −8.412 | −5.349 | 0.00 | 0.00 |
| ATOM | 927 | CA | VAL | 110 | 4.526 | −9.523 | −4.455 | 0.00 | 0.00 |
| ATOM | 928 | C | VAL | 110 | 5.595 | −9.736 | −3.370 | 0.00 | 0.00 |
| ATOM | 929 | O | VAL | 110 | 5.249 | −10.185 | −2.278 | 0.00 | 0.00 |
| ATOM | 930 | CB | VAL | 110 | 4.228 | −10.801 | −5.279 | 0.00 | 0.00 |
| ATOM | 931 | CG1 | VAL | 110 | 4.290 | −12.110 | −4.473 | 0.00 | 0.00 |
| ATOM | 932 | CG2 | VAL | 110 | 2.814 | −10.701 | −5.883 | 0.00 | 0.00 |
| ATOM | 933 | H | VAL | 110 | 5.095 | −8.644 | −6.301 | 1.00 | 99.99 |
| ATOM | 934 | N | LEU | 111 | 6.864 | −9.373 | −3.610 | 0.00 | 0.00 |
| ATOM | 935 | CA | LEU | 111 | 7.889 | −9.415 | −2.568 | 0.00 | 0.00 |
| ATOM | 936 | C | LEU | 111 | 7.591 | −8.396 | −1.466 | 0.00 | 0.00 |
| ATOM | 937 | O | LEU | 111 | 7.632 | −8.750 | −0.288 | 0.00 | 0.00 |
| ATOM | 938 | CB | LEU | 111 | 9.294 | −9.189 | −3.157 | 0.00 | 0.00 |
| ATOM | 939 | CG | LEU | 111 | 9.802 | −10.327 | −4.068 | 0.00 | 0.00 |
| ATOM | 940 | CD1 | LEU | 111 | 11.103 | −9.891 | −4.757 | 0.00 | 0.00 |
| ATOM | 941 | CD2 | LEU | 111 | 10.057 | −11.628 | −3.292 | 0.00 | 0.00 |
| ATOM | 942 | H | LEU | 111 | 7.116 | −9.015 | −4.521 | 1.00 | 99.99 |
| ATOM | 943 | N | LEU | 112 | 7.252 | −7.156 | −1.847 | 0.00 | 0.00 |
| ATOM | 944 | CA | LEU | 112 | 6.854 | −6.108 | −0.913 | 0.00 | 0.00 |
| ATOM | 945 | C | LEU | 112 | 5.460 | −6.346 | −0.311 | 0.00 | 0.00 |
| ATOM | 946 | O | LEU | 112 | 5.132 | −5.721 | 0.698 | 0.00 | 0.00 |
| ATOM | 947 | CB | LEU | 112 | 6.958 | −4.728 | −1.587 | 0.00 | 0.00 |
| ATOM | 948 | CG | LEU | 112 | 8.387 | −4.206 | −1.871 | 0.00 | 0.00 |
| ATOM | 949 | CD1 | LEU | 112 | 9.353 | −4.393 | −0.688 | 0.00 | 0.00 |
| ATOM | 950 | CD2 | LEU | 112 | 9.042 | −4.756 | −3.139 | 0.00 | 0.00 |
| ATOM | 951 | H | LEU | 112 | 7.233 | −6.937 | −2.834 | 1.00 | 99.99 |
| ATOM | 952 | N | ALA | 113 | 4.666 | −7.274 | −0.866 | 0.00 | 0.00 |
| ATOM | 953 | CA | ALA | 113 | 3.404 | −7.696 | −0.277 | 0.00 | 0.00 |
| ATOM | 954 | C | ALA | 113 | 3.618 | −8.559 | 0.969 | 0.00 | 0.00 |
| ATOM | 955 | O | ALA | 113 | 2.930 | −8.356 | 1.969 | 0.00 | 0.00 |
| ATOM | 956 | CB | ALA | 113 | 2.547 | −8.426 | −1.311 | 0.00 | 0.00 |
| ATOM | 957 | H | ALA | 113 | 4.973 | −7.744 | −1.706 | 1.00 | 99.99 |
| ATOM | 958 | N | LEU | 114 | 4.583 | −9.491 | 0.927 | 0.00 | 0.00 |
| ATOM | 959 | CA | LEU | 114 | 4.974 | −10.298 | 2.081 | 0.00 | 0.00 |
| ATOM | 960 | C | LEU | 114 | 5.779 | −9.482 | 3.103 | 0.00 | 0.00 |
| ATOM | 961 | O | LEU | 114 | 5.748 | −9.823 | 4.285 | 0.00 | 0.00 |
| ATOM | 962 | CB | LEU | 114 | 5.771 | −11.536 | 1.621 | 0.00 | 0.00 |
| ATOM | 963 | CG | LEU | 114 | 4.931 | −12.778 | 1.245 | 0.00 | 0.00 |
| ATOM | 964 | CD1 | LEU | 114 | 4.166 | −13.350 | 2.450 | 0.00 | 0.00 |

-continued pdb file of the α3β2 model

| | | | | | | | | | |
|---|---|---|---|---|---|---|---|---|---|
| ATOM | 965 | CD2 | LEU | 114 | 3.961 | −12.538 | 0.081 | 0.00 | 0.00 |
| ATOM | 966 | H | LEU | 114 | 5.105 | −9.614 | 0.070 | 1.00 | 99.99 |
| ATOM | 967 | N | THR | 115 | 6.437 | −8.388 | 2.684 | 0.00 | 0.00 |
| ATOM | 968 | CA | THR | 115 | 7.061 | −7.429 | 3.597 | 0.00 | 0.00 |
| ATOM | 969 | C | THR | 115 | 6.004 | −6.808 | 4.520 | 0.00 | 0.00 |
| ATOM | 970 | O | THR | 115 | 6.203 | −6.724 | 5.732 | 0.00 | 0.00 |
| ATOM | 971 | CB | THR | 115 | 7.850 | −6.357 | 2.822 | 0.00 | 0.00 |
| ATOM | 972 | OG1 | THR | 115 | 8.856 | −6.976 | 2.049 | 0.00 | 0.00 |
| ATOM | 973 | CG2 | THR | 115 | 8.536 | −5.343 | 3.744 | 0.00 | 0.00 |
| ATOM | 974 | H | THR | 115 | 6.462 | −8.179 | 1.695 | 1.00 | 99.99 |
| ATOM | 975 | HG1 | THR | 115 | 9.358 | −6.292 | 1.600 | 1.00 | 99.99 |
| ATOM | 976 | N | VAL | 116 | 4.865 | −6.420 | 3.937 | 0.00 | 0.00 |
| ATOM | 977 | CA | VAL | 116 | 3.714 | −5.834 | 4.610 | 0.00 | 0.00 |
| ATOM | 978 | C | VAL | 116 | 2.840 | −6.870 | 5.349 | 0.00 | 0.00 |
| ATOM | 979 | O | VAL | 116 | 1.930 | −6.491 | 6.087 | 0.00 | 0.00 |
| ATOM | 980 | CB | VAL | 116 | 2.821 | −5.132 | 3.593 | 0.00 | 99.99 |
| ATOM | 981 | CG1 | VAL | 116 | 1.467 | −4.828 | 4.229 | 0.00 | 99.99 |
| ATOM | 982 | CG2 | VAL | 116 | 3.477 | −3.829 | 3.151 | 0.00 | 99.99 |
| ATOM | 983 | N | PHE | 117 | 3.110 | −8.171 | 5.174 | 0.00 | 0.00 |
| ATOM | 984 | CA | PHE | 117 | 2.400 | −9.253 | 5.851 | 0.00 | 0.00 |
| ATOM | 985 | C | PHE | 117 | 3.141 | −9.726 | 7.108 | 0.00 | 0.00 |
| ATOM | 986 | O | PHE | 117 | 2.504 | −10.191 | 8.048 | 0.00 | 0.00 |
| ATOM | 987 | CB | PHE | 117 | 2.221 | −10.413 | 4.862 | 0.00 | 0.00 |
| ATOM | 988 | CG | PHE | 117 | 1.273 | −11.497 | 5.337 | 0.00 | 0.00 |
| ATOM | 989 | CD1 | PHE | 117 | 1.772 | −12.711 | 5.847 | 0.00 | 0.00 |
| ATOM | 990 | CD2 | PHE | 117 | −0.117 | −11.289 | 5.264 | 0.00 | 0.00 |
| ATOM | 991 | CE1 | PHE | 117 | 0.881 | −13.709 | 6.281 | 0.00 | 0.00 |
| ATOM | 992 | CE2 | PHE | 117 | −1.006 | −12.283 | 5.705 | 0.00 | 0.00 |
| ATOM | 993 | CZ | PHE | 117 | −0.507 | −13.495 | 6.215 | 0.00 | 0.00 |
| ATOM | 994 | H | PHE | 117 | 3.853 | −8.430 | 4.541 | 1.00 | 99.99 |
| ATOM | 995 | N | LEU | 118 | 4.470 | −9.571 | 7.159 | 0.00 | 0.00 |
| ATOM | 996 | CA | LEU | 118 | 5.248 | −9.706 | 8.388 | 0.00 | 0.00 |
| ATOM | 997 | C | LEU | 118 | 5.076 | −8.470 | 9.290 | 0.00 | 0.00 |
| ATOM | 998 | O | LEU | 118 | 5.266 | −8.568 | 10.503 | 0.00 | 0.00 |
| ATOM | 999 | CB | LEU | 118 | 6.733 | −9.887 | 8.025 | 0.00 | 0.00 |
| ATOM | 1000 | CG | LEU | 118 | 7.045 | −11.202 | 7.277 | 0.00 | 0.00 |
| ATOM | 1001 | CD1 | LEU | 118 | 8.486 | −11.161 | 6.750 | 0.00 | 0.00 |
| ATOM | 1002 | CD2 | LEU | 118 | 6.867 | −12.436 | 8.174 | 0.00 | 0.00 |
| ATOM | 1003 | H | LEU | 118 | 4.952 | −9.227 | 6.340 | 1.00 | 99.99 |
| ATOM | 1004 | N | LEU | 119 | 4.684 | −7.327 | 8.702 | 0.00 | 0.00 |
| ATOM | 1005 | CA | LEU | 119 | 4.344 | −6.095 | 9.399 | 0.00 | 0.00 |
| ATOM | 1006 | C | LEU | 119 | 3.168 | −6.312 | 10.329 | 0.00 | 0.00 |
| ATOM | 1007 | O | LEU | 119 | 3.315 | −6.088 | 11.531 | 0.00 | 0.00 |
| ATOM | 1008 | CB | LEU | 119 | 4.091 | −4.980 | 8.368 | 0.00 | 0.00 |
| ATOM | 1009 | CG | LEU | 119 | 3.542 | −3.613 | 8.849 | 0.00 | 0.00 |
| ATOM | 1010 | CD1 | LEU | 119 | 3.637 | −2.659 | 7.650 | 0.00 | 0.00 |
| ATOM | 1011 | CD2 | LEU | 119 | 2.071 | −3.607 | 9.296 | 0.00 | 0.00 |
| ATOM | 1012 | H | LEU | 119 | 4.577 | −7.325 | 7.698 | 1.00 | 99.99 |
| ATOM | 1013 | N | LEU | 120 | 2.020 | −6.742 | 9.780 | 0.00 | 0.00 |
| ATOM | 1014 | CA | LEU | 120 | 0.847 | −7.006 | 10.594 | 0.00 | 0.00 |
| ATOM | 1015 | C | LEU | 120 | 1.196 | −8.082 | 11.617 | 0.00 | 0.00 |
| ATOM | 1016 | O | LEU | 120 | 0.868 | −7.887 | 12.770 | 0.00 | 0.00 |
| ATOM | 1017 | CB | LEU | 120 | −0.389 | −7.303 | 9.718 | 0.00 | 0.00 |
| ATOM | 1018 | CG | LEU | 120 | −0.420 | −8.605 | 8.891 | 0.00 | 0.00 |
| ATOM | 1019 | CD1 | LEU | 120 | −1.031 | −9.789 | 9.656 | 0.00 | 0.00 |
| ATOM | 1020 | CD2 | LEU | 120 | −1.238 | −8.408 | 7.606 | 0.00 | 0.00 |
| ATOM | 1021 | H | LEU | 120 | 1.965 | −6.893 | 8.783 | 1.00 | 99.99 |
| ATOM | 1022 | N | ILE | 121 | 1.952 | −9.132 | 11.261 | 0.00 | 0.00 |
| ATOM | 1023 | CA | ILE | 121 | 2.309 | −10.226 | 12.171 | 0.00 | 0.00 |
| ATOM | 1024 | C | ILE | 121 | 3.063 | −9.794 | 13.437 | 0.00 | 0.00 |
| ATOM | 1025 | O | ILE | 121 | 2.951 | −10.474 | 14.455 | 0.00 | 0.00 |
| ATOM | 1026 | CB | ILE | 121 | 3.044 | −11.338 | 11.371 | 0.00 | 0.00 |
| ATOM | 1027 | CG1 | ILE | 121 | 1.996 | −12.159 | 10.582 | 0.00 | 0.00 |
| ATOM | 1028 | CG2 | ILE | 121 | 3.910 | −12.280 | 12.235 | 0.00 | 0.00 |
| ATOM | 1029 | CD1 | ILE | 121 | 2.583 | −13.151 | 9.570 | 0.00 | 0.00 |
| ATOM | 1030 | H | ILE | 121 | 2.237 | −9.221 | 10.296 | 1.00 | 99.99 |
| ATOM | 1031 | N | SER | 122 | 3.779 | −8.666 | 13.408 | 0.00 | 0.00 |
| ATOM | 1032 | CA | SER | 122 | 4.547 | −8.154 | 14.544 | 0.00 | 0.00 |
| ATOM | 1033 | C | SER | 122 | 3.910 | −6.923 | 15.201 | 0.00 | 0.00 |
| ATOM | 1034 | O | SER | 122 | 4.356 | −6.504 | 16.269 | 0.00 | 0.00 |
| ATOM | 1035 | CB | SER | 122 | 5.983 | −7.919 | 14.082 | 0.00 | 0.00 |
| ATOM | 1036 | OG | SER | 122 | 6.054 | −6.966 | 13.038 | 0.00 | 0.00 |
| ATOM | 1037 | H | SER | 122 | 3.814 | −8.140 | 12.545 | 1.00 | 99.99 |
| ATOM | 1038 | HG | SER | 122 | 5.710 | −7.367 | 12.233 | 1.00 | 99.99 |
| ATOM | 1039 | N | LYS | 123 | 2.824 | −6.407 | 14.610 | 0.00 | 0.00 |
| ATOM | 1040 | CA | LYS | 123 | 1.865 | −5.507 | 15.238 | 0.00 | 0.00 |
| ATOM | 1041 | C | LYS | 123 | 0.606 | −6.239 | 15.731 | 0.00 | 0.00 |

-continued pdb file of the α3β2 model

| | | | | | | | | | |
|---|---|---|---|---|---|---|---|---|---|
| ATOM | 1042 | O | LYS | 123 | −0.209 | −5.615 | 16.411 | 0.00 | 0.00 |
| ATOM | 1043 | CB | LYS | 123 | 1.524 | −4.373 | 14.258 | 0.00 | 0.00 |
| ATOM | 1044 | CG | LYS | 123 | 2.444 | −3.153 | 14.412 | 0.00 | 0.00 |
| ATOM | 1045 | CD | LYS | 123 | 2.457 | −2.557 | 15.837 | 0.00 | 0.00 |
| ATOM | 1046 | CE | LYS | 123 | 3.740 | −2.934 | 16.588 | 0.00 | 0.00 |
| ATOM | 1047 | NZ | LYS | 123 | 3.804 | −2.279 | 17.906 | 0.00 | 0.00 |
| ATOM | 1048 | H | LYS | 123 | 2.554 | −6.785 | 13.712 | 1.00 | 99.99 |
| ATOM | 1049 | HZ1 | LYS | 123 | 3.039 | −2.591 | 18.485 | 1.00 | 99.99 |
| ATOM | 1050 | HZ2 | LYS | 123 | 4.684 | −2.505 | 18.349 | 1.00 | 99.99 |
| ATOM | 1051 | HZ3 | LYS | 123 | 3.755 | −1.276 | 17.784 | 1.00 | 99.99 |
| ATOM | 1052 | N | ILE | 124 | 0.460 | −7.540 | 15.426 | 0.00 | 0.00 |
| ATOM | 1053 | CA | ILE | 124 | −0.713 | −8.357 | 15.735 | 0.00 | 0.00 |
| ATOM | 1054 | C | ILE | 124 | −0.378 | −9.710 | 16.388 | 0.00 | 0.00 |
| ATOM | 1055 | O | ILE | 124 | −1.293 | −10.446 | 16.758 | 0.00 | 0.00 |
| ATOM | 1056 | CB | ILE | 124 | −1.737 | −8.470 | 14.570 | 0.00 | 0.00 |
| ATOM | 1057 | CG1 | ILE | 124 | −1.402 | −9.547 | 13.510 | 0.00 | 0.00 |
| ATOM | 1058 | CG2 | ILE | 124 | −2.030 | −7.099 | 13.925 | 0.00 | 0.00 |
| ATOM | 1059 | CD1 | ILE | 124 | −2.384 | −10.723 | 13.496 | 0.00 | 0.00 |
| ATOM | 1060 | H | ILE | 124 | 1.160 | −7.964 | 14.834 | 1.00 | 99.99 |
| ATOM | 1061 | H | ILE | 124 | 1.160 | −7.964 | 14.834 | 1.00 | 99.99 |
| HETATM | 1062 | N | NME | 125 | 0.912 | −10.026 | 16.573 | 0.00 | 0.00 |
| HETATM | 1063 | H | NME | 125 | 1.620 | −9.385 | 16.248 | 0.00 | 0.00 |
| HETATM | 1064 | CA | NME | 125 | 1.375 | −11.257 | 17.196 | 0.00 | 0.00 |
| CONECT | 210 | 211 | 212 | | | | | | |
| CONECT | 423 | 424 | 425 | | | | | | |
| CONECT | 635 | 636 | 637 | | | | | | |
| CONECT | 848 | 849 | 850 | | | | | | |
| CONECT | 1062 | 1063 | 1064 | | | | | | |
| SPDBVT | 1.0000000000 | | 0.0000000000 | | | 0.0000000000 | | | |
| SPDBVT | 0.0000000000 | | 1.0000000000 | | | 0.0000000000 | | | |
| SPDBVT | 0.0000000000 | | 0.0000000000 | | | 1.0000000000 | | | |
| SPDBVT | 0.0000000000 | | 0.0000000000 | | | 0.0000000000 | | | |
| SPDBVT | 0.0000000000 | | 0.0000000000 | | | 0.0000000000 | | | |
| SPDBVV default; | | | | | | | | | |
| SPDBVV | 8.228955557850 | | 1111.571236645071 | | | 20.000000000000 | | | |
| SPDBVV | 0.9458704269 | | −0.2510394381 | | | −0.2056899028 | | | |
| SPDBVV | −0.2749012337 | | −0.9566045536 | | | −0.0966283586 | | | |
| SPDBVV | −0.1725063688 | | 0.1479423148 | | | −0.9738350087 | | | |
| SPDBVV | −0.2540000081 | | 0.0170000009 | | | −0.6704999804 | | | |
| SPDBVV | 0.0000000000 | | 0.0000000000 | | | 0.0000000000 | | | |
| SPDBVf | 3 3 3 3 | 33 3 | 3 3 | 3 | 3 3 | 3 3 | 3 | 3 3 | 3 3 3 |
| SPDBVf | 3 3 3 3 | 33 3 | 3 3 | 3 | 3 3 | 3 3 | 3 | 3 3 | 3 3 3 |
| SPDBVf | 3 3 3 3 | 33 3 | 3 3 | 3 | 3 3 | 3 3 | 3 | 3 3 | 3 3 3 |
| SPDBVf | 3 3 3 3 | 33 3 | 3 3 | 3 | 3 3 | 3 3 | 3 | 3 3 | 3 3 3 |
| SPDBVf | 3 3 3 3 | 33 3 | 3 3 | 3 | 3 3 | 3 3 | 3 | 3 3 | 3 3 3 |
| SPDBVf | 3 3 3 3 | 33 3 | 3 3 | 3 | 3 3 | 3 3 | 3 | 3 3 | 3 3 3 |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |
| SPDBVl | 1.00 1.00 1.00 1.0000 | | | 1.00 1.00 1.0000 | | | 1.00 1.00 1.00 | | |

| | | | |
|---|---|---|---|
| pdb file of the α3β2 model | | | |
| SPDBVb | 0.00 | 0.00 | 0.20 |
| END | | | |

What is claimed is:

1. A compound that is a derivative of dextromethorphan having the nitrogen-bound methyl group substituted by a $C_{1-6}$ alkyl group bearing an imidazolidine group.

2. The compound of claim 1, that is a non-competitive inhibitor of a nicotinic acetylcholine receptor and binds to the lumen of the pore of said receptor with a $\Delta G$ of $-8.5$ kcal/mol or less.

3. The compound of claim 1, that is a non-competitive inhibitor of $Rb^+$ efflux of a ligand-gated neurotransmitter ion channel with an $IC_{50}$ of less than 10 μM.

4. A compound having the structure

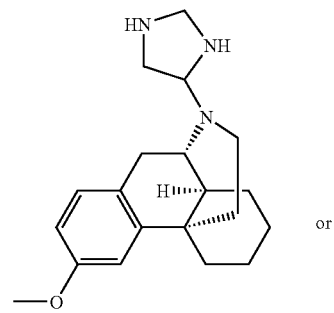

or

-continued
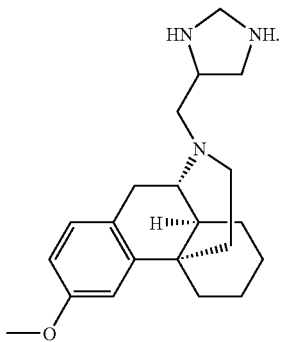
5. The compound
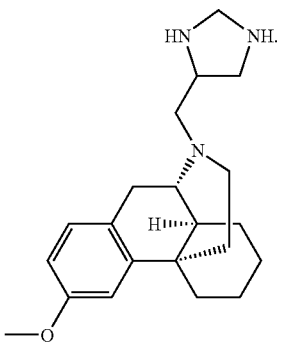
* * * * *